(12) United States Patent
Cech et al.

(10) Patent No.: US 6,309,867 B1
(45) Date of Patent: Oct. 30, 2001

(54) TELOMERASE

(75) Inventors: Thomas R. Cech; Toru Nakamura, both of Boulder, CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/430,323

(22) Filed: Oct. 29, 1999

Related U.S. Application Data

(63) Continuation of application No. 08/854,050, filed on May 9, 1997, which is a continuation-in-part of application No. 08/851,843, filed on May 6, 1997, now Pat. No. 6,093,809, which is a continuation-in-part of application No. 08/846,017, filed on Apr. 25, 1997, now abandoned, which is a continuation-in-part of application No. 08/844,419, filed on Apr. 18, 1997, now abandoned, which is a continuation-in-part of application No. 08/724,643, filed on Oct. 1, 1996, now abandoned.

(51) Int. Cl.[7] ........................................ C12N 9/12
(52) U.S. Cl. ............................. 435/194; 435/194
(58) Field of Search ............................... 435/194

(56) References Cited

U.S. PATENT DOCUMENTS 6,093,809  *  7/2000  Cech et al. .......................... 536/23.5

OTHER PUBLICATIONS

Nakamura et al, Telomerase catalytic subunit homologs from fission yeast and human, Science, 1997, 277, 955–959.*

* cited by examiner

Primary Examiner—Nashaat T. Nashed
Assistant Examiner—Malgorzata A. Walicka
(74) Attorney, Agent, or Firm—David J. Earp; Randolph T. Apple; William M. Smith

(57) ABSTRACT

The present invention is directed to novel telomerase nucleic acids and amino acids. In particular, the present invention is directed to nucleic acid and amino acid sequences encoding various telomerase protein subunits and motifs, including the 123 kDa and 43 kDa telomerase protein subunits of *Euplotes aediculatus*, and related sequences from Schizosaccharomyces, Saccharomyces sequences, and human telomerase. The present invention is also directed to polypeptides comprising these telomerase protein subunits, as well as functional polypeptides and ribonucleoproteins that contain these subunits.

1 Claim, 78 Drawing Sheets

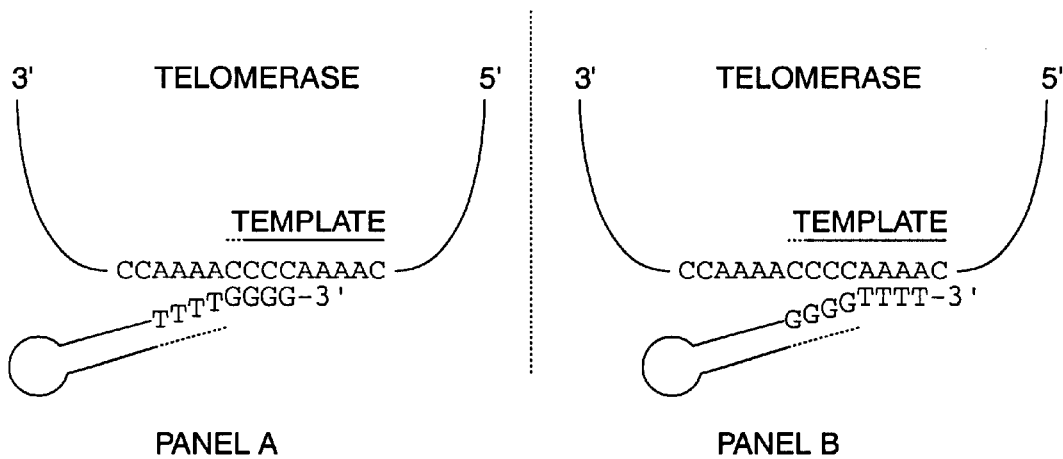

FIG. 7

```
   1  CCCCAAAACC CCAAAACCCC AAAACCCCTA TAAAAAAAGA AAAAATTGAG
  51  GTAGTTTAGA AATAAAATAT TATTCCCGCA CAAATGGAGA TGGATATTGA
 101  TTTGGATGAT ATAGAAAATT TACTTCCTAA TACATTCAAC AAGTATAGCA
 151  GCTCTTGTAG TGACAAGAAA GGATGCAAAA CATTGAAATC TGGCTCGAAA
 201  TCGCCTTCAT TGACTATTCC AAAGTTGCAA AAACAATTAG AGTTCTACTT
 251  CTCGGATGCA AATCTTTATA ACGATTCTTT CTTGAGAAAA TTAGTTTTAA
 301  AAAGCGGAGA GCAAAGAGTA GAAATTGAAA CATTACTAAT GTTTAAATAA
 351  AATCAGGTAA TGAGGATTAT TCTATTTTTT AGATCACTTC TTAAGGAGCA
 401  TTATGGAGAA AATTACTTAA TACTAAAAGG TAAACAGTTT GGATTATTTC
 451  CCTAGCCAAC AATGATGAGT ATATTAAATT CATATGAGAA TGAGTCAAAG
 501  GATCTCGATA CATCAGACTT ACCAAAGACA AACTCGCTAT AAAACGCAAG
 551  AAAAAGTTTG ATAATCGAAC AGCAGAAGAA CTTATTGCAT TTACTATTCG
 601  TATGGGTTTT ATTACAATTG TTTTAGGTAT CGACGGTGAA CTCCCGAGTC
 651  TTGAGACAAT TGAAAAAGCT GTTTACAACT GAAGGAATCG CAGTTCTGAA
 701  AGTTCTGATG TGTATGCCAT TATTTTGTGA ATTAATCTCA AATATCTTAT
 751  CTCAATTTAA TGGATAGCTA TAGAAACAAA CCAAATAAAC CATGCAAGTT
 801  TAATGGAATA TACGTTAAAT CCTTTGGGAC AAATGCACAC TGAATTTATA
 851  TTGGATTCTT AAAGCATAGA TACACAGAAT GCTTTAGAGA CTGATTTAGC
 901  TTACAACAGA TTACCTGTTT TGATTACTCT TGCTCATCTC TTATATCTTT
 951  AAAAGAAGCA GGCGAAATGA AAGAAGACT AAAGAAAGAG ATTTCAAAAT
1001  TTGTTGATTC TTCTGTAACC GGAATTAACA ACAAGAATAT TAGCAACGAA
1051  AAAGAAGAAG AGCTATCACA ATCCTGATTC TTAAAGATTT CAAAAATTCC
1101  AGGTAAGAGA GATACATTCA TTAAAATTCA TATATTATAG TTTTTCATTT
1151  CACAGCTGTT ATTTTCTTTT ATCTTAACAA TATTTTTTGA TTAGCTGGAA
1201  GTAAAAGTA TCAAATAAGA GAAGCGCTAG ACTGAGGTAA CTTAGCTTAT
1251  TCACATTCAT AGATCGACCT TCATATATCC AATACGATGA TAAGGAAACA
1301  GCAGTCATCC GTTTTAAAAA TAGTGCTATG AGGACTAAAT TTTTAGAGTC
1351  AAGAAATGGA GCCGAAATCT TAATCAAAAA GAATTGCGTC GATATTGCAA
1401  AAGAATCGAA CTCTAAATCT TTCGTTAATA AGTATTACCA ATCTTGATTG
1451  ATTGAAGAGA TTGACGAGGC AACTGCACAG AAGATCATTA AAGAAATAAA
1501  GTAACTTTTA TTAATTAGAG AATAAACTAA ATTACTAATA TAGAGATCAG
1551  CGATCTTCAA TTGACGAAAT AAAAGCTGAA CTAAAGTTAG ACAATAAAAA
1601  ATACAAACCT TGGTCAAAAT ATTGAGGAAG GAAAAGAAGA CCAGTTAGCA
1651  AAAGAAAAAA TAAGGCAATA AATAAAATGA GTACAGAAGT GAAGAAATAA
1701  AAGATTTATT TTTTTCAATA ATTTATTGAA AAGAGGGGTT TTGGGGTTTT
1751  GGGGTTTTGG GG
```

FIG. 11

```
   1  AAAACCCCAA AACCCCAAAA CCCCTTTTAG AGCCCTGCAG TTGGAAATAT
  51  AACCTCAGTA TTAATAAGCT CAGATTTTAA ATATTAATTA CAAAACCTAA
 101  ATGGAGGTTG ATGTTGATAA TCAAGCTGAT AATCATGGCA TTCACTCAGC
 151  TCTTAAGACT TGTGAAGAAA TTAAAGAAGC TAAAACGTTG TACTCTTGGA
 201  TCCAGAAAGT TATTAGATGA AGAAATCAAT CTCAAAGTCA TTATAAAGAT
 251  TTAGAAGATA TTAAATATT TGCGCAGACA AATATTGTTG CTACTCCACG
 301  AGACTATAAT GAAGAAGATT TTAAAGTTAT TGCAAGAAAA GAAGTATTTT
 351  CAACTGGACT AATGATCGAA CTTATTGACA AATGCTTAGT TGAACTTCTT
 401  TCATCAAGCG ATGTTTCAGA TAGACAAAAA CTTCAATGAT TTGGATTTCA
 451  ACTTAAGGGA AATCAATTAG CAAAGACCCA TTTATTAACA GCTCTTTCAA
 501  CTCAAAAGCA GTATTTCTTT CAAGACGAAT GGAACCAAGT TAGAGCAATG
 551  ATTGGAAATG AGCTCTTCCG ACATCTCTAC ACTAAATATT TAATATTCCA
 601  GCGAACTTCT GAAGGAACTC TTGTTCAATT TTGCGGGAAT AACGTTTTTG
 651  ATCATTTGAA AGTCAACGAT AAGTTTGACA AAAAGCAAAA AGGTGGAGCA
 701  GCAGACATGA ATGAACCTCG ATGTTGATCA ACCTGCAAAT ACAATGTCAA
 751  GAATGAGAAA GATCACTTTC TCAACAACAT CAACGTGCCG AATTGGAATA
 801  ATATGAAATC AAGAACCAGA ATATTTTATT GCACTCATTT TAATAGAAAT
 851  AACCAATTCT TCAAAAAGCA TGAGTTTGTG AGTAACAAAA ACAATATTTC
 901  AGCGATGGAC AGAGCTCAGA CGATATTCAC GAATATATTC AGATTTAATA
 951  GAATTAGAAA GAAGCTAAAA GATAAGGTTA TCGAAAAAAT TGCCTACATG
1001  CTTGAGAAAG TCAAAGATTT TAACTTCAAC TACTATTTAA CAAAATCTTG
1051  TCCTCTTCCA GAAAATTGGC GGGAACGGAA ACAAAAAATC GAAAACTTGA
1101  TAAATAAAAC TAGAGAAGAA AAGTCGAAGT ACTATGAAGA GCTGTTTAGC
1151  TACACAACTG ATAATAAATG CGTCACACAA TTTATTAATG AATTTTTCTA
1201  CAATATACTC CCCAAAGACT TTTTGACTGG AAGAAACCGT AAGAATTTTC
1251  AAAAGAAAGT TAAGAAATAT GTGGAACTAA ACAAGCATGA ACTCATTCAC
1301  AAAAACTTAT TGCTTGAGAA GATCAATACA AGAGAAATAT CATGGATGCA
1351  GGTTGAGACC TCTGCAAAGC ATTTTTATTA TTTTGATCAC GAAAACATCT
1401  ACGTCTTATG GAAATTGCTC CGATGGATAT TCGAGGATCT CGTCGTCTCG
1451  CTGATTAGAT GATTTTTCTA TGTCACCGAG CAACAGAAAA GTTACTCCAA
1501  AACCTATTAC TACAGAAAGA ATATTTGGGA CGTCATTATG AAAATGTCAA
1551  TCGCAGACTT AAAGAAGGAA ACGCTTGCTG AGGTCCAAGA AAAAGAGGTT
1601  GAAGAATGGA AAAAGTCGCT TGGATTTGCA CCTGGAAAAC TCAGACTAAT
1651  ACCGAAGAAA ACTACTTTCC GTCCAATTAT GACTTTCAAT AAGAAGATTG
1701  TAAATTCAGA CCGGAAGACT ACAAAATTAA CTACAAATAC GAAGTTATTG
1751  AACTCTCACT TAATGCTTAA GACATTGAAG AATAGAATGT TAAAGATCC
1801  TTTTGGATTC GCTGTTTTTA ACTATGATGA TGTAATGAAA AAGTATGAGG
1851  AGTTGTTTG CAAATGGAAG CAAGTTGGAC AACCAAAACT CTTCTTTGCA
1901  ACTATGGATA TCGAAAAGTG ATATGATAGT GTAAACAGAG AAAAACTATC
1951  AACATTCCTA AAAACTACTA AATTACTTTC TTCAGATTTC TGGATTATGA
2001  CTGCACAAAT TCTAAGAGA AGAATAACA TAGTTATCGA TTCGAAAAAC
2051  TTTAGAAAGA AAGAAATGAA AGATTATTTT AGACAGAAAT TCCAGAAGAT
2101  TGCACTTGAA GGAGGACAAT ATCCAACCTT ATTCAGTGTT CTTGAAAATG
2151  AACAAAATGA CTTAAATGCA AAGAAACAT TAATTGTTGA AGCAAAGCAA
2201  AGAAATTATT TTAAGAAAGA TAACTTACTT CAACCAGTCA TTAATATTTG
2251  CCAATATAAT TACATTAACT TTAATGGGAA GTTTTATAAA CAAACAAAAG
2301  GAATTCCTCA AGGTCTTTGA GTTTCATCAA TTTTGTCATC ATTTTATTAT
2351  GCAACATTAG AGGAAAGCTC CTTAGGATTC CTTAGAGATG AATCAATGAA
```

FIG. 9

```
2401  CCCTGAAAAT CCAAATGTTA ATCTTCTAAT GAGACTTACA GATGACTATC
2451  TTTTGATTAC AACTCAAGAG AATAATGCAG TATTGTTTAT TGAGAAACTT
2501  ATAAACGTAA GTCGTGAAAA TGGATTTAAA TTCAATATGA AGAAACTACA
2551  GACTAGTTTT CCATTAAGTC CAAGCAAATT TGCAAAATAC GGAATGGATA
2601  GTGTTGAGGA GCAAAATATT GTTCAAGATT ACTGCGATTG GATTGGCATC
2651  TCAATTGATA TGAAAACTCT TGCTTTAATG CCAAATATTA ACTTGAGAAT
2701  AGAAGGAATT CTGTGTACAC TCAATCTAAA CATGCAAACA AAGAAAGCAT
2751  CAATGTGGCT CAAGAAGAAA CTAAAGTCGT TTTTAATGAA TAACATTACC
2801  CATTATTTTA GAAAGACGAT TACAACCGAA GACTTTGCGA ATAAAACTCT
2851  CAACAAGTTA TTTATATCAG GCGGTTACAA ATACATGCAA TGAGCCAAAG
2901  AATACAAGGA CCACTTTAAG AAGAACTTAG CTATGAGCAG TATGATCGAC
2951  TTAGAGGTAT CTAAAATTAT ATACTCTGTA ACCAGAGCAT TCTTTAAATA
3001  CCTTGTGTGC AATATTAAGG ATACAATTTT TGGAGAGGAG CATTATCCAG
3051  ACTTTTTCCT TAGCACACTG AAGCACTTTA TTGAAATATT CAGCACAAAA
3101  AAGTACATTT TCAACAGAGT TTGCATGATC CTCAAGGCAA AAGAAGCAAA
3151  GCTAAAAAGT GACCAATGTC AATCTCTAAT TCAATATGAT GCATAGTCGA
3201  CTATTCTAAC TTATTTTGGA AAGTTAATTT TCAATTTTTG TCTTATATAC
3251  TGGGGTTTTG GGGTTTTGGG GTTTTGGGG
```

FIG. 9
(CONTINUED)

```
   1  MEVDVDNQAD NHGIHSALKT CEEIKEAKTL YSWIQKVIRC RNQSQSHYKD
  51  LEDIKIFAQT NIVATPRDYN EEDFKVIARK EVFSTGLMIE LIDKCLVELL
 101  SSSDVSDRQK LQCFGFQLKG NQLAKTHLLT ALSTQKQYFF QDEWNQVRAM
 151  IGNELFRHLY TKYLIFQRTS EGTLVQFCGN NVFDHLKVND KFDKKQKGGA
 201  ADMNEPRCCS TCKYNVKNEK DHFLNNINVP NWNNMKSRTR IFYCTHFNRN
 251  NQFFKKHEFV SNKNNISAMD RAQTIFTNIF RFNRIRKKLK DKVIEKIAYM
 301  LEKVKDFNFN YYLTKSCPLP ENWRERKQKI ENLINKTREE KSKYYEELFS
 351  YTTDNKCVTQ FINEFFYNIL PKDFLTGRNR KNFQKKVKKY VELNKHELIH
 401  KNLLLEKINT REISWMQVET SAKHFYYFDH ENIYVLWKLL RWIFEDLVVS
 451  LIRCFFYVTE QQKSYSKTYY YRKNIWDVIM KMSIADLKKE TLAEVQEKEV
 501  EEWKKSLGFA PGKLRLIPKK TTFRPIMTFN KKIVNSDRKT TKLTTNTKLL
 551  NSHLMLKTLK NRMFKDPFGF AVFNYDDVMK KYEEFVCKWK QVGQPKLFFA
 601  TMDIEKCYDS VNREKLSTFL KTTKLLSSDF WIMTAQILKR KNNIVIDSKN
 651  FRKKEMKDYF RQKFQKIALE GGQYPTLFSV LENEQNDLNA KKTLIVEAKQ
 701  RNYFKKDNLL QPVINICQYN YINFNGKFYK QTKGIPQGLC VSSILSSFYY
 751  ATLEESSLGF LRDESMNPEN PNVNLLMRLT DDYLLITTQE NNAVLFIEKL
 801  INVSRENGFK FNMKKLQTSF PLSPSKFAKY GMDSVEEQNI VQDYCDWIGI
 851  SIDMKTLALM PNINLRIEGI LCTLNLNMQT KKASMWLKKK LKSFLMNNIT
 901  HYFRKTITTE DFANKTLNKL FISGGYKMQ CAKEYKDHFK KNLAMSSMID
 951  LEVSKIIYSV TRAFFKYLVC NIKDTIFGEE HYPDFFLSTL KHFIEIFSTK
1001  KYIFNRVCMI LKAKEAKLKS DQCQSLIQYD A
```

FIG. 10

```
      CCCCAAAACCCCAAAACCCCAAAACCCCTATAAAAAAAGAAAAAATTGAGGTAGTTTAGA
    1 ---------+---------+---------+---------+---------+---------+  60
      GGGGTTTTGGGGTTTTGGGGTTTTGGGGATATTTTTTTCTTTTTTAACTCCATCAAATCT a     P  Q  N  P  K  T  P  K  P  L  *  K  K  K  K  L  R  *  F  R  -
b      P  K  T  P  K  P  Q  N  P  Y  K  K  K  R  K  N  *  G  S  L  E -
c       . P  K  P  Q  N  P  K  T  P  I  K  K  E  K  I  E  V  V  *  K -

AATAAAATATTATTCCCGCACAAATGGAGATGGATATTGATTTGGATGATATAGAAAATT
   61 ---------+---------+---------+---------+---------+---------+ 120
      TTATTTTATAATAAGGGCGTGTTTACCTCTACCTATAACTAAACCTACTATATCTTTTAA a     N  K  I  L  F  P  H  K  W  R  W  I  L  I  W  M  I  *  K  I  -
b      I  K  Y  Y  S  R  T  N  G  D  G  Y  *  F  G  *  Y  R  K  F -
c       *  N  I  I  P  A  Q  M  E  M  D  I  D  L  D  D  I  E  N  L -

TACTTCCTAATACATTCAACAAGTATAGCAGCTCTTGTAGTGACAAGAAAGGATGCAAAA
  121 ---------+---------+---------+---------+---------+---------+ 180
      ATGAAGGATTATGTAAGTTGTTCATATCGTCGAGAACATCACTGTTCTTTCCTACGTTTT a     Y  F  L  I  H  S  T  S  I  A  A  L  V  V  T  R  K  D  A  K  -
b      T  S  *  Y  I  Q  Q  V  *  Q  L  L  *  *  Q  E  R  M  Q  N -
c       L  P  N  T  F  N  K  Y  S  S  S  C  S  D  K  K  G  C  K  T -

CATTGAAATCTGGCTCGAAATCGCCTTCATTGACTATTCCAAAGTTGCAAAAACAATTAG
  181 ---------+---------+---------+---------+---------+---------+ 240
      GTAACTTTAGACCGAGCTTTAGCGGAAGTAACTGATAAGGTTTCAACGTTTTTGTTAATC a     H  *  N  L  A  R  N  R  L  H  *  L  F  Q  S  C  K  N  N  *  -
b      I  E  I  W  L  E  I  A  F  I  D  Y  S  K  V  A  K  T  I  R -
c       L  K  S  G  S  K  S  P  S  L  T  I  P  K  L  Q  K  Q  L  E -

AGTTCTACTTCTCGGATGCAAATCTTTATAACGATTCTTTCTTGAGAAAATTAGTTTTAA
  241 ---------+---------+---------+---------+---------+---------+ 300
      TCAAGATGAAGAGCCTACGTTTAGAAATATTGCTAAGAAAGAACTCTTTTAATCAAAATT a     S  S  T  S  R  M  Q  I  F  I  T  I  L  S  *  E  N  *  F  *  -
b      V  L  L  L  G  C  K  S  L  *  R  F  F  L  E  K  I  S  F  K -
c       F  Y  F  S  D  A  N  L  Y  N  D  S  F  L  R  K  L  V  L  K -

AAAGCGGAGAGCAAAGAGTAGAAATTGAAACATTACTAATGTTTAAATAAAATCAGGTAA
  301 ---------+---------+---------+---------+---------+---------+ 360
      TTTCGCCTCTCGTTTCTCATCTTTAACTTTGTAATGATTACAAATTTATTTTAGTCCATT a     K  A  E  S  K  E  *  K  L  K  H  Y  *  C  L  N  K  I  R  *  -
b      K  R  R  A  K  S  R  N  *  N  I  T  N  V  *  I  K  S  G  N -
c       S  G  E  Q  R  V  E  I  E  T  L  L  M  F  K  *  N  Q  V  M -

TGAGGATTATTCTATTTTTTAGATCACTTCTTAAGGAGCATTATGGAGAAAATTACTTAA
  361 ---------+---------+---------+---------+---------+---------+ 420
      ACTCCTAATAAGATAAAAAATCTAGTGAAGAATTCCTCGTAATACCTCTTTTAATGAATT a     *  G  L  F  Y  F  L  D  H  F  L  R  S  I  M  E  K  I  T  *  -
b      E  D  Y  S  I  F  *  I  T  S  *  G  A  L  W  R  K  L  L  N -
c       R  I  I  L  F  F  R  S  L  L  K  E  H  Y  G  E  N  Y  L  I -
```

FIG. 12

```
        TACTAAAAGGTAAACAGTTTGGATTATTTCCCTAGCCAACAATGATGAGTATATTAAATT
    421 ---------+---------+---------+---------+---------+---------+ 480
        ATGATTTCCATTTGTCAAACCTAATAAAGGGATCGGTTGTTACTACTCATATAATTTAA a   Y * K V N S L D Y F P S Q Q * * V Y * I   -
    b    T K R * T V W I I S L A N N D E Y I K F  -
    c     L K G K Q F G L F P * P T M M S I L N S -

CATATGAGAATGAGTCAAAGGATCTCGATACATCAGACTTACCAAAGACAAACTCGCTAT
    481 ---------+---------+---------+---------+---------+---------+ 540
        GTATACTCTTACTCAGTTTCCTAGAGCTATGTAGTCTGAATGGTTTCTGTTTGAGCGATA a   H M R M S Q R I S I H Q T Y Q R Q T R Y   -
    b    I * E * V K G S R Y I R L T K D K L A I  -
    c     Y E N E S K D L D T S D L P K T N S L * -

AAAACGCAAGAAAAAGTTTGATAATCGAACAGCAGAAGAACTTATTGCATTTACTATTCG
    541 ---------+---------+---------+---------+---------+---------+ 600
        TTTTGCGTTCTTTTTCAAACTATTAGCTTGTCGTCTTCTTGAATAACGTAAATGATAAGC a   K T Q E K V * * S N S R R T Y C I Y Y S   -
    b    K R K K K F D N R T A E E L I A F T I R  -
    c     N A R K S L I I E Q Q K N L L H L L F V -

TATGGGTTTTATTACAATTGTTTTAGGTATCGACGGTGAACTCCCGAGTCTTGAGACAAT
    601 ---------+---------+---------+---------+---------+---------+ 660
        ATACCCAAAATAATGTTAACAAAATCCATAGCTGCCACTTGAGGGCTCAGAACTCTGTTA a   Y G F Y Y N C F R Y R R * T P E S * D N   -
    b    M G F I T I V L G I D G E L P S L E T I  -
    c     W V L L Q L F * V S T V N S R V L R Q L -

TGAAAAAGCTGTTTACAACTGAAGGAATCGCAGTTCTGAAAGTTCTGATGTGTATGCCAT
    661 ---------+---------+---------+---------+---------+---------+ 720
        ACTTTTTCGACAAATGTTGACTTCCTTAGCGTCAAGACTTTCAAGACTACACATACGGTA a   * K S C L Q L K E S Q F * K F * C V C H   -
    b    E K A V Y N * R N R S S E S S D V Y A I  -
    c     K K L F T T E G I A V L K V L M C M P L -

TATTTTGTGAATTAATCTCAAATATCTTATCTCAATTTAATGGATAGCTATAGAAACAAA
    721 ---------+---------+---------+---------+---------+---------+ 780
        ATAAAACACTTAATTAGAGTTTATAGAATAGAGTTAAATTACCTATCGATATCTTTGTTT a   Y F V N * S Q I S Y L N L M D S Y R N K   -
    b    I L * I N L K Y L I S I * W I A I E T N  -
    c     F C E L I S N I L S Q F N G * L * K Q T -

CCAAATAAACCATGCAAGTTTAATGGAATATACGTTAAATCCTTTGGGACAAATGCACAC
    781 ---------+---------+---------+---------+---------+---------+ 840
        GGTTTATTTGGTACGTTCAAATTACCTTATATGCAATTTAGGAAACCCTGTTTACGTGTG a   P N K P C K F N G I Y V K S F G T N A H   -
    b    Q I N H A S L M E Y T L N P L G Q M H T  -
    c     K * T M Q V * W N I R * I L W D K C T L -

TGAATTTATATTGGATTCTTAAAGCATAGATACACAGAATGCTTTAGAGACTGATTTAGC
    841 ---------+---------+---------+---------+---------+---------+ 900
        ACTTAAATATAACCTAAGAATTTCGTATCTATGTGTCTTACGAAATCTCTGACTAAATCG a   * I Y I G F L K H R Y T E C F R D * F S   -
    b    E F I L D S * S I D T Q N A L E T D L A  -
    c     N L Y W I L K A * I H R M L * R L I * L -
```

FIG. 12
(CONTINUED)

```
        TTACAACAGATTACCTGTTTTGATTACTCTTGCTCATCTCTTATATCTTTAAAAGAAGCA
   901  ---------+---------+---------+---------+---------+---------+  960
        AATGTTGTCTAATGGACAAAACTAATGAGAACGAGTAGAGAATATAGAAATTTTCTTCGT a     L  Q  Q  I  T  C  F  D  Y  S  C  S  S  L  I  S  L  K  E  A  -
   b      Y  N  R  L  P  V  L  I  T  L  A  H  L  L  Y  L  *  K  K  Q  -
   c       T  T  D  Y  L  F  *  L  L  L  L  I  S  Y  I  F  K  R  S  R -

GGCGAAATGAAAAGAAGACTAAAGAAAGAGATTTCAAAATTTGTTGATTCTTCTGTAACC
   961  ---------+---------+---------+---------+---------+---------+ 1020
        CCGCTTTACTTTTCTTCTGATTTCTTTCTCTAAAGTTTTAAACAACTAAGAAGACATTGG a     G  E  M  K  R  R  L  K  K  E  I  S  K  F  V  D  S  S  V  T  -
   b      A  K  *  K  E  D  *  R  K  R  F  Q  N  L  L  I  L  L  *  P  -
   c       R  N  E  K  K  T  K  E  R  D  F  K  I  C  *  F  F  C  N  R -

GGAATTAACAACAAGAATATTAGCAACGAAAAAGAAGAAGAGCTATCACAATCCTGATTC
  1021  ---------+---------+---------+---------+---------+---------+ 1080
        CCTTAATTGTTGTTCTTATAATCGTTGCTTTTTCTTCTTCTCGATAGTGTTAGGACTAAG a     G  I  N  N  K  N  I  S  N  E  K  E  E  E  L  S  Q  S  *  F  -
   b      E  L  T  T  R  I  L  A  T  K  K  K  K  S  Y  H  N  P  D  S  -
   c       N  *  Q  Q  E  Y  *  Q  R  K  R  R  R  A  I  T  I  L  I  L -

TTAAAGATTTCAAAAATTCCAGGTAAGAGAGATACATTCATTAAAATTCATATATTATAG
  1081  ---------+---------+---------+---------+---------+---------+ 1140
        AATTTCTAAAGTTTTTAAGGTCCATTCTCTCTATGTAAGTAATTTTAAGTATATAATATC a     L  K  I  S  K  I  P  G  K  R  D  T  F  I  K  I  H  I  L  *  -
   b      *  R  F  Q  K  F  Q  V  R  E  I  H  S  L  K  F  I  Y  Y  S  -
   c       K  D  F  K  N  S  R  *  E  R  Y  I  H  *  N  S  Y  I  I  V -

TTTTTCATTTCACAGCTGTTATTTTCTTTTATCTTAACAATATTTTTTGATTAGCTGGAA
  1141  ---------+---------+---------+---------+---------+---------+ 1200
        AAAAAGTAAAGTGTCGACAATAAAAGAAAATAGAATTGTTATAAAAAACTAATCGACCTT a     F  F  I  S  Q  L  L  F  S  F  I  L  T  I  F  F  D  *  L  E  -
   b      F  S  F  H  S  C  Y  F  L  L  S  *  Q  Y  F  L  I  S  W  K  -
   c       F  H  F  T  A  V  I  F  F  Y  L  N  N  I  F  *  L  A  G  S -

GTAAAAAGTATCAAATAAGAGAAGCGCTAGACTGAGGTAACTTAGCTTATTCACATTCAT
  1201  ---------+---------+---------+---------+---------+---------+ 1260
        CATTTTTCATAGTTTATTCTCTTCGCGATCTGACTCCATTGAATCGAATAAGTGTAAGTA a     V  K  S  I  K  *  E  K  R  *  T  E  V  T  *  L  I  H  I  H  -
   b      *  K  V  S  N  K  R  S  A  R  L  R  *  L  S  L  F  T  F  I  -
   c       K  K  Y  Q  I  R  E  A  L  D  *  G  N  L  A  Y  S  H  S  * -

AGATCGACCTTCATATATCCAATACGATGATAAGGAAACAGCAGTCATCCGTTTTAAAAA
  1261  ---------+---------+---------+---------+---------+---------+ 1320
        TCTAGCTGGAAGTATATAGGTTATGCTACTATTCCTTTGTCGTCAGTAGGCAAAATTTTT a     R  S  T  F  I  Y  P  I  R  *  *  G  N  S  S  H  P  F  *  K  -
   b      D  R  P  S  Y  I  Q  Y  D  D  K  E  T  A  V  I  R  F  K  N  -
   c       I  D  L  H  I  S  N  T  M  I  R  K  Q  Q  S  S  V  L  K  I -

TAGTGCTATGAGGACTAAATTTTTAGAGTCAAGAAATGGAGCCGAAATCTTAATCAAAAA
  1321  ---------+---------+---------+---------+---------+---------+ 1380
        ATCACGATACTCCTGATTTAAAAATCTCAGTTCTTTACCTCGGCTTTAGAATTAGTTTTT a     *  C  Y  E  D  *  I  F  R  V  K  K  W  S  R  N  L  N  Q  K  -
   b      S  A  M  R  T  K  F  L  E  S  R  N  G  A  E  I  L  I  K  K  -
   c       V  L  *  G  L  N  F  *  S  Q  E  M  E  P  K  S  *  S  K  R -
```

*FIG. 12*
*(CONTINUED)*

```
        GAATTGCGTCGATATTGCAAAAGAATCGAACTCTAAATCTTTCGTTAATAAGTATTACCA
1381    ---------+---------+---------+---------+---------+---------+  1440
        CTTAACGCAGCTATAACGTTTTCTTAGCTTGAGATTTAGAAAGCAATTATTCATAATGGT a       E  L  R  R  Y  C  K  R  I  E  L  *  I  F  R  *  *  V  L  P   -
b        N  C  V  D  I  A  K  E  S  N  S  K  S  F  V  N  K  Y  Y  Q  -
c          I  A  S  I  L  Q  K  N  R  T  L  N  L  S  L  I  S  I  T  N-

ATCTTGATTGATTGAAGAGATTGACGAGGCAACTGCACAGAAGATCATTAAAGAAATAAA
1441    ---------+---------+---------+---------+---------+---------+  1500
        TAGAACTAACTAACTTCTCTAACTGCTCCGTTGACGTGTCTTCTAGTAATTTCTTTATTT a       I  L  I  D  C  R  D  *  R  G  N  C  T  E  D  H  *  R  N  K   -
b        S  *  L  I  E  E  I  D  E  A  T  A  Q  K  I  I  K  E  I  K  -
c          L  D  *  L  K  R  L  T  R  Q  L  H  R  R  S  L  K  K  *  S-

GTAACTTTTATTAATTAGAGAATAAACTAAATTACTAATATAGAGATCAGCGATCTTCAA
1501    ---------+---------+---------+---------+---------+---------+  1560
        CATTGAAAATAATTAATCTCTTATTTGATTTAATGATTATATCTCTAGTCGCTAGAAGTT a       V  T  F  I  N  *  R  I  N  *  I  T  N  I  E  I  S  D  L  Q   -
b        *  L  L  L  I  R  E  *  T  K  L  L  I  *  R  S  A  I  F  N  -
c          N  F  Y  *  L  E  N  K  L  N  Y  *  Y  R  D  Q  R  S  S  I-

TTGACGAAATAAAAGCTGAACTAAAGTTAGACAATAAAAAATACAAACCTTGGTCAAAAT
1561    ---------+---------+---------+---------+---------+---------+  1620
        AACTGCTTTATTTTCGACTTGATTTCAATCTGTTATTTTTATGTTTGGAACCAGTTTTA a       L  T  K  *  K  L  N  *  S  *  T  I  K  N  T  N  L  G  Q  N   -
b        *  R  N  K  S  *  T  K  V  R  Q  *  K  I  Q  T  L  V  K  I  -
c          D  E  I  K  A  E  L  K  L  D  N  K  K  Y  K  P  W  S  K  Y-

ATTGAGGAAGGAAAAGAAGACCAGTTAGCAAAAGAAAAAATAAGGCAATAAATAAAATGA
1621    ---------+---------+---------+---------+---------+---------+  1680
        TAACTCCTTCCTTTTCTTCTGGTCAATCGTTTTCTTTTTTATTCCGTTATTTATTTTACT a       I  E  E  G  K  E  D  Q  L  A  K  E  K  I  R  Q  *  I  K  *   -
b        L  R  K  E  K  K  T  S  *  Q  K  K  K  *  G  N  K  *  N  E  -
c          *  G  R  K  R  R  P  V  S  K  R  K  N  K  A  I  N  K  M  S-

GTACAGAAGTGAAGAAATAAAAGATTTATTTTTTTCAATAATTTATTGAAAAGAGGGGTT
1681    ---------+---------+---------+---------+---------+---------+  1740
        CATGTCTTCACTTCTTTATTTTCTAAATAAAAAAGTTATTAAATAACTTTTCTCCCCAA a       V  Q  K  *  R  N  K  R  F  I  F  F  N  N  L  L  K  R  G  V   -
b        Y  R  S  E  E  I  K  D  L  F  F  S  I  I  Y  *  K  E  G  F  -
c          T  E  V  K  K  *  K  I  Y  F  F  Q  *  F  I  E  K  R  G  F-

TTGGGGTTTTGGGGTTTTGGGG
1741    ---------+---------+--  1762
        AACCCCAAAACCCCAAAACCCC a       L  G  F  W  G  F  G    -
b        W  G  F  G  V  L  G   -
c          G  V  L  G  F  W    -
```

*FIG. 12*
(CONTINUED)

```
  2 EVDVQNQADNHGIHSALKTCEEIKEAKTLYSWIQKVIRCRNQSQSHYKDL  51
    |:::  |  :.::|:   :|       |.::|     ::. .   |  |..|.|.|
 19 ELELEMQENQNDIQVRVK....IDDPKQY..LVNVTAACLLQEGSYYQDK  62

52 EDIKIFAQTNIVATPRDYNEEDFKVIARKEVF.STGLMIELIDKCLVELL 100
    ::       ..::     :  .|.|  ..|...|:  ...:|  |   ...::|.:
 63 DERRYIITKALL....EVAESDPEFICQLAVYIRNELYIRTTTNYIVAF. 107

101 SSSDVSDRQKLQCFGFQLKGNQLAKTHLLTALSTQKYFFQDEWNQVRAM  150
                     ..:  ...:    ...:  |:    :..:.    |:.||   :
108 ............CVVHKNTQPFIEKYFNKAVLLPNDLLEVCEFAQVLYI 144

151 IGNELFRHLYTKYLIFQRTSEGTLVQFCGNNVFDHLKVNDKFDKKQKGGA 200
    ::..  | :||              | .: :.:|. ..|....  :::  ::
145 FDATEFKNLY............LDRILSQDIRKELTFRKCLQRCVRSKF 181

201 ADMNE...PRCCSTCKYNVKNEKDHFLNNINVPNWNNMKSRTRIFYCTHF 247
    ..:||    .::|..:   . |....::|. .| ..|:. |.:
182 SEFNEYQLGKYCTES..QRKKTMFRYLSVTNKQKWDQTKKK......... 220

248 NRNNQFFKKHEFVSNKNNISAMDRAQTIFTNIFRFNRIRKKLKDKVIEKI 297
    |.:  ...|   :.  ..:::  |  .: :          :|:..:    |  ||. |:.||
221 .RKENLLTKLQAIKESEDKSKRETG.....DIMNVEDAIKALKPAVMKKI 264

298 AYMLEKVKDFNFNYYLTKSCPLPENWRERKQKIENLINKTREEKSKYYEE 347
    |  . .:|                    :. |  ..:  |.|   |.|    ::.
265 AKRQNAMK..... ............KHMKAPKIPNSTLESKYLTFKD  294

348 LFSYTTDNKCVTQFINEFFYNILPKDFLTGRNRKNFQKKVKKYVELNKHE 397
    |:..    ...        .|  .|.||.|.:            ..:|  .|
295 LIKFCHISEP.....KERVYKILGKKYPKTEEEYKAAFGDSASAPFN.PE 338

398 LIHKNLLLEKINTREISWMQVETSAKHFYYFDHENIYVLWKLLRWIFEDL 447
    |   |..  :|     .|:|  .:|   :.. |. :    .|  ...   :||  : :
339 LAGKRMKIEISKTWENELSAKGNTAEVWDNLISSNQLPYMAMLRNLSN.. 386

448 VVSLIRCFFYVTEQQKSYSKTYYYRKNIWDVIMKMSIADLKKETLAEVQE 497
                                 |:|   ::.|
387 ..............................ILKAGVSD............ 394

498 KEVEEWKKSLGFAPGKLRLIPKKTTFRPIMTFNKKIVNSDRKTTKLTTNT 547
                                                    ||:..
395 ...............................................TTHS  398

548 KLLNSHLMLKTLKNRMFKDPFGFAVFNYDDVMKKYEEFVCKWKQVGQPKL 597
    |                                :|.  |.|:..|:
399 IVINK.................................ICEPKAVENSKM 415

598 FFATMDIEKCYDSVNREKLSTFLKTTKLLSSDFWIMTAQILKRKNNIVID 647
    |    :.  ..  :.||  |  |:..  :|..|   .:    :.:|| | :   |::
416 F..PLQFFSAIEAVN.EAVTKGFKAKK...RENMNLKGQIEAVKE..VVE 457

648 SKNFRKKEMKDYFRQKFQKIALEGGQYPTLFSVLENEQNDLNAKKTLIVE 697
    ..:  |||:|              .||..: ..:..|   |. ..:.  .. |  :.
458 KTDEEKKDM...........ELEQTEEGEFVKVNEGIGKQYINSIELAIK 496

698 AKQRNYFKKDNLLQPVINICQYNYINFNGKFYKQTKGIPQGLCVSSILSS 747
    .. :...   |   :::.   .   :      |.  :::..|  ... :|:
497 IAVNKNLDEIKGHTAIFSDVSGSMSTSMSGGAKKYGSVRTCLECALVLGL 546

748 FYYATLEESSLGFLRDESMNPENPNVNLLMRLTDDYLLITTQENNAVLFI 797
    :    .|.||  :::..|   .....   :::  :
547 MVKQRCEKSSFYIFSSPSSQCNKCYLEVDL.................... 576
```

FIG. 13

```
798  EKLINVSRENGFKFNMKK.LQTSFPLSPSKFAKYGMDSVEEQNIVQDYCD  846
         .::::: .|.| ||.. .|::. ...: ::::|  .  ....|
577  .......PGDELRPSMQKLLQEKGKLGGG..TDFPYECIDEWTKNKTHVD  617

847  WIGISIDMKTLALMPNINLRIEGILCTLNLNMQTKKASMWLKKKLKSFLM  896
     |.|  ||.. .  .:||:|  .:|:. .:              ||.|. :
618  NIVILSDMMIAEGYSDINVRGSSIVNSI.............KKYKDEVN  653

897  NNITHYFRKTITTEDFANKTLNKLFISGGYKYMQCAKEYKD.HFKKNLAM  945
     ||. :   .:. |:::          |::. :.|:.: :: | ::|
654  PNIKIF...AVDLEGYG.............KCLNLGDEFNENNYIKIFGM  687

946  SSMIDLEVSKIIYSVTRAFFKYLVCNIKDTIFGEEHYPDFFLSTLKHFIE  995
     |. |              :|::  ... :.             :::|
688  SDSI..............LKFISAKQGGA................NMVE  706

996  IFSTKKYIFNRVC  1008
     ::  |.: :.::.
707  VI..KNFALQKIG  717
```

*FIG. 13*
(CONTINUED)

```
132  LSTQKQYFFQDEWNQVRAMIGNEL.FRHLYTKYLIFQRTSE..GTLVQFC  178
     :|  ..|       ....|  ||||  :  :  .. ::.. |   | |.
  1  MSRRNQ.......KKPQAPIGNETNLDFVLQNLEVYKSQIEHYKTQQQQI   43

179  GNNVFDHLKVNDKFDKKQKGGAADMNEPRCCSTCKYNVKNEKDHFLNNIN  228
     :: :. ||...:. :. ..|...| :|        | .|...:.:|...:|
 44  KEEDLKLLKFKNQDQDGNSGNDDDDEE.........NNSNKQQELLRRVN   84

229  VPNWNNMKSRTRIFYCTHFNRNNQFFKKHEFVSNKNNISAMDRAQTIFTN  278
     ::... |::||     |:.|      ...  :.. |
 85  ...............QIKQQVQLIKK...VGSKVEKDLNLNEDENKKN  114

279  IFRFNRIRKKLKDKVIEKIAYMLEKVKDFNFNYYLTKSCPLPENWRERKQ  328
     :. ..::.   ...|. .   :  |  :::::  |..|.. ::|| .
115  GLSEQQVKEEQLRTITEEQVKYQNLVFNMDYQLDLNESGGHRRHRRETDY  164

329  KIENLINKTREEKSKYYEELFSYTTDNKCVTQFINE..FFYNILPKDFLTG  377
     ..|.:::  .:::|           ..:|. |: | : ||:::.
165  DTEKWFEISHDQK..............NYVSIYANQKTSYCWWLKDYFNK  200

378  RNRKNFQKKVKKYVELNKHELIHKNLLLEKINTREISWMQVETSAKHFYY  427
     .|  .::. .: :.   ..|:.  :  : :.|.  :  |:   |:..
201  NNYDHLNVSINRLE..TEAEFYAFDDFSQTIKLTNNSYQTVNID......  242

428  FDHENIYVLWKLLRWI..FEDLVVSLIRCFFYVTEQQKSYSKTYYYRKNI  475
     .: :|  ..:: |||:|  :| : :  ||: :  |.| .:.|. . ..|
243  VNFDNNLCILALLRFLLSLERFNILNIRSSY..TRNQYNFEKIGELLETI  290

476  WDVIMKMSIADLKKETLAEVQEKEVEEWKKSLGFAPGKLRLIPKKTTFRP  525
     :.|:.. ..       ..:| .::   ..:     |. | |.  |.
291  FAVVFSHR..........HLQGIHLQVPCEAFQYLVNSSSQISVKDSQLQ  330

526  IMTFNKKIVNSDRKTTKLTTNTKLLNSHLMLKTLKNRMFKDPFGFAVFNY  575
     :  |...:    |   |.|:   |:|..    .| :..   :.. || |.
331  VYSFSTDLKLVD..TNKVQDYFKFLQEFPRLTHVSQQAIPVSATNAVENL  378
```

*FIG. 14*

```
576  DDVMKKYEEFVCKWKQVGQPKLF.. ....FATMDIEKCYDS..VNREK     615
     : .:||       :. | |.|       :. . .:| ...  :.:|
379  NVLLKKVKH  ANLNLVSIPTQFNFDFYFVNLQHLKLEFGLEPNILTKQK    426

516  LSTFL......KTTKLLSSDFWIMTAQILKRKNNI..VIDSKNFRKKEMK    657
     |...|      |. |:|  |:.  ||    ||.  ...  ||:....
427  LENLLLSIKQSKNLKFLRLNFYTYVAQETSRKQILKQATTIKNLKNNKNQ    476

558  DYFRQKFQKIALEGGQYPTLFSVLEN..EQNDLNAKKTLIVEAKQRNYFK    705
     . . .       |:      | |     |:|:...    ::|.| |
477  EETPETKDETPSESTSGMKFFDHLSELTELEDFSVN....LQATQEIY..    520

706  KDNLLQPVINICQYNYINFNGKFYKQTKGIPQGLCVSSILSSFYYATLEE    755
     | |   |        .|     :.  :  ...|       |.||:
521  .DSLHKLLIRSTNLKKFKLSYKYEMEKSKMDTFIDLKNI.....YETLNN    564

756  SSLGFLRDESMNPENPNVNLLMRLTDDYLLITTQENNAVLFIEKLINVSR    305
     |:  |  | .||: |    ||:           .:..::   ||.
565  .....LKRCSVNISNPHGNISYELTN.........KDSTFYKFKLTLNQE    500

806  ENGFKFNMKKLQTSFPLSPSKFAKYGMDSVEEQNIVQDYCDWIGISIDMK    855
     |:.:|   |..|.:.   | ||.: .|:|. : :::...|...|: : ::.
601  LQHAKYTFK..QNEFQFNNVKSAKIESSSLESLEDIDSLCKSIASCKNLQ    648

856  TLALMPNINLRIEGILCTLNLNMQT..KKASMWLKK..KLKSFLMNNITH    901
     .:.:      |  ::|:. |:....   |.. :::|.  .||.:    .|.
649  NVNI.......IASLLYPNNIQKNPFNKPNLLFFKQFEQLKNLENVSINC    691

902  YFRKTI...TTEDFANKTLNKLFISGGYKYMQCAKEYKDHFKKNLAMSSM    948
     .:.|     |   |:....   |||   |   .:|:   :|..  ||.    .:...:
692  ILDQHILNSISEFLEKNKKIKAFILKRYYLLQYYLDYTKLFKTLQQLPEL    741

949  IDLEVSKIIYSVT..............RAFFKYLVCNIKDT..IFGEEHY    982
     ::   ...  :      |                  :||:. |.  ||:.    .:.      .:
742  NQVYINQQLEELTVSEVHKQVWENHKQKAFYEPLCEFIKESSQTLQLIDF    791

983  PDFFLS   TLKHFIEIFSTKKY IFNRVCMILKAKEAKLKSDQCQSLIQ   1028
     .:   :|     .|    |  | :|..||   .|:     ...     |    ...::.|.|::.
792  DQNTVSDDSIKKILESISESKYHHYLRLNPSQSSSLIKSENEEIQELLK    840
```

FIG. 14
(CONTINUED)

```
4    DIDLDDIENLLPNTFNKYSSSCSDKKGCKTLKSGSKSPSLTIPK......    47
     ::. ..||.    :.::...| |..  :||.|....  :|| .|.
617  NVKSAKIESSSLESLEDIDSLCKSIASCKNLQNVNIIASLLYPNNIQKNP    666

48   .......LQKQLEFYFSDANLYNDSFLRKLVLKSGEQRVE....IETLLM    86
     :   ||:|  . .|:  :::|    :|.|  .:  :|       |..:::
667  FNKPNLLFFKQFEQLKNLENVSINCILDQHILNSISEFLEKNKKIKAFIL    716
```

FIG. 15

```
  1 MEMDIDLDDIENL.....LPNTFNKYSSSCSDKKGCKTLKSGSKSPS...  42
    |: |.. .||    ...|.. |:| |...:. . | ||  ...:
491 IELAIKIAVNKNLDEIKGHTAIFSDVSGSMSTSMSGGAKKYGSVRTCLEC  540

43 .LTIPKLQKQ......LEFYFSDANLYNDSFLRKLVLKSGEQRVEIETLL  85
    |.:  : ||       : :: |... :|.::|  .: |.::| |..::.||
541 ALVLGLMVKQRCEKSSFYIFSSPSSQCNKCYL.EVDLPGDELRPSMQKLL  589
```

FIG. 16

```
telomerase p43  LQKQLEFYFSDANLYNDSFLRKLVLKSGEQRVEIETLLM
human La        ICHQUEYYFGDFNLPRDKFLKEQI.KLDEGWVPLEIMIK
Xenopus LaA     ICEQIEYYFGDHNLPRDKFLKQQI.LLDDGWVPLETMIK
Drosophila La   ILRQVEYYFGDANLNRDKFLREQIGKNEDGWVPLSVLVT
S. c. Lhp1p     CLKQVEFYFSEFNFPYDRFLRTTAEK.NDGWVPISTIAT
```

FIG. 18

```
   1 aactcattta attactaatt taatcaacaa gattgataaa aagcagtaaa taaaacccaa
  61 tagatttaat ttagaaagta tcaattgaaa aatggaaatt gaaaacaact aagcacaata
 121 gccaaaagcc gaaaaattgt ggtgggaact tgaattagag atgcaagaaa accaaaatga
 181 tatataagtt agggttaaga ttgacgatcc taagcaatat ctcgtgaacg tcactgcagc
 241 atgtttgttg taggaaggta gttactacta agataaagat gaagaagat atatcatcac
 301 taaagcactt cttgaggtgg ctgagtctga tcctgagttc atctgctagt tggcagtcta
 361 catccgtaat gaactttaca tcagaactac cactaactac attgtagcat ttgtgttgt
 421 ccacaagaat actcaaccat tcatcgaaaa gtacttcaac aaagcagtac ttttgcctaa
 481 tgacttactg gaagtctgtg aatttgcata ggttctctat attttgatg caactgaatt
 541 caaaaatttg tatcttgata ggatactttc ataagatatt cgtaaggaac tcactttccg
 601 taagtgttta caaagatgcg tcagaagcaa gttttctgaa ttcaacgaat actaacttgg
 661 taagtattgc actgaatcct aacgtaagaa acaatgttc cgttacctct cagttaccaa
 721 caagtaaaag tgggattaaa ctaagaagaa gagaaagag aatctcttaa ccaaacttta
 781 ggcaataaag gaatctgaag ataagtccaa gagagaaact ggagacataa tgaacgttga
 841 agatgcaatc aaggctttaa aaccagcagt tatgaagaaa atagccaaga gatagaatgc
 901 catgaagaaa cacatgaagg cacctaaaat tcctaactct accttggaat caaagtactt
 961 gaccttcaag gatctcatta agttctgcca tatttctgag cctaaagaaa gagtctataa
1021 gatccttggt aaaaaatacc ctaagaccga gaggaatac aaagcagcct ttggtgattc
1081 tgcatctgca cccttcaatc ctgaattggc tggaaagcgt atgaagattg aaatctctaa
1141 aacatggaa atgaactca gtgcaaaagg caacactgct gaggtttggg ataatttaat
1201 ttcaagcaat taactcccat atatggccat gttacgtaac ttgtctaaca tcttaaaagc
1261 cggtgtttca gatactacac actctattgt gatcaacaag atttgtgagc ccaaggccgt
1321 tgagaactcc aagatgttcc ctcttcaatt ctttagtgcc attgaagctg ttaatgaagc
1381 agttactaag ggattcaagg ccaagaagag agaaaatatg aatcttaaag gtcaaatcga
1441 agcagtaaag gaagttgttg aaaaaaccga tgaagagaag aaagatatgg agttggagta
1501 aaccgaagaa ggagaatttg ttaaagtcaa cgaagaagaatt ggcaagcaat acattaactc
1561 cattgaactt gcaatcaaga tagcagttaa caagaattta gatgaaatca aaggacacac
1621 tgcaatcttc tctgatgttt ctggttctat gagtacctca atgtcaggtg gagccaagaa
1681 gtatggttcc gttcgtactt gtctcgagtg tgcattagtc cttggtttga tggtaaaata
1741 acgttgtgaa aagtcctcat tctacatctt cagttcacct agttctcaat gcaataagtg
1801 ttacttagaa gttgatctcc ctggagacga actccgtcct tctatgtaaa aacttttgca
1861 agagaaagga aacttggtg gtggtactga tttcccctat gagtgcattg atgaatggac
1921 aaagaataaa actcacgtag acaatatcgt tattttgtct gatatgatga ttgcagaagg
1981 atattcagat atcaatgtta gaggcagttc cattgttaac agcatcaaaa agtacaagga
2041 tgaagtaaat cctaacatta aaatctttgc agttgactta gaaggttacg gaaagtgcct
2101 taatctaggt gatgagttca atgaaaacaa ctacatcaag atattcggta tgagcgattc
2161 aatcttaaag ttcatttcag ccaagcaagg aggagcaaat atggtcgaag ttatcaaaaa
2221 ctttgccctt caaaaaatag gacaaaagtg agtttcttga gattcttcta taacaaaaat
2281 ctcaccccac ttttttgttt tattgcatag ccattatgaa atttaaatta ttatctattt
2341 atttaagtta cttacatagt ttatgtatcg cagtctatta gcctattcaa atgattctgc
2401 aaagaacaaa aaagattaaa a
```

FIG. 19

```
                                    Motif A                                                              Motif B h--hDh---h--h                                          h---+-QG---SP
Consensus               GQPKLFFATMDIEKCYDSVNREKLSTFLKTTKLL--100-KFYKQTKGIPQGLCVSSILSSFYYATLEESSLGFL
telomerase p123         KNRNLHCTYDDYKKAFDSIPHSWLIQVLEIYKIN- 28-RQIAIKKGIYQGDSLSPLWFCLALNPLSHQLHNDR
Dong (LINE)             FGGSNWFREVDLKKCFDTISHDLIIKELKRYISD- 26-HVPVGPRVCVQGAPTSPALCNAVLLRLDRRLAGLA
al S.c. (groupII)       LKKKKSVTVLDVGDAYFSVPLDEDFRKYTAFTIP-  7-GIRYQYNVLPQGWKGSPAIFQSSMTKILEPFRKQN
HIV-RT                  VLPELYFMKFDVKSCYDSIPRMECMRILKDALKN- 68-KCYIREDGLFQGSSLSAPIVDLVYDDLLEFYSEFK
L8543.12

Motif C                                Motif D                  Motif E h--YhDDhhh                                  Gh-h---K                h-hLGh-h
Consensus               -14-LMRLTDDYLLITTQENN-0-AVLFIEKLINVSRENGFKFNMKKLQT-23-QDYCDWIGISI
telomerase p123         -16-HLIYMDDIKLYAKNDKE-0-MKKLIDTTIFSNDISMQFGLDKCKT-25-KCLYKYLGFQQ
Dong (LINE)             -55-YVRYADDILIGVLGSKN-2-KIIKRDLNNFLNS.LGLTINEEKTLI- 4-ETPARFLGYNI
al S.c. (groupII)       - 4-IYQYMDDLYVGSHLEIG-1-HRTKIEELRQHLLRWGLTTPDKKHQK- 0-EPPFLWMGYEL
HIV-RT                  - 8-ILKLADDFLIISTDQQQ.........VINIKKLAMGGFQKYNAKANR-41-IRSKSSKGIFR
L8543.12
```

FIG. 17

MEIENNQAQQPKAEKLWWELELEMQENQNDIQVRVKIDDPKQYL
VNVTAACLLQEGSYYQDKDERRYIITKALLEVAESDPEFICQLA
VYIRNELYIRTTTNYIVAFCVVHKNTQPFIEKYFNKAVLLPNDL
LEVCEFAQVLYIFDATEFKNLYLDRILSQDIRKELTFRKCLQRC
VRSKFSEFNEYQLGKYCTESQRKKTMFRYLSVTNKQKWDQTKKK
RKENLLTKLQAIKESEDKSKRETGDIMNVEDAIKALKPAVMKKI
AKRQNAMKKHMKAPKIPNSTLESKYLTFKDLIKFCHISEPKERV
YKILGKKYPKTEEEYKAAFGDSASAPFNPELAGKRMKIEISKTW
ENELSAKGNTAEVWDNLISSNQLPYMAMLRNLSNILKAGVSDTT
HSIVINKICEPKAVENSKMFPLQFFSAIEAVNEAVTKGFKAKKR
ENMNLKGQIEAVKEVVEKTDEEKKDMELEQTEEGEFVKVNEGIG
KQYINSIELAIKIAVNKNLDEIKGHTAIFSDVSGSMSTSMSGGA
KKYGSVRTCLECALVLGLMVKQRCEKSSFYIFSSPSSQCNKCYL
EVDLPGDELRPSMQKLLQEKGKLGGGTDFPYECIDEWTKNKTHV
DNIVILSDMMIAEGYSDINVRGSSIVNSIKKYKDEVNPNIKIFA
VDLEGYGKCLNLGDEFNENNYIKIFGMSDSILKFISAKQGGANM
VEVIKNFALQKIGQK

FIG. 20

MSRRNQKKPQAPIGNETNLDFVLQNLEVYKSQIEHYKTQQQQIK
EEDLKLLKFKNQDQDGNSGNDDDDEENNSNKQQELLRRVNQIKQ
QVQLIKKVGSKVEKDLNLNEDENKKNGLSEQQVKEEQLRTITEE
QVKYQNLVFNMDYQLDLNESGGHRRHRRETDYDTEKWFEISHDQ
KNYVSIYANQKTSYCWWLKDYFNKNNYDHLNVSINRLETEAEFY
AFDDFSQTIKLTNNSYQTVNIDVNFDNNLCILALLRFLLSLERF
NILNIRSSYTRNQYNFEKIGELLETIFAVVFSHRHLQGIHLQVP
CEAFQYLVNSSSQISVKDSQLQVYSFSTDLKLVDTNKVQDYFKF
LQEFPRLTHVSQQAIPVSATNAVENLNVLLKKVKHANLNLVSIP
TQFNFDFYFVNLQHLKLEFGLEPNILTKQKLENLLLSIKQSKNL
KFLRLNFYTYVAQETSRKQILKQATTIKNLKNNKNQEETPETKD
ETPSESTSGMKFFDHLSELTELEDFSVNLQATQEIYDSLHKLLI
RSTNLKKFKLSYKYEMEKSKMDTFIDLKNIYETLNNLKRCSVNI
SNPHGNISYELTNKDSTFYKFKLTLNQELQHAKYTFKQNEFQFN
NVKSAKIESSSLESLEDIDSLCKSIASCKNLQNVNIIASLLYPN
NIQKNPFNKPNLLFFKQFEQLKNLENVSINCILDQHILNSISEF
LEKNKKIKAFILKRYYLLQYYLDYTKLFKTLQQLPELNQVYINQ
QLEELTVSEVHKQVWENHKQKAFYEPLCEFIKESSQTLQLIDFD
QNTVSDDSIKKILESISESKYHHYLRLNPSQSSSLIKSENEEIQ
ELLKACDEKGVLVKAYYKFPLCLPTGTYYDYNSDRW

FIG. 22

MKILFEFIQDKLDIDLQTNSTYKENLKCGHFNGLDEILTTCFAL
PNSRKIALPCLPGDLSHKAVIDHCIIYLLTGELYNNVLTFGYKI
ARNEDVNNSLFCHSANVNVTLLKGAAWKMFHSLVGTYAFVDLLI
NYTVIQFNGQFFTQIVGNRCNEPHLPPKWVQRSSSSSATAAQIK
QLTEPVTNKQFLHKLNINSSSFFPYSKILPSSSSIKKLTDLREA
IFPTNLVKIPQRLKVRINLTLQKLLKRHKRLNYVSILNSICPPL
EGTVLDLSHLSRQSPKERVLKFIIVILQKLLPQEMFGSKKNKGK
IIKNLNLLLSLPLNGYLPFDSLLKKLRLKDFRWLFISDIWFTKH
NFENLNQLAICFISWLFRQLIPKIIQTFFYCTEISSTVTIVYFR
HDTWNKLITPFIVEYFKTYLVENNVCRNHNSYTLSNFNHSKMRI
IPKKSNNEFRIIAIPCRGADEEEFTIYKENHKNAIQPTQKILEY
LRNKRPTSFTKIYSPTQIADRIKEFKQRLLKKFNNVLPELYFMK
FDVKSCYDSIPRMECMRILKDALKNENGFFVRSQYFFNTNTGVL
KLFNVVNASRVPKPYELYIDNVRTVHLSNQDVINVVEMEIFKTA
LWVEDKCYIREDGLFQGSSLSAPIVDLVYDDLLEFYSEFKASPS
QDTLILKLADDFLIISTDQQQVINIKKLAMGGFQKYNAKANRDK
ILAVSSQSDDDTVIQFCAMHIFVKELEVWKHSSTMNNFHIRSKS
SKGIFRSLIALFNTRISYKTIDTNLNSTNTVLMQIDHVVKNISE
CYKSAFKDLSINVTQNMQFHSFLQRIIEMTVSGCPITKCDPLIE
YEVRFTILNGFLESLSSNTSKFKDNIILLRKEIQHLQAYIYIYI
HIVN

FIG. 23

```
   1 tcaatactat taattaataa ataaaaaaaa gcaaactaca aagaaaatgt caaggcgtaa
  61 ctaaaaaaag ccataggctc ctataggcaa tgaaacaaat cttgattttg tattacaaaa
 121 tctagaagtt tacaaaagcc agattgagca ttataagacc tagtagtaat agatcaaaga
 181 ggaggatctc aagcttttaa agttcaaaaa ttaagattag gatggaaact ctggcaacga
 241 tgatgatgat gaagaaaaca actcaaataa ataataagaa ttattaagga gagtcaatta
 301 gattaagtag caagtttaat tgataaaaaa agttggttct aaggtagaga aagatttgaa
 361 tttgaacgaa gatgaaaaca aaagaatgg actttctgaa tagcaagtga aagaagagta
 421 attaagaacg attactgaag aataggttaa gtattaaaat ttagtattta acatggacta
 481 ccagttagat ttaaatgaga gtggtggcca tagaagacac agaagagaaa cagattatga
 541 tactgaaaaa tggtttgaaa tatctcatga ccaaaaaaat tatgtatcaa tttacgccaa
 601 ctaaaagaca tcatattgtt ggtggcttaa agattatttt aataaaaaca attatgatca
 661 tcttaatgta agcattaaca gactagaaac tgaagccgaa ttctatgcct ttgatgattt
 721 ttcacaaaca atcaaactta ctaataattc ttactagact gttaacatag acgttaattt
 781 tgataataat ctctgtatac tcgcattgct tagatttta ttatcactag aaagattcaa
 841 tattttgaat ataagatctt cttatacaag aaattaatat aattttgaga aaattggtga
 901 gctacttgaa actatcttcg cagttgtctt ttctcatcgc cacttacaag gcattcattt
 961 acaagttcct tgcgaagcgt tctaatattt agttaactcc tcatcataaa ttagcgttaa
1021 agatagctaa ttataggtat actctttctc tacagactta aaattagttg acactaacaa
1081 agtccaagat tattttaagt tcttataaga attccctcgt tgactcatg taagctagta
1141 ggctatccca gttagtgcta ctaacgctgt agagaacctc aatgttttac ttaaaaaggt
1201 caagcatgct aatcttaatt tagtttctat ccctacctaa ttcaattttg atttctactt
1261 tgttaattta taacatttga aattagagtt tggattagaa ccaaatattt tgacaaaaca
1321 aaagcttgaa aatctacttt tgagtataaa ataatcaaaa aatcttaaat ttttaagatt
1381 aaactttac acctacgttg cttaagaaac ctccagaaaa cagatattaa acaagctac
1441 aacaatcaaa aatctcaaaa acaataaaaa tcaagaagaa actcctgaaa ctaaagatga
1501 aactccaagc gaaagcacaa gtggtatgaa atttttgat catctttctg aattaaccga
1561 gcttgaagat ttcagcgtta acttgtaagc tacccaagaa atttatgata gcttgcacaa
1621 acttttgatt agatcaacaa atttaaagaa gttcaaatta agttacaaat atgaaatgga
1681 aaagagtaaa atggatacat tcatagatct taagaatatt tatgaaacct taaacaatct
1741 taaagatgc tctgttaata tatcaaatcc tcatggaaac atttcttatg aactgacaaa
1801 taaagattct acttttata aatttaagct gaccttaaac taagaattat aacacgctaa
1861 gtatactttt aagtagaacg aatttttaatt taataacgtt aaaagtgcaa aaattgaatc
1921 ttcctcatta gaaagcttag aagatattga tagtctttgc aaatctattg cttcttgtaa
1981 aaatttacaa aatgttaata ttatcgccag tttgctctat cccaacaata tttagaaaaa
2041 tcctttcaat aagcccaatc ttctattttt caagcaattt gaataattga aaaatttgga
2101 aatgtatct atcaactgta ttcttgatca gcatatactt aattctattt cagaattcat
2161 agaaaagaat aaaaaaataa aagcattcat tttgaaaaga tattatttat tacaatatta
2221 tcttgattat actaaattat ttaaaacact tcaatagtta cctgaattaa attaagtta
2281 cattaattag caattagaag aattgactgt gagtgaagta cataagtaag tatgggaaaa
2341 ccacaagcaa aaagctttct atgaaccatt atgtgagttt atcaaagaat catcctaaac
2401 cctttagcta atagattttg accaaaacac tgtaagtgat gactctatta aaaagatttt
2461 agaatctata tctgagtcta agtatcatca ttatttgaga ttgaaccta gttaatctag
2521 cagtttaatt aaatctgaaa acgaagaaat ttaagaactt ctcaaagctt gcgacgaaaa
2581 aggtgtttta gtaaaagcat actataaatt ccctctatgt ttaccaactg gtacttatta
2641 cgattacaat tcagatagat ggtgattaat taaatattag tttaaataaa tattaaatat
2701 tgaatatttc tttgcttatt atttgaataa tacatacaat agtcatttt agtgttttga
2761 atatattta gttatttaat tcattatttt aagtaaataa ttattttca atcatttttt
2821 aaaaaatcg
```

FIG. 21

Oxytricha    LCVSYILSSFYYANLEENALQFLRKESMDPEKPETNLLMRLT
Euplotes     LCVSSILSSFYYATLEESSLGFLRDESMNPENPNVNLLMRLT

*FIG. 24*

```
ATTTATACTCATGAAAATCTTATTCGAGTTCATTCAAGACAAGCTTGACATTGATCTACA
GACCAACAGTACTTACAAAGAAAATTTAAAATGTGGTCACTTCAATGGCCTCGATGAAAT
TCTAACTACGTGTTTCGCACTACCAAATTCAAGAAAAATAGCATTACCATGCCTTCCTGG
TGACTTAAGCCACAAAGCAGTCATTGATCACTGCATCATTTACCTGTTGACGGGCGAATT
ATACAACAACGTACTAACATTTGGCTATAAAATAGCTAGAAATGAAGATGTCAACAATAG
TCTTTTTTGCCATTCTGCAAATGTTAACGTTACGTTACTGAAAGGCGCTGCTTGGAAAAT
GTTCCACAGTTTGGTCGGTACATACGCATTCGTTGATTTATTGATCAATTATACAGTAAT
TCAATTTAATGGGCAGTTTTTCACTCAAATCGTGGGTAACAGATGTAACGAACCTCATCT
GCCGCCCAAATGGGTCCAACGATCATCCTCATCATCCGCAACTGCTGCGCAAATCAAACA
ACTTACAGAACCAGTGACAAATAAACAATTCTTACACAAGCTCAATATAAATTCCTCTTC
TTTTTTTCCTTATAGCAAGATCCTTCCTTCATCATCATCTATCAAAAAGCTAACTGACTT
GAGAGAAGCTATTTTTCCCACAAATTTGGTTAAAATTCCTCAGAGACTAAAGGTACGAAT
TAATTTGACGCTGCAAAAGCTATTAAAGAGACATAAGCGTTTGAATTACGTTTCTATTTT
GAATAGTATTTGCCCACCATTGGAAGGGACCGTATTGGACTTGTCGCATTTGAGTAGGCA
ATCACCAAAGGAACGAGTCTTGAAATTTATCATTGTTATTTACAGAAGTTATTACCCCA
AGAAATGTTTGGCTCAAAGAAAATAAGGAAAAATTATCAAGAATCTAAATCTTTTATT
AAGTTTACCCTTAAATGGCTATTTACCATTTGATAGTTTGTTGAAAAAGTTAAGATTAAA
GGATTTTCGGTGGTTGTTCATTTCTGATATTTGGTTCACCAAGCACAATTTTGAAAACTT
GAATCAATTGGCGATTTGTTTCATTTCCTGGCTATTTAGACAACTAATTCCCAAAATTAT
ACAGACTTTTTTTTACTGCACCGAAATATCTTCTACAGTGACAATTGTTTACTTTAGACA
TGATACTTGGAATAAACTTATCACCCCTTTTATCGTAGAATATTTTAAGACGTACTTAGT
CGAAAACAACGTATGTAGAAACCATAATAGTTACACGTTGTCCAATTTCAATCATAGCAA
AATGAGGATTATACCAAAAAAAGTAATAATGAGTTCAGGATTATTGCCATCCCATGCAG
AGGGGCAGACGAAGAAGAATTCACAATTTATAAGGAGAATCACAAAAATGCTATCCAGCC
CACTCAAAAATTTTAGAATACCTAAGAAACAAAAGGCCGACTAGTTTTACTAAAATATA
TTCTCCAACGCAAATAGCTGACCGTATCAAAGAATTTAAGCAGAGACTTTTAAAGAAATT
TAATAATGTCTTACCAGAGCTTTATTTCATGAAATTTGATGTCAAATCTTGCTATGATTC
CATACCAAGGATGGAATGTATGAGGATACTCAAGGATGCGCTAAAAAATGAAAATGGGTT
TTTCGTTAGATCTCAATATTTCTTCAATACCAATACAGGTGTATTGAAGTTATTTAATGT
TGTTAACGCTAGCAGAGTACCAAAACCTTATGAGCTATACATAGATAATGTGAGGACGGT
TCATTTATCAAATCAGGATGTTATAAACGTTGTAGAGATGGAAATATTTAAAACAGCTTT
GTGGGTTGAAGATAAGTGCTACATTAGAGAAGATGGTCTTTTTCAGGGCTCTAGTTTATC
TGCTCCGATCGTTGATTTGGTGTATGACGATCTTCTGGAGTTTTATAGCGAGTTTAAAGC
CAGTCCTAGCCAGGACACATTAATTTTAAAACTGGCTGACGATTTCCTTATAATATCAAC
AGACCAACAGCAAGTGATCAATATCAAAAAGCTTGCCATGGGCGGATTTCAAAAATATAA
TGCGAAAGCCAATAGAGACAAAATTTTAGCCGTAAGCTCCCAATCAGATGATGATACGGT
TATTCAATTTTGTGCAATGCACATATTTGTTAAAGAATTGGAAGTTTGGAAACATTCAAG
CACAATGAATAATTTCCATATCCGTTCGAAATCTAGTAAAGGGATATTTCGAAGTTTAAT
AGCGCTGTTTAACACTAGAATCTCTTATAAAACAATTGACACAAATTTAAATTCAACAAA
CACCGTTCTCATGCAAATTGATCATGTTGTAAAGAACATTTCGGAATGTTATAAATCTGC
TTTTAAGGATCTATCAATTAATGTTACGCAAAATATGCAATTTCATTCGTTCTTACAACG
CATCATTGAAATGACAGTCAGCGGTTGTCCAATTACGAAATGTGATCCTTTAATCGAGTA
TGAGGTACGATTCACCATATTGAATGGATTTTGGAAAGCCTATCTTCAAACACATCAAA
ATTTAAAGATAATATCATTCTTTTGAGAAAGGAAATTCAACACTTGCAAGC
```

*FIG. 26*

```
                                    Motif 0
human                 AKFLHWLMSVYVVELLRSFFYVTETTFQKNR
tez1    ISEIEWLVLGKRSNAKMCLSDFEKRKQIFAEFIYWLYNSFIIPILQSFFYITESSDLRNR
EST2    LKDFRWLFISD---IWFTKHNFENLNQLAICFISWLFRQLIPKIIQTFFYCTEISSTVT-
p123    TREISWMQVET-SAKHFYYFDHEN-IYVLWKLLRWIFEDLVVSLIRCFFYVTEQQKSYSK
                          .        .           .  .....***.**

Motif 1
human    LFFYRKSVWSKLQSIGIRQHLKRVQLRDVSEAEVRQHREARPALLTSRLRFIPKP--DGL
tez1     TVYFRKDIWKLLCRPFI-TSMKMEAFEKINENNVRMDTQK-TTLPPAVIRLLPKK--NTF
EST2     IVYFRHDTWNKLITPFIVEYFKTYLVENNVCRNHNSYTLS--NFNHSKMRIIPKKSNNEF
p123     TYYYRKNIWDVIMKMSI-ADLKKETLAEVQEKEVEEWKKS-LGFAPGKLRLIPKK--TTF
          .*. *        .      .                      .    *  .**

Motif 2
human    RPIVNMDYVVGARTFRREKRAERLTSRVKALF-SVLNYERA
tez1     RLITN-LRKRFLIKMGSNKKMLVSTNQTLRPVASILKHLINEESSGIPFNLEVYMKLLTF
EST2     RIIAIPCRGADEEEFTIYKENHKNAIQPTQKILEYLRNKRPTSFTKIYSPTQIADRIKEF
p123     RPIMTFNKKIVNSDRKTTKLTTNTKLLNSHLMLKTLKN-RMFKDPFGFAVFNYDDVMKKY
         *                                    *                   .

KKDLLKHRMFGR-KKYFVRIDIKSCYDRIKQDLMFRIVKK-KLKDPEFVIRKYATIHATS
tez1     KQRLLKKFNNVLPELYFMKFDVKSCYDSIPRMECMRILKD-ALKNENGFFVRSQYFFNTN
EST2     EEFVCKWKQVGQPKLFFATMDIEKCYDSVNREKLSTFLKTTKLLSSDFWIMTAQILKRKN
p123     *        *         *  ***  * *   .                 .
                                Motif 3 (A)
```

FIG. 25

AKFLHWLMSVYVVELLRSFFYVTETTFQKNRLFFYRKSVWSKLQSIGIRQHLKR
VQLRDVSEAEVRQHREARPALLTSRLRFIPKPDGLRPIVNMDYVVGARTFRREK
RAERLTSRVKALFSVLNYERA

FIG. 27

GCCAAGTTCCTGCACTGGCTGATGAGTGTGTACGTCGTCGAGCTGCTCAGGTC
TTTCTTTTATGTCACGGAGACCACGTTTCAAAAGAACAGGCTCTTTTTCTACC
GGAAGAGTGTCTGGAGCAAGTTGCAAAGCATTGGAATCAGACAGCACTTGAAG
AGGGTGCAGCTGCGGGACGTGTCGGAAGCAGAGGTCAGGCAGCATCGGGAAGC
CAGGCCCGCCCTGCTGACGTCCAGACTCCGCTTCATCCCCAAGCCTGACGGGC
TGCGGCCGATTGTGAACATGGACTACGTCGTGGGAGCCAGAACGTTCCGCAGA
GAAAAGAGGGCCGAGCGTCTCACCTCGAGGGTGAAGGCACTGTTCAGCGTGCT
CAACTACGAGCGGGCGCG

FIG. 28

MTEHHTPKSRILRFLENQYVYLCTLNDYVQLVLRGSPASSYSNICERLRSDVQTSFSIFLHSTVVGF
DSKPDEGVQFSSPKCSQSELIANVVKQMFDESFERRRNLLMKGFSMNHEDFRAMHVNGVQNDLVSTF
PNYLISILESKNWQLLLEIIGSDAMHYLLSKGSIFEALPNDNYLQISGIPLFKNNVFEETVSKKRKR
TIETSITQNKSARKEVSWNSISISRFSIFYRSSYKKFKQDLYFNLHSICDRNTVHMWLQWIFPRQFG
LINAFQVKQLHKVIPLVSQSTVVPKRLLKVYPLIEQTAKRLHRISLSKVYNHYCPYIDTHDDEKILS
YSLKPNQVFAFLRSILVRVFPKLIWGNQRIFEIILKDLETFLKLSRYESFSLHYLMSNIKISEIEWL
VLGKRSNAKMCLSDFEKRKQIFAEFIYWLYNSFIIPILQSFFYITESSDLRNRTVYFRKDIWKLLCR
PFITSMKMEAFEKINENNVRMDTQKTTLPPAVIRLLPKKNTFRLITNLRKRFLIKMGSNKKMLVSTN
QTLRPVASILKHLINEESSGIPFNLEVYMKLLTFKKDLLKHRMFGRKKYFVRIDIKSCYDRIKQDLM
FRIVKKKLKDPEFVIRKYATIHATSDRATKNFVSEAFSYFDMVPFEKVVQLLSMKTSDTLFVDFVDY
WTKSSSEIFKMLKEHLSGHIVKIGNSQYLQKVGIPQGSILSSFLCHFYMEDLIDEYLSFTKKKGSVL
LRVVDDFLFITVNKKDAKKFLNLSLRGFEKHNFSTSLEKTVINFENSNGIINNTFFNESKKRMPFFG
FSVNMRSLDTLLACPKIDEALFNSTSVELTKHMGKSFFYKILRSSLASFAQVFIDITHNSKFNSCCN
IYRLGYSMCMRAQAYLKRMKDIFIPQRMFITDLLNVIGRKIWKKLAEILGYTSRRFLSSAEVKWLFC
LGMRDGLKPSFKYHPCFEQLIYQFQSLTDLIKPLRPVLRQVLFLHRRIAD

FIG. 29

```
ggtaccgatttacttccttccttccttcataagctaattgcttcctgcgaacgctcctaaatctctgaaatctcttacaaga
actcaataacaataccaagtcaaattccaattgtattagtgatcgataaatatttctatttatcggtcgtta
caagtatataagaacaaaagaacaactccttccccctaaagactttactttattaatttactttcaaatatattcg
ggttcgcttactttaatcgtgtactgttttagctgctacttctagccaacgcgtgtttctaccccgtcattgatat
agctcttggagtagctcacagaaatccttacaaatcttctgatgagactatattagattcattacagtcgtgcatattc
ttaacatggagccttacacactttagatgagtcgcatgatgagtatttggtatcatccaacgtttgccttgaaaag
gttgataattatttgcaaaaatcatgtccttagtgtggttaatccgaaagttttttgatgctgcacacgtctagcatg
attgagatattcaaaaattttctatccactacaactccttaacgcggttttatttttctatttctcatgttgtt
ccaaatatgtatcctcgtattaggcttttttcgtttactcctgaatcgtacctttttcactattccccctaatga
ataatctaaattagttcgcttataattgcatatagctatcattatatataaaaaatcctatatataattaatcaatatttgcggtc
gatactttgcaaaacattttattgtcgtagtcagtaggacacttgctttcgctttcagagaatcaatatgcttagagaagcgatgaagtacaaacg
actattttaaaacgttatgatcgatcagtaggacacttgctttcgctttcagagaatcaatatgcttagagaagcgatgaagtacaaacg
GACCGAACACCATACCCCAAAGCAGGAATTCTCGCTTCGTAGTCGGCTCGACTGTAGTCGGCTTGATTTTTGTTTTGTGTTGAGAAGTGTTCAATTTTCTTCTCCAAA
ATGTACAACTTGTTTGAGAGGGTCGCCGGCAAGCTCGTAGTCGGCTTGATTTTTGTTGAGAAGTGTTCAATTTTCTTCTCCAAA
TCCTTTCTATTTTCTTCATTCGAGgtatatatatttgttttgattttctattcgggatagctcatatatgggcagCTAATAGC
ATGCTCACAGTCAGAGgtataatatttcattcgagtcgatagctcatattcgggatagctcatatatgggcagCTAATAGC
GAATGTTGTAAAACAGATGTTCGATGAAAGTTTCGATGAAGTCTACTGATGAAGAATCTACTGATGAAGAAGGGTTTCCATGGtaaggt
attctaattgtgaaatatttaccttgcaattactgtttcaaagagattgtatttaaccgataaagaATCATGAAGATTTC
GAGCCATGCATGTAAACGGAGTACAAAATGATCTCGTTTCTACTTTTCCTAATTACCTTATATCTATACTGAGTCAAAA
AATTGGCAACTTTTGTTAGAAATgtaaataccggttaagatgttgcgcacttgaacaagactgacaagtatagTATCGG
CAGTGATGCCATGCATTACTTATTATCCAAAGGAAGTATTTTTGAGGCTCTTCCAAATGACAATTACCTTCAGATTTCTG
GCATACCACTTTTTAAAATAATGTGTTTGAGGAAAACTGTGTCAAAAAAGAAAGCGAACCATTGAAACATCCATTACT
CAAAATAAAAGCGCCCGCAAAGAAGTTTCCTGGAATAGACAAGTTCAATTAGTAGGTTTAGCATTTTTTACAGGTCATCCTA
TAAGAAGTTTAAGCAAGtaactaatactgttatcctcataactaatttttagATCTATATTTTAACTTACACTCTATTT
GTGATCGGAACACAGTACACATGTGGCTTCAATGGATTTTTCCAAGGCAATTTGGACTTATAAACGCATTTCAAGTGAAG
CAATTGCACAAAGTGATTCCACTGGTATCACAGAGTACAGTTGTGCCCAAACGCTCTCCTAAAGGTATACCCTTTAATTGA
ACAAACAGCAAAGCGACTCCATCGTATTTCCTTAAAGCCGAACCAGGTGTTTGCGTTTCACAACCATTATTGCCATATATTGACACCCACGATG
ATGAAAAAATCTGGGGTAACACTTGTTGATTTGAGATGATATTGAGATATATGAGATATATCGAGTCTTTAGTTTACATTATTTAATGAGTAACATAAGTCAAATGCG
AATTAATCTGGGGTAACACTTTTGATTTTGAGATATATGAGATATATCGAGTCTTTAGTTTACATTATTTAATGAGTAACATAAGTCAAATGCG
accagACCTTGCTAAGTGATTTTTTTTATATCACTGAATCAATGAAATCAAGTGATTACGAAGCGTTTAGTTATTTATTTTAGAAAGATATTT
AAAATGTGCTTAAGTGATTTGATTTGAGAAACGCAAGCAAATCAGATTTGAGATGATACTCATCATGAACTGTTTATTTTAGAAAGATATTT
ACCTATTTTACAATCTTTTTTTTATATCACTGAATCAATGAAATCAAGTGATTACGAAGCGTTTGAAAATAAACGAGtatttaaagtatt
GAAACTCTTGTGCCGACCCTTTATTCAGAACAATGTTAGATGATGATACTCAGAAAACTACTTTGCCTCCAGCAGTTATTCGTC
TATTACCTAAGAAGAATACCTTCGTCTCATTAGCAGATGGGTTCAAACAAAAATGTTAGTCAGTACGAACCAAACTTTACG
caatgtactttacttctaatctctattattagcagATGGGTTCAAACAAAAATGTTAGTCAGTACGAACCAAACTTTACG
ACCTGTGCATCGATACTGAAACATTTAATCAATGAAGAAAGTAGTGTATTCCATTTAACTTGGAGGTTTACATGAAGC
```

FIG. 30

```
TTCTTACTTTTAAGAAGGATCTTCTTAAGCACCGAATGTTTGGgtaattataatgcgcgattcctcattattaatttt
gcagGCGTAAGAAGTATTTGTACGGATAGATATAAATCCTGTTGTTATGATCGAATAAAGCAAGATTTGATGTTTCGATT
GTTAAAAGAAACTCAAGGATCCCGAATTTGTAATTCGAAAGTATGCAACCATACATGCAACAAGTGACCGAGCTACAAA
AACTTTGTTAGTGAGGCGTTTCCTATTGtaagttttttcattggaattttttaacaaattcttttttagTTGAT
ATGGTGCCTTTGAAAAAGTCGTGCAGTTACTTTCTATGAAAACATCAGATACTTTGTTGTTGTGATTTGTGATTATTG
GACCAAAGTTCTTCTGAATTTTAAAATGCTCAAGGAACATCTCTCTGACACATTGTTAAGtataccaattgttga
attgtaataacactaatgaaactagATAGGAAATTCTCAATAACCTTCAAAAAGTTGGTATCCCTCAGGGCTCAATTCTGT
CATCTTTTTGTGTCATTTCTATATGGAAGATTTGATGAATAACCTATCGTTTACGAAAGAAGGATCAGTGTTG
TTACGAGTAGTCGACGATTTCCTCTTATAACAGTTAATAAAAGGATGCAAAAAATTTTGAATTATCTTAAGAGg
tgagttgctgtcattcctaagtctaaccgttgaagGATTTGAGAAACACAATTTTCTACGAGCCTGGAGAAACAGTA
ATAAACTTTGAAAATAGTAATGGGATAATAAACAATACTTTTTTTAATGAAAGCAAGAAAAGAATGCCATTCTTCGTTT
CTCTGTGAACATGAGGTCTCTGATACATTGTTAGCATGTCCTAAAATTGATGAAGCCTTATTAACTCTACATCTGTAG
AGCTGACGAAACATATGGGAAATCTTTTTTTTACAAAATTCTAAGtatactgtaactaatagctgacaaata
atcagATCGAGCCTTGCATCCTTTGCACAAGTATTTATTGACATTACCCACAATTCAAAATTCAATTCTTGCTGCAATAT
ATATAGGCTAGGATACTCTATGTGTATGAGAGCACAAGCATACTTAAAAGGATGAAGGATATATTTATTCCCAAAGAA
TGTTCATAACGGgtgagtacttatttaactagaaagtcattaacctttcttgtcctctgaatgtactgt
AATTTGAAAAGTTGGCCGAAATATTAGGATATACGAGTAGGCGTTTCTTGTCCTCTGGAATGACTTATCAAGCCGTAAGACCAGTTTGCG
cggtctcgagacttcagcagcaatattgacacatcagGCTTTTTTGTCTTGGAATGACTTCAGTCATTCAGTCCTTATCAAGCCGCTAAGACCAGTTTGCG
TATCATCCATGCTTCGAACAGTACGTAATATACCAATTCAGTCATTGACTGATCTTATCAAGCCTATCAAGCTTATTACTGGTGTC
ACAGGTGTTATTTTACATAGAAGAATAGCTGATTAAtgtcatttcaatttattatatacatcctttattactggtgtc
ttaaacaatattattactaagtatagctgaccccaagcaagcatactatagatctctagtaagtaaaattaatctc
gttattagtttttgattgacttgtcttatcttttaagaaagattgacagtgttgctgactactgccacatg
cccattaaacgggagtggttaaacattaaaagtaataacatgaggctaatctccttcatttagaataaggaaaagtggttt
tctataatgaataatgcccgcactaagtcaaaaagacgaagattatctcttcaaacaaggggattaagcatatccgaagg
aaagagagtaataacccagtgttgttgaagaagcaagataattggaacaagcttctgcagatgacaggctaaatt
ttggtgaccgaatttggtaaagcccaggttatccatgtggccggctgtttgtttttcctgactcaatttgcatgggtgaaag
agtttgaataactaagctcattaatgtctttatataagttttgtttcctgacttcctcaaagcgaagtcaaagaacttattg
aaatagtgttaagccattatggattccgaaatagccaaattctttgttccttaaggaggaatctccaccgatgaggaaaatgactctaaaggat
aagcttatgaggcttcaaaactctcctgattcaaaaagaaaatatcattgggagacatctcttgatgaatcagatgcggagagtat
gctgagagagcctaatttttgcaataactcttctatttctgaaatgtatggtcctactgtcgcttcgacttctgtagctcta
cgcagttaagtgaccaaaggtacc
```

*FIG. 30*
(CONTINUED)

```
EST2 pep          FFYCTEISST VTIVYFRHDT WN----KLIT P-----FIVE YFK-TYLVEN    40
Euplotes pep      FFYVTEQQKS YSKTYYYRKN IWDVI-MKMS IAD----LKK ETLA--EVQE    43
Trans of tetrahymen  ------KHKE GSQIFYYRKP IWKLVSKLTI VKVRIQFSEK NKQMKNNFYQ    44

Consensus         FFY.TE..K. .S..YYYRK. IW....-KL. .....-F..K ........V..    50

EST2 pep          NVCRNHNSY- ---------- ---------- TLSNFNHSKM RHIPKKSNNE    79
Euplotes pep      KEVEEWKKSL ---------- ---------- ---GFAPGKG RLIPKKTT--    78
Trans of tetrahymen  KIQLEEENLE KVEEKLIPED SFQKYPQGKL ---GKL     RHIPKK----    92

Consensus         K...E..... .......... .......... ...F..GKL  RHIPKK....   100

EST2 pep          ADEEEFTIYK ENHKNAIQPT QKILEYLRNK RPTSFTKIYS PTQIADRIKE   129
Euplotes pep      IVNSDRKTTK LTTNTKLLNS HLMLKTLKN- -RMFK----- -DPFGFAVFN   120
Trans of tetrahymen  DKQKNIK--- ---------- QLVFRNLKD- ---ML-G---- -QKIGYSVFD   130

Consensus         ....K..K LN.N.L.S QL.L.LKN- ---------- ...IG..VF.   150

EST2 pep          FKQRLLKKFN NVL------- -PELYFMKFD VKSCYD                 157
Euplotes pep      YD-DVMKKYE EFVCKWKQVH CPKLFFATMD IEKCYD                 155
Trans of tetrahymen  NK-QISEKFA QFIEKWKNKG RPCLYYVTL-                        158

Consensus         .K-....KKF. .F..KWK..G .P.LYF.T.D ...CYD                 186
```

FIG. 31

S-1: FFY VTE TTF QKN RLF FYR KSV WSK
S-2: RQH LKR VQL RDV SEA EVR QHR EA
S-3: ART FRR EKR AER LTS RVK ALF SVL NYE

A-1: AKF LHW LMS VYV VEL LRS FFY VTE TTF Q
A-2: LFF YRK SVW SKL QSI GIR QHL KRV QLR DVS
A-3: PAL LTS RLR FIP KPD GLR PIV NMD YVV

FIG. 32

```
Poly 4
              t       t       c
       t a    a   g   c   c   t c g
5'-   cag acc aaa gga att cca taa gg -3'
       Q   T   K   G   I   P   Q   G
                    4(B')

5(c')

D   D   Y   L   L   I   T
3'-   ctg ctg atg gag gag tag tgg -5'
       a   a   a a a a a   a   a
                   t   t   t   t
                       c       c
                       Poly 1
```

FIG. 34

```
Ot          LCVSYILSSFYYANLEENALQFLRKESMDPEKPETNLLMRLT
Ea_p123  KGIPQGLCVSSILSSFYYATLEESSLGFLRDESMNPENPNVNLLMRLTDDYLLIT
Sp_M2         SILSSFLCHFYMEDLIDEYLSFTKKK------GSVLLRVV
Sc_p103  DGLFQGSSLSAPIVDLVYDDLLEFYSEFKASPS-----QDTLILKLADDFLIIS
                  *  .      *   .           *           ......

Q   K   V   G   I   P   Q   G                  <---Actual Genomic Sequence.
caa aaa gtt ggt atc cct cag gg......

Poly 4
    t       t       c
t a   a   g c   c   t c g
cag acc aaa gga att cca taa gg ----> ag acc aaa gga att cca tca ggC T

```
GAA GAT TTG ATT GAT GAA TAC CTA TCG TTT ACG AAA AAG AAA GGA TCA GTG TTG TTA CGA
CTT CTA AAC TAA CTA CTT ATG GAT AGC AAA TGC TTC TTT CCT AGT CAC AAC AAT GCT
 E   D   L   I   D   E   Y   L   S   F   T   K   K   K   G   S   V   L   L   R

GTA GTC gac gac tac ctc ctc atc acc
CAT CAG ctg ctg atg gag gag tag tgg
 V   V   D   D   Y   L   I   T <---- ctg ctg atg gag gag tag tgg
          a   a   a a a a   t t t t
                            c   c
                 Poly 1

......gac gat ttc ctc ttt ata aca......    <---Actual Genomic Sequence
       D   D   F   L   F   I   T
```

FIG. 36
(CONTINUED)

```
                          Motif 0
S.p. Tez1p  (429). WLYNSFIIPILQSFFYITESSDLRNRTVYFRKDIW  ...(35)...
S.c. Est2p  (366). WLFRQLIPKIIQTFFYCTEISSTVT-IVYFRHDTW  ...(35)...
E.a. p123   (441). WIFEDLVVSLIRCFFYTEQQKSYSKTYYRKNIW   ...(35)...
                         * ***  **
                *
         Motif 1            Motif 2         K
         p hh  h K            hR h          R
S.p. Tez1p  AVIRLLPKK--NTFRLITN-LRKRF  ...(61)...
S.c. Est2p  SKMRIIPKKSNNEFRIIAIPCRGAD  ...(62)...
E.a. p123   GKLRLIPKK--TTFRPIMTFNKKIV  ...(61)...
             * ***       *        **
                *

Motif 3(A)  AF            K
                  h  hDh   GY      h
S.p. Tez1p  KKYFVRIDIKSCYDRIKQDLMFRIVK  ...(89)....
S.c. Est2p  ELYFMKFDVKSCYDSIPRMECMRILK  ...(75)....
E.a. p123   KLFFATMDIEKCYDSVNREKLSTFLK  ...(107)...
             *    *    ***
                  *

Motif 4(B')
             hPQG     pP  hh    h
S.p. Tez1p  YLQKVGIPQGSILSSFLCHFYMEDLIDEYLSF  ...(6)....
S.c. Est2p  YIREDGLFQGSSLSAPIVDLVYDDLLEFYSEF  ...(8)....
E.a. p123   YKQTKGIPQGLCVSSILSSFYYATLEESSLGF  ...(14)...
             *      **
                *

Y Motif 5(C)
         h  F DDhhh
S.p. Tez1p  VLLRVVDDFLFITVNKKDAKKFLNLSLRGFEKHNFSTSLEKTVINFENS  .(205)
S.c. Est2p  LILKLADDFLIISTDQQQVINIKKLAMGGFQKYNAKANRDKILAVSSQS  .(173)
E.a. p123   LLMRLTDDYLLITTQENNAVLFIEKLINVSRENGFKFNMKKLQTSFPLS  .(209)
                   *

Motif 6(D)
                       Gh h  cK   h
S.p. Tez1p
S.c. Est2p
E.a. p123
                   *
```

| | | | |
|---|---|---|---|
| Sp_Tip1p | 1 | - - - - - - - - - - M T E H H T P K S R I L R F L E N Q Y V Y L C T | 24 |
| Sc_Est2p | 1 | - - - - - - - - - - - - - - - - - - - - - - - - - - M K I L F E F | 7 |
| Ea_p123 | 1 | M E V D V D N Q A D N H G I H S A L K T C E E I K E A K T L Y S W | 33 |

| | | | |
|---|---|---|---|
| Sp_Tip1p | 25 | L N D Y V Q L V L R G S P A S S Y S N I C E R L R S D V Q T S F S | 57 |
| Sc_Est2p | 8  | I Q D K L D I D L Q T N - - S T Y K - - - E N L K C G H F N G L D | 35 |
| Ea_p123  | 34 | I Q K V I R C R N Q S Q - - S H Y K - - - D L E D I K I F A Q T N | 61 |

| | | | |
|---|---|---|---|
| Sp_Tip1p | 58 | I F L H S T V V G F D S K P D E G V Q F S S P K C S Q S E L I A N | 90 |
| Sc_Est2p | 36 | E I L T C F A L P N S R - K I A L P C L P G D L S H K A V I D H | 67 |
| Ea_p123  | 62 | I V A T P R D Y N E E D F K V I A R K E V F S T G L M I E L I D K | 94 |

| | | | |
|---|---|---|---|
| Sp_Tip1p | 91 | V V K Q M F D E S F E R R R - N L L M K G F S M N H E D F R A M H | 122 |
| Sc_Est2p | 68 | C I Y L L T G E L Y N - - N V L T F G Y K I A R N E D - - - - | 93 |
| Ea_p123  | 95 | C L V E L L S S S D V S D R Q K L Q C F G F Q L K G N Q - - - - | 122 |

| | | | |
|---|---|---|---|
| Sp_Tip1p | 123 | V N G V Q N D L V S T F P N Y L I S I L E S K N W Q L L E I L G | 155 |
| Sc_Est2p | 94  | - - - V N N S L F C H S A N V N V T L L K G A A W K M F H S L V G | 123 |
| Ea_p123  | 123 | - - - L A K T H L L T A L S T Q K Q Y F F Q D E W N Q V R A M I G | 152 |

| | | | |
|---|---|---|---|
| Sp_Tip1p | 156 | S D A M H Y L L S K G S I F E A L P N D N Y L Q I S G L P L F K N | 188 |
| Sc_Est2p | 124 | T Y A F V D L L I N Y T V I Q F N - G Q F F T Q I V G N R C N E P | 155 |
| Ea_p123  | 153 | N E L F R H L Y T K Y L I F Q R T S E G T L V Q F C G N N V F D H | 185 |

| | | | |
|---|---|---|---|
| Sp_Tip1p | 189 | N V F E E T V S K K R K R T I E T S I T Q N - - - K S A R K E V S | 218 |
| Sc_Est2p | 156 | H L P P K W V Q - - R S S S S S A T A A Q I - - - K Q L T E P V T | 183 |
| Ea_p123  | 186 | L K V N D K F D K - K Q K G G A A D M N E P R C C S T C K Y N V K | 217 |

```
Sp_Tip1p   426  EFIYWLYNSFIPILQSFFYITESSDLRNRTVY          458
Sc_Est2p   363  CFISWLFRQLIPKLIQTFFFYCTEISSTVT-IVY        394
Ea_p123    438  KLLRWIFEDLVVSLIRCFFYVTEQQKSYSKTYY         470

Sp_Tip1p   459  FRKDIWKLLCRPFFITSMKMEAFEKINENNVRMD        491
Sc_Est2p   395  FRHDTWNKLITPFIVEYFKTYLVENNVCRNHNS         427
Ea_p123    471  YRKNIWDVIMKMSIADLKKETLAEVQEKEVEEW         503

Sp_Tip1p   492  TQKTTLPPAVIRLLPKK--NTFRLITNLRKRFL         522
Sc_Est2p   428  YTLSNFNHSKMRIIPKKSNNEFRI--AIPCRGAD        460
Ea_p123    504  KKSLGFAPGKLRLIPKK--TIFRPIMTFNKKIV         534

Sp_Tip1p   523  IKMGSNKKMLVSTNQTLRPVASILKHLINE---         552
Sc_Est2p   461  EEE--FTIYKENHKNAIQPTQKILEYLRNKRPT         491
Ea_p123    535  NSD--RKTTKLTTNTKLLNSHLMLKTLKNR-MF         564

Sp_Tip1p   553  ESSGIPFNLEVYMKLLTFKKDLLKHRMFGR-KK         584
Sc_Est2p   492  SFTKLYSPTQIADRIKEFKQRLLKKFNNVLPEL         524
Ea_p123    565  KDPFGFAVFNYDDVMKKYEEFVCKWKQVGQPKL         597

Sp_Tip1p   585  YFVRIDIKSCYDRIKQDLMFRIVKKKLKDPE-F         616
Sc_Est2p   525  YFMKFDVKSCYDSIPRMECMRILKDALKNENGF         557
Ea_p123    598  FFATMDIEKCYDSVNREKLSTFLKTTKLLSSDF         630

Sp_Tip1p   617  VLRKYATIHATSDRATKN------------            634
Sc_Est2p   558  FVRSQYFFNTNTG-----------------            570
Ea_p123    631  WIMTAQILKRKNNIVIDSKNFRKKEMKDYFRQK         663
```

A.

```
Sp_Tip1p  635  FVSEAFSYFDMVPFEKVVQLLS--MKTSDTLFV  665
Sc_Est2p  571  -----VLKLFNVVNASR--VPKPYELYI       591
Ea_p123   664  FQKIALEGGQYPTLFSVLENEQNDLNAKKTLIV  696

Sp_Tip1p  666  DFVDYWTKSSSEIFKMLKEHLSGHIVKIGNSQY  698
Sc_Est2p  592  DNVRTVHLSNQDVINVVEMEIFKTALWVEDKCY  624
Ea_p123   697  EAKQRNYFKKDNLLQPVINICQYNYINFNGKFY  729

Sp_Tip1p  699  LQKVGIPQGSILSSFLCHFYMEDLIDEYLSFTK  731
Sc_Est2p  625  IREDGLFQGSSLSAPIVDLVYDDLLEFYSEFKA  657
Ea_p123   730  KQTKGIPQGLCVSSILSSFYYATLEESSLGFLR  762

Sp_Tip1p  732  KKG-----SVLLRVVDDFLFITVNKKDAKK    756
Sc_Est2p  658  SPSQD-----TLIKLADDFLI--STDQQQVIN   684
Ea_p123   763  DESMNPENPNVNLLMRLTDDYLLITQENNAVL  795

Sp_Tip1p  757  FLNLSLRGFEKHNFSTSLEKTVINFENSNG---  786
Sc_Est2p  685  IKKLAMGGFQKYNAKANRDKILAVSSQSD---   713
Ea_p123   796  FIEKLINVSRENGFKFNMKKLQTSFPLSPSKFA  828

Sp_Tip1p  787  ----INNTFFNESKKRMPFFGFSVNMRSLDTLL  816
Sc_Est2p  714  ----DDTVIQFCA--MHIFVKELEVWKHSSTM  739
Ea_p123   829  KYGMDSVEEQNIVQDYCDWIGISIDMKTLALMP  861

Sp_Tip1p  817  ACPKIDEALFNSTSVELTKHMGKSFFYKILRSS  849
Sc_Est2p  740  NNFHIRSKSSKGIFRSLIALFNTRISYKTIDTN  772
Ea_p123   862  NINLRIEGILCTLNLNMQTKKASMWLKKLKSF  894
```

| | | | |
|---|---|---|---|
| Sp_Tip1p | 850 | LASFAQVFIDITHNSKFNSCCNIYRLGYSMCMR | 882 |
| Sc_Est2p | 773 | LNSTNTVLMQIDHVVKNISEC- - - - - - - | 793 |
| Ea_p123 | 895 | LMNNITHYFRKTTTEDFANKTLNKLFISGGYK | 927 |
| | | | |
| Sp_Tip1p | 883 | AQAYLKRMKDIFIPQRMFITDLLNVIGRKIWKK | 915 |
| Sc_Est2p | 794 | - - -YKSAFKDLSIN- -VTQNMQFHSFLQRIIEM | 821 |
| Ea_p123 | 928 | YMQCAKEYKDHFKKNLAMSSMIDLEVSKIIYSV | 960 |
| | | | |
| Sp_Tip1p | 916 | LAEILGYTSRRFLSSAEVKWLFCLGMRDGLKPS | 948 |
| Sc_Est2p | 822 | TVSGCPITKCDPLIEYEVRFTILNGFLESLSSN | 854 |
| Ea_p123 | 961 | TRAFFKYLVCNIKDTIFGEEHYPDFFLSTLKHF | 993 |
| | | | |
| Sp_Tip1p | 949 | FKYHPCFEQLIYQFQSLTDLIKPLRPVLRQVLF | 981 |
| Sc_Est2p | 855 | TS- - - - - - -KFKDNILLRKEIQHLQAYIY | 877 |
| Ea_p123 | 994 | IEIFS- - -TKKYIFNRVCMILKAKEAKLKSDQC | 1023 |
| | | | |
| Sp_Tip1p | 982 | LHRRIAD- | 988 |
| Sc_Est2p | 878 | IYIHIVN- | 884 |
| Ea_p123 | 1024 | QSLIQYDA | 1031 |

| | | | |
|---|---|---|---|
| Sp_Tip1p | 1 | - - - - - - - - - M T E H H T P K S R I L R F L E N Q Y V Y L C T | 24 |
| Sc_Est2p | 1 | - - - - - - - - - - - - - - - - - - - - - - - - M K I L F E F | 7 |
| Ea_p123 | 1 | M E V D V D N Q A D N H G I H S A L K T C E E I K E A K T L Y S W | 33 |
| Sp_Tip1p | 25 | L N D Y V Q L V L R G S P A S Y S N I C E R L R S D V Q T S F S | 57 |
| Sc_Est2p | 8 | I Q D K L D I D L Q T N - - S T Y K - - - E N L K C G H F N G L D | 35 |
| Ea_p123 | 34 | I Q K V I R C R N Q S Q - - S H Y K - - - D L E D I K I F A Q T N | 61 |
| Sp_Tip1p | 58 | I F L H S T V V G F D S K P D E G V Q F S S S P K C S Q S E L I A N | 90 |
| Sc_Est2p | 36 | E I L T T C F A L P N S R - K I A L P C L P G D L S H K A V I D H | 67 |
| Ea_p123 | 62 | I V A T P R D Y N E E D F K V I A R K E V F S T G L M I E L I D K | 94 |
| Sp_Tip1p | 91 | V V K Q M F D E S F E R R R - N L L M K G F S M N H E D F R A M H | 122 |
| Sc_Est2p | 68 | C I I Y L L T G E L Y N - - N V L T F G Y K I A R N E D - - - - | 93 |
| Ea_p123 | 95 | C L V E L L S S S D V S D R Q K L Q C F G F Q L K G N Q - - - - | 122 |
| Sp_Tip1p | 123 | V N G V Q N D L V S T F P N Y L I S I L E S K N W Q L L L E I I G | 155 |
| Sc_Est2p | 94 | - - V N N S L F C H S A N V N V T L L K G A A W K M F H S L V G | 123 |
| Ea_p123 | 123 | - - - L A K T H L L T A L S T Q K Q Y F F Q D E W N Q V R A M I G | 152 |
| Sp_Tip1p | 156 | S D A M H Y L L S K G S I F E A L P N D N Y L Q I S G I P L F K N | 188 |
| Sc_Est2p | 124 | T Y A F V D L L I N Y T V I Q F N - G Q F F T Q I V G N R C N E P | 155 |
| Ea_p123 | 153 | N E L F R H L Y T K Y L I F Q R T S E G T L V Q F C G N N V F D H | 185 |
| Sp_Tip1p | 189 | N V F E E T V S K K R K R T I E T S I T Q N - - - K S A R K E V S | 218 |
| Sc_Est2p | 156 | H L P P K W V Q - - R S S S S S A T A A Q I - - - K Q L T E P V T | 183 |
| Ea_p123 | 186 | L K V N D K F D K - K Q K G G A A D M N E P R C C S T C K Y N V K | 217 |

| | | | |
|---|---|---|---|
| Sp_Tip1p | 219 | WNSISISRFSIFYRSSYKKFKQDLYFNLHSICD | 251 |
| Sc_Est2p | 184 | N-------------KQFLHKLNINSSSFFP | 200 |
| Ea_p123 | 218 | NEK--DHFLNNINVPNWNNMKSRTRIFYCTHFN | 248 |

| | | | |
|---|---|---|---|
| Sp_Tip1p | 252 | RNTVHMWLQWIFPRQFGLINAFQVKQLHKVIPL | 284 |
| Sc_Est2p | 201 | -------YSKILPSSS---SIKKLTDLREAIFP | 223 |
| Ea_p123 | 249 | R-------NNQFFKKHEFVSNKNNISAMDRAQTI | 275 |

| | | | |
|---|---|---|---|
| Sp_Tip1p | 285 | VS----QSTVVPKRLLKVYPLIEQTAKRLHRIS | 313 |
| Sc_Est2p | 224 | TN----LVKIPQRLKVRINLTLQKLLKRHKRLN | 252 |
| Ea_p123 | 276 | FTNIFRFNRIRKKLKDKVIEKIAYMLEKVKDFN | 308 |

| | | | |
|---|---|---|---|
| Sp_Tip1p | 314 | LSKVYNHYCPYID-THDDEKILSYSLKPNQ--- | 342 |
| Sc_Est2p | 253 | YVSILNSICPPLEGTVLDLSHLSRQSPKER--- | 282 |
| Ea_p123 | 309 | FNYYLTKSCPLPENWRERKQKIENLINKTREEK | 341 |

| | | | |
|---|---|---|---|
| Sp_Tip1p | 343 | ------VFAFLRSILVRVFPKLI | 359 |
| Sc_Est2p | 283 | ------VLKFI--VILQKLLPQEM | 299 |
| Ea_p123 | 342 | SKYYEELFSYTTDNKCVTQFINEFFYNILPKDF | 374 |

| | | | |
|---|---|---|---|
| Sp_Tip1p | 360 | WGNQRIFEIILKDLETFLKLSRYESFSLHYLMS | 392 |
| Sc_Est2p | 300 | FGSKKNKGKI-IKNLNLLSLPLNGYLPFDSLLK | 332 |
| Ea_p123 | 375 | LTG-RNRKNFQKKVKKYVELNKHELIHKNLLLE | 406 |

| | | | |
|---|---|---|---|
| Sp_Tip1p | 393 | NIKISEIEWLVLGKRSNAKMCLSDFEKRKQIFA | 425 |
| Sc_Est2p | 333 | KLRLKDFRWLFIS--DIWFTKHNFENLNQLAI | 362 |
| Ea_p123 | 407 | KINTREISWMQVETS-AKHFYYFDHEN-IYVLW | 437 |

| | | | |
|---|---|---|---|
| Sp_Tip1p | 426 | EFIYWLYNSFIIPILQSFFYITESSDLRNRTVY | 458 |
| Sc_Est2p | 363 | CFISWLFRQLIPKIIQTFFYCTE-ISSTVT-IVY | 394 |
| Ea_p123 | 438 | KLLRWIFEDLVVSLIRCFFYVTEQQKSYSKTYY | 470 |
| Sp_Tip1p | 459 | FRKDIWKLLCRPFITSMKMEAFEKINENNVRMD | 491 |
| Sc_Est2p | 395 | FRHDTWNKLITPFIVEYFKTYLVENNVCRNHNS | 427 |
| Ea_p123 | 471 | YRKNIWDVIMKMSIADLKKETLAEVQEKEVEEW | 503 |
| Sp_Tip1p | 492 | TQKTTLPPAVIRLLPKK--NTFRLITNLRKRFL | 522 |
| Sc_Est2p | 428 | YTLSNFNHSKMRIIPKKSNNEFRI-AIPCRGAD | 460 |
| Ea_p123 | 504 | KKSLGFAPGKLRLIPKK--TTFRPIMTFNKKIV | 534 |
| Sp_Tip1p | 523 | IKMGSNKKMLVSTNQTLRPVASILKHLINE--- | 552 |
| Sc_Est2p | 461 | EEE--FTIYKENHKNAIQPTQKILEYLRNKRPT | 491 |
| Ea_p123 | 535 | NSD--RKTTKLTTNTKLLNSHLMLKTLKNR-MF | 564 |
| Sp_Tip1p | 553 | ESSGIPFNLEVYYMKLLTFKKDLLKHRMFGR-KK | 584 |
| Sc_Est2p | 492 | SFTKIYSPTQIADRIKEFKQRLLKKFNNVLPEL | 524 |
| Ea_p123 | 565 | KDPFGFAVFNYDDVMKKYEEFVCKWKQVGQPKL | 597 |
| Sp_Tip1p | 585 | YFVRIDIKSCYDRIKQDLMFRIVKKKLKDPE-F | 616 |
| Sc_Est2p | 525 | YFMKFDVKSCYDSIPRMECMRILKDALKNENGF | 557 |
| Ea_p123 | 598 | FFATMDIEKCYDSVNREKLSTFLKTTKLLSSDF | 630 |
| Sp_Tip1p | 617 | VIRKYATIHATSDRATKN-------------- | 634 |
| Sc_Est2p | 558 | FVRSQYFFNTNTG------------------ | 570 |
| Ea_p123 | 631 | WIMTAQILKRKNNIVIDSKNFRKKEMKDYFRQK | 663 |

| | | | |
|---|---|---|---|
| Sp_Tip1p | 635 | FVSEAFSYFDMVPFEK VQLLS - - MKTSDTLFV | 665 |
| Sc_Est2p | 571 | - - - - - VLKLFN VNASR - - VPKPYELY I | 591 |
| Ea_p123 | 664 | FQKIALEGGQYPTLFS V LENEQNDLNAKKTLIV | 696 |

| | | | |
|---|---|---|---|
| Sp_Tip1p | 666 | DFVDYWTKSSSEIFKMLKEHLSGHIVKIGNSQ Y | 698 |
| Sc_Est2p | 592 | DNVRTVHLSNQDVINVVEMEIFKTALWVEDKC Y | 624 |
| Ea_p123 | 697 | EAKQRNYFKKDNLLQPVINICQYNYINFNGKF Y | 729 |

| | | | |
|---|---|---|---|
| Sp_Tip1p | 699 | LQKVG I P Q G S I L SSFLCHFYMED L IDEYLS F TK | 731 |
| Sc_Est2p | 625 | IREDGLFQGSLSAPIVDLVYDDLLEFYSEFKA | 657 |
| Ea_p123 | 730 | KQTKG I P Q G LCV S SILSSFYYATL EESSLG F LR | 762 |

| | | | |
|---|---|---|---|
| Sp_Tip1p | 732 | KKG - - - - - SVLLRVV DDFLF I TVNKKDAKK | 756 |
| Sc_Est2p | 658 | SPSQD - - - - TLILKLADDFL I - STDQQQVIN | 684 |
| Ea_p123 | 763 | DESMNPENPNVNLLMRLTDDYL L L TTQENNAVL | 795 |

| | | | |
|---|---|---|---|
| Sp_Tip1p | 757 | FLNLSLRGFEKHNFSTSLE K TVINFEN S NG - - - - | 786 |
| Sc_Est2p | 685 | IKKLAMGGFQKYNAKANRD K ILAVSSQ S D - - - - | 713 |
| Ea_p123 | 796 | FIEKLINVSRENGFKFNM K K LQTSFPL S PSKFA | 828 |

| | | | |
|---|---|---|---|
| Sp_Tip1p | 787 | - - - IINNTFFNESKKRMPFFGFSVNMRSLDTLL | 816 |
| Sc_Est2p | 714 | - - - DDTVIQFCA - - MHIFVKELEVWKHSSTM | 739 |
| Ea_p123 | 829 | KYGMDSVEEQNIVQDYCDWIGISIDMKTLALMP | 861 |

| | | | |
|---|---|---|---|
| Sp_Tip1p | 817 | ACPKIDEALFNSTSVELTKHMGKSFF Y K ILRSS | 849 |
| Sc_Est2p | 740 | NNFHIRSKSSKGIFRSLIALFNTRISY K T IDTN | 772 |
| Ea_p123 | 862 | NINLRIEGILCTLNLMQTKKASMWL K K LKSF | 894 |

```
Sp_Tip1p  850  LASFAQVFIDITHNSKFNSCCNIYRLGYSMCMR     882
Sc_Est2p  773  LNSTNTVLMQIDHVVKNISEC-----            793
Ea_p123   895  LMNNITHYFRKTITTEDFANKTLNKLFISGGYK     927

Sp_Tip1p  883  AQAYLKRMKDIFIPQRMFITDLLNVIGRKIWKK      915
Sc_Est2p  794  ---YKSAFKDLSIN--VTQNMQFHSFLQRI-IEM     821
Ea_p123   928  YMQCAKEYKDHFKKNLAMSSMIDLEVSKILYSV      960

Sp_Tip1p  916  LAEILGYTSRRFLSSAEVKWLFCLGMRDGLKPS      948
Sc_Est2p  822  TVSGCPITKCDPLIEYEVRFTILNGFLESLSSN      854
Ea_p123   961  TRAFFKYLVCNIKDTIFGEEHYPDFFLSTLKHF      993

Sp_Tip1p  949  FKYHPCFEQLIYQFQSLTDLIKPLRPVLRQVLF      981
Sc_Est2p  855  TS-------KFKDNILLRKEIQHLQAYIY          877
Ea_p123   994  IEIFS---TKKYIFNRVCMILKAKEAKLKSDQC     1023

Sp_Tip1p  982  LHRRIAD-                              988
Sc_Est2p  878  IYIHIVN-                              884
Ea_p123  1024  QSLIQYDA                             1031
```

FIG. 42 (CONTINUED)

```
   1 ggtaccgattta ctttcctt cttcatagctaattgctcctcgaacgctcctaaatctctggaaatatttttacaaga   80
  81 actcaataacaat accaagtcaaattccaatatgaagtgttagtgatcgataatttctatttttatcggtcgtta  160
 161 ccaagtataaggacaaaagaacaacttcctcccctaaagacttttacttttattactttcaaatatatttcg  240
 241 ggttcgcttactttaatcgtgtactgtttagctgctacttctagcaaccgcgtgtttctaccccgtcattggatat  320
 321 agctcttggagtagctcacagaaatcttctgatgagactatattagattcattacagtccgtgcatattc  400
 401 ttaacatggagccttacacgtttagatgagtccctcgcatggagtcctctagtggttgctgcacgtctagcatg  560
 481 gttgataatattgcaaaatcatgtctatccactaccaactcctttaacgcgttttcgttcactgtctcctgttt  640
 561 attgagatattcaaaaatttctctgtattggcttataattgatagtagaaagattggtgattctactcgttattaaatcaa  640
 641 ccaaatatgtatcatctcgtattagcttataatttagctatcattatataaacaacatattatatatagtttaa  720
 721 ataatctaaattagtttcgtttataatttagctatcatttatataaaactctatataaatatatatgttaaa  800
 801 gatactttgcaaaaacattatttgatcagtaggacactttgcatatatgtcataatggttacttgtaacttgc  880
 881 actattttaaaacgttatgatcagtaggacactttgcatatatgtcataatggttacttgtaacttgc  958

959 ATG ACC GAA CAC CAC ATC ACC CCC AAA AGC AGG ATT CTT CGC TTT CTA GAG AAT CAA TAT GTA  1018
   1   M   T   E   H   H   I   T   P   K   S   R   I   L   R   F   L   E   N   Q   Y   V   20

1019 TAC CTA TGT ACC TTA AAT GAT TAT GTA CAA CTT GTT TTG AGA GGG TCG CCG GCA AGC TCG     1078
  21   Y   L   C   T   L   N   D   Y   V   Q   L   V   L   R   G   S   P   A   S   S     40

1079 TAT AGC AAT ATA TGC GAA CGC TTG AGA AGC GAT GTA CCA GAT GAA GGT GTT CAA TTT TCT CTT 1138
  41   Y   S   N   I   C   E   R   L   R   S   D   V   P   D   E   G   V   Q   F   S   L   60

1139 CAT TCG ACT GTA GTC GGC TTC GAC AGT AAG CCA GAT GAA GGT GTT CAA TTT TCT TCT CCA     1198
  61   H   S   T   V   V   G   F   D   S   K   P   D   E   G   V   Q   F   S   S   P     80

1199 AAA TGC TCA CAG TCA GAG gtatatattttctattcggatagctaatatgggcag                         1272
  81   K   C   S   Q   S   E                                                              86

1273 CTA ATA GCG AAT GTT GTA AAA CAG ATG TTC GAT GAA AGT TTT GAG CGT CGA AGG AAT CTA     1332
  87   L   I   A   N   V   V   K   Q   M   F   D   E   S   F   E   R   R   N   L         106

1333 CTG ATG AAA GGG TTT TCC ATG gtaaggtattctaattgtgaaatatttacctgtcaattactgtttcaaagaga   1405
 107   L   M   K   G   F   S   M                                                          113

1406 ttgtatttaaccgataaag AAT CAT GAA GAT TTT CGA GCC ATG CAT GTA AAC GGA GTA CAA AAT     1469
 114                       N   H   E   D   F   R   A   M   H   V   N   G   V   Q   N     128
```

```
2268 TTT GAG ATA ATA TTA AAA G gtattgtataaattattaccactaacgatttaccag AC CTC GAA ACT 2336
 366  F   E   I   I   L   K  D                                         L   E   T  375

2337 TTC TTG AAA TTA TCG AGA TAC GAG TCT TTT AGT TTA CAT TAT TTA ATG AGT AAC ATA AAG 2396
 376  F   L   K   L   S   R   Y   E   S   F   S   L   H   Y   L   M   S   N   I   K  395

2397 gtaatatgccaaattttttaccattaattaacaatcag ATT TCA GAA ATT GAA TGG CTA GTC CTT GGA 2465
 396                                         I   S   E   I   E   W   L   V   L   G  405

2466 AAA AGG TCA AAT GCG AAA ATG TGC TTA AGT GAT TTT GAG AAA CGC AAG CAA ATA TTT GCG 2525
 406  K   R   S   N   A   K   M   C   L   S   D   F   E   K   R   K   Q   I   F   A  425

2526 GAA TTC ATC TAC TGG CTA TAC AAT TCG TTT ATA ATA CCT ATT TTA CAA TCT TTT TTT TAT 2585
 426  E   F   I   Y   W   L   Y   N   S   F   I   I   P   I   L   Q   S   F   F   Y  445

2586 ATC ACT GAA TCA AGT GAT TTA CGA AAT CGA ACT GTT TAT TTT AGA AAA GAT ATT TGG AAA 2645
 446  I   T   E   S   S   D   L   R   N   R   T   V   Y   F   R   K   D   I   W   K  465

2646 CTC TTG TGC CGA CCC TTT ATT ACA TCA ATG AAA ATG GAA GCG TTT GAA AAA ATA AAC GAG 2705
 466  L   L   C   R   P   F   I   T   S   M   K   M   E   A   F   E   K   I   N   E  485

2706 gtatttaaagtattttttgcaaaaagctaatatttcag AAC AAT GTT AGG ATG GAT ACT CAG AAA ACT 2775
 486                                         N   N   V   R   M   D   T   Q   K   T  495

2776 ACT TTG CCT CCA GCA GTT ATT CGT CTA TTA CCT AAG AAT ACC TTT CGT CTC ATT ACG 2835
 496  T   L   P   P   A   V   I   R   L   L   P   K   N   T   F   R   L   I   T  515

2836 AAT TTA AGA AAA TTC TTA ATA AAG gtattaattttggtcatcaatgtactttacttctaatctatta 2906
 516  N   L   R   K   F   L   I   K                                              524

2907 ttagcag ATG GGT TCA AAC AAA ATG TTA GTC AGT ACG AAC CAA ACT TTA CGA CCT GTG 2967
 525        M   G   S   N   K   M   L   V   S   T   N   Q   T   L   R   P   V  542

2968 GCA TCG ATA CTG AAA CAT TTA ATC AAT GAA GAA AGT GGT ATT CCA TTT AAC TTG GAG 3027
 543  A   S   I   L   K   H   L   I   N   E   E   S   G   I   P   F   N   L   E  562

3028 GTT TAC ATG AAG CTT CTT ACT TTT AAG AAG GAT CTT CTT AAG CAC CGA ATG TTT GG gtaat 3088
 563  V   Y   M   K   L   L   T   F   K   K   D   L   L   K   H   R   M   F   G      581
```

FIG. 46
(CONTINUED)

```
3089 tatataatgcgcgattcctcattattttgcag G CGT AAG AAG TAT TTT GTA CGG ATA GAT ATA  3155
 582                                   R   K   K   Y   F   V   R   I   D   I    591

3156 AAA TCC TGT TAT GAT CGA ATA AAG CAA GAT TTG ATG TTT CGG ATT GTT AAA AAG CTC  3215
 592  K   S   C   Y   D   R   I   K   Q   D   L   M   F   R   I   V   K   K   L   611

3216 AAG GAT CCC GAA TTT GTA ATT CGA AAG TAT GCA ACC ATA CAT GCA ACA AGT GAC CGA GCT  3275
 612  K   D   P   E   F   V   I   R   K   Y   A   T   I   H   A   T   S   D   R   A   631

3276 ACA AAA AAC TTT GTT AGT GAG GCG TTT TCC TAT gtaagttattttttcattggaattttaacaa  3343
 632  T   K   N   F   V   S   E   A   F   S   Y                                   643

3344 attcttttag TT GAT ATG GTG CCT TTT GAA AAA GTC GTG CAG TTA CTT TCT ATG AAA ACA  3405
 644               D   M   V   P   F   E   K   V   V   Q   L   L   S   M   K   T   659

3406 TCA GAT ACT TTG TTT GAT TTT GTG GAT TAT TGG ACC AAA AGT TCT TCT GAA ATT TTT  3465
 660  S   D   T   L   F   D   F   V   D   Y   W   T   K   S   S   S   E   I   F   679

3466 AAA ATG CTC AAG GAA CAT CTC TCT GGA CAC ATT GTT AAG gtataccaattgttgaattgtaataaca  3532
 680  K   M   L   K   E   H   L   S   G   H   I   V   K                              692

3533 ctaatgaaactag ATA GGA AAT TCT CAA TAC CTT CAA AAA GTT GGT ATC CCT CAG GGC TCA  3593
 693                I   G   N   S   Q   Y   L   Q   K   V   G   I   P   Q   G   S    708

3594 ATT CTG TCA TCT TTT TTG TGT CAT TTC TAT ATG GAA GAT TTG ATT GAT GAA TAC CTA TCG  3653
 709  I   L   S   S   F   L   C   H   F   Y   M   E   D   L   I   D   E   Y   L   S   728

3654 TTT ACG AAA AAG AAA GGA TCA GTG GTG TTG TTA CGA GTA GTC GAC GAT TTC CTC TTT ATA ACA  3713
 729  F   T   K   K   K   G   S   V   V   L   L   R   V   V   D   D   F   L   F   I   T   748

3714 GTT AAT AAA AAG GAT GCA AAA AAG TTT TTG AAT TTA TCT TTA AGA G gtgagttgctgtcattcc  3777
 749  V   N   K   K   D   A   K   K   F   L   N   L   S   L   R   G                   764

3778 taagttctaaccgttgaag GA TTT GAG AAA CAC AAT TTC TCT ACG AGC CTG GAG AAA ACA GTA  3840
 765                        F   E   K   H   N   F   S   T   S   L   E   K   T   V    778

3841 ATA AAC TTT GAA AAT AGT AAT GGG ATA ATA AAC AAT ACT TTT TTT AAT GAA AGC AAG AAA  3900
 779  I   N   F   E   N   S   N   G   I   I   N   N   T   F   F   N   E   S   K   K   798
```

```
3901 AGA ATG CCA TTC TTC GGT TTC TCT GTG AAC ATG AGG TCT CTT GAT ACA TTG TTA GCA TGT 3960
 799  R   M   P   F   F   G   F   S   V   N   M   R   S   L   D   T   L   L   A   C   818

3961 CCT AAA ATT GAT GAA GCC TTA TTT AAC TCT ACA TCT GTA GAG CTG ACG AAA CAT ATG GGG 4020
 819  P   K   I   D   E   A   L   F   N   S   T   S   V   E   L   T   K   H   M   G   838

4021 AAA TCT TTT TTT TAC AAA ATT CTA AG gtatactgtgtaactgtgaatatagctgacaaataatcag A TCG 4089
 839  K   S   F   F   Y   K   I   L   R                                           S   848

4090 AGC CTT GCA TCC TTT GCA CAA GTA TTT ATT GAC ATT ACC CAC AAT TCA AAA TTC AAT TCT 4149
 849  S   L   A   S   F   A   Q   V   F   I   D   I   T   H   N   S   K   F   N   S   868

4150 TGC TGC AAT ATA TAT AGG CTA GGA TAC TCT ATG TGT AGA GCA CAA GCA TAC TTA AAA 4209
 869  C   C   N   I   Y   R   L   G   Y   S   M   C   R   A   Q   A   Y   L   K   888

4210 AGG ATG AAG GAT ATA TTT ATT CCC CAA AGA ATG TTC ATA ACG G gtgagtacttatttaactaga 4274
 889  R   M   K   D   I   F   I   P   Q   R   M   F   I   T   D                       903

4275 aaagtcattaattaaccttag AT CTT TTG AAT GTT ATT GGA AGA AAA ATT TGG AAA AAG TTG GCC 4339
 904                         L   L   N   V   I   G   R   K   I   W   K   K   L   A   917

4340 GAA ATA TTA GGA TAT ACG AGT CGT AGG CGT TTC TCC TCT GCA GAA GTC AAA TG gtacgtgtc 4401
 918  E   I   L   G   Y   T   S   R   R   R   F   S   S   A   E   V   K   W            935

4402 ggtctcgagacttcagcaatattgacacatcag G CTT TTT TGT CTT GGA ATG TAC CAA TTT CAG ACT 4468
 936                                    L   F   C   L   G   M   Y   Q   F   Q   T   946

4469 CCC TCT TTC AAA TAT CAT CCA TGC TTC GAA CAG CTA ATA TAC TTA TTT TTA CAT AGA AGA ATA 4528
 947  P   S   F   K   Y   H   P   C   F   E   Q   L   I   Y   L   F   L   H   R   R   I   966

4529 GAT CTT ATC AAG CCG CTA AGA CCA GTT TTG CGA CAG GTG TTA TTT AGA CAA GTA CTT ACT 4588
 967  D   L   I   K   P   L   R   P   V   L   R   Q   V   L   F   R   Q   V   L   T   986

4589 GCT GAT TAA tgtcatttcaattattattatacatccttattactggtgtcttaaacaatattattactaagtata 4665
 987  A   D   *                                                                       989
```

```
4666  gctgaccccaaagcaagcatactataggatttctagtaaattaatctcgttattagttttgattgacttgtct  4745
4746  ttatccttatacttttaagaaagattgacagtggttgctgactactgccacatgcccattaaacggagtggttaaaca  4825
4826  ttaaaagtaatacatgaggctaatctcctttcatttagaataaggaaagtggttttctataatgaataatgcccgcacta  4905
4906  atgcaaaaagacgaagattatcttctaaacaaggggattaagcatatccgaaggaaagagagtaatatacccagtgtt  4985
4986  gttgaagaaagcaaggataatttggaacaagcttctgcagatgacaggctaaatttggtgaccgaatttggtaaaagc  5065
5066  cccaggttatccatgtggccggcttgcctgtactgagacgaaaagaaactaaggatagtttgaatactaatagctcatta  5145
5146  atgtcttatataggtttgttttttcctgacttcaattttgcatggtgaaaagaaatagttaagcttatgat  5225
5226  tccgaaatagccaaatttcttggttcctccaccgatgaggaagtctaaagcgggaaatagcttattcagctgctgaggagaagcctaattttgc  5305
5306  tcctgatttaaaggaggaatcttcctgggagacatctcttgatgaatcagatgcggagagtatctccagcgagtatctccttgatgtcaata  5385
5386  aaaaagaaaaatatcattgggagacatctcttgatgaatcagatgcggagagtatctccagcgagtatctccttgatgtcaata  5465
5466  acttctatttctgaaatgtatggtcctactgtcgcttcgtcgtactgtcgcttcgtcgtactgtcgcttcgtcgtactgtcgcttcgtcgtactg  5544
```

*FIG. 46*
(CONTINUED)

```
                                           1
                                           met ser val tyr val val glu leu leu
GCCAAGTTCCTGCACTGGCTG    ATG AGT GTG TAC GTC GTC GAG CTG CTC 10                                                        20
arg ser phe phe tyr val thr glu thr thr phe gln lys asn arg
AGG TCT TTC TTT TAT GTC ACG GAG ACC ACG TTT CAA AAG AAC AGG 30
leu phe phe tyr arg lys ser val trp ser lys leu gln ser ile
CTC TTT TTC TAC CGG AAG AGT GTC TGG AGC AAG TTG CAA AGC ATT 40                                              50
gly ile arg gln his leu lys arg val gln leu arg glu leu ser
GGA ATC AGA CAG CAC TTG AAG AGG GTG CAG CTG CGG GAG CTG TCG 60
glu ala glu val arg gln his arg glu ala arg pro ala leu leu
GAA GCA GAG GTC AGG CAG CAT CGG GAA GCC AGG CCC GCC CTG CTG 70                                                        80
thr ser arg leu arg phe ile pro lys pro asp gly leu arg pro
ACG TCC AGA CTC CGC TTC ATC CCC AAG CCT GAC GGG CTG CGG CCG 90
ile val asn met asp tyr val val gly ala arg thr phe arg arg
ATT GTG AAC ATG GAC TAC GTC GTG GGA GCC AGA ACG TTC CGC AGA 100                                              110
glu lys     ala glu arg leu thr ser arg val lys ala leu phe
GAA AAG ARG GCC GAG CGT CTC ACC TCG AGG GTG AAG GCA CTG TTC 120
ser val leu asn tyr glu arg ala arg arg pro gly leu leu gly
AGC GTG CTC AAC TAC GAG CGG GCG CGG CGC CCC GGC CTC CTG GGC 130                                              140
ala ser val leu gly leu asp asp ile his arg ala trp arg thr
GCC TCT GTG CTG GGC CTG GAC GAT ATC CAC AGG GCC TGG CGC ACC 150
phe val leu arg val arg ala gln asp pro pro pro glu leu tyr
TTC GTG CTG CGT GTG CGG GCC CAG GAC CCG CCG CCT GAG CTG TAC 160                                              170
phe val lys val asp val thr gly ala tyr asp thr ile pro gln
TTT GTC AAG GTG GAT GTG ACG GGC GCG TAC GAC ACC ATC CCC CAG 180
asp arg leu thr glu val ile ala ser ile ile lys pro gln asn
GAC AGG CTC ACG GAG GTC ATC GCC AGC ATC ATC AAA CCC CAG AAC 190                                              200
thr tyr cys val arg arg tyr ala val val gln lys ala ala met
ACG TAC TGC GTG CGT CGG TAT GCC GTG GTC CAG AAG GCC GCC ATG
```

*FIG. 47*

```
                            210
gly thr ser ala arg pro ser arg ala thr ser tyr val gln cys
GGC ACG TCC GCA AGG CCT TCA AGA GCC ACG TCC TAC GTC CAG TGC 220                                      230
gln gly ile pro gln gly ser ile leu ser thr leu leu cys ser
CAG GGG ATC CCG CAG GGC TCC ATC CTC TCC ACG CTG CTC TGC AGC 240
leu cys tyr gly asp met glu asn lys leu phe ala gly ile arg
CTG TGC TAC GGC GAC ATG GAG AAC AAG CTG TTT GCG GGG ATT CGG 250                                      260
arg asp gly leu leu leu arg leu val asp asp phe leu leu val
CGG GAC GGG CTG CTC CTG CGT TTG GTG GAT GAT TTC TTG TTG GTG 270
thr pro his leu thr his ala lys thr phe leu arg thr leu val
ACA CCT CAC CTC ACC CAC GCG AAA ACC TTC CTC AGG ACC CTG GTC 280                                      290
arg gly val pro glu tyr gly cys val val asn leu arg lys thr
CGA GGT GTC CCT GAG TAT GGC TGC GTG GTG AAC TTG CGG AAG ACA 300
val val asn phe pro val glu asp glu ala leu gly gly thr ala
GTG GTG AAC TTC CCT GTA GAA GAC GAG GCC CTG GGT GGC ACG GCT 310                                      320
phe val gln met pro ala his gly leu phe pro trp cys gly leu
TTT GTT CAG ATG CCG GCC CAC GGC CTA TTC CCC TGG TGC GGC CTG 330
leu leu asp thr arg thr leu glu val gln ser asp tyr ser ser
CTG CTG GAT ACC CGG ACC CTG GAG GTG CAG AGC GAC TAC TCC AGC 340                                      350
tyr ala arg thr ser ile arg ala ser leu thr phe asn arg gly
TAT GCC CGG ACC TCC ATC AGA GCC AGT CTC ACC TTC AAC CGC GGC 360
phe lys ala gly arg asn met arg arg lys leu phe gly val leu
TTC AAG GCT GGG AGG AAC ATG CGT CGC AAA CTC TTT GGG GTC TTG 370                                      380
arg leu lys cys his ser leu phe leu asp leu gln val asn ser
CGG CTG AAG TGT CAC AGC CTG TTT CTG GAT TTG CAG GTG AAC AGC 390
leu gln thr val cys thr asn ile tyr lys ile leu leu leu gln
CTC CAG ACG GTG TGC ACC AAC ATC TAC AAG ATC CTC CTG CTG CAG 400                                      410
ala tyr arg phe his ala cys val leu gln leu pro phe his gln
GCG TAC AGG TTT CAC GCA TGT GTG CTG CAG CTC CCA TTT CAT CAG
```

*FIG. 47*
(CONTINUED)

```
                         420
gln val trp lys asn pro his phe ser cys ala ser ser leu thr
CAA GTT TGG AAG AAC CCA CAT TTT TCC TGC GCG TCA TCT CTG ACA 430                                      440
arg leu pro leu leu leu his pro glu ser gln glu arg arg asp
CGG CTC CCT CTG CTA CTC CAT CCT GAA AGC CAA GAA CGC AGG GAT 450
val ala gly gly gln gly arg arg arg pro ser ala leu arg gly
GTC GCT GGG GGC CAA GGG CGC CGC CGG CCC TCT GCC CTC CGA GGC 460                                          470
arg ala val ala val pro pro ser ile pro ala gln ala asp ser
CGT GCA GTG GCT GTG CCA CCA AGC ATT CCT GCT CAA GCT GAC TCG 480
thr pro cys his leu arg ala thr pro gly val thr gln asp ser
ACA CCG TGT CAC CTA CGT GCC ACT CCT GGG GTC ACT CAG GAC AGC 490                                              500
pro asp ala ala glu ser glu ala pro gly asp asp ala asp cys
CCA GAC GCA GCT GAG TCG GAA GCT CCC GGG GAC GAC GCT GAC TGC 510
pro gly gly arg ser gln pro gly thr ala leu arg leu gln asp
CCT GGA GGC CGC AGC CAA CCC GGC ACT GCC CTC AGA CTT CAA GAC 520                                      530
his pro gly leu met ala thr arg pro gln pro gly arg glu gln
CAT CCT GGA CTG ATG GCC ACC CGC CCA CAG CCA GGC CGA GAG CAG 540
thr pro ala ala leu ser arg arg ala tyr thr ser gln gly gly
ACA CCA GCA GCC CTG TCA CGC CGG GCT TAT ACG TCC CAG GGA GGG 550                                              560
arg gly gly pro his pro gly leu his arg trp glu ser glu ala
AGG GGC GGC CCA CAC CCA GGC CTG CAC CGC TGG GAG TCT GAG GCC

564
OP
TGA GTGAGTGTTTGGCCGAGGCCTGCATGTCCGGCTGAAGGCTGAGTGTCCGGCTGAGGC

CTGAGCGAGTGTCCAGCCAAGGGCTGAGTGTCCAGCACACCTGCGTTTTCACTTCCCCAC

AGGCTGGCGTTCGGTCCACCCCAGGGCCAGCTTTTCCTCACCAGGAGCCCGGCTTCCACT

CCCCACATAGGAATAGTCCATCCCCAGATTCGCCATTGTTCACCCTTCGCCCTGCCTTCC

TTTGCCTTCCACCCCCACCATTCAGGTGGAGACCCTGAGAAGGACCCTGGGAGCTTTGGG

AATTTGGAGTGACCAAAGGTGTGCCCTGTACACAGGCGAGGACCCTGCACCTGGATGGGG

GTCCCTGTGGGTCAAATTGGGGGGAGGTGCTGTGGGAGTAAAATACTGAATATATGAGTT

TTTCAGTTTTGGAAAAAAAAAAAAAAAAAAAAAAAAAAAA
```

FIG. 47
(CONTINUED)

```
Motif -1
Ep p123          ...LVVSLIRCFFYVTEQQKSYSKT...
Sp Tez1          ...FIIPILQSFFYITESSDLRNRT...
Sc Est2          ...LIPKIIQTFFYCTEISSTVTIV...
Hs TCP1          ...YVVELLRSFFYVTETTFQKNRL...
consensus              FFY TE K
Motif 0                 p hhh   K    hR  h    R
Ep p123          ...KSLGFAPGKLRLIPKKT--TFRPIMTFNKKIV...
Sp Tez1          ...QKTTLPPAVIRLLPKKN--TFRLITNLRKRFL...
Sc Est2          ...TLSNFNHSKMRIIPKKSNNEFRIIAIPCRGAD...
Hs TCP1          ...ARPALLTSRLRFIPKPD--GLRPIVNMDYVVG...
consensus               R  PK       R I AF
Motif A            h   hDh   GY    h
Ep p123          ...PKLFFATMDIEKCYDSVNREKLSTFLK...
Sp Tez1          ...RKKYFVRIDIKSCYDRIKQDLMFRIVK...
Sc Est2          ...PELYFMKFDVKSCYDSIPRMECMRILK...
Hs TCP1          ...PELYFVKVDVTGAYDTIPQDRLTEVIA...//...
consensus            F   D   YD Motif B                    hPQG    pS  hh
Ep p123          ...NGKFYKQTKGIPQGLCVSSILSSFYYA...
Sp Tez1          ...GNSQYLQKVGIPQGSILSSFLCHFYME...
Sc Est2          ...EDKCYIREDGLFQGSSLSAPIVDLYD...
Hs TCP1          ...RATSYVQCQGIPQGSILSTLLCSLCYG...
consensus                  G QG    S Y
Motif C            h   F DD hhh
Ep p123          ...PNVNLLMRLTDDYLLITTQENN...
Sp Tez1          ...KKGSVLLRVVDDFLFITVNKKD...
Sc Est2          ...SQDTLILKLADDFLIISTDQQQ...
Hs TCP1          ...RRDGLLLRLVDDFLLVTPHLTH...
consensus              DD L Motif D               Gh  h   cK
Ep p123          ...NVSRENGFKFNMKKL...
Sp Tez1          ...LNLSLRGFEKHNFST...
Sc Est2          ...KKLAMGGFQKYNAKA...
Hs TCP1          ...LRTLVRGVPEYGCVV...
consensus              G
```

*FIG. 48*

```
   1   GCAGCGCTGC GTCCTGCTGC GCACGTGGGA AGCCCTGGCC CCGGCCACCC
  51   CCGCGATGCC GCGCGCTCCC CGCTGCCGAG CCGTGCGCTC CCTGCTGCGC
 101   AGCCACTACC GCGAGGTGCT GCCGCTGGCC ACGTTCGTGC GGCGCCTGGG
 151   GCCCCAGGGC TGGCGGCTGG TGCAGCGCGG GGACCCGGCG GCTTTCCGCG
 201   CGNTGGTGGC CCANTGCNTG GTGTGCGTGC CCTGGGANGN ANGGCNGCCC
 251   CCCGCCGCCC CCTCCTTCCG CCAGGTGTCC TGCCTGAANG ANCTGGTGGC
 301   CCGAGTGCTG CANANGCTGT GCGANCGCGG CGCGAANAAC GTGCTGGCCT
 351   TCGGCTTCGC GCTGCTGGAC GGGGCCCGCG GGGCCCCCC CGAGGCCTTC
 401   ACCACCAGCG TGCGCAGCTA CCTGCCCAAC ACGGTGACCG ACGCACTGCG
 451   GGGGAGCGGG GCGTGGGGGC TGCTGCTGCG CCGCGTGGGC GACGACGTGC
 501   TGGTTCACCT GCTGGCACGC TGCGCGNTNT TTGTGCTGGT GGNTCCCAGC
 551   TGCGCCTACC ANGTGTGCGG GCCGCCGCTG TACCAGCTCG GCGCTGCNAC
 601   TCAGGCCCGG CCCCCGCCAC ACGCTANTGG ACCCGAANGC GTCTGGGATC
 651   CAACGGGCCT GGAACCATAG CGTCAGGGAG GCCGGGGTCC CCCTGGGCTG
 701   CCAGCCCCGG GTGCGAGGAG GCGCGGGGGC AGTGCCAGCC GAAGTCTGCC
 751   GTTGCCCAAG AGGCCCAGGC GTGGCGCTGC CCCTGAGCCG GAGCGGACGC
 801   CCGTTGGGCA GGGGTCCTGG GCCCACCCGG GCAGGACGCC TGGACCGAGT
 851   GACCGTGGTT TCTGTGTGGT GTCACCTGCC AGACCCGCCG AAGAAGCCAC
 901   CTCTTTGGAG GGTGCGCTCT CTGGCACGCG CCACTCCCAC CCATCCGTGG
 951   GCCGCCAGCA CCACGCGGGC CCCCCATCCA CATCGCGGCC ACCACGTCCT
1001   GGGACACGCC TTGTCCCCCG GTGTACGCCG AGACCAAGCA CTTCCTCTAC
1051   TCCTCAGGCG ACAAGNACAC TGCGNCCCTC CTTCCTACTC AATATATCTG
1101   AGGCCCAGCC TGACTGGCGT TCGGGAGGTT CGTGGAGACA NTCTTTCTGG
1151   TTCCAGGCCT TGGATGCCAG GATTCCCCGC AGGTTGCCCC GCCTGCCCCA
1201   GCGNTACTGG CAAATGCGGC CCCTGTTTCT GGAGCTGCTT GGGAACCACG
1251   CGCAGTGCCC CTACGGGGTG TTCCTCAAGA CGCACTGCCC GCTGCGAGCT
1301   GCGGTCACCC CAGCAGCCGG TGTCTGTGCC CGGGAGAAGC CCCAGGGCTC
1351   TGTGGCGGCC CCCGAGGAGG AGGAACACAG ACCCCCGTCG CCTGGTGCAG
1401   CTGCTCCGCC AGCACAGCAG CCCCTGGCAG GTGTACGGCT TCGTGCGGGC
1451   CTGCCTGCGC CGGCTGGTGC CCCCAGGCCT CTGGGCTCC AGGCACAACG
1501   AACGCCGCTT CCTCAGGAAC ACCAAGAAGT TCATCTCCCT GGGGAAGCAT
1551   GCCAAGCTCT CGCTGCAGGA GCTGACGTGG AAGATGAGCG TGCGGGACTG
1601   CGCTTGGCTG CGCAGGAGCC CAGGGGTTGG CTGTGTTCCG GCCGCAGAGC
1651   ACCGTCTGCG TGAGGAGATC CTGGCCAAGT TCCTGCACTG GCTGATGAGT
1701   GTGTACGTCG TCGAGCTGCT CAGGTCTTTC TTTTATGTCA CGGAGACCAC
1751   GTTTCAAAAG AACAGGCTCT TTTTCTACCG GAAGAGTGTC TGGAGCAAGT
1801   TGCAAAGCAT TGGAATCAGA CAGCACTTGA AGAGGGTGCA GCTGCGGGAG
1851   CTGTCGGAAG CAGAGGTCAG GCAGCATCGG GAAGCCAGGC CCGCCCTGCT
1901   GACGTCCAGA CTCCGCTTCA TCCCCAAGCC TGACGGGCTG CGGCCGATTG
1951   TGAACATGGA CTACGTCGTG GGAGCCAGAA CGTTCCGCAG AGAAAAGAGG
2001   GCCGAGCGTC TCACCTCGAG GGTGAAGGCA CTGTTCAGCG TGCTCAACTA
2051   CGAGCGGGCG CGGCGCCCCG GCCTCCTGGG CGCCTCTGTG CTGGGCCTGG
2101   ACGATATCCA CAGGGCCTGG CGCACCTTCG TGCTGCGTGT GCGGGCCCAG
2151   GACCCGCCGC CTGAGCTGTA CTTTGTCAAG GTGGATGTGA CGGGCGCGTA
2201   CGACACCATC CCCCAGGACA GGCTCACGGA GGTCATCGCC AGCATCATCA
2251   AACCCCAGAA CACGTACTGC GTGCGTCGGT ATGCCGTGGT CCAGAAGGCC
2301   GCCCATGGGC ACGTCCGCAA GGCCTTCAAG AGCCACGTCT CTACCTTGAC
2351   AGACCTCCAG CCGTACATGC GACAGTTCGT GGCTCACCTG CAGGANAACA
2401   GCCCGCTGAG GGATGCCGTC GTCATCGAGC AGAGCTCCTC CCTGAATGAG
2451   GCCAGCAGTG GCCTCTTCGA CGTCTTCCTA CGCTTCATGT GCCACCACGC
```

FIG. 50

```
2501  CGTGCGCATC AGGGGCAAGT CCTACGTCCA GTGCCAGGGG ATCCCGCAGG
2551  GCTCCATCCT CTCCACGCTG CTCTGCAGCC TGTGCTACGG CGACATGGAG
2601  AACAAGCTGT TTGCGGGGAT TCGGCGGGAC GGGCTGCTCC TGCGTTTGGT
2651  GGATGATTTC TTGTTGGTGA CACCTCACCT CACCCACGCG AAAACCTTCC
2701  TCAGGACCCT GGTCCGAGGT GTCCCTGAGT ATGGCTGCGT GGTGAACTTG
2751  CGGAAGACAG TGGTGAACTT CCCTGTAGAA GACGAGGCCC TGGGTGGCAC
2801  GGCTTTTGTT CAGATGCCGG CCCACGGCCT ATTCCCTGG TGCGGCCTGC
2851  TGCTGGATAC CCGGACCCTG GAGGTGCAGA GCGACTACTC CAGCTATGCC
2901  CGGACCTCCA TCAGAGCCAG TCTCACCTTC AACCGCGGCT TCAAGGCTGG
2951  GAGGAACATG CGTCGCAAAC TCTTTGGGGT CTTGCGGCTG AAGTGTCACA
3001  GCCTGTTTCT GGATTTGCAG GTGAACAGCC TCCAGACGGT GTGCACCAAC
3051  ATCTACAAGA TCCTCCTGCT GCAGGCGTAC AGGTTTCACG CATGTGTGCT
3101  GCAGCTCCCA TTTCATCAGC AAGTTTGGAA GAACCCCACA TTTTTCCTGC
3151  GCGTCATCTC TGACACGGCC TCCCTCTGCT ACTCCATCCT GAAAGCCAAG
3201  AACGCAGGGA TGTCGCTGGG GGCCAAGGGC GCCGCCGGCC CTCTGCCCTC
3251  CGAGGCCGTG CAGTGGCTGT GCCACCAAGC ATTCCTGCTC AAGCTGACTC
3301  GACACCGTGT CACCTACGTG CCACTCCTGG GGTCACTCAG GACAGCCCAG
3351  ACGCAGCTGA GTCGGAAGCT CCCGGGGACG ACGCTGACTG CCCTGGAGGC
3401  CGCAGCCAAC CCGGCACTGC CCTCAGACTT CAAGACCATC CTGGACTGAT
3451  GGCCACCCGC CCACAGCCAG GCCGAGAGCA GACACCAGCA GCCCTGTCAC
3501  GCCGGGCTCT ACGTCCCAGG GAGGGAGGGG CGGCCCACAC CCAGGCCCGC
3551  ACCGCTGGGA GTCTGAGGCC TGAGTGAGTG TTTGGCCGAG GCCTGCATGT
3601  CCGGCTGAAG GCTGAGTGTC CGGCTGAGGC CTGAGCGAGT GTCCAGCCAA
3651  GGGCTGAGTG TCCAGCACAC CTGCCGTCTT CACTTCCCCA CAGGCTGGCG
3701  CTCGGCTCCA CCCCAGGGCC AGCTTTTCCT CACCAGGAGC CCGGCTTCCA
3751  CTCCCCACAT AGGAATAGTC CATCCCCAGA TTCGCCATTG TTCACCCCTC
3801  GCCCTGCCCT CCTTTGCCTT CCACCCCCAC CATCCAGGTG GAGACCCTGA
3851  GAAGGACCCT GGGAGCTCTG GAATTTGGA GTGACCAAAG GTGTGCCCTG
3901  TACACAGGCG AGGACCCTGC ACCTGGATGG GGGTCCCTGT GGGTCAAATT
3951  GGGGGGAGGT GCTGTGGGAG TAAAATACTG AATATATGAG TTTTTCAGTT
4001  TTGAAAAAAA AAAAAAAAAA AAAAAAAA
```

*FIG. 50*
*(CONTINUED)*

```
     GCAGCGCTGCGTCCTGCTGCGCACGTGGGAAGCCCTGGCCCCGGCCACCCCCGCGATGCC
   1 ----------+---------+---------+---------+---------+---------+  60
     CGTCGCGACGCAGGACGACGCGTGCACCCTTCGGGACCGGGGCCGGTGGGGCGCTACGG a      A  A  L  R  P  A  A  H  V  G  S  P  G  P  G  H  P  R  D  A  -
b       Q  R  C  V  L  L  R  T  W  E  A  L  A  P  A  T  P  A  M  P  -
c        S  A  A  S  C  C  A  R  G  K  P  W  P  R  P  P  P  R  C  R -

GCGCGCTCCCCGCTGCCGAGCCGTGCGCTCCCTGCTGCGCAGCCACTACCGCGAGGTGCT
  61 ----------+---------+---------+---------+---------+---------+ 120
     CGCGCGAGGGGCGACGGCTCGGCACGCGAGGGACGACGCGTCGGTGATGGCGCTCCACGA a      A  R  S  P  L  P  S  R  A  L  P  A  A  Q  P  L  P  R  G  A  -
b       R  A  P  R  C  R  A  V  R  S  L  L  R  S  H  Y  R  E  V  L  -
c        A  L  P  A  A  E  P  C  A  P  C  C  A  A  T  T  A  R  C  C -

GCCGCTGGCCACGTTCGTGCGGCGCCTGGGGCCCCAGGGCTGGCGGCTGGTGCAGCGCGG
 121 ----------+---------+---------+---------+---------+---------+ 180
     CGGCGACCGGTGCAAGCACGCCGCGGACCCCGGGGTCCCGACCGCCGACCACGTCGCGCC a      A  A  G  H  V  R  A  A  P  G  A  P  G  L  A  A  G  A  A  R  -
b       P  L  A  T  F  V  R  R  L  G  P  Q  G  W  R  L  V  Q  R  G  -
c        R  W  P  R  S  C  G  A  W  G  P  R  A  G  G  W  C  S  A  G -

GGACCCGGCGGCTTTCCGCGCGNTGGTGGCCCANTGCNTGGTGTGCGTGCCCTGGGANGN
 181 ----------+---------+---------+---------+---------+---------+ 240
     CCTGGGCCGCCGAAAGGCGCGCNACCACCGGGTNACGNACCACACGCACGGGACCCTNCN a      G  P  G  G  F  P  R  ?  G  G  P  ?  ?  G  V  R  A  L  G  ?  -
b       D  P  A  A  F  R  A  ?  V  A  ?  C  ?  V  C  V  P  W  ?  ?  -
c        T  R  R  L  S  A  R  W  W  P  ?  A  W  C  A  C  P  G  ?  ? -

ANGGCNGCCCCCGCCGCCCCCTCCTTCCGCCAGGTGTCCTGCCTGAANGANCTGGTGGC
 241 ----------+---------+---------+---------+---------+---------+ 300
     TNCCGNCGGGGGGCGGCGGGGGAGGAAGGCGGTCCACAGGACGGACTTNCTNGACCACCG a      ?  A  A  P  R  R  P  L  L  P  P  G  V  L  P  E  ?  ?  G  G  -
b       ?  ?  P  P  A  A  P  S  F  R  Q  V  S  C  L  ?  ?  L  V  A  -
c        G  ?  P  P  P  P  P  P  S  A  R  C  P  A  *  ?  ?  W  W  P -

CCGAGTGCTGCANANGCTGTGCGANCGCGGCGCGAANAACGTGCTGGCCTTCGGCTTCGC
 301 ----------+---------+---------+---------+---------+---------+ 360
     GGCTCACGACGTNTNCGACACGCTNGCGCCGCGCTTNTTGCACGACCGGAAGCCGAAGCG a      P  S  A  A  ?  A  V  R  ?  R  R  E  ?  R  A  G  L  R  L  R  -
b       R  V  L  ?  ?  L  C  ?  R  G  A  ?  N  V  L  A  F  G  F  A  -
c        E  C  C  ?  ?  C  A  ?  A  A  R  ?  T  C  W  P  S  A  S  R -

GCTGCTGGACGGGGCCCGCGGGGGCCCCCCCGAGGCCTTCACCACCAGCGTGCGCAGCTA
 361 ----------+---------+---------+---------+---------+---------+ 420
     CGACGACCTGCCCCGGGCGCCCCCGGGGGGGCTCCGGAAGTGGTGGTCGCACGCGTCGAT a      A  A  G  R  G  P  R  G  P  P  R  G  L  H  H  Q  R  A  Q  L  -
b       L  L  D  G  A  R  G  G  P  P  E  A  F  T  T  S  V  R  S  Y  -
c        C  W  T  G  P  A  G  A  P  P  R  P  S  P  P  A  C  A  A  T -

CCTGCCCAACACGGTGACCGACGCACTGCGGGGGAGCGGGGCGTGGGGGCTGCTGCTGCG
 421 ----------+---------+---------+---------+---------+---------+ 480
     GGACGGGTTGTGCCACTGGCTGCGTGACGCCCCCTCGCCCCGCACCCCCGACGACGACGC a      P  A  Q  H  G  D  R  R  T  A  G  E  R  G  V  G  A  A  A  A  -
b       L  P  N  T  V  T  D  A  L  R  G  S  G  A  W  G  L  L  L  R  -
c        C  P  T  R  *  P  T  H  C  G  G  A  G  R  G  G  C  C  A  -
```

GGNTCCCAGCTGCGCCTACCANGTGTGCGGGCCGCCGCTGTACCAGCTCGGCGCTGCNAC
541   ---------+---------+---------+---------+---------+---------+ 600
      CCNAGGGTCGACGCGGATGGTNCACACGCCCGGCGGCGACATGGTCGAGCCGCGACGNTG a       G  S  Q  L  R  L  P  ?  V  R  A  A  A  V  P  A  R  R  C  ?   -
b          ?  P  S  C  A  Y  ?  V  C  G  P  P  L  Y  Q  L  G  A  A  T -
c             ?  P  A  A  P  T  ?  C  A  G  R  R  C  T  S  S  A  L  ?  L -

TCAGGCCCGGCCCCCGCCACACGCTANTGGACCCGAANGCGTCTGGGATCCAACGGGCCT
601   ---------+---------+---------+---------+---------+---------+ 660
      AGTCCGGGCCGGGGGCGGTGTGCGATNACCTGGGCTTNCGCAGACCCTAGGTTGCCCGGA a       S  G  P  A  P  A  T  R  ?  W  T  R  ?  R  L  G  S  N  G  P   -
b          Q  A  R  P  P  P  H  A  ?  G  P  E  ?  V  W  D  P  T  G  L -
c             R  P  G  P  R  H  T  L  ?  D  P  ?  A  S  G  I  Q  R  A  W -

GGAACCATAGCGTCAGGGAGGCCGGGGTCCCCCTGGGCTGCCAGCCCCGGGTGCGAGGAG
661   ---------+---------+---------+---------+---------+---------+ 720
      CCTTGGTATCGCAGTCCCTCCGGCCCCAGGGGGACCCGACGGTCGGGGCCCACGCTCCTC a       G  T  I  A  S  G  R  P  G  S  P  W  A  A  S  P  G  C  E  E   -
b          E  P  *  R  Q  G  G  R  G  P  P  G  L  P  A  P  G  A  R  R -
c             N  H  S  V  R  E  A  G  V  P  L  G  C  Q  P  R  V  R  G  G -

GCGCGGGGGCAGTGCCAGCCGAAGTCTGCCGTTGCCCAAGAGGCCCAGGCGTGGCGCTGC
721   ---------+---------+---------+---------+---------+---------+ 780
      CGCGCCCCCGTCACGGTCGGCTTCAGACGGCAACGGGTTCTCCGGGTCCGCACCGCGACG a       A  R  G  Q  C  Q  P  K  S  A  V  A  Q  E  A  Q  A  W  R  C   -
b          R  G  G  S  A  S  R  S  L  P  L  P  K  R  P  R  R  G  A  A -
c             A  G  A  V  P  A  E  V  C  R  C  P  R  G  P  G  V  A  L  P -

CCCTGAGCCGGAGCGGACGCCCGTTGGGCAGGGGTCCTGGGCCCACCCGGGCAGGACGCC
781   ---------+---------+---------+---------+---------+---------+ 840
      GGGACTCGGCCTCGCCTGCGGGCAACCCGTCCCCAGGACCCGGGTGGGCCCGTCCTGCGG a       P  *  A  G  A  D  A  R  W  A  G  V  L  G  P  P  G  Q  D  A   -
b          P  E  P  E  R  T  P  V  G  Q  G  S  W  A  H  P  G  R  T  P -
c             L  S  R  S  G  R  P  L  G  R  G  P  G  P  T  R  A  G  R  L -

TGGACCGAGTGACCGTGGTTTCTGTGTGGTGTCACCTGCCAGACCCGCCGAAGAAGCCAC
841   ---------+---------+---------+---------+---------+---------+ 900
      ACCTGGCTCACTGGCACCAAAGACACACCACAGTGGACGGTCTGGGCGGCTTCTTCGGTG a       W  T  E  *  P  W  F  L  C  G  V  T  C  Q  T  R  R  R  S  H   -
b          G  P  S  D  R  G  F  C  V  V  S  P  A  R  P  A  E  E  A  T -
c             D  R  V  T  V  V  S  V  W  C  H  L  P  D  P  P  K  K  P  P -

CTCTTTGGAGGGTGCGCTCTCTGGCACGCGCCACTCCCACCCATCCGTGGGCCGCCAGCA
901   ---------+---------+---------+---------+---------+---------+ 960
      GAGAAACCTCCCACGCGAGAGACCGTGCGCGGTGAGGGTGGGTAGGCACCCGGCGGTCGT a       L  F  G  G  C  A  L  W  H  A  P  L  P  P  I  R  G  P  P  A   -
b          S  L  E  G  A  L  S  G  T  R  H  S  H  P  S  V  G  R  Q  H -
c             L  W  R  V  R  S  L  A  R  A  T  P  T  H  P  W  A  A  S  T -

CCACGCGGGCCCCCCATCCACATCGCGGCCACCACGTCCTGGGACACGCCTTGTCCCCCG
961   ---------+---------+---------+---------+---------+---------+ 1020
      GGTGCGCCCGGGGGGTAGGTGTAGCGCCGGTGGTGCAGGACCCTGTGCGGAACAGGGGGC
```

GTGTACGCCGAGACCAAGCACTTCCTCTACTCCTCAGGCGACAAGNACACTGCGNCCCTC
   1021  ---------+---------+---------+---------+---------+---------+ 1080
         CACATGCGGCTCTGGTTCGTGAAGGAGATGAGGAGTCCGCTGTTCNTGTGACGCNGGGAG a        V  Y  A  E  T  K  H  F  L  Y  S  S  G  D  K  ?  T  A  ?  L   -
b           C  T  P  R  P  S  T  S  S  T  P  Q  A  T  ?  T  L  R  P  S -
c              V  R  R  D  Q  A  L  P  L  L  R  R  Q  ?  H  C  ?  P  P -

CTTCCTACTCAATATATCTGAGGCCCAGCCTGACTGGCGTTCGGGAGGTTCGTGGAGACA
   1081  ---------+---------+---------+---------+---------+---------+ 1140
         GAAGGATGAGTTATATAGACTCCGGGTCGGACTGACCGCAAGCCCTCCAAGCACCTCTGT a        L  P  T  Q  Y  I  *  G  P  A  *  L  A  F  G  R  F  V  E  T   -
b           F  L  L  N  I  S  E  A  Q  P  D  W  R  S  G  G  S  W  R  ? -
c              S  Y  S  I  Y  L  R  P  S  L  T  G  V  R  E  V  R  G  D  ?-

NTCTTTCTGGTTCCAGGCCTTGGATGCCAGGATTCCCCGCAGGTTGCCCCGCCTGCCCCA
   1141  ---------+---------+---------+---------+---------+---------+ 1200
         NAGAAAGACCAAGGTCCGGAACCTACGGTCCTAAGGGGCGTCCAACGGGGCGGACGGGGT a        ?  F  L  V  P  G  L  G  C  Q  D  S  P  Q  V  A  P  P  A  P   -
b           S  F  W  F  Q  A  L  D  A  R  I  P  R  R  L  P  R  L  P  Q -
c              L  S  G  S  R  P  W  M  P  G  F  P  A  G  C  P  A  C  P  S-

GCGNTACTGGCAAATGCGGCCCCTGTTTCTGGAGCTGCTTGGGAACCACGCGCAGTGCCC
   1201  ---------+---------+---------+---------+---------+---------+ 1260
         CGCNATGACCGTTTACGCCGGGGACAAAGACCTCGACGAACCCTTGGTGCGCGTCACGGG a        A  ?  L  A  N  A  A  P  V  S  G  A  A  W  E  P  R  A  V  P   -
b           R  Y  W  Q  M  R  P  L  F  L  E  L  L  G  N  H  A  Q  C  P -
c              ?  T  G  K  C  G  P  C  F  W  S  C  L  G  T  T  R  S  A  P-

CTACGGGGTGTTCCTCAAGACGCACTGCCCGCTGCGAGCTGCGGTCACCCCAGCAGCCGG
   1261  ---------+---------+---------+---------+---------+---------+ 1320
         GATGCCCCACAAGGAGTTCTGCGTGACGGGCGACGCTCGACGCCAGTGGGGTCGTCGGCC a        L  R  G  V  P  Q  D  A  L  P  A  A  S  C  G  H  P  S  S  R   -
b           Y  G  V  F  L  K  T  H  C  P  L  R  A  A  V  T  P  A  A  G -
c              T  G  C  S  S  R  R  T  A  R  C  E  L  R  S  P  Q  Q  P  V-

TGTCTGTGCCCGGGAGAAGCCCCAGGGCTCTGTGGCGGCCCCCGAGGAGGAGGAACACAG
   1321  ---------+---------+---------+---------+---------+---------+ 1380
         ACAGACACGGGCCCTCTTCGGGGTCCCGAGACACCGCCGGGGGCTCCTCCTCCTTGTGTC a        C  L  C  P  G  E  A  P  G  L  C  G  G  P  R  G  G  G  T  Q   -
b           V  C  A  R  E  K  P  Q  G  S  V  A  A  P  E  E  E  E  H  R -
c              S  V  P  G  R  S  P  R  A  L  W  R  P  P  R  R  R  N  T  D-

ACCCCCGTCGCCTGGTGCAGCTGCTCCGCCAGCACAGCAGCCCCTGGCAGGTGTACGGCT
   1381  ---------+---------+---------+---------+---------+---------+ 1440
         TGGGGGCAGCGGACCACGTCGACGAGGCGGTCGTGTCGTCGGGGACCGTCCACATGCCGA a        T  P  V  A  W  C  S  C  S  A  S  T  A  A  P  G  R  C  T  A   -
b           P  P  S  P  G  A  A  A  P  P  A  Q  Q  P  L  A  G  V  R  L -
c              P  R  R  L  V  Q  L  L  R  Q  H  S  S  P  W  Q  V  Y  G  F-

TCGTGCGGGCCTGCCTGCGCCGGCTGGTGCCCCCAGGCCTCTGGGGCTCCAGGCACAACG
   1441  ---------+---------+---------+---------+---------+---------+ 1500
         AGCACGCCCGGACGGACGCGGCCGACCACGGGGGTCCGGAGACCCCGAGGTCCGTGTTGC
```

AACGCCGCTTCCTCAGGAACACCAAGAAGTTCATCTCCCTGGGGAAGCATGCCAAGCTCT
  1501  ---------+---------+---------+---------+---------+---------+ 1560
        TTGCGGCGAAGGAGTCCTTGTGGTTCTTCAAGTAGAGGGACCCCTTCGTACGGTTCGAGA a    N A A S S G T P R S S S P W G S M P S S  -
b     T P L P Q E H Q E V H L P G E A C Q A L -
c      R R F L R N T K K F I S L G K H A K L S -

CGCTGCAGGAGCTGACGTGGAAGATGAGCGTGCGGGACTGCGCTTGGCTGCGCAGGAGCC
  1561  ---------+---------+---------+---------+---------+---------+ 1620
        GCGACGTCCTCGACTGCACCTTCTACTCGCACGCCCTGACGCGAACCGACGCGTCCTCGG a    R C R S * R G R * A C G T A L G C A G A  -
b     A A G A D V E D E R A G L R L A A Q E P -
c      L Q E L T W K M S V R D C A W L R R S P -

CAGGGGTTGGCTGTGTTCCGGCCGCAGAGCACCGTCTGCGTGAGGAGATCCTGGCCAAGT
  1621  ---------+---------+---------+---------+---------+---------+ 1680
        GTCCCCAACCGACACAAGGCCGGCGTCTCGTGGCAGACGCACTCCTCTAGGACCGGTTCA a    Q G L A V F R P Q S T V C V R R S W P S  -
b     R G W L C S G R R A P S A * G D P G Q V -
c      G V G C V P A A E H R L R E E I L A K F -

TCCTGCACTGGCTGATGAGTGTGTACGTCGTCGAGCTGCTCAGGTCTTTCTTTTATGTCA
  1681  ---------+---------+---------+---------+---------+---------+ 1740
        AGGACGTGACCGACTACTCACACATGCAGCAGCTCGACGAGTCCAGAAAGAAAATACAGT a    S C T G * * V C T S S S C S G L S F M S  -
b     P A L A D E C V R R R A A Q V F L L C H -
c      L H W L M S V Y V V E L L R S F F Y V T -

CGGAGACCACGTTTCAAAAGAACAGGCTCTTTTTCTACCGGAAGAGTGTCTGGAGCAAGT
  1741  ---------+---------+---------+---------+---------+---------+ 1800
        GCCTCTGGTGCAAAGTTTTCTTGTCCGAGAAAAGATGGCCTTCTCACAGACCTCGTTCA a    R R P R F K R T G S F S T G R V S G A S  -
b     G D H V S K E Q A L F L P E E C L E Q V -
c      E T T F Q K N R L F F Y R K S V W S K L -

TGCAAAGCATTGGAATCAGACAGCACTTGAAGAGGGTGCAGCTGCGGGAGCTGTCGGAAG
  1801  ---------+---------+---------+---------+---------+---------+ 1860
        ACGTTTCGTAACCTTAGTCTGTCGTGAACTTCTCCCACGTCGACGCCCTCGACAGCCTTC a    C K A L E S D S T * R G C S C G S C R K  -
b     A K H W N Q T A L E E G A A A G A V G S -
c      Q S I G I R Q H L K R V Q L R E L S E A -

CAGAGGTCAGGCAGCATCGGGAAGCCAGGCCCGCCCTGCTGACGTCCAGACTCCGCTTCA
  1861  ---------+---------+---------+---------+---------+---------+ 1920
        GTCTCCAGTCCGTCGTAGCCCTTCGGTCCGGGCGGGACGACTGCAGGTCTGAGGCGAAGT a    Q R S G S I G K P G P P C * R P D S A S  -
b     R G Q A A S G S Q A R P A D V Q T P L H -
c      E V R Q H R E A R P A L L T S R L R F I -

TCCCCAAGCCTGACGGGCTGCGGCCGATTGTGAACATGGACTACGTCGTGGGAGCCAGAA
  1921  ---------+---------+---------+---------+---------+---------+ 1980
        AGGGGTTCGGACTGCCCGACGCCGGCTAACACTTGTACCTGATGCAGCACCCTCGGTCTT
```

CGTTCCGCAGAGAAAAGAGGGCCGAGCGTCTCACCTCGAGGGTGAAGGCACTGTTCAGCG
1981 ---------+---------+---------+---------+---------+---------+ 2040
     GCAAGGCGTCTCTTTTCTCCCGGCTCGCAGAGTGGAGCTCCCACTTCCGTGACAAGTCGC a   R S A E K R G P S V S P R G * R H C S A   -
b     V P Q R K E G R A S H L E G E G T V Q R -
c       F R R E K R A E R L T S R V K A L F S V -

TGCTCAACTACGAGCGGGCGCGGCGCCCCGGCCTCCTGGGCGCCTCTGTGCTGGGCCTGG
2041 ---------+---------+---------+---------+---------+---------+ 2100
     ACGAGTTGATGCTCGCCCGCGCCGCGGGGCCGGAGGACCCGCGGAGACACGACCCGGACC a   C S T T S G R G A P A S W A P L C W A W   -
b     A Q L R A G A A P R P P G R L C A G P G -
c       L N Y E R A R R P G L L G A S V L G L D -

ACGATATCCACAGGGCCTGGCGCACCTTCGTGCTGCGTGTGCGGGCCCAGGACCCGCCGC
2101 ---------+---------+---------+---------+---------+---------+ 2160
     TGCTATAGGTGTCCCGGACCGCGTGGAAGCACGACGCACACGCCCGGGTCCTGGGCGGCG a   T I S T G P G A P S C C V C G P R T R R   -
b     R Y P Q G L A H L R A A C A G P G P A A -
c       D I H R A W R T F V L R V R A Q D P P P -

CTGAGCTGTACTTTGTCAAGGTGGATGTGACGGGCGCGTACGACACCATCCCCCAGGACA
2161 ---------+---------+---------+---------+---------+---------+ 2220
     GACTCGACATGAAACAGTTCCACCTACACTGCCCGCGCATGCTGTGGTAGGGGGTCCTGT a   L S C T L S R W M * R A R T T P S P R T   -
b     * A V L C Q G G C D G R V R H H P P G Q -
c       E L Y F V K V D V T G A Y D T I P Q D R -

GGCTCACGGAGGTCATCGCCAGCATCATCAAACCCCAGAACACGTACTGCGTGCGTCGGT
2221 ---------+---------+---------+---------+---------+---------+ 2280
     CCGAGTGCCTCCAGTAGCGGTCGTAGTAGTTTGGGGTCTTGTGCATGACGCACGCAGCCA a   G S R R S S P A S S N P R T R T A C V G   -
b     A H G G H R Q H H Q T P E H V L R A S V -
c       L T E V I A S I I K P Q N T Y C V R R Y -

ATGCCGTGGTCCAGAAGGCCGCCCATGGGCACGTCCGCAAGGCCTTCAAGAGCCACGTCT
2281 ---------+---------+---------+---------+---------+---------+ 2340
     TACGGCACCAGGTCTTCCGGCGGGTACCCGTGCAGGCGTTCCGGAAGTTCTCGGTGCAGA a   M P W S R R P P M G T S A R P S R A T S   -
b     C R G P E G R P W A R P Q G L Q E P R L -
c       A V V Q K A A H G H V R K A F K S H V S -

CTACCTTGACAGACCTCCAGCCGTACATGCGACAGTTCGTGGCTCACCTGCAGGANAACA
2341 ---------+---------+---------+---------+---------+---------+ 2400
     GATGGAACTGTCTGGAGGTCGGCATGTACGCTGTCAAGCACCGAGTGGACGTCCTNTTGT a   L P * Q T S S R T C D S S W L T C R ? T   -
b     Y L D R P P A V H A T V R G S P A G ? Q -
c       T L T D L Q P Y M R Q F V A H L Q ? N S -

GCCCGCTGAGGGATGCCGTCGTCATCGAGCAGAGCTCCTCCCTGAATGAGGCCAGCAGTG
2401 ---------+---------+---------+---------+---------+---------+ 2460
     CGGGCGACTCCCTACGGCAGCAGTAGCTCGTCTCGAGGAGGGACTTACTCCGGTCGTCAC
```

GCCTCTTCGACGTCTTCCTACGCTTCATGTGCCACCACGCCGTGCGCATCAGGGGCAAGT
    2461 ---------+---------+---------+---------+---------+---------+ 2520
         CGGAGAAGCTGCAGAAGGATGCGAAGTACACGGTGGTGCGGCACGCGTAGTCCCCGTTCA a        A S S T S S Y A S C A T T P C A S G A S  -
b         P L R R L P T L H V P P R R A H Q G Q V  -
c          L F D V F L R F M C H H A V R I R G K S -

CCTACGTCCAGTGCCAGGGGATCCCGCAGGGCTCCATCCTCTCCACGCTGCTCTGCAGCC
    2521 ---------+---------+---------+---------+---------+---------+ 2580
         GGATGCAGGTCACGGTCCCCTAGGGCGTCCCGAGGTAGGAGAGGTGCGACGAGACGTCGG a        P T S S A R G S R R A P S S P R C S A A  -
b         L R P V P G D P A G L H P L H A A L Q P  -
c          Y V Q C Q G I P Q G S I L S T L L C S L -

TGTGCTACGGCGACATGGAGAACAAGCTGTTTGCGGGGATTCGGCGGGACGGGCTGCTCC
    2581 ---------+---------+---------+---------+---------+---------+ 2640
         ACACGATGCCGCTGTACCTCTTGTTCGACAAACGCCCCTAAGCCGCCCTGCCCGACGAGG a        C A T A T W R T S C L R G F G G T G C S  -
b         V L R R H G E Q A V C G D S A G R A A P  -
c          C Y G D M E N K L F A G I R R D G L L L -

TGCGTTTGGTGGATGATTTCTTGTTGGTGACACCTCACCTCACCCACGCGAAAACCTTCC
    2641 ---------+---------+---------+---------+---------+---------+ 2700
         ACGCAAACCACCTACTAAAGAACAACCACTGTGGAGTGGAGTGGGTGCGCTTTTGGAAGG a        C V W W M I S C W * H L T S P T R K P S  -
b         A F G G * F L V G D T S P H P R E N L P  -
c          R L V D D F L L V T P H L T H A K T F L -

TCAGGACCCTGGTCCGAGGTGTCCCTGAGTATGGCTGCGTGGTGAACTTGCGGAAGACAG
    2701 ---------+---------+---------+---------+---------+---------+ 2760
         AGTCCTGGGACCAGGCTCCACAGGGACTCATACCGACGCACCACTTGAACGCCTTCTGTC a        S G P W S E V S L S M A A W * T C G R Q  -
b         Q D P G P R C P * V W L R G E L A E D S  -
c          R T L V R G V P E Y G C V V N L R K T V -

TGGTGAACTTCCCTGTAGAAGACGAGGCCCTGGGTGGCACGGCTTTTGTTCAGATGCCGG
    2761 ---------+---------+---------+---------+---------+---------+ 2820
         ACCACTTGAAGGGACATCTTCTGCTCCGGGACCCACCGTGCCGAAAACAAGTCTACGGCC a        W * T S L * K T R P W V A R L L F R C R  -
b         G E L P C R R R G P G W H G F C S D A G  -
c          V N F P V E D E A L G G T A F V Q M P A -

CCCACGGCCTATTCCCCTGGTGCGGCCTGCTGCTGGATACCCGGACCCTGGAGGTGCAGA
    2821 ---------+---------+---------+---------+---------+---------+ 2880
         GGGTGCCGGATAAGGGGACCACGCCGGACGACGACCTATGGGCCTGGGACCTCCACGTCT a        P T A Y S P G A A C W I P G P W R C R  -
b         P R P I P L V R P A A G Y P D P G G A E  -
c          H G L F P W C G L L L D T R T L E V Q S -

GCGACTACTCCAGCTATGCCCGGACCTCCATCAGAGCCAGTCTCACCTTCAACCGCGGCT
    2881 ---------+---------+---------+---------+---------+---------+ 2940
         CGCTGATGAGGTCGATACGGGCCTGGAGGTAGTCTCGGTCAGAGTGGAAGTTGGCGCCGA
```

TCAAGGCTGGGAGGAACATGCGTCGCAAACTCTTTGGGGTCTTGCGGCTGAAGTGTCACA
   2941 ---------+---------+---------+---------+---------+---------+ 3000
        AGTTCCGACCCTCCTTGTACGCAGCGTTTGAGAAACCCCAGAACGCCGACTTCACAGTGT a       S R L G G T C V A N S L G S C G * S V T    -
b       Q G W E E H A S Q T L W G L A A E V S Q    -
c         K A G R N M R R K L F G V L R L K C H S  -

GCCTGTTTCTGGATTTGCAGGTGAACAGCCTCCAGACGGTGTGCACCAACATCTACAAGA
   3001 ---------+---------+---------+---------+---------+---------+ 3060
        CGGACAAAGACCTAAACGTCCACTTGTCGGAGGTCTGCCACACGTGGTTGTAGATGTTCT a       A C F W I C R * T A S R R C A P T S T R    -
b       P V S G F A G E Q P P D G V H Q H L Q D    -
c         L F L D L Q V N S L Q T V C T N I Y K I  -

TCCTCCTGCTGCAGGCGTACAGGTTTCACGCATGTGTGCTGCAGCTCCCATTTCATCAGC
   3061 ---------+---------+---------+---------+---------+---------+ 3120
        AGGAGGACGACGTCCGCATGTCCAAAGTGCGTACACACGACGTCGAGGGTAAAGTAGTCG a       S S C C R R T G F T H V C C S S H F I S    -
b       P P A A G V Q V S R M C A A A P I S S A    -
c         L L L Q A Y R F H A C V L Q L P F H Q Q  -

AAGTTTGGAAGAACCCCACATTTTTCCTGCGCGTCATCTCTGACACGGCCTCCCTCTGCT
   3121 ---------+---------+---------+---------+---------+---------+ 3180
        TTCAAACCTTCTTGGGGTGTAAAAAGGACGCGCAGTAGAGACTGTGCCGGAGGGAGACGA a       K F G R T P H F S C A S S L T R P P S A    -
b       S L E E P H I F P A R H L * H G L P L L    -
c         V W K N P T F F L R V I S D T A S L C Y  -

ACTCCATCCTGAAAGCCAAGAACGCAGGGATGTCGCTGGGGGCCAAGGGCGCCGCCGGCC
   3181 ---------+---------+---------+---------+---------+---------+ 3240
        TGAGGTAGGACTTTCGGTTCTTGCGTCCCTACAGCGACCCCCGGTTCCCGCGGCGGCCGG a       T P S * K P R T Q G C R W G P R A P P A    -
b       L H P E S Q E R R D V A G G Q G R R R P    -
c         S I L K A K N A G M S L G A K G A A G P  -

CTCTGCCCTCCGAGGCCGTGCAGTGGCTGTGCCACCAAGCATTCCTGCTCAAGCTGACTC
   3241 ---------+---------+---------+---------+---------+---------+ 3300
        GAGACGGGAGGCTCCGGCACGTCACCGACACGGTGGTTCGTAAGGACGAGTTCGACTGAG a       L C P P R P C S G C A T K H S C S S * L    -
b       S A L R G R A V A V P P S I P A Q A D S    -
c         L P S E A V Q W L C H Q A F L L K L T R  -

GACACCGTGTCACCTACGTGCCACTCCTGGGGTCACTCAGGACAGCCCAGACGCAGCTGA
   3301 ---------+---------+---------+---------+---------+---------+ 3360
        CTGTGGCACAGTGGATGCACGGTGAGGACCCCAGTGAGTCCTGTCGGGTCTGCGTCGACT a       D T V S P T C H S W G H S G Q P R R S *    -
b       T P C H L R A T P G V T Q D S P D A A E    -
c         H R V T Y V P L L G S L R T A Q T Q L S  -

GTCGGAAGCTCCCGGGGACGACGCTGACTGCCCTGGAGGCCGCAGCCAACCCGGCACTGC
   3361 ---------+---------+---------+---------+---------+---------+ 3420
        CAGCCTTCGAGGGCCCCTGCTGCGACTGACGGGACCTCCGGCGTCGGTTGGGCCGTGACG
```

CCTCAGACTTCAAGACCATCCTGGACTGATGGCCACCCGCCCACAGCCAGGCCGAGAGCA
   3421 ---------+---------+---------+---------+---------+---------+ 3480
        GGAGTCTGAAGTTCTGGTAGGACCTGACTACCGGTGGGCGGGTGTCGGTCCGGCTCTCGT a    P  Q  T  S  R  P  S  W  T  D  G  H  P  P  T  A  R  P  R  A  -
b      L  R  L  Q  D  H  P  G  L  M  A  T  R  P  Q  P  G  R  E  Q -
c        S  D  F  K  T  I  L  D  *  W  P  P  A  H  S  Q  A  E  S  R -

GACACCAGCAGCCCTGTCACGCCGGGCTCTACGTCCCAGGGAGGGAGGGGCGGCCCACAC
   3481 ---------+---------+---------+---------+---------+---------+ 3540
        CTGTGGTCGTCGGGACAGTGCGGCCCGAGATGCAGGGTCCCTCCCTCCCCGCCGGGTGTG a    D  T  S  S  P  V  T  P  G  S  T  S  Q  G  G  R  G  G  P  H  -
b      T  P  A  A  L  S  R  R  A  L  R  P  R  E  G  G  A  A  H  T -
c        H  Q  Q  P  C  H  A  G  L  Y  V  P  G  R  E  G  R  P  T  P -

CCAGGCCCGCACCGCTGGGAGTCTGAGGCCTGAGTGAGTGTTTGGCCGAGGCCTGCATGT
   3541 ---------+---------+---------+---------+---------+---------+ 3600
        GGTCCGGGCGTGGCGACCCTCAGACTCCGGACTCACTCACAAACCGGCTCCGGACGTACA a    P  G  P  H  R  W  E  S  E  A  *  V  S  V  W  P  R  P  A  C  -
b      Q  A  R  T  A  G  S  L  R  P  E  *  V  F  G  R  G  L  H  V -
c        R  P  A  P  L  G  V  *  G  L  S  E  C  L  A  E  A  C  M  S -

CCGGCTGAAGGCTGAGTGTCCGGCTGAGGCCTGAGCGAGTGTCCAGCCAAGGGCTGAGTG
   3601 ---------+---------+---------+---------+---------+---------+ 3660
        GGCCGACTTCCGACTCACAGGCCGACTCCGGACTCGCTCACAGGTCGGTTCCCGACTCAC a    P  A  E  G  *  V  S  G  *  G  L  S  E  C  P  A  K  G  *  V  -
b      R  L  K  A  E  C  P  A  E  A  *  A  S  V  Q  P  R  A  E  C -
c        G  *  R  L  S  V  R  L  R  P  E  R  V  S  S  Q  G  L  S  V -

TCCAGCACACCTGCCGTCTTCACTTCCCCACAGGCTGGCGCTCGGCTCCACCCCAGGGCC
   3661 ---------+---------+---------+---------+---------+---------+ 3720
        AGGTCGTGTGGACGGCAGAAGTGAAGGGGTGTCCGACCGCGAGCCGAGGTGGGGTCCCGG a    S  S  T  P  A  V  F  T  S  P  Q  A  G  A  R  L  H  P  R  A  -
b      P  A  H  L  P  S  S  L  P  H  R  L  A  L  G  S  T  P  G  P -
c        Q  H  T  C  R  L  H  F  P  T  G  W  R  S  A  P  P  Q  G  Q -

AGCTTTTCCTCACCAGGAGCCCGGCTTCCACTCCCCACATAGGAATAGTCCATCCCCAGA
   3721 ---------+---------+---------+---------+---------+---------+ 3780
        TCGAAAAGGAGTGGTCCTCGGGCCGAAGGTGAGGGGTGTATCCTTATCAGGTAGGGGTCT a    S  F  S  S  P  G  A  R  L  P  L  P  T  *  E  *  S  I  P  R  -
b      A  F  P  H  Q  E  P  G  F  H  S  P  H  R  N  S  P  S  P  D -
c        L  F  L  T  R  S  P  A  S  T  P  H  I  G  I  V  H  P  Q  I -

TTCGCCATTGTTCACCCCTCGCCCTGCCCTCCTTTGCCTTCCACCCCCACCATCCAGGTG
   3781 ---------+---------+---------+---------+---------+---------+ 3840
        AAGCGGTAACAAGTGGGGAGCGGGACGGGAGGAAACGGAAGGTGGGGGTGGTAGGTCCAC a    F  A  I  V  H  P  S  P  C  P  P  L  P  S  T  P  T  I  Q  V  -
b      S  P  L  F  T  P  R  P  A  L  L  C  L  P  P  P  P  S  R  W -
c        R  H  C  S  P  L  A  L  P  S  F  A  F  H  P  H  H  P  G  G -

GAGACCCTGAGAAGGACCCTGGGAGCTCTGGGAATTTGGAGTGACCAAAGGTGTGCCCTG
   3841 ---------+---------+---------+---------+---------+---------+ 3900
        CTCTGGGACTCTTCCTGGGACCCTCGAGACCCTTAAACCTCACTGGTTTCCACACGGGAC
```

TACACAGGCGAGGACCCTGCACCTGGATGGGGGTCCCTGTGGGTCAAATTGGGGGAGGT
  3901   ---------+---------+---------+---------+---------+---------+ 3960
         ATGTGTCCGCTCCTGGGACGTGGACCTACCCCCAGGGACACCCAGTTTAACCCCCCTCCA a        Y  T  G  E  D  P  A  P  G  W  G  S  L  W  V  K  L  G  G  G  -
b           T  Q  A  R  T  L  H  L  D  G  G  P  C  G  S  N  W  G  E  V  -
c              H  R  R  G  P  C  T  W  M  G  V  P  V  G  Q  I  G  G  R  C -

GCTGTGGGAGTAAAATACTGAATATATGAGTTTTTCAGTTTTGAAAAAAAAAAAAAAAAA
  3961   ---------+---------+---------+---------+---------+---------+ 4020
         CGACACCCTCATTTTATGACTTATATACTCAAAAAGTCAAAACTTTTTTTTTTTTTTTTT a        A  V  G  V  K  Y  *  I  Y  E  F  F  S  F  E  K  K  K  K  K  -
b           L  W  E  *  N  T  E  Y  M  S  F  S  V  L  K  K  K  K  K  -
c              C  G  S  K  I  L  N  I  *  V  F  Q  F  *  K  K  K  K  K -

AAAAAAAAA
  4021   --------- 4029
         TTTTTTTTT a        K  K  K  -
b           K  K  -
c              K  K  -
```

FIG. 51
(CONTINUED)

```
                                                                    1
                                                                   met
GCAGCGCTGCGTCCTGCTGCGCACGTGGGAAGCCCTGGCCCCGGCCACCCCGCG ATG 10
pro arg ala pro arg cys arg ala val arg ser leu leu arg ser
CCG CGC GCT CCC CGC TGC CGA GCC GTG CGC TCC CTG CTG CGC AGC 20                                          30
his tyr arg glu val leu pro leu ala thr phe val arg arg leu
CAC TAC CGC GAG GTG CTG CCG CTG GCC ACG TTC GTG CGG CGC CTG 40
gly pro gln gly trp arg leu val gln arg gly asp pro ala ala
GGG CCC CAG GGC TGG CGG CTG GTG CAG CGC GGG GAC CCG GCG GCT 50                                          60
phe arg ala leu val ala gln cys leu val cys val pro trp asp
TTC CGC GCG CTG GTG GCC CAG TGC CTG GTG TGC GTG CCC TGG GAC 70
ala arg pro pro pro ala ala pro ser phe arg gln val ser cys
GCA CGG CCG CCC CCC GCC GCC CCC TCC TTC CGC CAG GTG TCC TGC 80                                          90
leu lys glu leu val ala arg val leu gln arg leu cys glu arg
CTG AAG GAG CTG GTG GCC CGA GTG CTG CAG AGG CTG TGC GAG CGC 100
gly ala lys asn val leu ala phe gly phe ala leu leu asp gly
GGC GCG AAG AAC GTG CTG GCC TTC GGC TTC GCG CTG CTG GAC GGG 110                                         120
ala arg gly gly pro pro glu ala phe thr thr ser val arg ser
GCC CGC GGG GGC CCC CCC GAG GCC TTC ACC ACC AGC GTG CGC AGC 130
tyr leu pro asn thr val thr asp ala leu arg gly ser gly ala
TAC CTG CCC AAC ACG GTG ACC GAC GCA CTG CGG GGG AGC GGG GCG 140                                         150
trp gly leu leu leu arg arg val gly asp asp val leu val his
TGG GGG CTG CTG CTG CGC CGC GTG GGC GAC GAC GTG CTG GTT CAC 160
leu leu ala arg cys ala leu phe val leu val ala pro ser cys
CTG CTG GCA CGC TGC GCG CTC TTT GTG CTG GTG GCT CCC AGC TGC 170                                         180
ala tyr gln val cys gly pro pro leu tyr gln leu gly ala ala
GCC TAC CAG GTG TGC GGG CCG CCG CTG TAC CAG CTC GGC GCT GCC 190
thr gln ala arg pro pro pro his ala ser gly pro arg arg arg
ACT CAG GCC CGG CCC CCG CCA CAC GCT AGT GGA CCC CGA AGG CGT
```

*FIG. 53*

```
              200                                           210
leu gly cys glu arg ala trp asn his ser val arg glu ala gly
CTG GGA TGC GAA CGG GCC TGG AAC CAT AGC GTC AGG GAG GCC GGG 220
val pro leu gly leu pro ala pro gly ala arg arg arg gly gly
GTC CCC CTG GGC CTG CCA GCC CCG GGT GCG AGG AGG CGC GGG GGC 230                                           240
ser ala ser arg ser leu pro leu pro lys arg pro arg arg gly
AGT GCC AGC CGA AGT CTG CCG TTG CCC AAG AGG CCC AGG CGT GGC 250
ala ala pro glu pro glu arg thr pro val gly gln gly ser trp
GCT GCC CCT GAG CCG GAG CGG ACG CCC GTT GGG CAG GGG TCC TGG 260                                           270
ala his pro gly arg thr arg gly pro ser asp arg gly phe cys
GCC CAC CCG GGC AGG ACG CGT GGA CCG AGT GAC CGT GGT TTC TGT 280
val val ser pro ala arg pro ala glu glu ala thr ser leu glu
GTG GTG TCA CCT GCC AGA CCC GCC GAA GAA GCC ACC TCT TTG GAG
              290                                           300
gly ala leu ser gly thr arg his ser his pro ser val gly arg
GGT GCG CTC TCT GGC ACG CGC CAC TCC CAC CCA TCC GTG GGC CGC 310
gln his his ala gly pro pro ser thr ser arg pro pro arg pro
CAG CAC CAC GCG GGC CCC CCA TCC ACA TCG CGG CCA CCA CGT CCC 320                                           330
trp asp thr pro cys pro pro val tyr ala glu thr lys his phe
TGG GAC ACG CCT TGT CCC CCG GTG TAC GCC GAG ACC AAG CAC TTC 340
leu tyr ser ser gly asp lys glu gln leu arg pro ser phe leu
CTC TAC TCC TCA GGC GAC AAG GAG CAG CTG CGG CCC TCC TTC CTA 350                                           360
leu ser ser leu arg pro ser leu thr gly ala arg arg leu val
CTC AGC TCT CTG AGG CCC AGC CTG ACT GGC GCT CGG AGG CTC GTG 370
glu thr ile phe leu gly ser arg pro trp met pro gly thr pro
GAG ACC ATC TTT CTG GGT TCC AGG CCC TGG ATG CCA GGG ACT CCC 380                                           390
arg arg leu pro arg leu pro gln arg tyr trp gln met arg pro
CGC AGG TTG CCC CGC CTG CCC CAG CGC TAC TGG CAA ATG CGG CCC 400
leu phe leu glu leu leu gly asn his ala gln cys pro tyr gly
CTG TTT CTG GAG CTG CTT GGG AAC CAC GCG CAG TGC CCC TAC GGG 410                                           420
val leu leu lys thr his cys pro leu arg ala ala val thr pro
GTG CTC CTC AAG ACG CAC TGC CCG CTG CGA GCT GCG GTC ACC CCA
```

```
                                    430
ala ala gly val cys ala arg glu lys pro gln gly ser val ala
GCA GCC GGT GTC TGT GCC CGG GAG AAG CCC CAG GGC TCT GTG GCG 440                                 450
ala pro glu glu glu asp thr asp pro arg arg leu val gln leu
GCC CCC GAG GAG GAG GAC ACA GAC CCC CGT CGC CTG GTG CAG CTG 460
leu arg gln his ser ser pro trp gln val tyr gly phe val arg
CTC CGC CAG CAC AGC AGC CCC TGG CAG GTG TAC GGC TTC GTG CGG 470                                 480
ala cys leu arg arg leu val pro pro gly leu trp gly ser arg
GCC TGC CTG CGC CGG CTG GTG CCC CCA GGC CTC TGG GGC TCC AGG 490
his asn glu arg arg phe leu arg asn thr lys lys phe ile ser
CAC AAC GAA CGC CGC TTC CTC AGG AAC ACC AAG AAG TTC ATC TCC 500                                 510
leu gly lys his ala lys leu ser leu gln glu leu thr trp lys
CTG GGG AAG CAT GCC AAG CTC TCG CTG CAG GAG CTG ACG TGG AAG 520
met ser val arg asp cys ala trp leu arg arg ser pro gly val
ATG AGC GTG CGG GAC TGC GCT TGG CTG CGC AGG AGC CCA GGG GTT 530                                 540
gly cys val pro ala ala glu his arg leu arg glu glu ile leu
GGC TGT GTT CCG GCC GCA GAG CAC CGT CTG CGT GAG GAG ATC CTG 550
ala lys phe leu his trp leu met ser val tyr val val glu leu
GCC AAG TTC CTG CAC TGG CTG ATG AGT GTG TAC GTC GTC GAG CTG 560                                 570
leu arg ser phe phe tyr val thr glu thr thr phe gln lys asn
CTC AGG TCT TTC TTT TAT GTC ACG GAG ACC ACG TTT CAA AAG AAC 580
arg leu phe phe tyr arg lys ser val trp ser lys leu gln ser
AGG CTC TTT TTC TAC CGG AAG AGT GTC TGG AGC AAG TTG CAA AGC 590                                 600
ile gly ile arg gln his leu lys arg val gln leu arg glu leu
ATT GGA ATC AGA CAG CAC TTG AAG AGG GTG CAG CTG CGG GAG CTG
                            610
ser glu ala glu val arg gln his arg glu ala arg pro ala leu
TCG GAA GCA GAG GTC AGG CAG CAT CGG GAA GCC AGG CCC GCC CTG 620                                 630
leu thr ser arg leu arg phe ile pro lys pro asp gly leu arg
CTG ACG TCC AGA CTC CGC TTC ATC CCC AAG CCT GAC GGG CTG CGG 640
pro ile val asn met asp tyr val val gly ala arg thr phe arg
CCG ATT GTG AAC ATG GAC TAC GTC GTG GGA GCC AGA ACG TTC CGC
```

FIG. 53
(CONTINUED)

```
                        650                                          660
arg glu lys arg ala glu arg leu thr ser arg val lys ala leu
AGA GAA AAG AGG GCC GAG CGT CTC ACC TCG AGG GTG AAG GCA CTG 670
phe ser val leu asn tyr glu arg ala arg arg pro gly leu leu
TTC AGC GTG CTC AAC TAC GAG CGG GCG CGG CGC CCC GGC CTC CTG 680                                          690
gly ala ser val leu gly leu asp asp ile his arg ala trp arg
GGC GCC TCT GTG CTG GGC CTG GAC GAT ATC CAC AGG GCC TGG CGC 700
thr phe val leu arg val arg ala gln asp pro pro glu leu
ACC TTC GTG CTG CGT GTG CGG GCC CAG GAC CCG CCG CCT GAG CTG 710                                          720
tyr phe val lys val asp val thr gly ala tyr asp thr ile pro
TAC TTT GTC AAG GTG GAT GTG ACG GGC GCG TAC GAC ACC ATC CCC 730
gln asp arg leu thr glu val ile ala ser ile ile lys pro gln
CAG GAC AGG CTC ACG GAG GTC ATC GCC AGC ATC ATC AAA CCC CAG 740                                          750
asn thr tyr cys val arg arg tyr ala val val gln lys ala ala
AAC ACG TAC TGC GTG CGT CGG TAT GCC GTG GTC CAG AAG GCC GCC 760
his gly his val arg lys ala phe lys ser his val ser thr leu
CAT GGG CAC GTC CGC AAG GCC TTC AAG AGC CAC GTC TCT ACC TTG 770                                          780
thr asp leu gln pro tyr met arg gln phe val ala his leu gln
ACA GAC CTC CAG CCG TAC ATG CGA CAG TTC GTG GCT CAC CTG CAG 790
glu thr ser pro leu arg asp ala val val ile glu gln ser ser
GAG ACC AGC CCG CTG AGG GAT GCC GTC GTC ATC GAG CAG AGC TCC 800                                          810
ser leu asn glu ala ser ser gly leu phe asp val phe leu arg
TCC CTG AAT GAG GCC AGC AGT GGC CTC TTC GAC GTC TTC CTA CGC 820
phe met cys his his ala val arg ile arg gly lys ser tyr val
TTC ATG TGC CAC CAC GCC GTG CGC ATC AGG GGC AAG TCC TAC GTC 830                                          840
gln cys gln gly ile pro gln gly ser ile leu ser thr leu leu
CAG TGC CAG GGG ATC CCG CAG GGC TCC ATC CTC TCC ACG CTG CTC 850
cys ser leu cys tyr gly asp met glu asn lys leu phe ala gly
TGC AGC CTG TGC TAC GGC GAC ATG GAG AAC AAG CTG TTT GCG GGG 860                                          870
ile arg arg asp gly leu leu leu arg leu val asp asp phe leu
ATT CGG CGG GAC GGG CTG CTC CTG CGT TTG GTG GAT GAT TTC TTG
```

*FIG. 53*
*(CONTINUED)*

```
                                        880
leu val thr pro his leu thr his ala lys thr phe leu arg thr
TTG GTG ACA CCT CAC CTC ACC CAC GCG AAA ACC TTC CTC AGG ACC
                890                                 900
leu val arg gly val pro glu tyr gly cys val val asn leu arg
CTG GTC CGA GGT GTC CCT GAG TAT GGC TGC GTG GTG AAC TTG CGG
                                910
lys thr val val asn phe pro val glu asp glu ala leu gly gly
AAG ACA GTG GTG AAC TTC CCT GTA GAA GAC GAG GCC CTG GGT GGC
                920                                 930
thr ala phe val gln met pro ala his gly leu phe pro trp cys
ACG GCT TTT GTT CAG ATG CCG GCC CAC GGC CTA TTC CCC TGG TGC
                                940
gly leu leu leu asp thr arg thr leu glu val gln ser asp tyr
GGC CTG CTG CTG GAT ACC CGG ACC CTG GAG GTG CAG AGC GAC TAC
                950                                 960
ser ser tyr ala arg thr ser ile arg ala ser leu thr phe asn
TCC AGC TAT GCC CGG ACC TCC ATC AGA GCC AGT CTC ACC TTC AAC
                                970
arg gly phe lys ala gly arg asn met arg arg lys leu phe gly
CGC GGC TTC AAG GCT GGG AGG AAC ATG CGT CGC AAA CTC TTT GGG
                980                                 990
val leu arg leu lys cys his ser leu phe leu asp leu gln val
GTC TTG CGG CTG AAG TGT CAC AGC CTG TTT CTG GAT TTG CAG GTG
                                1000
asn ser leu gln thr val cys thr asn ile tyr lys ile leu leu
AAC AGC CTC CAG ACG GTG TGC ACC AAC ATC TAC AAG ATC CTC CTG
                1010                                1020
leu gln ala tyr arg phe his ala cys val leu gln leu pro phe
CTG CAG GCG TAC AGG TTT CAC GCA TGT GTG CTG CAG CTC CCA TTT
                                1030
his gln gln val trp lys asn pro thr phe phe leu arg val ile
CAT CAG CAA GTT TGG AAG AAC CCC ACA TTT TTC CTG CGC GTC ATC
                1040                                1050
ser asp thr ala ser leu cys tyr ser ile leu lys ala lys asn
TCT GAC ACG GCC TCC CTC TGC TAC TCC ATC CTG AAA GCC AAG AAC
                                1060
ala gly met ser leu gly ala lys gly ala ala gly pro leu pro
GCA GGG ATG TCG CTG GGG GCC AAG GGC GCC GCC GGC CCT CTG CCC
                1070                                1080
ser glu ala val gln trp leu cys his gln ala phe leu leu lys
TCC GAG GCC GTG CAG TGG CTG TGC CAC CAA GCA TTC CTG CTC AAG
                                1090
leu thr arg his arg val thr tyr val pro leu leu gly ser leu
CTG ACT CGA CAC CGT GTC ACC TAC GTG CCA CTC CTG GGG TCA CTC
```

FIG. 53
(CONTINUED)

```
                          1100                                           1110
arg thr ala gln thr gln leu ser arg lys leu pro gly thr thr
AGG ACA GCC CAG ACG CAG CTG AGT CGG AAG CTC CCG GGG ACG ACG 1120
leu thr ala leu glu ala ala ala asn pro ala leu pro ser asp
CTG ACT GCC CTG GAG GCC GCA GCC AAC CCG GCA CTG CCC TCA GAC 1130        1132
phe lys thr ile leu asp OP
TTC AAG ACC ATC CTG GAC TGA TGGCCACCCGCCCACAGCCAGGCCGAGAGCAGA

CACCAGCAGCCCTGTCACGCCGGGCTCTACGTCCCAGGGAGGGAGGGGCGGCCCACACCC

AGGCCCGCACCGCTGGGAGTCTGAGGCCTGAGTGAGTGTTTGGCCGAGGCCTGCATGTCC

GGCTGAAGGCTGAGTGTCCGGCTGAGGCCTGAGCGAGTGTCCAGCCAAGGGCTGAGTGTC

CAGCACACCTGCCGTCTTCACTTCCCCACAGGCTGGCGCTCGGCTCCACCCCAGGGCCAG

CTTTTCYTCACCAGGAGCCCGGCTTCCACTCCCCACATAGGAATAGTCCATCCCCAGATT

CGCCATTGTTCACCCYTCGCCCTGCCYTCCTTTGCCTTCCACCCCCACCATCCAGGTGGA

GACCCTGAGAAGGACCCTGGGAGCTCTGGGAATTTGGAGTGACCAAAGGTGTGCCCTGTA

CACAGGCGAGGACCCTGCACCTGGATGGGGGTCCCTGTGGGTCAAATTGGGGGAGGTGC

TGTGGGAGTAAAATACTGAATATATGAGTTTTTCAGTTTTGRAAAAAAAAAAAAAAAAAA

AAAAAAAAAA
```

*FIG. 53*
(CONTINUED)

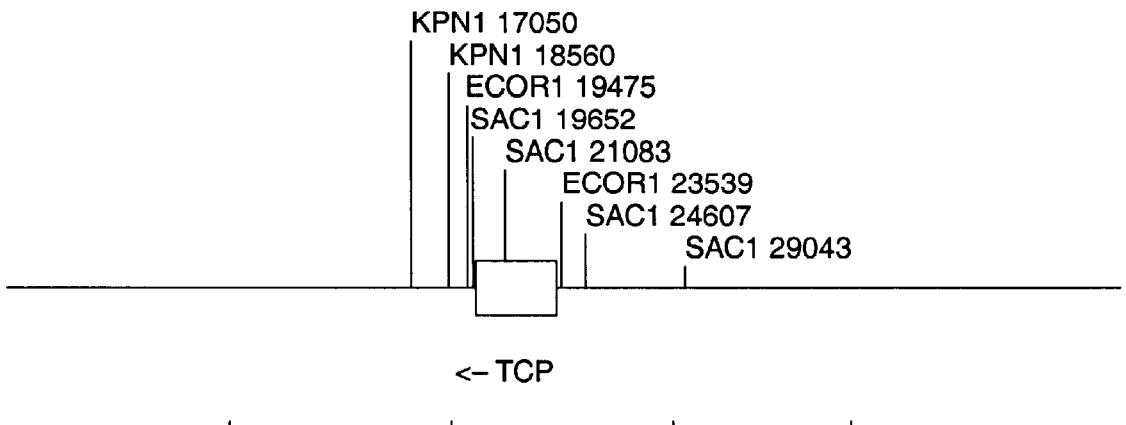

*FIG. 54*

TELOMERASE

The present application is a continuation of U.S. patent application Ser. No. 08/854,050, filed May 9, 1997, which is a continuation-in-part application of U.S. patent application Ser. No. 08/851,843, filed May 6, 1997 now U.S. Pat. No. 6,093,809, which is a continuation-in-part application of U.S. patent application Ser. No. 08/846,017, filed Apr. 25, 1997 now abandoned, which is a continuation-in-part of U.S. patent application Ser. No. 08/844,419, filed Apr. 18, 1997 now abandoned, which is a continuation-in-part of U.S. patent application Ser. No. 08/724,643, filed Oct. 1, 1996 now abandoned.

FIELD OF THE INVENTION

The present invention is related to novel telomerase genes and proteins. In particular, the present invention is directed to a telomerase isolated from *Euplotes aediculatus*, the two polypeptide subunits of this telomerase, as well as sequences of the Schizosaccharomyces, Tetrahymena, and human homologs of the *E. aediculatus* telomerase.

BACKGROUND OF THE INVENTION

Telomeres, the protein-DNA structures physically located on the ends of the eukaryotic organisms, are required for chromosome stability and are involved in chromosomal organization within the nucleus (See e.g., Zakian, Science 270:1601 [1995]; Blackburn and Gall, J. Mol. Biol., 120:33 [1978]; Oka et al., Gene 10:301 [1980]; and Klobutcher et al., Proc. Natl. Acad. Sci., 78:3015 [1981]). Telomeres are believed to be essential in such organisms as yeasts and probably most other eukaryotes, as they allow cells to distinguish intact from broken chromosomes, protect chromosomes from degradation, and act as substrates for novel replication mechanisms. Telomeres are generally replicated in a complex, cell cycle and developmentally regulated, manner by "telomerase," a telomere-specific DNA polymerase. However, telomerase-independent means for telomere maintenance have been described. In recent years, much attention has been focused on telomeres, as telomere loss has been associated with chromosomal changes such as those that occur in cancer and aging.

Telomeric DNA

In most organisms, telomeric DNA has been reported to consist of a tandem array of very simple sequences, which in many cases are short and precise. Typically, telomeres consist of simple repetitive sequences rich in G residues in the strand that runs 5' to 3' toward the chromosomal end. For example, telomeric DNA in Tetrahymena is comprised of sequence $T_2G_4$, while in Oxytricha, the sequence is $T_4G_4$, and in humans the sequence is $T_2AG_3$ (See e.g., Zakian, Science 270:1601 [1995]; and Lingner et al., Genes Develop., 8:1984 [1994]). However, heterogenous telomeric sequences have been reported in some organisms (e.g., the sequence $TG_{1-3}$ in Saccharomyces). In addition, the repeated telomeric sequence in some organisms is much longer, such as the 25 base pair sequence of *Kluyveromyces lactis*. Moreover, the telomeric structure of some organisms is completely different. For example, the telomeres of Drosophila are comprised of a transposable element (See, Biessman et al., Cell 61:663 [1990]; and F.-m Sheen and Levis, Proc. Natl. Acad. Sci., 91:12510 [1994]).

The telomeric DNA sequences of many organisms have been determined (See e.g., Zakian, Science 270:1601 [1995]). However, it has been noted that as more telomeric sequences become known, it is becoming increasingly difficult to identify even a loose consensus sequence to describe them (Zakian, supra). Furthermore, it is known that the average amount of telomeric DNA varies between organisms. For example, mice may have as many as 150 kb (kilobases) of telomeric DNA per telomere, while the telomeres of Oxytricha macronuclear DNA molecules are only 20 bp in length (Kipling and Cooke, Nature 347:400 [1990]; Starling et al., Nucleic Acids Res., 18:6881 [1990]; and Klobutcher et al., Proc. Natl. Acad. Sci. 78:3015 [1981]). Moreover, in most organisms, the amount of telomeric DNA fluctuates. For example, the amount of telomeric DNA at individual yeast telomeres in a wild-type may range from approximately 200 to 400 bp, with this amount of DNA increasing and decreasing stoichastically (Shampay and Blackburn, Proc. Natl. Acad. Sci., 85:534 [1988]). Heterogeneity and spontaneous changes in telomere length may reflect a complex balance between the processes involved in degradation and lengthening of telomeric tracts. In addition, genetic, nutritional and other factors may cause increases or decreases in telomeric length (Lustig and Petes, Natl. Acad. Sci., 83:1398 [1986]; and Sandell et al., Cell 91:12061 [1994]). The inherent heterogeneity of virtually all telomeric DNAs suggests that telomeres are not maintained via conventional replicative processes.

In addition to the telomeres themselves, the regions located adjacent to telomeres have been studied. For example, in most organisms, the sub-telomeric regions immediately internal to the simple repeats consist of middle repetitive sequences, designated as telomere-associated ("TA") DNA. These regions bear some similarity with the transposon telomeres of Drosophila. In Saccharomyces, two classes of TA elements, designated as "X" and "Y," have been described (Chan and Tye, Cell 33:563 [1983]). These elements may be found alone or in combination on most or all telomeres.

Telomeric Structural Proteins

Various structural proteins that interact with telomeric DNA have been described which are distinct from the protein components or the telomerase enzyme. Such structural proteins comprise the "telosome" of Saccharomyces chromosomes (Wright et al., Genes Develop., 6:197 [1992]) and of ciliate macronuclear DNA molecules (Gottschling and Cech, Cell 38:501 [1984]; and Blackburn and Chiou, Proc. Natl. Acad. Sci., 78:2263 [1981]). The telosome is a non-nucleosomal, but discrete chromatin structure that encompasses the entire terminal array of telomeric repeats. In Saccharomyces, the DNA adjacent to the telosome is packaged into nucleosomes. However, these nuclcosomes are reported to differ from those in most other regions of the yeast genome, as they have features that are characteristic of transcriptionally inactive chromatin (Wright et al., Genes Develop., 6:197 [1992]; and Braunstein et al., Genes Develop., 7:592 [1993]). In mammals, most of the simple repeated telomeric DNA is packaged in closely spaced nucleosomes (Makarov et al., Cell 73:775 [1993]; and Tommerup et al., Mol. Cell. Biol., 14:5777 [1994]). However, the telomeric repeats located at the very ends of the human chromosomes are found in a telosome-like structure.

Telomer Replication

Complete replication of the ends of linear eukaryotic chromosomes presents special problems for conventional methods of DNA replication. For example, conventional DNA polymerases cannot begin DNA synthesis de novo, rather, they require RNA primers which are later removed during replication. In the case of telomeres, removal of the RNA primer from the lagging-strand end would necessarily leave a 5'-terminal gap, resulting in the loss of sequence if the parental telomere was blunt-ended (Watson, Nature New Biol., 239:197 [1972]; Olovnikov, J. Theor. Biol., 41:181 [1973]). However, the described telomeres have 3' overhangs (Klobutcher et al., Proc. Natl. Acad. Sci., 58:3015 [1981]; Henderson and Blackburn, Mol. Cell. Biol., 9:345 [1989]; and Wellinger et al., Cell 72:51 [1993]). For these molecules, it is possible that removal of the lagging-strand 5'-terminal RNA primer could regenerate the 3' overhang without loss of sequence on this side of the molecule. However, loss of sequence information on the leading-strand end would occur, because of the lack of a complementary strand to act as template in the synthesis of a 3' overhang (Zahler and Prescott, Nucleic Acids Res., 16:6953 [1988]; Lingner el al., Science 269:1533 [1995]).

Nonetheless, complete replication of the chromosomes must occur. While conventional DNA polymerases cannot accurately reproduce chromosomal DNA ends, specialized factors exist to ensure their complete replication. Telomerase is a key component in this process. Telomerase is a ribonucleoprotein (RNP) particle and polymerase that uses a portion of its internal RNA moiety as a template for telomere repeat DNA synthesis (Yu et al., Nature 344:126 [1990]; Singer and Gottschling, Science 266:404 [1994]; Autexier and Greider, Genes Develop., 8:563 [1994]; Gilley et al., Genes Develop., 9:2214 [1995]; McEachern and Blackburn, Nature 367:403 [1995]; Blackburn, Ann. Rev. Biochem., 61:113 [1992];. Greider, Ann. Rev. Biochem., 65:337 [1996]). The activity of this enzyme depends upon both its RNA and protein components to circumvent the problems presented by end replication by using RNA (i.e., as opposed to DNA) to template the synthesis of telomeric DNA. Telomerases extend the G strand of telomeric DNA. A combination of factors, including telomerase processivity, frequency of action at individual telomeres, and the rate of degradation of telomeric DNA, contribute to the size of the telomeres (i.e., whether they are lengthened, shortened, or maintained at a certain size). In vitro, telomerases may be extremely processive, with the Tetrahymena telomerase adding an average of approximately 500 bases to the G strand primer before dissociation of the enzyme (Greider, Mol. Cell. Biol., 114572 [1991]).

Importantly, telomere replication is regulated both by developmental and cell cycle factors. It has been hypothesized that aspects of telomere replication may act as signals in the cell cycle. For example, certain DNA structures or DNA-protein complex formations may act as a checkpoint to indicate that chromosomal replication has been completed (See e.g., Wellinger et al., Mol. Cell. Biol., 13:4057 [1993]). In addition, it has been observed that in humans, telomerase activity is not detectable in most somatic tissues, although it is detected in many tumors (Wellinger, supra). This telomere length may serve as a mitotic clock, which serves to limit the replication potential of cells in vivo and/or in vitro. What remains needed in the art is a method to study the role of telomeres and their replication in normal as well as abnormal cells (i.e., cancerous cells). An understanding of telomerase and its function is needed in order to develop means for use of telomerase as a target for cancer therapy or anti-aging processes.

SUMMARY OF THE INVENTION

The present invention provides compositions and methods for purification and use of telomerase. In particular, the present invention is directed to telomerase and co-purifying polypeptides obtained from *Euplotes aediculatus*, as well as other organisms (e.g., Schizosaccharomyces, Tetrahymena, and humans). The present invention also provides methods useful for the detection and identification of telomerase homologs in other species and genera of organisms.

The present invention provides heretofore unknown telomerase subunit proteins of *E. aediculatus* of approximately 123 kDa and 43 kDa, as measured on SDS-PAGE. In particular, the present invention provides substantially purified 123 kDa and 43 kDa telomerase protein subunits.

One aspect of the invention features isolated and substantially purified polynucleotides which encode telomerase subunits (i.e., the 123 kDa and 43 kDa protein subunits). In a particular aspect, the polynucleotide is the nucleotide sequence of SEQ ID NO:1, or variants thereof. In an alternative embodiment, the present invention provides fragments of the isolated (i.e., substantially purified) polynucleotide encoding the telomerase 123 kDa subunit of at least 10 amino acid residues in length. The invention further contemplates fragments of this polynucleotide sequence (i.e., SEQ ID NO:1) that are at least 6 nucleotides, at least 25 nucleotides, at least 30 nucleotides, at least 100 nuclcotides, at least 250 nucleotides, and at least 500 nucleotides in length. In addition, the invention features polynucleotide sequences that hybridize under stringent conditions to SEQ ID NO:1, or fragments thereof. The present invention further contemplates a polynucleotide sequence comprising the complement of the nucleic acid of SEQ ID NO:1, or variants thereof.

The present invention also provides the polynucleotide with the sequence of SEQ ID NO:3. In particular, the present invention provides the polynucleotide sequence comprising at least a portion of the nucleic acid sequence of SEQ ID NO:3, or variants, thereof. In one embodiment, the present invention provides fragments of the isolated (i.e., substantially purified) polynucleotide encoding the telomerase 43 kDa subunit of at least 10 amino acid residues in length. The invention also provides an isolated polynucleotide sequence encoding the polypeptide of SEQ ID NOS:4–6, or variants thereof. The invention further contemplates fragments of this polynucleotide sequence (i.e., SEQ ID NO:3) that are at least 5 nucleotides, at least 20 nucleotides, at least 100 nucleotides, at least 250 nucleotides, and at least 500 nucleotides in length. In addition, the invention features polynucleotide sequences that hybridize under stringent conditions to SEQ ID NO:3, or fragments thereof. The present invention further contemplates a polynucleotide sequence comprising the complement of the nucleic acid of SEQ ID NO:3, or variants thereof.

The present invention provides a substantially purified polypeptide comprising at least a portion of the amino acid sequence of SEQ ID NO:2, or variants thereof. In one embodiment, the portion of the polypeptide sequence comprises fragments of SEQ ID NO:2, having a length greater than 10 amino acids. However, the invention also contemplates polypeptide sequences of various lengths, the sequences of which are included within SEQ ID NO:2, ranging from 5–500 amino acids. The present invention also provides an isolated polynucleotide sequence encoding the polypeptide of SEQ ID NO:2, or variants, thereof.

The present invention provides a substantially purified polypeptide comprising at least a portion of the amino acid sequence selected from the group consisting of SEQ ID NO:4–6, or variants thereof. In one embodiment, the portion of the polypeptide comprises fragments of SEQ ID NO:4, having a length greater than 10 amino acids. In an alternative embodiment, the portion of the polypeptide comprises fragments of SEQ ID NO:5, having a length greater than 10 amino acids. In yet another alternative embodiment, the portion of the polypeptide comprises fragments of SEQ ID NO:6, having a length greater than 10 amino acids. The present invention also contemplates polypeptide sequences of various lengths, the sequences of which are included within SEQ ID NOS:4, 5, and/or 6, ranging from 5 to 500 amino acids.

The present invention also provides a telomerase complex comprised of at least one purified 123 kDa telomerase protein subunit at least one a purified 43 kDa telomerase protein subunit, and purified RNA. In a preferred embodiment, the telomerase complex comprises one purified 123 kDa telomerase protein subunit, one purified 43 kDa telomerase protein subunit, and purified telomerase RNA. In one preferred embodiment, the telomerase complex comprises an 123 kDa and/or telomerase protein subunit obtained from *Euplotes aediculatus*. It is contemplated that the 123 kDa telomerase protein subunit of the telomerase complex be encoded by SEQ ID NO:1. It is also contemplated that the 123 kDa telomerase protein subunit of the telomerase complex be comprised of SEQ ID NO:2. It is also contemplated that the 43 kDa telomerase protein subunit of the telomerase complex be obtained from *Euplotes aediculatus*. It is further contemplated that the 43 kDa telomerase subunit of the telomerase complex be encoded by SEQ ID NO:3. It is also contemplated that the 43 kDa telomerase protein subunit of the telomerase complex be comprised of the amino acid sequence selected from the group consisting of SEQ ID NO:4, SEQ ID NO:5, and SEQ ID NO:6. It is contemplated that the purified RNA of the telomerase complex be comprised of the RNA encoded by such sequences as those disclosed by Linger et al., (Lingner et al., Genes Develop., 8:1985 [1994]). In a preferred embodiment, the telomerase complex is capable of replicating telomeric DNA.

The present invention also provides methods for identifying telomerase protein subunits in eukaryotic organisms other than *E. aediculatus*. These methods are comprised of multiple steps. The first step is the synthesis of at least one probe or primer oligonucleotide that encodes at least a portion of the amino acid sequence of SEQ ID NOS:2, 4, 5, or 6. In the alternative, the synthesized probe or primer oligonucleotides are complementary to at least a portion of the amino acid sequence of SEQ ID NO:2, 4, 5, or 6. The next step comprises exposing at least one of the probe or primer oligonucleotide(s) to nucleic acid comprising the genome or, in the alternative, the expressed portion of the genome of the other organism (i.e., the non-*E. aediculatus* organism), under conditions suitable for the formation of nucleic acid hybrids. Next, the hybrids are identified with or without amplification, using a DNA polymerase (e.g. Taq, or any other suitable polymerase known in the art). Finally, the sequence of the hybrids are determined using methods known in the art, and the sequences of the derived amino acid sequences analyzed for their similarity to SEQ ID NOS:2, 4, 5, or 6.

The present invention also provides methods for identifying nucleic acid sequences encoding telomerase protein subunits in eukaryotic organisms comprising the steps of: providing a sample suspected of containing nucleic acid encoding an eukaryotic telomerase protein subunit; at least one oligonucleotide primer complementary to the nucleic acid sequence encoding at least a region of an *Euplotes aediculatus* telomerase protein subunit; and iii) a polymerase; exposing the sample to the at least one oligonucleotide primer and the polymerase under conditions such that the nucleic acid encoding the eukaryotic telomerase protein subunit is amplified; determining the sequence of the eukaryotic telomerase protein subunit; and comparing the sequence of the eukaryotic telomerase protein subunit and the *Euplotes aediculatus* telomerase protein subunit. In one preferred embodiment, the *Euplotes aediculatus* telomerase subunit comprises at least a portion of SEQ ID NO:1. In an alternative preferred embodiment, the *Euplotes aediculatus* telomerase subunit comprises at least a portion of SEQ ID NO:3.

Thus, the present invention also provides methods for identification of telomerase protein subunits in eukaryotic organisms other than *E. aediculatus*. In addition, the present invention provides methods for comparisons between the amino acid sequences of SEQ ID NOS:2, 4, 5, or 6, and the amino acid sequences derived from gene sequences of other organisms or obtained by direct amino acid sequence analysis of protein. The amino acid sequences shown to have the greatest degree of identity (i.e., homology) to SEQ ID NOS:2, 4, 5, or 6, may then selected for further testing. Sequences of particular importance are those that share identity with the reverse transcriptase motif of the Euplotes sequence. Once identified, the proteins with the sequences showing the greatest degree of identity may be tested for their role in telomerase activity by genetic or biochemical methods, including the methods set forth in the Examples below.

The present invention also provides methods for purification of telomerase comprising the steps of providing a sample containing telomerase, an affinity oligonucleotide, a displacement oligonucleotide; exposing the sample to the affinity oligonucleotide under conditions wherein the affinity oligonucleotide binds to the telomerase to form a telomerase-oligonucleotide complex; and exposing the oligonucleotide-telomerase complex to the displacement oligonucleotide under conditions such that the telomerase is released from the template. In a preferred embodiment, the method comprises the further step of eluting the telomerase. In another preferred embodiment, the affinity oligonucleotide comprises an antisense portion and a biotin residue. It is contemplated that during the exposing step, the biotin residue of the affinity oligonucleotide binds to an avidin bead and the antisense portion binds to the telomerase. It is also contemplated that during the exposing step, the displacement oligonucleotide binds to the affinity oligonucleotide.

The present invention further provides substantially purified polypeptides comprising the amino acid sequence comprising SEQ ID NOS:63, 64, 65, 67, and 69. In another embodiment, the present invention also provides purified, isolated polynucleotide sequences encoding the polypeptides comprising the amino acid sequences of SEQ ID NOS:63, 64, 65, 67, and 68, 69. The present invention contemplates portions or fragments of SEQ ID NOS:63, 64, 65, 67, and 69, of various lengths. In one embodiment, the portion of polypeptide comprises fragments of lengths greater than 10 amino acids. However, the present invention also contemplates polypeptide sequences of various lengths, the sequences of which are included within SEQ ID NOS:63, 64, 65, 67, and 69, ranging from 5 to 500 amino acids (as appropriate, based on the length of SEQ ID NOS:63, 64, 65, 67, and 69).

The present invention also provides nucleic acid sequences comprising SEQ ID NOS:55, 62, 66, and 68, or variants thereof. The present invention further provides fragments of the isolated polynucleotide sequences that are at least 6 nucleotides, at least 25 nucleotides, at least 30 nucleotides, at least 50 nucleotides, at least 100 nucleotides, at least 250 nucleotides, and at least 500 nucleotides in length (as appropriate for the length of the sequence of SEQ ID NOS:55, 62, 66, and 68, or variants thereof).

In particularly preferred embodiments, the polynucleotide hybridizes specifically to telomerase sequences, wherein the telomerase sequences are selected from the group consisting of human, *Euplotes aediculatus*, Oxytricha, Schizosaccharomyces, and Saccharomyces telomerase sequences. In other preferred embodiments, the present invention provides polynucleotide sequences comprising the complement of nucleic acid sequences selected from the group consisting of SEQ ID NOS:55, 62, 66, and 68, or variants thereof. In yet other preferred embodiments, the present invention provides polynucleic acid sequences that hybridize under stringent conditions to at least one nucleic acid sequence selected from the group consisting of SEQ ID NO:55, 62, 66, and 68. In a further embodiment, the polynucleotide sequence comprises a purified, synthetic nucleotide sequence having a length of about ten to thirty nucleotides.

In alternative preferred embodiments, the present invention provides polynucleotide sequences corresponding to the human telomerase, including SEQ ID NOS:173 and 224, and their complementary sequences. The invention further contemplates fragments of these polynucleotide sequence (i.e., SEQ ID NOS:173, and 224) that are at least 5 nucleotides, at least 20 nucleotides, at least 100 nucleotides, at least 250 nucleotides, and at least 500 nucleotides in length. The invention further contemplates fragments of the complements of these polynucleotide sequences (i.e., SEQ ID NOS:173, and 224) that are at least 5 nuclcotides, at least 20 nucleotides, at least 100 nucleotides, at least 250 nucleotides, and at least 500 nucleotides in length. In addition, the invention features polynucleotide sequences that hybridize under stringent conditions to SEQ ID NOS:173 and 224, and/or fragments, and/or the complementary sequences thereof. The present invention further contemplates a polynucleotide sequence comprising the complement of the nucleic acids of SEQ ID NOS: 173 and 224, or variants thereof. In a further embodiment, the polynucleotide sequence comprises a purified, synthetic nucleotide sequence corresponding to a fragment of SEQ ID NOS:173 and/or 224, having a length of about ten to thirty nucleotides. The present invention further provides plasmid pGRN121 (ATCC accession ##20916), and the lambda clone 25-1.1 (ATCC accession #209024).

The present invention further provides substantially purified polypeptides comprising the amino acid sequence comprising SEQ ID NOS:173–223, and 225. In another embodiment, the present invention also provides purified, isolated polynucleotide sequences encoding the polypeptides comprising the amino acid sequences of SEQ ID NOS:174–223, and 225. The present invention contemplates portions or fragments of SEQ ID NOS:174–223, and 225, of various lengths. In one embodiment, the portion of polypeptide comprises fragments of lengths greater than 10 amino acids. However, the present invention also contemplates polypeptide sequences of various lengths, the sequences of which are included within SEQ ID NOS:174–223, and 225, ranging from 5 to 1100 amino acids (as appropriate, based on the length of SEQ ID NOS:174–223, and 225).

The present invention also provides methods for detecting the presence of nucleotide sequences encoding at least a portion of human telomerase in a biological sample, comprising the steps of, providing: a biological sample suspected of containing nucleic acid corresponding to the nucleotide sequence set forth in SEQ ID NO:62; the nucleotide of SEQ ID NO:62 or fragment(s) thereof, combining the biological sample with the nucleotide under conditions such that a hybridization complex is formed between the nucleic acid and the nucleotide; and detecting the hybridization complex.

In one embodiment of the method the nucleic acid corresponding to the nucleotide sequence of SEQ ID NO:62, is ribonucleic acid, while in an alternative embodiment, the nucleotide sequence is deoxyribonucleic acid. In yet another embodiment of the method the detected hybridization complex correlates with expression of the polynucleotide of SEQ ID NO:62, in the biological sample. In yet another embodiment of the method, detection of the hybridization complex comprises conditions that permit the detection of alterations in the polynucleotide of SEQ ID NO:62 in the biological sample.

The present invention also provides antisense molecules comprising the nucleic acid sequence complementary to at least a portion of the polynucleotide of SEQ ID NO:55, 62, 66, 67, and 68. In an alternatively preferred embodiment, the present invention also provides pharmaceutical compositions comprising antisense molecules of SEQ ID NOS:55, 62, 67, and 68, and a pharmaceutically acceptable excipient and/or other compound (e.g., adjuvant).

In yet another embodiment, the present invention provides polynucleotide sequences contained on recombinant expression vectors. In one embodiment, the expression vector containing the polynucleotide sequence is contained within a host cell.

The present invention also provides methods for producing polypeptides comprising the amino acid sequence of SEQ ID NOS:61, 63, 65, 67, or 68, the method comprising the steps of: culturing a host cell under conditions suitable for the expression of the polypeptide; and recovering the polypeptide from the host cell culture.

The present invention also provides purified antibodies that binds specifically to a polypeptide comprising at least a portion of the amino acid sequence of SEQ ID NOS:55, 63, 64, 65, 67, and/or 69. In one embodiment, the present invention provides a pharmaceutical composition comprising at least one antibody, and a pharmaceutically acceptable excipient.

The present invention further provides methods for the detection of human telomerase in a biological sample comprising the steps of: providing a biological sample suspected of expressing human telomerase protein; and at least one antibody that binds specifically to at least a portion of the amino acid sequence of SEQ ID NOS:55, 63, 64, 65, 67, and/or 69; combining the biological sample and antibody (ies) under conditions such that an antibody:protein complex is formed; and detecting the complex wherein the presence of the complex correlates with the expression of the protein in the biological sample.

The present invention further provides substantially purified peptides comprising the amino acid sequence selected from the group consisting of SEQ ID NOS:71, 73, 75, 77, 79, 82, 83, 83, 85, and 101. In an alternative embodiment, the present invention provides purified, isolated polynucleotide sequences encoding the polypeptide corresponding to these sequences. In preferred embodiments, the polynucleotide hybridizes specifically to telomerase sequences, wherein the telomerase sequences are selected from the group consisting of human, *Euplotes aediculatus*, Oxytricha, Schizosaccharomyces, Saccharomyces and Tetrahymena telomerase sequences. In yet another embodiment, the polynucleotide sequence comprises the complement of a nucleic acid sequence selected from the group consisting of SEQ ID NOS:70, 72, 74, 76, 78, 80, 81, 100, 173, 224, and variants thereof. In a further embodiment, the polynucleotide sequence that hybridizes under stringent conditions to a nucleic acid sequence selected from the group consisting of SEQ ID NOS:66, 68, 80, and 81. In yet another embodiment, the polynucleotide sequence is selected from the group consisting of SEQ ID NOS:70, 72, 74, 76, 78, 87, 88, 89, 90, 91, 92, 93, 94, 95, 96, 97, 98, 99, 102, 103, 104, 105, 106, 107, 108, 109, 110, 111, 173, and 224. In an alternative embodiment, the nucleotide sequence comprises a purified, synthetic nucleotide sequence having a length of about ten to fifty nucleotides.

The present invention also provides methods for detecting the presence of nucleotide sequences encoding at least a portion of human telomerase in a biological sample, comprising the steps of, providing: a biological sample suspected of containing nucleic acid corresponding to the nucleotide sequence of SEQ ID NO:100, and/or SEQ ID NO:173, and/or SEQ ID NO:224; the nucleotide of SEQ ID NO:100, and/or SEQ ID NO:173, and/or SEQ ID NO:224. or fragment(s) thereof; combining the biological sample with the nucleotide under conditions such that a hybridization complex is formed between the nucleic acid and the nucleotide; and detecting the hybridization complex.

In one embodiment of the method the nucleic acid corresponding to the nucleotide sequence of SEQ ID NO:100, and/or SEQ ID NO:173, and/or SEQ ID NO:224. is ribonucleic acid, while in an alternative embodiment, the nucleotide sequence is deoxyribonucleic acid. In yet another embodiment of the method the detected hybridization complex correlates with expression of the polynucleotide of SEQ ID NO:100. and/or SEQ ID NO:173, and/or SEQ ID NO:224, in the biological sample. In yet another embodiment of the method, detection of the hybridization complex comprises conditions that permit the detection of alterations in the polynucleotide of SEQ ID NO:100 and/or SEQ ID NO:173, and/or SEQ ID NO:224, in the biological sample.

The present invention also provides antisense molecules comprising the nucleic acid sequence complementary to at least a portion of the polynucleotide of SEQ ID NO:82, 100, 113, and 117. In an alternatively preferred embodiment, the present invention also provides pharmaceutical compositions comprising antisense molecules of SEQ ID NOS:82, 100, 173, 224, and a pharmaceutically acceptable excipient and/or other compound (e.g., adjuvant).

In yet another embodiment, the present invention provides polynucleotide sequences contained on recombinant expression vectors. In one embodiment, the expression vector containing the polynucleotide sequence is contained within a host cell.

The present invention also provides methods for producing polypeptides comprising the amino acid sequence of SEQ ID NOS:82, 83, 84, 85, 86, 101, 174, 223, and/or 225, the method comprising the steps of: culturing a host cell under conditions suitable for the expression of the polypeptide; and recovering the polypeptide from the host cell culture.

The present invention also provides purified antibodies that binds specifically to a polypeptide comprising at least a portion of the amino acid sequence of SEQ ID NOS:71, 73, 75, 77, 79, 82, 83, 84, 85, 101, 174, 223, and/or 225. In one embodiment, the present invention provides a pharmaceutical composition comprising at least one antibody, and a pharmaceutically acceptable excipient.

The present invention further provides methods for the detection of human telomerase in a biological sample comprising the steps of: providing a biological sample suspected of expressing human telomerase protein; and at least one antibody that binds specifically to at least a portion of the amino acid sequence of SEQ ID NOS:71, 73, 75, 77, 79, 82, 83, 84, 85, 87, 101, 174, 223, and/or 225, combining the biological sample and antibody(ies) under conditions such that an antibody:protein complex is formed; and detecting the complex wherein the presence of the complex correlates with the expression of the protein in the biological sample.

DESCRIPTION OF THE FIGURES

FIG. 7 shows the putative alignments of telomerase RNA template, with SEQ ID NOS:43 and 44 in Panel A, and SEQ ID NOS:45 and 46 in Panel B.

FIG. 9 shows the DNA sequence of the gene encoding the 123 kDa telomerase protein subunit (SEQ ID NO:1).

FIG. 10 shows the amino acid sequence of the 123 kDa telomerase protein subunit (SEQ ID NO:2).

FIG. 11 shows the DNA sequence of the gene encoding the 43 kDa telomerase protein subunit (SEQ ID NO:3).

FIG. 12 shows the DNA sequence, as well as the amino acid sequences of all three open reading frames of the 43 kDa telomerase protein subunit (SEQ ID NOS:4–6).

FIG. 13 shows a sequence comparison between the 123 kDa telomerase protein subunit of *E. aediculatus* (SEQ ID NO:2) and the 80 kDa polypeptide subunit of *T. thermophila* (SEQ ID NO:52).

FIG. 14 shows a sequence comparison between the 123 kDa telomerase protein subunit of *E.aediculatus* (SEQ ID NO:2) and the 95 kDa telomerase polypeptide of *T. thermophila* (SEQ ID NO:54).

FIG. 15 shows the best-fit alignment between a portion of the "La-domain" of the 43 kDa telomerase protein subunit of *E. aediculatus* (SEQ ID NO:9) and a portion of the 95 kDa polypeptide subunit of *T. thermophila* (SEQ ID NO:10).

FIG. 16 shows the best-fit alignment between a portion of the "La-domain" of the 43 kDa telomerase protein subunit of *E. aediculatus* (SEQ ID NO:11) and a portion of the 80 kDa polypeptide subunit of *T. thermophila* (SEQ ID NO:12).

FIG. 17 shows the alignment and motifs of the polymerase domain of the 123 kDa telomerase protein subunit of *E. aediculatus* (SEQ ID NOS:13 and 18) and the polymerase domains of various reverse transcriptases (SEQ ID NOS:14–17, and 19–22).

FIG. 18 shows the alignment of a domain of the 43 kDa telomerase protein subunit (SEQ ID NO:23) with various La proteins (SEQ ID NOS:24–27).

FIG. 19 shows the nucleotide sequence encoding the *T. thermophila* 80 kDa protein subunit (SEQ ID NO:51).

FIG. 20 shows the amino acid sequence of the *T. thermophilia* 80 kDa protein subunit (SEQ ID NO:52).

FIG. 21 shows the nucleotide sequence encoding the *T. thermophila* 95 kDa protein subunit (SEQ ID NO:53).

FIG. 22 shows the amino acid sequence of the *T. thermophila* 95 kDa protein subunit (SEQ ID NO:54).

FIG. 23 shows the amino acid sequence of L8543.12 ("Est2p") (SEQ ID NO:55).

FIG. 24 shows the alignment of the Oxytricha PCR product (SEQ ID NO:58) with the Euplotes sequence (SEQ ID NO:59).

FIG. 25 shows the alignment of the human telomere amino acid motifs (SEQ ID NO:67), with portions of the tez1 sequence (SEQ ID NO:63) Est2p (SEQ ID NO:64), and the Euplotes p123 (SEQ ID NO:65).

FIG. 26 shows the DNA sequence of Est2 (SEQ ID NO:66).

FIG. 27 shows the amino acid sequence of a cDNA clone (SEQ ID NO:67) encoding human telomerase peptide motifs.

FIG. 28 shows the DNA sequence of a cDNA clone (SEQ ID NO:62) encoding human telomerase peptide motifs.

FIG. 29 shows the amino acid sequence of tez1 (SEQ ID NO:69).

FIG. 30 shows the DNA sequence of tez1 (SEQ ID NO:68).

FIG. 31 shows the alignment of EST2p (SEQ ID NO:83), Euplotes (SEQ ID NO:84), and Tetrahymena (SEQ ID NO:85) sequences, as well as consensus sequence.

FIG. 32 shows the sequences of peptides useful for production of antibodies.

FIG. 34 (SEQ ID NOS:118–121) shows two degenerate primers used in PCR to identify the *S. pombe* homolog of the *E. aediculatus* p123 sequences.

FIG. 36 (SEQ ID NOS: 58, 118, 121–130) shows the alignment of the M2 PCR product with *E. aediculatus* p123, *S. cerevisiae*, and Oxytricha telomerase protein sequences.

FIG. 41 (SEQ ID NOS: 133–147) shows the alignment of RT domains from telomerase catalytic subunits.

FIG. 42 (SEQ ID NOS: 2, 55, 69) shows the alignment of three telomerase sequences.

FIG. 46 shows the DNA (SEQ ID NO:68) and amino acid (SEQ ID NO:69) sequence of tez1, with the coding regions indicated.

FIG. 47 shows the DNA (SEQ ID NO:100) and amino acid (SEQ ID NO:101) of the ORF encoding an approximately 63 kDa telomerase protein or fragment thereof.

FIG. 48 (SEQ ID NOS: 148–171) shows an alignment of reverse transcriptase motifs from various sources.

FIG. 50 provides the results of preliminary nucleic acid sequencing analysis of human telomerase (SEQ ID NO:173).

FIG. 51 provides the preliminary nucleic acid (SEQ ID NO: 173) and deduced ORF sequences (SEQ ID NOS: 174–223) of human telomerase.

FIG. 53 provides the nucleic acid (SEQ ID NO:224) and deduced ORF sequence (SEQ ID NO:225) of human telomerase.

FIG. 54 provides a restriction map of lambda clone 25-1.1 (ATCC accession #209024).

DEFINITIONS

Figure 1:
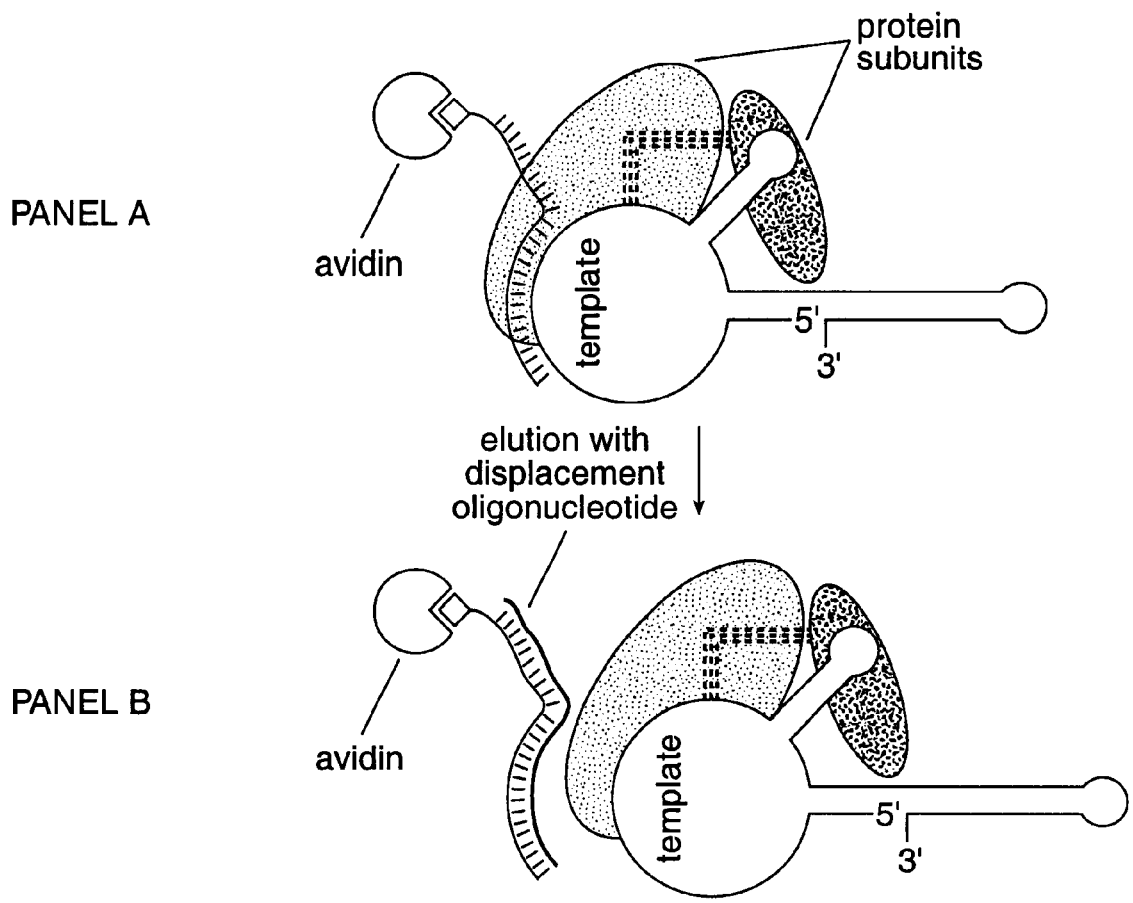
FIG. 1 is a schematic diagram of the affinity purification of telomerase showing the binding and displacement elution steps.

To facilitate understanding the invention, a number of terms are defined below.

As used herein, the term "ciliate" refers to any of the protozoans belonging to the phylum Ciliaphora.

As used herein, the term "eukaryote" refers to organisms distinguishable from "prokaryotes." It is intended that the term encompass all organisms with cells that exhibit the usual characteristics of eukaryotes such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "polyploid" refers to cells or organisms which contain more than two sets of chromosomes.

As used herein, the term "macronucleus" refers to the larger of the two types of nuclei observed in the ciliates. This structure is also sometimes referred to as the "vegetative" nucleus. Macronuclei contain many copies of each gene and are transcriptionally active.

As used herein, the term "micronucleus" refers to the smaller of the two types of nuclei observed in the ciliates. This structure is sometimes referred to as the "reproductive" nucleus, as it participates in meiosis and autogamy. Micronuclei are diploid and are transcriptionally inactive.

As used herein, the term "ribonucleoprotein" refers to a complex macromolecule containing both RNA and protein.

As used herein, the term "telomerase polypeptide," refers to a polypeptide which is at least a portion of the Euplotes telomerase structure. The term encompasses the 123 kDa and 43 kDa polypeptide or protein subunits of the Euplotes telomerase. It is also intended that the term encompass variants of these protein subunits. It is further intended to encompass the polypeptides encoded by SEQ ID NOS: 1 and 3. As molecular weight measurements may vary, depending upon the technique used, it is not intended that the present invention be precisely limited to the 123 kDa or 43 kDa molecular masses of the polypeptides encoded by SEQ ID NOS:1 and 3, as determined by any particular method such as SDS-PAGE.

As used herein, the terms "telomerase" and "telomerase complex" refer to functional telomerase enzymes. It is intended that the terms encompass the complex of proteins and nucleic acids found in telomerases. For example, the terms encompass the 123 kDa and 43 kDa telomerase protein subunits and RNA of *E. aediculatus*.

As used herein, the term "capable of replicating telomeric DNA" refers to functional telomerase enzymes which are capable of performing the function of replicating DNA located in telomeres. It is contemplated that this term encompass the replication of telomeres, as well as sequences and structures that are commonly found located in telomeric regions of chromosomes. For example, "telomeric DNA" includes, but is not limited to the tandem array of repeat sequences found in the telomeres of most organisms. "Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to peptide or protein sequence. "Peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid (Nielsen et al., Anticancer Drug Des 8:53–63 [1993]).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, naturally occurring sequences.

A "substitution" results from the replacement of one or more nucleotides or amino acids by different nucleotides or amino acids, respectively.

As used herein, the term "purified" refers to the removal of contaminant(s) from a sample. As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

As used herein, the term "probe" refers to an oligonucleotide (i.e., a sequence of nucleotides), whether occurring naturally as in a purified restriction digest or produced synthetically, which is capable of hybridizing to another oligonucleotide or polynucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

As used herein, the term "target" refers to the region of nucleic acid bounded by the primers used for polymerase chain reaction. Thus, the "target" is sought to be sorted out from other nucleic acid sequences. A "segment" is defined as a region of nucleic acid within the target sequence. "Amplification" is defined as the production of additional copies of a nucleic acid sequence and is generally carried out using polymerase chain reaction (PCR) or other technologies well known in the art (e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the method of K. B. Mullis (U.S. Pat. Nos. 4,683,195 and 4,683,202, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "polymerase" refers to any polymerase suitable for use in the amplification of nucleic acids of interest. It is intended that the term encompass such DNA polymerases as Taq DNA polymerase obtained from *Thermus aquaticus*, although other polymerases, both thermostable and thermolabile are also encompassed by this definition.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or DATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for insertion into recombinant vectors.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted, low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing" (Coombs, *Dictionary of Biotechnology*, Stockton Press, New York N.Y. [1994].

"Stringency" typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridisation, in *Nucleic Acid Hybridisation* (1985). Other references include more sophisticated computations which take structural as well as sequence characteristics into account for the calculation of $T_m$.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH [fluorescent in situ hybridization]).

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein the term "portion" when in reference to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:2" encompasses the full-length 123 kDa telomerase protein subunit and fragments thereof.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

The term "sample" as used herein is used in its broadest sense. A biological sample suspected of containing nucleic acid encoding telomerase subunits may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "correlates with expression of a polynucleotide," as used herein, indicates that the detection of the presence of ribonucleic acid (RNA) complementary to a telomerase sequence by hybridization assays is indicative of the presence of mRNA encoding eukaryotic telomerases, including human telomerases in a sample, and thereby correlates with expression of the telomerase mRNA from the gene encoding the protein.

"Alterations in the polynucleotide" as used herein comprise any alteration in the sequence of polynucleotides encoding telomerases, including deletions, insertions, and point mutations that may be detected using hybridization assays. Included within this definition is the detection of alterations to the genomic DNA sequence which encodes telomerase (e.g., by alterations in pattern of restriction enzyme fragments capable of hybridizing to any sequence such as SEQ ID NOS: 1 or 3 [e.g., RFLP analysis], the inability of a selected fragment of any sequence to hybridize to a sample of genomic DNA [e.g., using allele-specific oligonucleotide probes], improper or unexpected hybridization, such as hybridization to a locus other than the normal chromosomal locus for the telomere or telomerase genes e.g., using FISH to metaphase chromosomes spreads, etc.]).

A "variant" in regard to amino acid sequences is used to indicate an amino acid sequence that differs by one or more amino acids from another, usually related amino acid. The variant may have "conservative" changes, wherein a substituted amino acid has similar structural or chemical properties (e.g., replacement of leucine with isoleucine). More rarely, a variant may have "non-conservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software. Thus, it is contemplated that this definition will encompass variants of telomerase and/or telomerase protein subunits. For example, the polypeptides encoded by the three open reading frames (ORFs) of the 43 kDa polypeptide gene may be considered to be variants of each other. Such variants can be tested in functional assays, such as telomerase assays to detect the presence of functional telomerase in a sample.

The term "derivative" as used herein refers to the chemical modification of a nucleic acid encoding telomerase structures, such as the 123 kDa or 43 kDa protein subunits of the E. aediculatus telomerase, or other telomerase proteins or peptides. Illustrative of such modifications would be replacement of hydrogen by an alkyl, acyl, or amino group. A nucleic acid derivative would encode a polypeptide which retains essential biological characteristics of naturally-occurring telomerase or its subunits.

The term "biologically active" refers to telomerase molecules or peptides having structural, regulatory, or biochemical functions of a naturally occurring telomerase molecules or peptides. Likewise, "immunologically active," defines the capability of the natural, recombinant, or synthetic telomerase proteins or any oligopeptide thereof, to induce a specific immune response in appropriate animals or cells, and to bind with specific antibodies.

"Affinity purification" as used herein refers to the purification of ribonucleoprotein particles, through the use of an "affinity oligonucleotide" (i.e., an antisense oligonucleotides) to bind the particle, followed by the step of eluting the particle from the oligonucleotide by means of a "displacement oligonucleotide." In the present invention, the displacement oligonucleotide has a greater degree of complementarity with the affinity oligonucleotide, and therefore produces a more thermodynamically stable duplex than the particle and the affinity oligonucleotide. For example, telomerase may be bound to the affinity oligonucleotide and then eluted by use of a displacement oligonucleotide which binds to the affinity oligonucleotide. In essence, the displacement oligonucleotide displaces the telomerase from the affinity oligonucleotide, allowing the elution of the telomerase. Under sufficiently mild conditions, the method results in the enrichment of functional ribonucleoprotein particles. Thus, the method is useful for the purification of telomerase from a mixture of compounds.

GENERAL DESCRIPTION OF THE INVENTION

The present invention provides purified telomerase preparations and telomerase protein subunits useful for investigations of the activities of telomerases, including potential nuclease activities. In particular, the present invention is directed to the telomerase and co-purifying polypeptides obtained from *Euplotes aediculatus*. This organism, a hypotrichous ciliate, was chosen for use in this invention as it contains an unusually large number of chromosomal ends (Prescott, Microbiol. Rev., 58:233 [1994]), because a very large number of gene-sized DNA molecules are present in its polyploid macronucleus. Tetrahymena, a holotrichous ciliate commonly used in previous studies of telomerase and telomeres, is as evolutionarily distant from Euplotes as plants are from mammals (Greenwood et al., J. Mol. Evol., 3:163 [1991]).

The homology found between the 123 kDa *E. aediculatus* telomerase subunit and the L8543.12 sequence (i.e., Est2 of *Saccharomyces cerevisiae*; See, Lendvay et al., Genetics 144:1399–1412 [1996]), Schizosaccharomyces, and human motifs, provides a strong basis for predicting that full human telomerase molecule comprises a protein that is large, basic, and includes such reverse transcriptase motifs. Thus, the compositions and methods of the present invention is useful for the identification of other telomerases, from a wide variety of species. The present invention describes the use of the 123 kDa reverse transcriptase motifs in a method to identify similar motifs in organisms that are distantly related to Euplotes (e.g., Oxytricha), as well as organisms that are not related to Euplotes (e.g., Saccharomyces, Schizosaccharomyces, humans, etc.).

The present invention also provides additional methods for the study of the structure and function of distinct forms of telomerase. It is contemplated that the telomerase proteins of the present invention will be useful in diagnostic applications, evolutionary (e.g., phylogenetic) investigations, as well as development of compositions and methods for cancer therapy or anti-aging regimens. Although the telomerase protein subunits of the present invention themselves have utility, it further contemplated that the polypeptides of the present invention will be useful in conjunction with the RNA moiety of the telomerase enzyme (i.e., a complete telomerase).

It is also contemplated that methods and compositions of this invention will lead to the discovery of additional unique telomerase structures and/or functions. In addition, the present invention provides novel methods for purification of functional telomerase, as well as telomerase proteins. This affinity based method described in Example 3, is an important aspect in the purification of functionally active telomerase. A key advantage of this procedure is the ability to use mild elution conditions, during which proteins that bind non-specifically to the column matrix are not eluted.

DETAILED DESCRIPTION OF THE INVENTION

The present invention is directed to the nucleic and amino acid sequences of the protein subunits of the *E. aediculatus* telomerase, as well as the nucleic and amino acid sequences of the telomerases from other organisms, including humans. In addition, the present invention is directed to the purification of functional telomerase. As described below the present invention also comprises various forms of telomerase, including recombinant telomerase and telomerase protein subunits, obtained from various organisms.

The 123 kDa and 43 kDa Telomerase Subunit Protein Sequences

The nucleic acid and deduced amino acid sequences of the 123 and 43 kDa protein subunits are shown in FIGS. 1–6. In accordance with the invention, any nucleic acid sequence which encodes *E. aediculatus* telomerase or its subunits can be used to generate recombinant molecules which express the telomerase or its subunits.

It will be appreciated by those skilled in the art that as a result of the degeneracy of the genetic code, a multitude of telomerase subunit protein sequences, some bearing minimal homology to the nucleotide sequences of any known and naturally occurring gene, may be produced. The invention contemplates each and every possible variation of nucleotide sequence that could be made by selecting combinations based on possible codon choices, taking into account the use of the codon "UGA" as encoding cysteine in *E. aediculatus*. Other than the exception of the "UGA" codon, these combinations are made in accordance with the standard triplet genetic code as applied to the nucleotide sequence encoding naturally occurring *E. aediculatus* telomerase, and all such variations are to be considered as being specifically disclosed. For example, the amino acid sequences encoded by each of the three open reading frames of the 43 kDa nucleotide sequence are specifically included (SEQ ID NOS:4–6). It is contemplated that any variant forms of telomerase subunit protein be encompassed by the present invention, as long as the proteins are functional in assays such as those described in the Examples.

Although nucleotide sequences which encode *E. aediculatus* telomerase protein subunits and their variants are preferably capable of hybridizing to the nucleotide sequence of the naturally occurring sequence under appropriately selected conditions of stringency, it may be advantageous to produce nucleotide sequences encoding *E. aediculatus* telomerase protein subunits or their derivatives possessing a substantially different codon usage, including the "standard" codon usage employed by human and other systems. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding telomerase subunits and their derivatives without altering the encoded amino acid sequences include the production of RNA transcripts having more desirable properties, such as a greater or a shorter half-life, than transcripts produced from the naturally occurring sequence.

It is now possible to produce a DNA sequence, or portions thereof, encoding telomerase protein subunits and their derivatives entirely by synthetic chemistry, after which the synthetic gene may be inserted into any of the many available DNA vectors and cell systems using reagents that are well known in the art. Moreover, synthetic chemistry may be used to introduce mutations into a sequence encoding *E. aediculatus* protein subunits or any portion thereof, as well as sequences encoding yeast or human telomerase proteins, subunits, or any portion thereof.

Also included within the scope of the present invention are polynucleotide sequences that are capable of hybridizing to the nuclcotide sequence of FIGS. 9, 11, 12, and 26, under various conditions of stringency. Hybridization conditions are based on the melting temperature ($T_m$) of the nucleic acid binding complex or probe, as taught in Berger and Kimmel (Berger and Kimmel, *Guide to Molecular Cloning Techniques*, Meth. Enzymol., vol. 152, Academic Press, San Diego Calif. [1987]) incorporated herein by reference, and may be used at a defined "stringency".

Altered nucleic acid sequences encoding telomerase protein subunits which may be used in accordance with the invention include deletions, insertions or substitutions of different nucleotides resulting in a polynucleotide that encodes the same or a functionally equivalent telomerase subunit. The protein may also show deletions, insertions or substitutions of amino acid residues which produce a silent change and result in a functionally equivalent telomerase subunit. Deliberate amino acid substitutions may be made on the basis of similarity in polarity, charge, solubility, hydrophobicity, hydrophilicity, and/or the amphipathic nature of the residues as long as the biological activity of the telomerase subunit is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine; and phenylalanine, tyrosine.

Methods for DNA sequencing are well known in the art and employ such enzymes as the Klenow fragment of DNA polymerase I, Sequenase® (US Biochemical Corp, Cleveland Ohio), Taq DNA polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elimer).

Also included within the scope of the present invention are alleles encoding human telomerase proteins and subunits. As used herein, the term "allele" or "alielic sequence" is an alternative form of the nucleic acid sequence encoding human telomerase proteins or subunits. Alleles result from mutations (i.e., changes in the nucleic acid sequence), and generally produce altered mRNAs or polypeptides whose structure and/or function may or may not be altered. An given gene may have no, one or many allelic forms. Common mutational changes that give rise to alleles are generally ascribed to natural deletions, additions, or substitutions of amino acids. Each of these types of changes may occur alone, or in combination with the others, one or more times within a given sequence.

Human Telomerase Motifs

The present invention also provides nucleic and amino acid sequence information for human telomerase motifs. These sequences were first identified in a BLAST search conducted using the Euplotes 123 kDa peptide, and a homologous sequence from Schizosaccharomyces, designated as "tez1." FIG. 25 shows the sequence alignment of the Euplotes ("p123"), Schizosaccharomyces ("tez1"), Est2p (i.e., the *S. cerevisiae* protein encoded by the Est2 nucleic acid sequence, and also referred to herein as "L8543.12"), and the human homolog identified in this comparison search. The amino acid sequence of this aligned portion is provided in SEQ ID NO:67 (the cDNA sequence is provided in SEQ ID NO:62), while the portion of tez1 shown in FIG. 25 is provided in SEQ ID NO:63. The portion of Est2 shown in this Figure is also provided in SEQ ID NO:64, while the portion of p123 shown is also provided in SEQ ID NO:65.

As shown in FIG. 25, there are regions that are highly conserved among these proteins. For example, as shown in this Figure, there are regions of identity in "Motif 0," "Motif 1, "Motif 2," and "Motif 3." The identical amino acids are indicated with an asterisk (*), while the similar amino acid residues are indicated by a circle (●). This indicates that there are regions within the telomerase motifs that are conserved among a wide variety of eukaryotes, ranging from yeast to ciliates, to humans. It is contemplated that additional organisms will likewise contain such conserved regions of sequence.

FIG. 27 shows the amino acid sequence of the cDNA clone encoding human telomerase motifs (SEQ ID NO:67), while FIG. 28 shows the DNA sequence of the clone. FIG. 29 shows the amino acid sequence of tez1 (SEQ ID NO:69), while FIG. 30 shows the DNA sequence of tez1 (SEQ ID NO:68). In FIG. 30, the introns and other non-coding regions are shown in lower case, while the exons (i.e., coding regions are shown in upper case.

Extending The Polynucleotide Sequence

The polynucleotide sequence encoding telomerase, or telomerase protein subunits, or their functional equivalents, may be extended utilizing partial nucleotide sequence and various methods known in the art to detect upstream sequences such as promoters and regulatory elements. For example, Gobinda et al. (Gobinda et al., PCR Meth. Applic. 2:318–22 [1993]) describe "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia et al., Nucleic Acids Res 16:8186 [1988]). The primers may be designed using OLIGO® 4.06 Primer Analysis Software (National Biosciences Inc, Plymouth Minn. [1992]), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom et al. PCR Methods Applic 1:111–19 [1991]), a method for PCR amplification of DNA fragments adjacent to a known sequence in human and yeast artificial chromosome DNA, may also be used. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker et al., Nucleic Acids Res 19:3055–60 [1991]), a method for targeted gene walking. Alternatively, PCR, nested primers, PromoterFinder™ (Clontech, Palo Alto Calif.) and PromoterFinder libraries can be used to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled devise camera. Output/light intensity is converted to electrical signal using, appropriate software (e.g., Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez et al., Anal Chem 65:2851–8 [1993]).

Expression of the Nucleotide Sequence

In accordance with the present invention, polynucleotide sequences which encode telomerase, telomerase protein subunits, or their functional equivalents, may be used in recombinant DNA molecules that direct the expression of telomerase or telomerase subunits by appropriate host cells.

The nucleotide sequences of the present invention can be engineered in order to alter either or both telomerase subunits for a variety of reasons, including but not limited to, alterations which modify the cloning, processing and/or expression of the gene product. For example, mutations may be introduced using techniques which are well known in the art (e.g., site-directed mutagenesis to insert new restriction sites, to alter glycosylation patterns, to change codon preference, to produce splice variants, etc.).

In an alternate embodiment of the invention, the sequence encoding the telomerase subunit(s) may be synthesized, whole or in part, using chemical methods well known in the art (See e.g., Caruthers et al., Nucleic Acids Res. Symp. Ser., 215–223 [1980]; and Horn et al. Nucleic Acids Res. Symp. Ser., 225–232 [1980]). Alternatively, the protein itself could be produced using chemical methods to synthesize a telomerase subunit amino acid sequence, in whole or in part. For example, peptide synthesis can be performed using various solid-phase techniques (Roberge, et al. Science 269:202 [1995]) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (e.g., Creighton, *Proteins, Structures and Molecular Principles*, W H Freeman and Co, New York N.Y. [1983]). The composition of the synthetic peptides may be confirmed by amino acid analysis or sequencing (e.g., the Edman degradation procedure; Creighton, supra). Additionally the amino acid sequences of telomerase subunit proteins, or any part thereof, may be altered during direct synthesis and/or combined using chemical methods with sequences from other proteins, or any part thereof, to produce a variant polypeptide.

Expression Systems

In order to express a biologically active telomerase protein subunit, the nucleotide sequence encoding the subunit or the functional equivalent, is inserted into an appropriate expression vector (i.e., a vector which contains the necessary elements for the transcription and translation of the inserted coding sequence). In order to express a biologically active telomerase enzyme, the nucleotide sequence encoding the telomerase protein subunits are inserted into appropriate expression vectors and the nucleotide sequence encoding the telomerase RNA subunit is inserted into the same or another vector for RNA expression. The protein and RNA subunits are then either expressed in the same cell or expressed separately, and then mixed to achieve a reconstituted telomerase.

Methods which are well known to those skilled in the art can be used to construct expression vectors containing a telomerase protein subunit sequence and appropriate transcriptional or translational controls. These methods include in vitro recombinant DNA techniques, synthetic techniques and in vivo recombination or genetic recombination. Such techniques are described in Sambrook et al. (Sambrook et al., *Molecular Cloning, A Laboratory Manual*, Cold Spring Harbor Press, Plainview N.Y. [1989]), and Ausubel et al. (Ausubel et al., *Current Protocols in Molecular Biology*, John Wiley & Sons, New York N.Y. [1989]). These same methods may be used to convert the UGA codons, which encode cysteine in Euplotes, to the UGU or UGC codon for cysteine recognized by the host expression system.

A variety of expression vector/host systems may be utilized to contain and express a telomerase subunit-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" of these systems vary in their strength and specificities and are those non-translated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla Calif.) or pSport1 (Gibco BRL) and ptrp-lac hybrids and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from the mammalian genes or from mammalian viruses are most appropriate. If it is necessary to generate a cell line that contains multiple copies of the sequence encoding telomerase or telomerase protein subunits, vectors based on SV40 or EBV may be used with an appropriate selectable marker.

In bacterial systems, a number of expression vectors may be selected depending upon the use intended for the telomerase protein or subunit. For example, when large quantities of telomerase protein, subunit, or peptides, are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the sequence encoding the telomerase or protein subunit may be ligated into the vector in frame with sequences for the amino-terminal Met and the subsequent 7 residues of β-galactosidase so that a hybrid protein is produced (e.g., pIN vectors; Van Heeke and Schuster, J. Biol. Chem., 264:5503–5509 [1989]) and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor Xa protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al. (supra) and Grant et al., Meth. Enzymol., 153:516–544 (1987).

In cases where plant expression vectors are used, the expression of a sequence encoding telomerase or protein subunit, may be driven by any of a number of promoters. For example, viral promoters such as the 35S and 19S promoters of CaMV (Brisson et al., Nature 310:511–514 [1984]) may be used alone or in combination with the omega leader sequence from TMV (Takamatsu et al., EMBO J., 6:307–311 [1987]). Alternatively, plant promoters such as the small subunit of RUBISCO (Coruzzi et al. EMBO J., 3:1671–1680 [1984]; Broglie et al., Science 224:838–843 [1984]) or heat shock promoters (Winter and Sinibaldi Results Probl. Cell Differ., 17:85–105 [1991]) may be used. These constructs can be introduced into plant cells by direct DNA transformation or pathogen-mediated transfection (for reviews of such techniques, see Hobbs or Murry, in *McGraw Hill Yearbook of Science and Technology* McGraw Hill New York N.Y., pp. 191–196 [1992]; or Weissbach and Weissbach, *Methods for Plant Molecular Biology*, Academic Press, New York N.Y., pp. 421–463 [1988]).

An alternative expression system which could be used to express telomerase or telomerase protein subunit is an insect system. In one such system, *Autographa californica* nuclear polyhedrosis virus (AcNPV) is used as a vector to express foreign genes in *Spodoptera frugiperda* cells or in Trichoplusia larvae. The sequence encoding the telomerase sequence of interest may be cloned into a nonessential region of the virus, such as the polyhedrin gene, and placed under control of the polyhedrin promoter. Successful insertion of the sequence encoding the telomerase protein or telomerase protein subunit will render the polyhedrin gene inactive and produce recombinant virus lacking coat protein. The recombinant viruses are then used to infect *S. frugiperda* cells or Trichoplusia larvae in which the telomerase sequence is expressed (Smith et al., J. Virol., 46:584 [1983]; Engelhard et al., Proc. Natl. Acad. Sci. 91:3224–7 [1994]).

In mammalian host cells, a number of viral-based expression systems may be utilized. In cases where an adenovirus is used as an expression vector, a sequence encoding telomerase protein or telomerase protein subunit, may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk, Proc. Natl. Acad. Sci., 81:3655–59 [1984]). In addition, transcription enhancers, such as the Rous sarcoma virus (RSV) enhancer, may be used to increase expression in mammalian host cells.

Specific initiation signals may also be required for efficient translation of a sequence encoding telomerase protein subunits. These signals include the ATG initiation codon and adjacent sequences. In cases where the sequence encoding a telomerase protein subunit, its initiation codon and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf et al., Results Probl. Cell Differ., 20:125 [1994]; and Bittner et al., Meth. Enzymol., 153:516 [1987]).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO (ATCC CCL 61 and CRL 9618), HeLa (ATCC CCL 2), MDCK (ATCC CCL 34 and CRL 6253), HEK 293 (ATCC CRL 1573), WI-38 (ATCC CCL 75) (ATCC: American Type Culture Collection, Rockville, Md.), etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express telomerase or a telomerase subunit protein may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler et al., Cell 11:223–32 [1977]) and adenine phosphoribosyltransferase (Lowy et al., Cell 22:817 [1980]) genes which can be employed in tk or aprt− cells, respectively. Also, antimetabolitc, antibiotic or herbicide resistance can be used as the basis for selection; for example, dhfr which confers resistance to methotrexate (Wigler et al., Proc. Nati. Acad. Sci., 77:3567 [1980]); npt, which confers resistance to the aminoglycosides neomycin and G-418 (Colbere-Garapin et al., J. Mol. Biol., 150:1 [1981]) and als or pat, which confer resistance to chlorsulfuron and phosphinotricin acetyltransferase, respectively (Murry, In McGraw Hill *Yearbook of Science and Technolog*, McGraw Hill, New York N.Y., pp 191–196, [1992]). Additional selectable genes have been described, for example, trpB, which allows cells to utilize indole in place of tryptophan, or hisD, which allows cells to utilize histinol in place of histidine (Hartman and Mulligan, Proc. Natl. Acad. Sci., 85:8047 [1988]). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes et al., Meth. Mol. Biol., 55:121 [1995]).

Identification of Transformants Containing the Polynucleotide Sequence

Although the presence/absence of marker gene expression suggests that the gene of interest is also present, its presence and expression should be confirmed. For example, if the sequence encoding a telomerase protein subunit is inserted within a marker gene sequence, recombinant cells containing the sequence encoding the telomerase protein subunit can be identified by the absence of marker gene function. Alternatively, a marker gene can be placed in tandem with the sequence encoding telomerase protein subunit under the control of a single promoter. Expression of the marker gene in response to induction or selection usually indicates expression of the tandem sequence as well.

Alternatively, host cells which contain the coding sequence for telomerase or a telomerase protein subunit and express the telomerase or protein subunit be identified by a variety of procedures known to those of skill in the art. These procedures include, but are not limited to, DNA-DNA or DNA-RNA hybridization and protein bioassay or immunoassay techniques which include membrane, solution, or chip-based technologies for the detection and/or quantification of the nucleic acid or protein.

The presence of the polynucleotide sequence encoding telomerase protein subunits can be detected by DNA-DNA or DNA-RNA hybridization or amplification using probes, portions, or fragments of the sequence encoding the subunit. Nucleic acid amplification based assays involve the use of oligonucleotides or oligomers based on the nucleic acid sequence to detect transformants containing DNA or RNA encoding the telomerase subunit. As used herein "oglionucleotides" or "oligomers" refer to a nucleic acid sequence of approximately 10 nucleotides or greater and as many as approximately 100 nucleotides, preferably between 15 to 30 nucleotides, and more preferably between 20–25 nucleotides which can be used as a probe or amplimer.

A variety of protocols for detecting and measuring the expression of proteins (e.g., telomerase or a telomerase protein subunits) using either polyclonal or monoclonal antibodies specific for the protein are known in the art. Examples include enzyme-linked immunosorbent assay (ELISA), radioimmunoassay (RIA) and fluorescent activated cell sorting (FACS). These and other assays are described, among other places, in Hampton et al., *Serological Methods a Laboratory Manual*, APS Press, St Paul Minn. [1990]) and Maddox et al., J. Exp. Med., 158:1211 [1983]).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR. amplification using a labeled nucleotide. Alternatively, a telomerase protein subunit sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemilumincscent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241, herein incorporated by reference. Also, recombinant immunoglobulins may be produced as shown in U.S. Pat. No. 4,816,567 incorporated herein by reference.

Purification of Recombinant Telomerase and Telomerase Subunit Proteins

In addition to the method of purification described in Example 3 below, it is contemplated that additional methods of purifying recombinantly produced telomerase or telomerase protein subunits will be used. For example, host cells transformed with a nucleotide sequence encoding telomerase or telomerase subunit protein(s) may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing the telomerase or subunit protein encoding sequence can be designed with signal sequences which direct secretion of the telomerase or telomerase subunit protein through a prokaryotic or eukaryotic cell membrane. Other recombinant constructions may join the sequence encoding the telomerase or subunit protein to a nucleotide sequence encoding a polypeptide domain.

Telomerase or telomerase subunit protein(s) may also be expressed as recombinant proteins with one or more additional polypeptide domains added to facilitate protein purification. Such purification facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and telomerase or telomerase protein subunits is useful to facilitate purification. One such expression vector provides for expression of a fusion protein comprising the sequence encoding telomerase or telomerase protein subunits and nucleic acid sequence encoding 6 histidine residues followed by thioredoxin and an enterokinase cleavage site. The histidine residues facilitate purification while the enterokinase cleavage site provides a means for purifying the telomerase or telomerase protein subunit from the fusion protein. Literature pertaining to vectors containing fusion proteins is available in the art (See e.g., Kroll et al., DNA Cell. Biol., 12:441–53 [1993]).

In addition to recombinant production, fragments of telomerase subunit protein may be produced by direct peptide synthesis using solid-phase techniques (See e.g., Merrifield, J. Am. Chem. Soc., 85:2149 [1963]). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of telomere protein subunit may be chemically synthesized separately and combined using chemical methods to produce the full length molecule.

Uses of Telomerase and Telomerase Subunit Proteins

The rationale for use of the nucleotide and peptide sequences disclosed herein is based in part on the homology between the *E. aediculatus* telomerase 123 kDa protein subunit, the yeast protein L8543.12 (Est2), Schizosaccharomyces, and the human motifs observed during the development of the present invention. In particular, the yeast and 123 kDa protein contain the reverse transcriptase motif in their C-terminal regions, they share similarity in regions outside the reverse transcriptase motif, they are similarly basic (with a pI of 10.1 for the 123 kDa protein and of 10.0 for the yeast), and they are both large (123 kDa and 103 kDa). Furthermore, in view of the reverse transcriptase motifs, these subunits are believed to comprise the catalytic core of their respective telomerases. Indeed, the reverse transcriptase motifs of the 123 kDa *E. aediculatus* telomerase protein subunit is shown in the present invention to be useful for the identification of similar sequences in other organisms.

As *E. aediculatus* and *S. cerevisiae* are so phylogenetically distant, it is contemplated that this homology provides a strong basis for predicting that human and other telomerases will contain a protein that is large, basic, and includes such reverse transcriptase motifs. Indeed, motifs have been identified within a clone encoding the human homolog of the telomerase protein. It is further contemplated that this protein is essential for human telomerase catalytic activity. This observation should prove valuable for amplification of the human telomerase gene by PCR or other methods, for screening for telomerase sequences in human and other animals, as well as for prioritizing candidate telomerase proteins or genes identified by genetic, biochemical, or nucleic acid hybridization methods. It is also contemplated that the telomerase proteins of the present invention will find use in tailing DNA 3' ends in vitro.

It is contemplated that expression of telomerase and/or telomerase subunit proteins in cell lines will find use in the development of diagnostics for tumors and aging factors. The nucleotide sequence may be used in hybridization or PCR technologies to diagnose the induced expression of messenger RNA sequences early in the disease process. Likewise the protein can be used to produce antibodies useful in ELISA assays or a derivative diagnostic format. Such diagnostic tests may allow different classes of human tumors or other cell-proliferative diseases to be distinguished and thereby facilitate the selection of appropriate treatment regimens.

It is contemplated that the finding of the reverse transcriptase motifs in the telomerase proteins of the present invention will be used to develop methods to test known and yet to be described reverse transcriptase inhibitors, including nucleosides, and non-nucleosides for anti-telomerase activity.

It is contemplated that the amino acid sequence motifs disclosed herein will lead to the development of drugs (e.g., telomerase inhibitors) useful in humans and/or other animals, that will arrest cell division in cancers or other disorders characterized by proliferation of cells. It is also contemplated that the telomerase proteins will find use in methods for targeting and directing RNA or RNA-tethered drugs to specific sub-cellular compartments such as the nucleus or sub-nuclear organelles, or to telomeres.

In one embodiment of the diagnostic method of the present invention, normal or standard values for telomerase mRNA expression are established as a baseline. This can be accomplished by a number of assays such as quantitating the amount of telomerase mRNA in tissues taken from normal subjects, either animal or human, with nucleic probes derived from the telomerase or telomerase protein subunit sequences provided herein (either DNA or RNA forms) using techniques which are well known in the art (e.g., Southern blots, Northern blots, dot or slot blots). The standard values obtained from normal samples may be compared with values obtained from samples from subjects potentially affected by disease (e.g., tumors or disorders related to aging). Deviation between standard and subject values can establish the presence of a disease state. In addition, the deviation can indicate, within a disease state, a particular clinical outcome (e.g., metastatic or non-metastatic).

The nucleotide sequence encoding telomerase or telomerase protein subunits is useful when placed in an expression vector for making quantities of protein for therapeutic use. The antisense nucleotide sequence of the telomerase gene is potentially useful in vectors designed for gene therapy directed at neoplasia including metastases. Additionally, the inhibition of telomerase expression may be useful in detecting the development of disturbances in the aging process or problems occurring during chemotherapy. Alternatively, the telomerase or telomerase protein subunit encoding nucleotide sequences may used to direct the expression of telomerase or subunits in situations where it is desirable to increase the amount of telomerase activity.

Telomere Subunit Protein Antibodies

It is contemplated that antibodies directed against the telomerase subunit proteins will find use in the diagnosis and treatment of conditions and diseases associated with expression of telomerase (including the over-expression and the absence of expression). Such antibodies include, but are not limited to, polyclonal, monoclonal, chimeric, single chain, Fab fragments and fragments produced by a Fab expression library. Given the phylogenetic conservation of the reverse transcriptase motif in the 123 kDa subunit of the Euplotes telomerase, it is contemplated that antibodies directed against this subunit may be useful for the identification of homologous subunits in other organisms, including humans. It is further contemplated that antibodies directed against the motifs provided in the present invention will find use in treatment and/or diagnostic areas.

Telomerase subunit proteins used for antibody induction need not retain biological activity; however, the protein fragment, or oligopeptide must be immunogenic, and preferably antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of telomerase subunit protein amino acids may be fused with those of another protein such as keyhole limpet hemocyanin and antibody produced against the chimeric molecule. Complete telomerase used for antibody induction can be produced by co-expression of protein and RNA components in cells, or by reconstitution in vitro from components separately expressed or synthesized.

For the production of antibodies, various hosts including goats, rabbits, rats, mice, etc may be immunized by injection with telomerase protein, protein subunit, or any portion, fragment or oligopeptide which retains immunogenic properties. Depending on the host species, various adjuvants may be used to increase immunological response. Such adjuvants are commercially available, and include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmctte-Guerin) and *Corynebacterium parvum* are potentially useful adjuvants.

Monoclonal antibodies to telomerase or telomerase protein subunits be prepared using any technique which provides for the production of antibody molecules by continuous cell lines in culture. These include but are not limited to the hybridoma technique originally described by Koehler and Milstein (Koehler and Milstein, Nature 256:495–497 [1975]), the human B-cell hybridoma technique (Kosbor et al., Immunol. Today 4:72 [1983]; Cote el al., Proc. Natl. Acad. Sci., 80:2026–2030 [1983]) and the EBV-hybridoma technique (Cole et al., *Monoclonal Antibodies and Cancer Therapy*, Alan R Liss Inc, New York N.Y., pp 77–96 [1985]).

Antibodies may also be produced by inducing in vivo production in the lymphocyte population or by screening recombinant immunoglobulin libraries or panels of highly specific binding reagents as disclosed in Orlandi et al. (Orlandi et al.,Proc. Natl. Acad. Sci., 86: 3833 [1989]; and Winter and Milstein, Nature 349:293 [1991]).

Antibody fragments which contain specific binding sites for telomerase or telomerase protein subunits may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., Science 256:1275 [1989]).

A variety of protocols for competitive binding or immunoradiometric assays using either polyclonal or monoclonal antibodies with established specificities are well known in the art. Such immunoassays typically involve the formation of complexes between telomerase or telomerase protein subunit and its specific antibody and the measurement of complex formation. A two-site, monoclonal-based immunoassay utilizing monoclonal antibodies reactive to two noninterfering epitopes on a specific telomerase protein subunit is preferred in some situations, but a competitive binding assay may also be employed (See e.g., Maddox et al., J. Exp. Med., 158:1211 [1983]).

Peptides selected from the group comprising the sequences shown in FIG. 32 are used to generate polyclonal and monoclonal antibodies specifically directed against human and other telomerase proteins. The peptides are useful for inhibition of protein-RNA, protein-protein interaction within the telomerase complex, and protein-DNA interaction at telomeres. Antibodies produced against these peptides are then used in various settings, including but not limited to anti-cancer therapeutics capable of inhibiting telomerase activity, for purification of native telomerase for therapeutics, for purification and cloning other components of human telomerase and other proteins associated with human telomerase, and diagnostic reagents.

Diagnostic Assays Using Telomerase Specific Antibodies

Particular telomerase and telomerase protein subunit antibodies are useful for the diagnosis of conditions or diseases characterized by expression of telomerase or telomerase protein subunits, or in assays to monitor patients being treated with telomerase, its fragments, agonists or inhibitors (including antisense transcripts capable of reducing expression of telomerase). Diagnostic assays for telomerase include methods utilizing the antibody and a label to detect telomerase in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above. In particular, the present invention is useful for diagnosis of human disease, although it is contemplated that the present invention will find use in the veterinary arena.

A variety of protocols for measuring telomerase protein(s) using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two noninterfering epitopes on the telomerase proteins or a subunit is preferred, but a competitive binding assay may be employed. These assays are described, among other places, in Maddox (Maddox et al., J. Exp. Med., 158:1211 [1983]).

In order to provide a basis for diagnosis, normal or standard values for human telomerase expression must be established. This is accomplished by combining body fluids or cell extracts taken from normal subjects, either animal or human, with antibody to telomerase or telomerase subunit(s) under conditions suitable for complex formation which are well known in the art. The amount of standard complex formation may be quantified by comparing various artificial membranes containing known quantities of telomerase protein, with both control and disease samples from biopsied tissues. Then, standard values obtained from normal samples may be compared with values obtained from samples from subjects potentially affected by disease (e.g., metastases). Deviation between standard and subject values establishes the presence of a disease state.

Drug Screening

Telomerase or telomerase subunit proteins or their catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between telomerase or the subunit protein and the agent being tested, may be measured.

Another technique for drug screening which may be used for high throughput screening of compounds having suitable binding affinity to the telomerase or telomerase protein subunit is described in detail in "Determination of Amino Acid Sequence Antigenicity" by Geysen, (Geysen, WO Application 84/03564, published on Sep. 13, 1984, incorporated herein by reference). In summary, large numbers of different small peptide test compounds are synthesized on a solid substrate, such as plastic pins or some other surface. The peptide test compounds are reacted with fragments of telomerase or telomerase protein subunits and washed. Bound telomerase or telomerase protein subunit is then detected by methods well known in the art. Substantially purified telomerase or telomerase protein subunit can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding telomerase or subunit protein(s) specifically compete with a test compound for binding telomerase or the subunit protein. In this manner, the antibodies can be used to detect the presence of any peptide which shares one or more antigenic determinants with the telomerase or subunit protein.

Uses of the Polynucleotides Encoding Telomerase Subunit Proteins

A polynucleotide sequence encoding telomerase subunit proteins or any part thereof may be used for diagnostic and/or therapeutic purposes. For diagnostic purposes, the sequence encoding telomerase subunit protein of this invention may be used to detect and quantitate gene expression of the telomerase or subunit protein. The diagnostic assay is useful to distinguish between absence, presence, and excess expression of telomerase, and to monitor regulation of telomerase levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding telomerase subunit proteins or closely related molecules. The specificity of the probe, whether it is made from a highly specific region (e.g., 10 unique nucleotides in the 5' regulatory region), or a less specific region (e g., especially in the 3' region), and the stringency of the hybridization or amplification (maximal, high, intermediate or low) will determine whether the probe identifies only naturally occurring telomerase, telomerase subunit proteins or related sequences.

Probes may also be used for the detection of related sequences and should preferably contain at least 50% of the nucleotides from any of these telomerase subunit protein sequences. The hybridization probes of the subject invention may be derived from the nucleotide sequence provided by the present invention (e.g., SEQ ID NO:1, 3, 62, 66, or 68), or from genomic sequence including promoter, enhancer elements and introns of the naturally occurring sequence encoding telomerase subunit proteins. Hybridization probes may be labeled by a variety of reporter groups, including commercially available radionuclides such as $^{32}P$ or $^{35}S$, or enzymatic labels such as alkaline phosphatase coupled to the probe via avidin/biotin coupling systems, and the like.

Other means for producing specific hybridization probes for DNAs include the cloning of nucleic acid sequences encoding telomerase subunit proteins or derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding telomerase may be used for the diagnosis of conditions or diseases with which the abnormal expression of telomerase is associated. For example, polynucleotide sequences encoding human telomerase may be used in hybridization or PCR assays of fluids or tissues from biopsies to detect telomerase expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The human telomerase-encoding nucleotide sequences disclosed herein provide the basis for assays that detect activation or induction associated with disease (including metastasis); in addition, the lack of expression of human telomerase may be detected using the human and other telomerase-encoding nucleotide sequences disclosed herein. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding human telomerase in the sample indicates the presence of the associated disease. Alternatively, the loss of expression of human telomerase sequences in a tissue which normally expresses telomerase sequences indicates the presence of an abnormal or disease state.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for human telomerase expression must be established. This is accomplished by combining body fluids or cell extracts taken from normal subjects, either animal or human, with human telomerase or a portion thereof, under conditions suitable for hybridization or amplification. Standard hybridization may be quantified by comparing the values obtained for normal subjects with a dilution series of human telomerase run in the same experiment where a known amount of substantially purified human telomerase is used. Standard values obtained from normal samples may be compared with values obtained from samples from patients affected by telomerase-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, which may be used as described in U.S. Pat. Nos. 4,683,195, 4,683,202, and 4,965,188 (herein incorporated by reference) provides additional uses for oligonucleotides based upon the sequence encoding telomerase subunit proteins. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby et al., J. Immunol. Meth., 159:235–44 [1993]) or biotinylating [Duplaa et al., Anal. Biochem., 229–36 [1993]) nucleotides, co-amplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to other telomerase sequences, the polynucleotide encoding human telomerase disclosed herein may be useful in the treatment of metastasis; in particular, inhibition of human telomerase expression may be therapeutic.

Expression vectors derived from retroviruses, adenovirus, herpes or vaccinia viruses, or from various bacterial plasmids, may be used for delivery of nucleotide sequences (sense or antisense) to the targeted organ, tissue or cell population. Methods which are well known to those skilled in the art can be used to construct recombinant vectors which will express antisense of the sequence encoding human telomerase. See, for example, the techniques described in Sambrook et al. (supra) and Ausubel et al. (supra).

The polynucleotides comprising full length cDNA sequence and/or its regulatory elements enable researchers to use the sequence encoding human telomerase, including the various motifs as an investigative tool in sense (Youssoufian and Lodish, Mol. Cell. Biol., 13:98–104 [1993]) or antisense (Eguchi et al., Arn. Rev. Biochem., 60:631–652 [1991]) regulation of gene function. Such technology is now well known in the art, and sense or antisense oligomers, or larger fragments, can be designed from various locations along the coding or control regions.

Genes encoding human telomerase can be turned off by transfecting a cell or tissue with expression vectors which express high levels of a desired telomerase fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA or PNA, to the control regions of the sequence encoding human telomerase (i.e., the promoters, enhancers, and introns). Oligonucleotides derived from the transcription initiation site, (e.g., between −10 and +10 regions of the leader sequence) are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules (for a review of recent therapeutic advances using triplex DNA, see Gee et al., in Huber and Carr, *Molecular and Immunologic Approaches*, Futura Publishing Co, Mt Kisco N.Y. [1994]).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding human telomerase.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding human telomerase and/or telomerase protein subunits. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra, and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, the disclosure of which is herein incorporated by reference. Delivery by transfection and by liposome are quite well known in the art.

Furthermore, the nucleotide sequences encoding the various telomerase proteins and subunits disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences in Other Genomes

The nucleic acid sequence encoding *E. aediculatus, S. cerevisiae, S. pombe*, and human telomerase subunit proteins and sequence variants thereof, may also be used to generate hybridization probes for mapping the naturally occurring homologous genomic sequence in the human and other genomes. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed by Price (Price, Blood Rev., 7:127 [1993]) and Trask (Trask, Trends Genet 7:149 [1991]).

The technique of fluorescent in situ hybridization (FISH) of chromosome spreads has been described, among other places, in Verma et al. (Verma et al., *Human Chromosomes: A Manual of Basic Techniques*, Pergamon Press, New York N.Y. [1988]). Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the sequence encoding human telomerase on a physical chromosomal map and a specific disease (or predisposition to a specific disease) may help delimit the region of DNA associated with the disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps (See e.g., Hudson et al., Science 270:1945 [1995]). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques.

Pharmaceutical Compositions

The present invention also relates to pharmaceutical compositions which may comprise telomerase and/or or telomerase subunit nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents. drugs or hormones, in pharmaceutical compositions where it is mixed with suitable excipient(s), adjuvants, and/or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (e.g. directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and other compounds that facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, etc., suitable for ingestion by the patient.

Pharmaceutical preparations for oral use can be obtained through combination of active compounds with solid excipient, optionally grinding a resulting mixture, and processing the mixture of granules, after adding suitable additional compounds, if desired, to obtain tablets or dragee cores. Suitable excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art (e.g., by means of conventional mixing, dissolving, granulating, dragee-making, levigating, emulsifying, encapsulating, entrapping or lyophilizing processes).

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5, that is combined with buffer prior to use.

After pharmaceutical compositions comprising a compound of the invention formulated in a acceptable carrier have been prepared, they can be placed in an appropriate container and labeled for treatment of an indicated condition. For administration of human telomerase proteins, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays or in any appropriate animal model. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state (e.g., tumor size and location; age, weight and gender of the patient; diet, time and frequency of administration, drug combination(s), reaction sensitivities, and tolerance/response to therapy). Long acting pharmaceutical compositions might be administered every 3 to 4 days, every week, or once every two weeks depending on half-life and clearance rate of the particular formulation. Guidance as to particular dosages and methods of delivery is provided in the literature (See, U.S. Pat. Nos. 4,657,760; 5,206,344; and 5,225,212, herein incorporated by reference). Those skilled in the art will employ different formulations for nucleotides than for proteins or their inhibitors. Similarly, delivery of polynucleotides or polypeptides will be specific to particular cells, conditions, locations, etc.

It is contemplated, for example, that human telomerase can be used as a therapeutic molecule combat disease (e.g., cancer) and/or problems associated with aging. It is further contemplated that antisense molecules capable of reducing the expression of human telomerase or telomerase protein subunits can be as therapeutic molecules to treat tumors associated with the aberrant expression of human telomerase. Still further it is contemplated that antibodies directed against human telomerase and capable of neutralizing the biological activity of human telomerase may be used as therapeutic molecules to treat tumors associated with the aberrant expression of human telomerase and/or telomerase protein subunits.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); RPN (ribonucleoprotein); remN (2'-O-methylribonucleotides); dNTP (deoxyribonucleotide); dH₂O (distilled water); DDT (dithiothreitol); PMSF (phenylmethylsulfonyl fluoride); TE (10 mM Tris HCl, 1 mM EDTA, approximately pH 7.2); KGlu (potassium glutamate); SSC (salt and sodium citrate buffer); SDS (sodium dodecyl sulfate); PAGE (polyacrylamide gel electrophoresis); Novex (Novex, San Diego, Calif.); BioRad (Bio-Rad Laboratories, Hercules, Calif.); Pharmacia (Pharmacia Biotech, Piscataway, N.J.); Boehringer-Mannheim (Boehringer-Mannheim Corp., Concord, Calif.); Amersham (Amersham, Inc., Chicago, Ill.); Stratagene (Stratagene Cloning Systems, La Jolla, Calif.); NEB (New England Biolabs, Beverly, Mass.); Pierce (Pierce Chemical Co., Rockford, Ill.); Beckman (Beckman Instruments, Fullerton, Calif.); Lab Industries (Lab Industries, Inc., Berkeley, Calif.); Eppendorf (Eppendorf Scientific, Madison, Wis.); and Molecular Dynamics (Molecular Dynamics, Sunnyvale, Calif.).

EXAMPLE 1

Growth of *Euplotes aediculatus*

In this Example, cultures of *E. aediculatus* were obtained from Dr. David Prescott, MCDB, University of Colorado. Dr. Prescott originally isolated this culture from pond water, although this organism is also available from the ATCC (ATCC #30859). Cultures were grown as described by Swanton et al., (Swanton et al., Chromosoma 77:203 [1980]), under non-sterile conditions, in 15-liter glass containers containing Chlorogonium as a food source. Organisms were harvested from the cultures when the density reached approximately $10^4$ cells/ml.

EXAMPLE 2

Preparation of Nuclear Extracts

In this Example, nuclear extracts of *E. aediculatus* were prepared using the method of Lingner et al., (Lingner et al., Genes Develop., 8:1984 [1994]), with minor modifications, as indicated below. Briefly, cells grown as described in Example 1 were concentrated with 15 μm Nytex filters and cooled on ice. The cell pellet was resuspended in a final volume of 110 ml TMS/PMSF/spermidinephosphate buffer. The stock TMS/PMSF/spermidine phosphate buffer was prepared by adding 0.075 g spermidine phosphate (USB) and 0.75 ml PMSF (from 100 mM stock prepared in ethanol) to 150 ml TMS. TMS comprised 10 mM Tris-acetate, 10 mM $MgCl_2$, 85.5752 g sucrose/liter, and 0.33297 g $CaCl_2$/liter, pH 7.5.

After resuspension in TMS/PMSF/spermidinephosphate buffer, 8.8 ml 10% NP-40 and 94.1 g sucrose were added and the mixture placed in a siliconized glass beaker with a stainless steel stirring rod attached to an overhead motor. The mixture was stirred until the cells were completely lysed (approximately 20 minutes). The mixture was then centrifuged for 10 minutes at 7500 rpm (8950×g), at 4° C., using a Beckman JS-13 swing-out rotor. The supernatant was removed and nuclei pellet was resuspended in TMS/PMSF/spermidine phosphate buffer, and centrifuged again, for 5 minutes at 7500 rpm (8950×g), at 4° C., using a Beckman JS-13 swing-out rotor.

The supernatant was removed and the nuclei pellet was resuspended in a buffer comprised of 50 mM Tris-acetate, 10 mM $MgCl_2$, 10% glycerol, 0.1% NP-40, 0.4 M KGlu, 0.5 mM PMSF, pH-7.5, at a volume of 0.5 ml buffer per 10 g of harvested cells. The resuspended nuclei were then dounced in a glass homogenizer with approximately 50 strokes, and then centrifuged for 25 minutes at 14,000 rpm at 4° C., in an Eppendorf centrifuge. The supernatant containing the nuclear extract was collected, frozen in liquid nitrogen, and stored at −80° C. until used.

EXAMPLE 3

Purification of Telomerase

In this Example, nuclear extracts prepared as described in Example 2 were used to purify *E. aediculatus* telomerase. In this purification protocol, telomerase was first enriched by chromatography on an Affi-Gel-heparin column, and then extensively purified by affinity purification with an antisense oligonucleotide. As the template region of telomerase RNA is accessible to hybridization in the telomerase RNP particle, an antisense oligonucleotide (i.e. the "affinity oligonucleotide") was synthesized that was complementary to this template region as an affinity bait for the telomerase. A biotin residue was included at the 5' end of the oligonucleotide to immobilize it to an avidin column.

Following the binding of the telomerase to the oligonucleotide, and extensive washing, the telomerase was eluted by use of a displacement oligonucleotide. The affinity oligonuclcotide included DNA bases that were not complementary to the telomerase RNA 5' to the telomerase-specific sequence. As the displacement oligonucleotide was complementary to the affinity oligonucleotide for its entire length, it was able to form a more thermodynamically stable duplex than the telomerase bound to the affinity oligonucleotidc. Thus, addition of the displacement oligonucleotide resulted in the elution of the telomerase from the column.

In this Example, the nuclear extracts prepared from 45 liter cultures were frozen until a total of 34 ml of nuclear extract was collected. This corresponded to 630 liters of culture (i.e., approximately $4 \times 10^9$ cells). The nuclear extract was diluted with a buffer to 410 ml, to provide final concentrations of 20 mM Tris-acetate, 1 mM $MgCl_2$, 0.1 mM EDTA, 33 mM KGlu, 10% (vol/vol) glycerol, 1 mM dithiothreitol (DTT), and 0.5 mM phenylmethylsulfonyl fluoride (PMSF), at a pH of 7.5.

The diluted nuclear extract was applied to an Affi-Gel-heparin gel column (Bio-Rad), with a 230 ml bed volume and 5 cm diameter, equilibrated in the same buffer and eluted with a 2-liter gradient from 33 to 450 mM KGlu. The column was run at 4° C., at a flow rate of 1 column volume/hour. Fractions of 50 mls each were collected and assayed for telomerase activity as described in Example 4. Telomerase was eluted from the column at approximately 170 mM KGlu. Fractions containing telomerase (approximately 440 ml) were pooled and adjusted to 20 mM Tris-acetate, 10 mM $MgCl_2$, 1 mM EDTA, 300 mM KGlu, 10% glycerol, 1 mM DTT, and 1% Nonidet P-40. This buffer was designated as "WB."

To this preparation, 1.5 nmol of each of two competitor DNA oligonucleotides (5'-TAGACCTGTTAGTGTACATTTGAATTGAAGC-3' (SEQ ID NO:28)) and (5'-TAGACCTGTTAGGTTGGATTTGTGGCATCA-3' (SEQ ID NO:29)), 50 µg yeast RNA (Sigma), and 0.3 nmol of biotin-labelled telomerase-specific oligonucleotide (5'-biotin-TAGACCTGTTA-(rmeG)$_2$-(rmeU)$_4$-(rmeG)$_4$-(rmeU)$_4$-remG-3')(SEQ ID NO:60), were added per ml of the pool. The 2-O-methyribonucleotides of the telomerase specific oligonucleotides were complementary to the telomerase RNA template region; the deoxyribonucleotides were not complementary. The inclusion of competitor, non-specific DNA oligonucleotides increased the efficiency of the purification, as the effects of nucleic acid binding proteins and other components in the mixture that would either bind to the affinity oligonucleotide or remove the telomerase from the mixture were minimized.

This material was then added to Ultralink immobilized neutravidin plus (Pierce) column material, at a volume of 60 µl of suspension per ml of pool. The column material was pre-blocked twice for 15 minutes each blocking, with a preparation of WB containing 0.01% Nonidet P-40, 0.5 mg BSA, 0.5 mg/ml lysozyme, 0.05 mg/ml glycogen, and 0.1 mg/ml yeast RNA. The blocking was conducted at 4° C., using a rotating wheel to thoroughly block the column material. After the first blocking step, and before the second blocking step, the column material was centrifuged at 200×g for 2 minutes to pellet the matrix.

The pool-column mixture was incubated for 8 minutes at 30° C., and then for an additional 2 hours at 4° C., on a rotating wheel (approximately 10 rpm; Labindustries) to allow binding. The pool-column mixture was then centrifuged 200×g for 2 minutes, and the supernatant containing unbound material was removed. The pool-column mixture was then washed. This washing process included the steps of rinsing the pool-column mixture with WB at 4° C., washing the mixture for 15 minutes with WB at 4° C., rinsing with WB, washing for 5 minutes at 30° C., with WB containing 0.6 M KGlu, and no Nonidet P-40, washing 5 minutes at 25° C. with WB, and finally, rinsing again with WB. The volume remaining after the final wash was kept small, in order to yield a ratio of buffer to column material of approximately 1:1.

Telomerase was eluted from the column material by adding 1 nmol of displacement deoxyoligonucleotide (5'-CA$_4$C$_4$A$_4$C$_2$TA$_2$CAG$_2$TCTA-3')(SEQ ID NO:30), per ml of column material and incubating at 25° C. for 30 minutes. The material was centrifuged for 2 minutes 14,000 rpm in a microcentrifuge (Eppendorf), and the cluate collected. The elution procedure was repeated twice more, using fresh displacement oligonucleotide each time. As mentioned above, because the displacement oligonucleotide was complementary to the affinity oligonucleotide, it formed a more thermodynamically stable complex with the affinity oligonucleotide than the telomerase. Thus, addition of the displacement oligonucleotide to an affinity-bound telomerase resulted in efficient elution of telomerase under native conditions. The telomerase appeared to be approximately 50% pure at this stage, as judged by analysis on a protein gel. The affinity purification of telomerase and elution with a displacement oligonucleotide is shown in FIG. 1 (panels A and B, respectively). In this Figure, the 2'-O-methyl sugars of the affinity oligonucleotide are indicated by the bold line. The black and shaded oval shapes in this Figure are intended to graphically represent the protein subunits of the present invention.

The protein concentrations of the extract and material obtained following Affi-Gel-heparin column chromatography, were determined using the method of Bradford (Bradford, Anal. Biochem., 72:248 [1976]), using BSA as the standards. Only a fraction of the telomerase preparation was further purified on a glycerol gradient.

The sedimentation coefficient of telomerase was determined by glycerol gradient centrifugation, as described in Example 8.

Table 1 below is a purification table for telomerase purified according to the methods of this Example. The telomerase was enriched 12-fold in nuclear extracts, as compared to whole cell extracts, with a recovery of 80%; 85% of telomerase was solubilized from nuclei upon extraction.

TABLE 1

Purification of Telomerase

| Fraction | Protein (mg) | Telomerase (pmol of RNP) | Telomerase/ Protein/pmol of RNP/mg | Recovery (%) | Purification Factor |
|---|---|---|---|---|---|
| Nuclear Extract | 2020 | 1720 | 0.9 | 100 | 1 |
| Heparin | 125 | 1040 | 8.3 | 60 | 10 |

TABLE 1-continued

Purification of Telomerase

| Fraction | Protein (mg) | Telomerase (pmol of RNP) | Telomerase/ Protein/pmol of RNP/mg | Recovery (%) | Purification Factor |
|---|---|---|---|---|---|
| Affinity | 0.3** | 680 | 2270 | 40 | 2670 |
| Glycerol Gradient | NA* | NA* | NA* | 25 | NA* |

*NA = Not available
**This value was calculated from the measured amount of telomerase (680 pmol), by assuming a purity of 50% (based on a protein gel).

EXAMPLE 4

Telomerase Activity

At each step in the purification of telomerase, the preparation was analyzed by three separate assays, one of which was activity, as described in this Example. In general, telomerase assays were done in 40 μl containing 0.003–0.3 μl of nuclear extract, 50 mM Tris-Cl (pH 7.5), 50 mM KGlu, 10 mM $MgCl_2$, 1 mM DTT, 125 μM dTTP, 125 μM dGTP, and approximately 0.2 pmoles of 5'-$^{32}$P-labelled oligonucleotide substrate (i.e., approximately 400,000 cpm). Oligonucleotide primers were heat-denatured prior to their addition to the reaction mixture. Reactions were assembled on ice and incubated for 30 minutes at 25° C. The reactions were stopped by addition of 200 μl of 10 mM Tris-Cl (pH 7.5), 15 mM EDTA, 0.6% SDS, and 0.05 mg/ml proteinase K, and incubated for at least 30 minutes at 45° C. After ethanol precipitation, the products were analyzed on denaturing 8% PAGE gels, as known in the art (See e.g., Sambrook et al., 1989).

EXAMPLE 5

Quantification of Telomerase Activity

In this Example, quantification of telomerase activity through the purification procedure is described. Quantitation was accomplished by assaying the elongation of oligonucleotide primers in the presence of dGTP and [α-$^{32}$P]dTTP. Briefly, 1 μM 5'-$(G_4T_4)_2$-3' oligonucleotide was extended in a 20 μl reaction mixture in the presence of 2 μl of [α-$^{32}$P] dTTP (10 mCi/ml, 400 Ci/mmol; 1 Ci=37 GBq), and 125 μM dGTP as described by (Lingner et al., Genes Develop., 8:1984 [1994]), and loaded onto an 8% PAGE sequencing gel as known in the art (See e.g., Sambrook et al., 1989).

Figure 3:
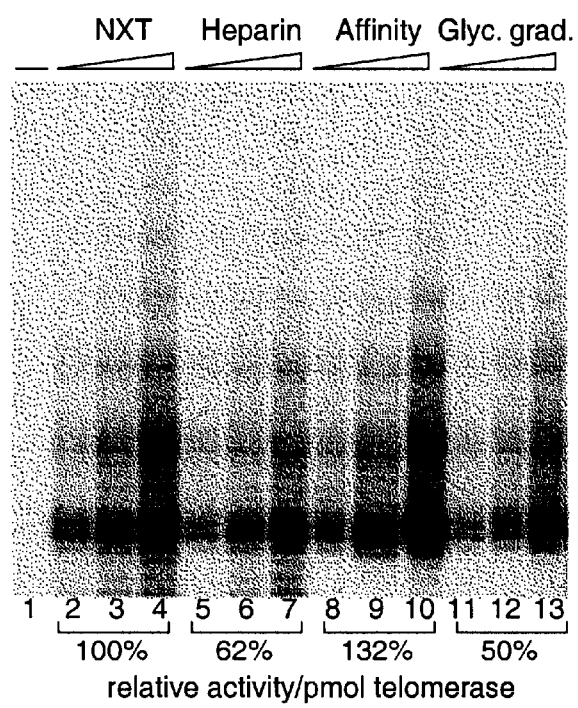
FIG. 3 shows telomerase activity through the purification protocol.

The results of this study are shown in FIG. 3. In lane 1, there is no telomerase present (i.e., a negative control); lanes 2, 5, 8, and 11 contained 0.14 fmol telomerase; lanes 3, 6, 9, and 12 contained 0.42 fmol telomerase; and lanes 4, 7, 10, and 13 contained 1.3 fmol telomerase. Activity was quantified using a PhosphorImager (Molecular Dynamics) using the manufacturer's instructions. It was determined that under these conditions, 1 fmol of affinity-purified telomerase incorporated 21 fmol of dTTP in 30 minutes.

As shown in this figure, the specific activity of the telomerase did not change significantly through the purification procedure. Affinity-purified telomerase was fully active. However, it was determined that at high concentrations, an inhibitory activity was detected and the activity of crude extracts was not linear. Thus, in the assay shown in FIG. 3, the crude extract was diluted 700–7000-fold. Upon purification, this inhibitory activity was removed and no inhibitory effect was detected in the purified telomerase preparations, even at high enzyme concentrations.

EXAMPLE 6

Gel Electrophoresis and Northern Blots

As indicated in Example 4, at each step in the purification of telomerase, the preparation was analyzed by three separate assays. This Example describes the gel electrophoresis and blotting procedures used to quantify telomerase RNA present in fractions and analyze the integrity of the telomerase ribonucleoprotein particle.

Denaturing Gels and Northern Blots

In this Example, synthetic T7-transcribed telomerase RNA of known concentration served as the standard. Throughout this investigation, the RNA component was used as a measure of telomerase.

A construct for phage T7 RNA polymerase transcription of *E. aediculatus* telomerase RNA was produced, using the polymerase chain reaction (PCR). The telomerase RNA gene was amplified with primers that annealed to either end of the gene. The primer that annealed at the 5' end also encoded a hammerhead ribozyme sequence to generate the natural 5' end upon cleavage of the transcribed RNA, a T7-promoter sequence, and an EcoRI site for subcloning. The sequence of this 5' primer was 5'-GCGGGAATTCT-AATACGACTCACTATAGGGAAGGAAACTCTGATG-AGGCCGAAAGGCCGAAACTCCACGAAAGTGGAG-TAAGTTTCTCGATAATTGATCTGTAG-3' (SEQ ID NO:31). The 3' primer included an EarI site for termination of transcription at the natural 3' end, and a BamHI site for cloning. The sequence of this 3' primer was 5'-CGGGGATCCTCTTCAAAAGATGAGAGGACAGC-AAAC-3' (SEQ ID NO:32). The PCR amplification product was cleaved with EcoRI and BamHI, and subcloned into the respective sites of pUC19 (NEB), to give "pEaT7." The correctness of this insert was confirmed by DNA sequencing. T7 transcription was performed as described by Zaug et al., Biochemistry 33:14935 [1994]), with EarI-linearized plasmid. RNA was gel-purified and the concentration was determined (an $A_{260}$ of 1=40 μg/ml). This RNA was used as a standard to determine the telomerase RNA present in various preparations of telomerase.

The signal of hybridization was proportional to the amount of telomerase RNA, and the derived RNA concentrations were consistent with, but slightly higher than those obtained by native gel electrophoresis. Comparison of the amount of whole telomerase RNA in whole cell RNA to serial dilutions of known T7 RNA transcript concentrations indicated that each *E. aediculatus* cell contained approximately 300,000 telomerase molecules.

Visualization of the telomerase was accomplished by Northern blot hybridization to its RNA component, using the methods described by Lingner et al. (Linger et al., Genes Develop., 8:1984 [1994]). Briefly, RNA (less than or equal to 0.5 μg/lane) was resolved on an 8% PAGE and electroblotted onto a Hybond-N membrane (Amersham), as known in the art (See e.g., Sambrook et al., 1989). The blot was hybridized overnight in 10 ml of 4×SSC, 10×Denhardt's solution, 0.1% SDS, and 50 μg/ml denatured herring sperm DNA,. After pre-hybridizing for 3 hours, $2 \times 10^6$ cpm probe/ml hybridization solution was added. The randomly labelled probe was a PCR-product that covered the entire telomerase RNA gene. The blot was washed with several buffer changes for 30 minutes in 2×SSC, 0.1% SDS, and then washed for 1 hour in 0.1×SSC and 0.1% SDS at 45° C.

Native Gels and Northern Blots

In this experiment, the purified telomerase preparation was run on native (i.e., non-denaturing) gels of 3.5% polyacrylamide and 0.33% agarose, as known in the art and described by Lamond and Sproat (Lamond and Sproat,

[1994], supra). The telomerase comigrated approximately with the xylene cyanol dye.

Figure 2:
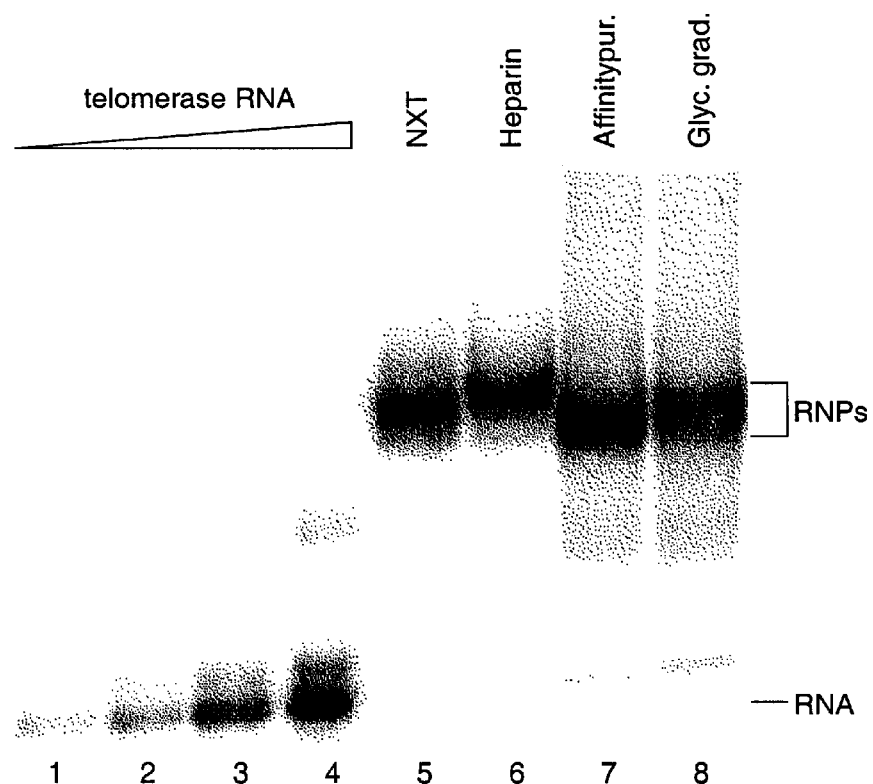
FIG. 2 is a photograph of a Northern blot of telomerase preparations obtained during the purification protocol.

The native gel results indicated that telomerase was maintained as an RNP throughout the purification protocol. FIG. 2 is a photograph of a Northern blot showing the mobility of the telomerase in different fractions on a non-denaturing gel as well as in vitro transcribed telomerase. In this figure, lane 1 contained 1.5 fmol telomerase RNA, lane 2 contained 4.6 fmol telomerase RNA, lane 3 contained 14 fmol telomerase RNA, lane 4 contained 41 fmol telomerase RNA, lane 5 contained nuclear extract (42 fmol telomerase), lane 6 contained Affi-Gel-heparin-purified telomerase (47 fmol telomerase), lane 7 contained affinity-purified telomerase (68 fmol), and lane 8 contained glycerol gradient-purified telomerase (35 fmol).

As shown in FIG. 2, in nuclear extracts, the telomerase was assembled into an RNP particle that migrated slower than unassembled telomerase RNA. Less than 1% free RNA was detected by this method. However, a slower migrating telomerase RNP complex was also sometimes detected in extracts. Upon purification on the Affi-Gel-heparin column, the telomerase RNP particle did not change in mobility (FIG. 2, lane 6). However, upon affinity purification the mobility of the RNA particle slightly increased (FIG. 2, lane 7), perhaps indicating that a protein subunit or fragment had been lost. On glycerol gradients, the affinity-purified telomerase did not change in size, but approximately 2% free telomerase RNA was detectable (FIG. 2, lane 8), suggesting that a small amount of disassembly of the RNP particle had occurred.

EXAMPLE 7
Telomerase Protein Composition

In this Example, the analysis of the purified telomerase protein composition are described.

Figure 4:
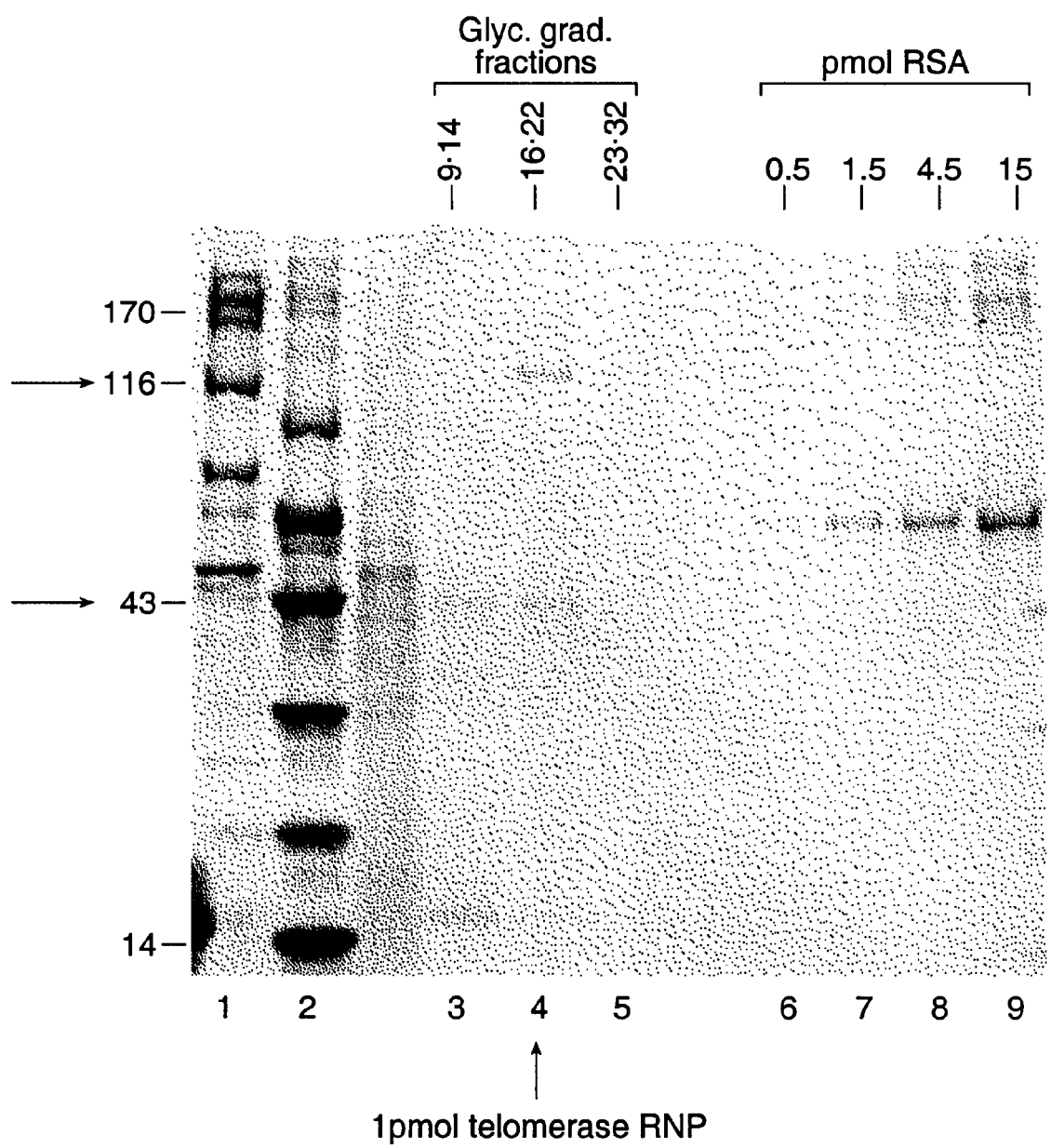
FIG. 4 is a photograph of a SDS-PAGE gel, showing the presence of an approximately 123 kDa polypeptide and an approximately 43 kDa doublet.

In this Example, glycerol gradient fractions obtained from Example 8, were separated on a 4–20% polyacrylamide gel (Novex). Following electrophoresis, the gel was stained with Coomassie brilliant blue. FIG. 4 shows a photograph of the gel. Lanes 1 and 2 contained molecular mass markers (Pharmacia) as indicated on the left side of the gel shown in FIG. 4. Lanes 3–5 contained glycerol gradient fraction pools as indicated on the top of the gel (i.e., lane 3 contained fractions 9–14, lane 4 contained fractions 15–22, and lane 5 contained fractions 23–32). Lane 4 contained the pool with 1 pmol of telomerase RNA. In lanes 6–9 BSA standards were run at concentrations indicated at the top of the gel in FIG. 4 (i.e., lane 6 contained 0.5 pmol BSA, lane 7 contained 1.5 pmol BSA, lane 8 contained 4.5 BSA, and lane 9 contained 15 pmol BSA).

As shown in FIG. 4, polypeptides with molecular masses of 120 and 43 kDa co-purified with the telomerase. The 43 kDa polypeptide was observed as a doublet. It was noted that the polypeptide of approximately 43 kDa in lane 3 migrated differently than the doublet in lane 4; it may be an unrelated protein. The 120 kDa and 43 kDa doublet each stained with Coomassie brilliant blue at approximately the level of 1 pmol, when compared with BSA standards. Because this fraction contained 1 pmol of telomerase RNA, all of which was assembled into an RNP particle (See, FIG. 2, lane 8), there appear to be two polypeptide subunits that are stoichiometric with the telomerase RNA. However, it is also possible that the two proteins around 43 kDa are separate enzyme subunits.

Affinity-purified telomerase that was not subjected to fractionation on a glycerol gradient contained additional polypeptides with apparent molecular masses of 35 and 37 kDa, respectively. This latter fraction was estimated to be at least 50% pure. However, the 35 kDa and 37 kDa polypeptides that were present in the affinity-purified material were not reproducibly separated by glycerol gradient centrifugation. These polypeptides may be contaminants, as they were not visible in all activity-containing preparations.

EXAMPLE 8
Sedimentation Coefficient

The sedimentation coefficient for telomerase was determined by glycerol gradient centrifugation. In this Example, nuclear extract and affinity-purified telomerase were fractionated on 15–40% glycerol gradients containing 20 mM Tris-acetate, with 1 mM $MgCl_2$, 0.1 mM EDTA, 300 mM KGlu, and 1 mM DTT, at pH 7.5. Glycerol gradients were poured in 5 ml (13×51 mm) tubes, and centrifuged using an SW55Ti rotor (Beckman) at 55,000 rpm for 14 hours at 4° C.

Marker proteins were run in a parallel gradient and had a sedimentation coefficient of 7.6 S for alcohol dehydrogenase (ADH), 113 S for catalase, 17.3 S for apoferritin, and 19.3 S for thyroglobulin. The telomerase peak was identified by native gel electrophoresis of gradient fractions followed by blot hybridization to its RNA component.

Figure 5:
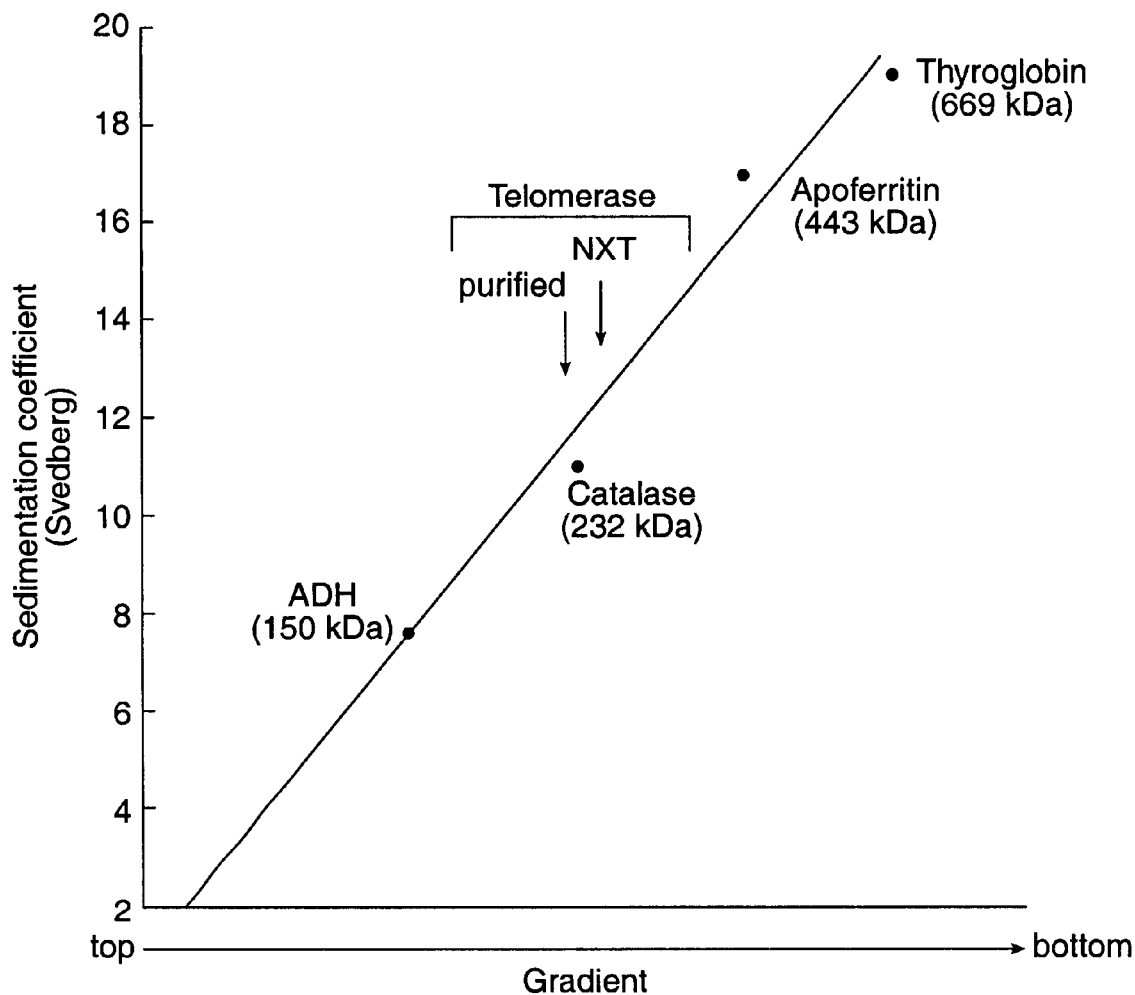
FIG. 5 is a graph showing the sedimentation coefficient of telomerase.

FIG. 5 is a graph showing the sedimentation coefficient for telomerase. As shown in this Figure, affinity-purified telomerase co-sedimented with catalase at 11.5 S, while telomerase in nuclear extracts sedimented slightly faster, peaking around 12.5 S. Therefore, consistent with the mobility of the enzyme in native gels, purified telomerase appears to have lost a proteolytic fragment or a loosely associated subunit.

The calculated molecular mass for telomerase, if it is assumed to consist of one 120 kDa protein subunit, one 43 kDa subunit, and one RNA subunit of 66 kDa, adds up to a total of 229 kDa. This is in close agreement with the 232 kDa molecular mass of catalase. However, the sedimentation coefficient is a function of the molecular mass, as well as the partial specific volume and the frictional coefficient of the molecule, both of which are unknown for the telomerase RNP.

EXAMPLE 9
Substrate Utilization

In this Example, the substrate requirements of telomerase were investigated. One simple model for DNA end replication predicts that after semi-conservative DNA replication, telomerase extends double-stranded, blunt-ended DNA molecules. In a variation of this model, a single-stranded 3' end is created by a helicase or nuclease after replication. This 3' end is then used by telomerase for binding and extension.

To determine whether telomerase is capable of elongating blunt-ended molecules, model hairpins were synthesized with telomeric repeats positioned at their 3' ends. These primer substrates were gel-purified, 5'-end labelled with polynucleotide kinase, heated at 0.4 μM to 80° C. for 5 minutes, and then slowly cooled to room temperature in a heating block, to allow renaturation and helix formation of the hairpins. Substrate mobility on a non-denaturing gel indicated that very efficient hairpin formation was present, as compared to dimerization.

In this Example, assays were performed with unlabelled 125 μM dGTP, 125 μM dTTP, and 0.02 μM 5'-end-labelled primer (5'-$^{32}$P-labelled oligonucleotide substrate) in 10 μl reaction mixtures that contained 20 mM Tris-acetate, with 10 mM $MgCl_2$, 50 mM KGlu, and 1 mM DTT, at pH 7.5. These mixtures were incubated at 25° C. for 30 minutes. Reactions were stopped by adding formamide loading buffer (i.e., TBE, formamide, bromthymol blue, and cyanol, Sambrook, 1989, supra).

Primers were incubated without telomerase ("−"), with 5.9 fmol of affinity-purified telomerase ("+"), or with 17.6 fmol of affinity-purified telomerase ("+++"). Affinity-purified telomerase used in this assay was dialyzed with a membrane having a molecular cut-off of 100 kDa, in order to remove the displacement oligonucleotide. Reaction products were separated on an 8% PAGE/urea gel containing 36% formamide, to denature the hairpins. The sequences of the primers used in this study, as well as their lane assignments are shown in Table 2.

TABLE 2

Primer Sequences

| Lane | Primer Sequence (5' to 3') | SEQ ID NO: |
|---|---|---|
| 1–3 | $C_4(A_4C_4)_3CACA(G_4T_4)_3G_4$ | SEQ ID NO:33 |
| 4–6 | $C_2(A_4C_4)_3CACA(G_4T_4)_3G_4$ | SEQ ID NO:34 |
| 7–9 | $(A_4C_4)_3CACA(G_4T_4)_3G_4$ | SEQ ID NO:35 |
| 10–12 | $A_2C_4(A_4C_4)_2CACA(G_4T_4)_3G_4$ | SEQ ID NO:36 |
| 13–15 | $C_4(A_4C_4)_2CACA(G_4T_4)_3$ | SEQ ID NO:37 |
| 16–18 | $(A_4C_4)_3CACA(G_4T_4)_3$ | SEQ ID NO:38 |
| 19–21 | $A_2C_4(A_4C_4)_2CACA(G_4T_4)_3$ | SEQ ID NO:39 |
| 22–24 | $C_4(A_4C_4)_2CACA(G_4T_4)_3$ | SEQ ID NO:40 |
| 25–27 | $C_2(A_4C_4)_2CACA(G_4T_4)_3$ | SEQ ID NO:41 |
| 28–30 | $(A_4C_4)_2CACA(G_4T_4)_3$ | SEQ ID NO:42 |

Figure 6:
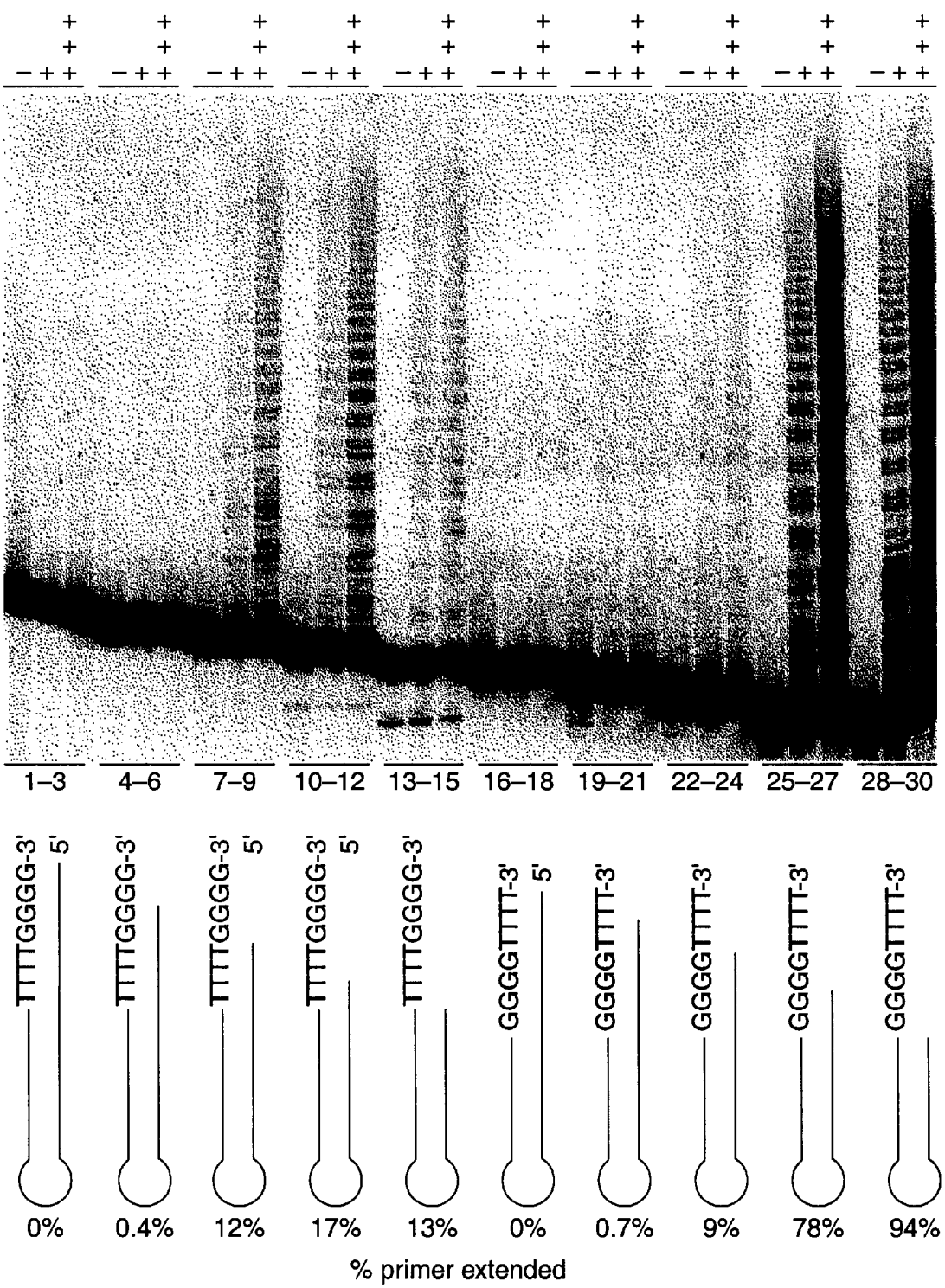
FIG. 6 is a photograph of a polyacrylamide/urea gel with 36% formamide.

The gel results are shown in FIG. 6. Lanes 1–15 contained substrates with telomeric repeats ending with four G residues. Lanes 16–30 contained substrates with telomeric repeats ending with four T residues. The putative alignment on the telomerase RNA template is indicated in FIG. 7 (SEQ ID NOS:43 and 44, and 45 and 46, respectively). It was assumed that the primer sets anneal at two very different positions in the template shown in FIG. 7 (i.e., 7A and 7B, respectively). This may have affected their binding and/or elongation rate.

Figure 8:
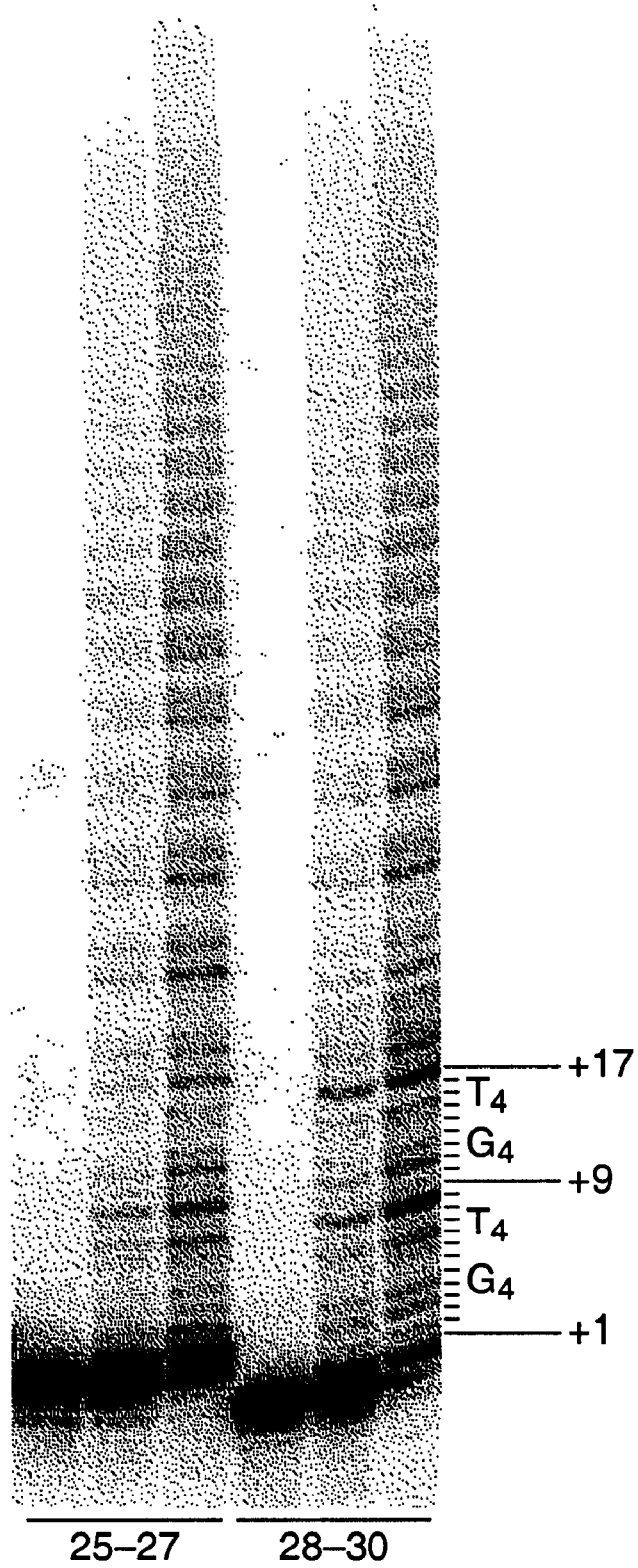
FIG. 8 is a photograph of lanes 25–30 of the gel shown in FIG. 6, shown at a lighter exposure level.

FIG. 8 shows a lighter exposure of lanes 25–30 in FIG. 6. The lighter exposure of FIG. 8 was taken in order to permit visualization of the nucleotides that are added and the positions of pausing in elongated products. Percent of substrate elongated for the third lane in each set was quantified on a PhosphorImager, as indicated on the bottom of FIG. 6.

The substrate efficiencies for these hairpins were compared with double-stranded telomere-like substrates with overhangs of differing lengths. A model substrate that ended with four G residues (see lanes 1–15 of FIG. 6), was not elongated when it was blunt ended (see lanes 1–3). However, slight extension was observed with an overhang length of two bases; elongation became efficient when the overhang was at least 4 bases in length. The telomerase acted in a similar manner with a double-stranded substrate that ended with four T residues, with a 6-base overhang required for highly efficient elongation. In FIG. 6, the faint bands below the primers in lanes 10–15 that are independent of telomerase represent shorter oligonucleotides in the primer preparations.

The lighter exposure of lanes 25–30 in FIG. 8 shows a ladder of elongated products, with the darkest bands correlating with the putative 5' boundary of the template (as described by Lingner et al., Genes Develop., 8:1984 [1994]). The abundance of products that correspond to other positions in the template suggested that pausing and/or dissociation occurs at sites other than the site of translocation with the purified telomerase.

As shown in FIG. 6, double-stranded, blunt-ended oligonucleotides were not substrates for telomerase. To determine whether these molecules would bind to telomerase, a competition experiment was performed. In this experiment, 2 nM of 5'-end labelled substrate with the sequence $(G_4T_4)_2$ (SEQ ID NO:61), or a hairpin substrate with a six base overhang respectively were extended with 0.125 nM telomerase (FIG. 6, lanes 25–27). Although the same unlabeled oligonucleotide substrates competed efficiently with labelled substrate for extension, no reduction of activity was observed when the double-stranded blunt-ended hairpin oligonucleotides were used as competitors, even in the presence of 100-fold excess hairpins.

These results indicated that double-stranded, blunt-ended oligonucleotides cannot bind to telomerase at the concentrations tested in this Example. Rather, a single-stranded 3' end is required for binding. It is likely that this 3' end is required to base pair with the telomerase RNA template.

EXAMPLE 10

Cloning & Sequencing of the 123 kDa Polypeptide

In this Example, the cloning of the 123 kDa polypeptide of telomerase (i.e., the 123 kDa protein subunit) is described. In this study, an internal fragment of the telomerase gene was amplified by PCR, with oligonucleotide primers designed to match peptide sequences that were obtained from the purified polypeptide obtained in Example 3, above. The polypeptide sequence was determined using the nanoES tandem mass spectroscopy methods known in the art and described by Calvio et al., RNA 1:724–733 [1995]). The oligonucleotide primers used in this Example had the following sequences, with positions that were degenerate shown in parentheses—5'-TCT(G/A)AA(G/A) TA(G/A)TG(T/G/A)GT(G/A/T/C)A(T/G/A)(G/A)TT(G/A) TTCAT-3' (SEQ ID NO:47), AND 5'-GCGGATCCATGAA (T/C)CC(A/T)GA(G/A)AA(T/C)CC(A/T)AA(T/C)GT-3' (SEQ ID NO:48).

A 50 $\mu$l reaction contained 0.2 mM dNTPs, 0.15 $\mu$g E. aediculatus chromosomal DNA, 0.5 $\mu$l Taq (Boehringer-Mannheim), 0.8 $\mu$g of each primer, and 1×reaction buffer (Boehringer-Mannheim). The reaction was incubated in a thermocycler (Perkin-Elmer), using the following—5 minutes at 95° C., followed by 30 cycles of 1 minute at 94° C., 1 minute at 52° C., and 2 minutes at 72° C. The reaction was completed by 10 minute incubation at 72° C.

A genomic DNA library was prepared from the chromosomal E. aediculatus DNA by cloning blunt-ended DNA into the SmaI site of pCR-Script plasmid vector (Stratagene). This library was screened by colony hybridization, with the radiolabelled, gel-purified PCR product. Plasmid DNA of positive clones was prepared and sequenced by the dideoxy method (Sanger el al., Proc. Natl. Acad. Sci., 74:5463 [1977]) or manually, through use of an automated sequencer (ABI). The DNA sequence of the gene encoding this polypeptide is shown in FIG. 9 (SEQ ID NO:1). The start codon in this sequence inferred from the DNA sequence, is located at nucleotide position 101, and the open reading frame ends at position 3193. The genetic code of Euplotes differs from other organisms in that the "UGA" codon encodes a cysteine residue. The amino acid sequence of the polypeptide inferred from the DNA sequence is shown in FIG. 10 (SEQ ID NO:2), and assumes that no unusual amino acids are inserted during translation and no post-translational modification occurs.

EXAMPLE 11

Cloning & Sequencing of the 43 kDa Polypeptide

In this Example, the cloning of the 43 kDa polypeptide of telomerase (i.e., the 43 kDa protein subunit) is described. In this study, an internal fragment of the telomerase gene was amplified by PCR, with oligonucleotide primers designed to match peptide sequences that were obtained from the purified polypeptide obtained in Example 3, above . The polypeptide sequence was determined using the nanoES tandem mass spectroscopy methods known in the art and described by Calvio et al., RNA 1:724–733 [1995]). The oligonucleotide primers used in this Example had the following sequences—5'-NNNGTNAC(C/T/A)GG(C/T/A)AT(C/T/A)AA(C/T)AA-3' (SEQ ID NO:49), and 5'-(T/G/A)GC(T/G/A)GT(C/T)TC(T/C)TG(G/A)TC(G/A)TT(G/A)TA-3' (SEQ ID NO:50). In this sequence, "N" indicates the presence of any of the four nucleotides (i. e., A, T, G, or C).

A 50 μl reaction contained 0.2 mM dNTPs, 0.2 μg *E. aediculatus* chromosomal DNA, 0.5 μl Taq (Boehringer-Mannheim), 0.8 μg of each primer, and 1×reaction buffer (Boehringer-Mannheim). The reaction was incubated in a thermocycler (Perkin-Elmer), using the following—5 minutes at 95° C., followed by 30 cycles of 1 minute at 94° C., 1 minute at 52° C., and 1 minutes at 72° C. The reaction was completed by 10 minute incubation at 72° C.

A genomic DNA library was prepared from the chromosomal *E. aediculatus* DNA by cloning blunt-ended DNA into the SmaI site of pCR-Script plasmid vector (Stratagene). This library was screened by colony hybridization, with the radiolabelled, gel-purified PCR product. Plasmid DNA of positive clones was prepared and sequenced by the dideoxy method (Sanger et al, Proc. Natl. Acad. Sci., 74:5463 [1977]) or manually, through use of an automated sequencer (ABI). The DNA sequence of the gene encoding this polypeptide is shown in FIG. 11 (SEQ ID NO:3). Three potential reading frames are shown for this sequence, as shown in FIG. 12. For clarity, the amino acid sequence is indicated below the nucleotide sequence in all three reading frames. These reading frames are designated as "a," "b," and "c" (SEQ ID NOS:4–6). A possible start codon is encoded at nucleotide position 84 in reading frame "c." They coding region could end at position 1501 in reading frame "b." Early stop codons, indicated by asterisks in this figure, occur in all three reading frames between nucleotide position 337–350.

The "La-domain" is indicated in bold-face type. Further downstream, the protein sequence appears to be encoded by different reading frames, as none of the three frames is uninterrupted by stop codons. Furthermore, peptide sequences from purified protein are encoded in all three frames. Therefore, this gene appears to contain intervening sequences, or in the alternative, the RNA is edited. Other possibilities include ribosomal frame-shifting or sequence errors. However, the homology to the La-protein sequence remains of significant interest. Again, in Euplotes, the "UGA" codon encodes a cysteine residue.

EXAMPLE 12
Amino Acid and Nucleic Acid Comparisons

In this Example, comparisons between various reported sequences and the sequences of the 123 kDa and 43 kDa telomerase subunit polypeptides were made.

Comparisons with the 123 kDa *E. aediculatus* Telomerase Subunit

The amino acid sequence of the 123 kDa *Euplotes aediculatus* polypeptide was compared with the sequence of the 80 kDa telomerase protein subunit of *Tetrahymena thermophila* (GenBank accession #U25641) in order to investigate their similarity. The nucleotide sequence as obtained from GenBank (SEQ ID NO:51) encoding this protein is shown in FIG. 19. The amino acid sequence of this protein as obtained from GenBank (SEQ ID NO:52) is shown in FIG. 20. The sequence comparison between the 123 kDa *E. aediculatus* and 80 kDa *T. thermophila* is shown in FIG. 13. In this figure, the *E. aediculatus* sequence is the upper sequence (SEQ ID NO:2), while the *T. thermophila* sequence is the lower sequence (SEQ ID NO:52). In this Figure, as well as FIGS. 14–16, identities are indicated by vertical bars, while single dots between the sequences indicate somewhat similar amino acids, and double dots between the sequences indicate more similar amino acids. The observed identity was determined to be approximately 19%, while the percent similarity was approximately 45%, values similar to what would be observed with any random protein sequence.

The amino acid sequence of the 123 kDa *Euplotes aediculatus* polypeptide was also compared with the sequence of the 95 kDa telomerase protein subunit of *Tetrahymena thermophilia* (GenBank accession #U25642), in order to investigate their similarity. The nucleotide sequence as obtained from GenBank (SEQ ID NO:53) encoding this protein is shown in FIG. 21. The amino acid sequence of this protein as obtained from GenBank (SEQ ID NO:54) is shown in FIG. 22. This sequence comparison is shown in FIG. 14. In this figure, the *E. aediculatus* sequence is the upper sequence (SEQ ID NO:2), while the *T. thermophila* sequence is the lower sequence (SEQ ID NO:54); identities are indicated by vertical bars. The observed identity was determined to be approximately 20%, while the percent similarity was approximately 43%, values similar to what would be observed with any random protein sequence.

Significantly, the amino acid sequence of the 123 kDa *E. aediculatus* polypeptide contains the five motifs (SEQ ID NOS:13 and 18) characteristic of reverse transcriptases. The 123 kDa polypeptide was also compared with the polymerase domains of various reverse transcriptases (SEQ ID NOS:14–17, and 19–22). FIG. 17 shows the alignment of the 123 kDa polypeptide with the putative yeast homolog (L8543.12 or ESTp)(SEQ ID NOS: 17 and 22). The amino acid sequence of L8543.12 (or ESTp) obtained from GenBank is shown in FIG. 23 (SEQ ID NO:55).

Four motifs (A, B, C, and D) were included in this comparison. In this FIG. 17, highly conserved residues are indicated by white letters on a black background. Residues of the *E. aediculatus* sequences that are conserved in the other sequence are indicated in bold; the "h" indicates the presence of a hydrophobic amino acid. The numerals located between amino acid residues of the motifs indicates the length of gaps in the sequences. For example, the "100" shown between motifs A and B reflects a 100 amino acid gap in the sequence between the motifs.

Genbank searches identified a yeast protein (Genbank accession #u20618), and gene "L8543.12" (Est2), containing amino acid sequence that shows some homology to the *E. aediculatus* 123 kDa telomerase subunit. Based on the observations that both proteins contain reverse transcriptase motifs in their C-terminal regions; both proteins share similarity in regions outside the reverse transcriptase motif; the proteins are similarly basic (pI=10.1 for *E. aediculatus* and pI=10.0 for the yeast); and both proteins are large (123 kDa for *E. aediculatus* and 103 kDa for the yeast), these sequences comprise the catalytic core of their respective telomerases. It is contemplated that based on this observation of homology in two phylogenetically distinct organisms as *E. aediculatus* and yeast, the human telomerase will contain a protein that has the same characteristics (i.e., reverse transcriptase motifs, is basic, and large [>100 kDa]).

Comparisons with the 43 kDa *E. aediculatus* Telomerase Subunit

The amino acid sequence of the "La-domain" of the 43 kDa *Euplotes aediculatus* polypeptide was compared with the sequence of the 95 kDa telomerase protein subunit of *Tetrahymena thermophilia* (described above) in order to investigate their similarity. This sequence comparison is shown in FIG. 15. In this figure, the E. aediculatus sequence is the upper sequence (SEQ ID NO:9), while the T. thermophila sequence is the lower sequence (SEQ ID NO:10); identities are indicated by vertical bars. The observed identity was determined to be approximately 23%, while the percent similarity was approximately 46%, values similar to what would be observed with any random protein sequence.

The amino acid sequence of the "La-domain" of the 43 kDa Euplotes aediculatus polypeptide was compared with the sequence of the 80 kDa telomerase protein subunit of Tetrahymena thermophila (described above) in order to investigate their similarity. This sequence comparison is shown in FIG. 16. In this figure, the E. aediculatus sequence is the upper sequence (SEQ ID NO:11), while the T. thermophila sequence is the lower sequence (SEQ ID NO:12); identities are indicated by vertical bars. The observed identity was determined to be approximately 26%, while the percent similarity was approximately 49%, values similar to what would be observed with any random protein sequence.

The amino acid sequence of a domain of the 43 kDa E. aediculatus polypeptide (SEQ ID NO:23) was also compared with La proteins from various other organisms (SEQ ID NOS:24–27). These comparisons are shown in FIG. 18. In this Figure, highly conserved residues are indicated by white letters on a black background. Residues of the E. aediculatus sequences that are conserved in the other sequence are indicated in bold.

EXAMPLE 13
Identification of Telomerase Protein Subunits in Another Organism

In this Example, the sequences identified in the previous Examples above, were used to identify the telomerase protein subunits of Oxytricha trifallax, a ciliate that is very distantly related to E. aediculatus. In this Example, primers were chosen based on the conserved region of the E. aediculatus 123 kDa polypeptide which comprised the reverse transcriptase domain motifs. Suitable primers were synthesized and used in a PCR reaction with total DNA from Oxytricha. The Oxytricha DNA was prepared according to methods known in the art. The PCR products were then cloned and sequenced using methods known in the art.

The oligonucleotide sequences used as the primers were as follows: 5'-(T/C)A(A/G)AC(T/A/C)AA(G/A)GG(T/A/C)AT(T/C)CC(C/T/A)(C/T)A(G/A)GG-3' (SEQ ID NO:56) and 5'-(G/A/T)GT(G/A/T)ATNA(G/A)NA(G/A)(G/A)TA(G/A)TC(G/A)TC-3' (SEQ ID NO:57). Positions that were degenerate are shown in parenthesis, with the alternative bases shown within the parenthesis. "N" represents any of the four nucleotides.

In the PCR reaction, a 50 µl reaction contained 0.2 mM dNTPs, 0.3 µg Oxytricha trifallax chromosomal DNA, 1 µl Taq polymerase (Boehringer-Mannheim), 2 micromolar of each primer, 1×reaction buffer (Boehringer-Mannheim). The reaction was incubated in a thermocycler (Perkin-Elmer) under the following conditions: 1×5 min at 95° C., 30 cycles consisting of 1 min at 94° C., 1 min at 53° C., and 1 min at 72° C., followed by 1×10 min at 72° C. The PCR-product was gel-purified and sequenced by the dideoxy-method, by methods known well in the art (e.g., Sanger et al, Proc. Natl. Acad. Sci. 74, 5463–5467 (1977).

The deduced amino acid sequence of the PCR product was determined and compared with the E. aediculatus sequence. FIG. 24 shows the alignment of these sequences, with the O. trifallax sequence (SEQ ID NO:58) shown in the top row, and the E. aediculatus sequence (SEQ ID NO:59) shown in the bottom row. As can be seen from this Figure, there is a great deal of homology between the O. trifallax polypeptide sequence identified in this Example with the E. aediculatus polypeptide sequence. Thus, it is clear that the sequences identified in the present invention are useful for the identification of homologous telomerase protein subunits in other eukaryotic organisms. Indeed, development of the present invention has identified homologous telomerase sequences in multiple, diverse species.

EXAMPLE 15
Identification of Tetrahymena Telomerase Sequences

In this Example, a Tetrahymena clone was produced that shares homology with the Euplotes sequences, and EST2p.

This experiment utilized PCR with degenerate oligonucleotide primers directed against conserved motifs to identify regions of homology between Tetrahymena, Euplotes, and EST2p sequences. The PCR method used in this Example is a novel method that is designed to specifically amplify rare DNA sequences from complex mixtures. This method avoids the problem of amplification of DNA products with the same PCR primer at both ends (i.e., single primer products) commonly encountered in PCR cloning methods. These single primer products produce unwanted background and can often obscure the amplification and detection of the desired two-primer product. The method used in these experiment preferentially selects for two-primer products. In particular, one primer is biotinylated and the other is not. After several rounds of PCR amplification, the products are purified using streptavidin magnetic beads and two primer products are specifically eluted using heat denaturation. This method finds use in settings other than the experiments described in this Example. Indeed, this method finds use in application in which it is desired to specifically amplify rare DNA sequences, including the preliminary steps in cloning methods such as 5' and 3; RACE, and any method that uses degenerate primers in PCR.

A first PCR run was conducted using Tetrahymena template macronuclear DNA isolated using methods known in the art, and the 24-mer forward primer with the sequence 5' biotin-GCCTATTT(TC)TT(TC)TA(TC)(GATC)(GATC)(GATC)AC(GATC)GA-3' (SEQ ID NO:70) designated as "K231," corresponding to the FFYXTE region (SEQ ID NO:71), and the 23-mer reverse primer with the sequence 5'-CCAGATAT(GATC)A(TGA)(GATC)A(AG)AA(AG)TC(AG)TC-3' (SEQ ID NO:72), designated as "K220," corresponding to the DDFL(FIL)I region (SEQ ID NO:73). This PCR reaction contained 2.5 µl DNA (50 ng), 4 µl of each primer (20 µM), 3 µl 10×PCR buffer, 3 µl 10×dNTPs, 2 µl Mg, 0.3 µl Taq, and 11.2 µl dH$_2$O. The mixture was cycled for 8 cycles of 94° C. for 45 seconds, 37° C. for 45 seconds, and 72 ° C. for 1 minute.

This PCR reaction was bound to 200 µl streptavidin magnetic beads, washed with 200 µl TE, resuspended in 20 µl dH$_2$O and then heat-denatured by boiling at 100° C. for 2 minutes. The beads were pulled down and the eluate removed. Then, 2.5 µl of this eluate was subsequently reamplified using the above conditions, with the exception being that 0.3 µl of α-$^{32}$P dATP was included, and the PCR was carried out for 33 cycles. This reaction was run a 5% denaturing polyacrylamide gel, and the appropriate region was cut out of the gel. These products were then reamplified for an additional 34 cycles, under the conditions listed above, with the exception being that a 42° C. annealing temperature was used.

A second PCR run was conducted using Tetrahymena macronuclear DNA template isolated using methods known in the art, and the 23-mer forward primer with the sequence 5'ACAATG(CA)G(GATC)(TCA)T(GATC)(TCA)T(GATC)

CC(GATC)AA(AG)AA-3' (SEQ ID NO:74), designated as "K228," corresponding to the region R(LI)(LI)PKK (SEQ ID NO:75), and a reverse primer with the sequence 5'-ACGAATC(GT)(GATC)GG(TAG)AT(GATC)(GC)(TA)(AG)TC(AG)TA(AG)CA 3' (SEQ ID NO:76), designated "K224," corresponding to the CYDSIPR region (SEQ ID NO:77). This PCR reaction contained 2.5 µl DNA (50 ng), 4 µl of each primer (20 µM), 3 µl 10×PCR buffer, 3 µl 10×dNTPs, 2 µl Mg, 0.3 µl α-$^{32}$dATP, 0.3 µl Taq, and 10.9 µl dH$_2$O. This reaction was run on a 5% denaturing polyacrylamide gel, and the appropriate region was cut out of the gel. These products were reamplified for an additional 34 cycles, under the conditions listed above, with the exception being that a 42° C. annealing temperature was used.

Ten µl of the reaction product from run 1 were bound to streptavidin-coated magnetic beads in 200 µl TE. The beads were washed with 200 µl TE, and then then resuspended in 20 µl of dH$_2$O, heat denatured, and the eluate was removed. Next, 2.5 µl of this eluate was reamplified for 33 cycles using the conditions indicated above. The reaction product from run 2 was then added to the beads and diluted with 30 µl 0.5×SSC. The mixture was heated from 94° C. to 50° C. The eluate was removed and the beads were washed three times in 0.5×SSC at 55° C. The beads were then resuspended in 20 µl dH$_2$O, heat denatured, and the eluate was removed, designated as "round 1 eluate" and saved.

To isolate the Tetrahymena band, the round 1 eluate was reamplified with the forward primer K228 (SEQ ID NO:74) and reverse primer K227 (SEQ ID NO:78) with the sequence 5'-CAATTCTC(AG)TA(AG)CA(GATC)(CG)(TA)(CT)TT(AGT)AT(GA)TC-3' (SEQ ID NO:78), corresponding to the DIKSCYD region (SEQ ID NO:79). The PCR reactions were conducted as described above. The reaction products were run on a 5% polyacrylamide gel; the band corresponding to approximately 295 nucleotides was cut from the gel and sequenced.

The clone designated as 168-3 was sequenced. The DNA sequence (including the primer sequences) was found to be: GATTACTCCCGAAGAAAGGATCTTTC-CGTCCAATCATGACTTTCTTAAGAAAG GACAAG-CAAAAAAATATTAAGTTAAATCTAAAT-TAAATTCTAATGGATAGCC AACTTGTGTTTAGGAATTTAAAAGACAT-GCTGGGATAAAACATAGGATACTC AGTCTTTGATAATAAACAAATTTCA-GAAAAATTTGCCTAATTCATAGAGAAA TGGAAAAATAAAGGAAGACCTCAGC-TATATTATGTCACTCTAGACATAAAGA CTTGCTAC (SEQ ID NO:80).

Additional sequence of this gene was obtained by PCR using one unique primer designed to match the sequence from 168-3 ("K297" with the sequence 5'-GACTGACATAATATACGTGA-3'; SEQ ID NO:111), and the K231 (FFYXTE) primer. The sequence of the fragment obtained from this reaction, together with 168-3 is as follows (without the primer sequences): AAACACAAG-GAAGGAAGTCAAATATTCTATTACCG-TAAACCAATATGGAAAT TAGTGAGTAAATTAACTAT-TGTCAAAGTAAGAATTTAGTTTTCTGAAAAGAA TAAATAAATGAAAAATAATTTTTAT-CAAAAAATTTAGCTTGAAGAGGAGAAT TTG-GAAAAAGTTGAAGAAAAATTGATACCA-GAAGATTCATTTTAGAAATACC CTCAAGGAAAGCTAAGGATTATAC-CTAAAAAAGGATCTTTCCGTCCAATCAT GACTTTCTTAAGAAAGGACAAG-CAAAAAAATATTAAGTTAAATCTAAATTAA ATTCTAATGGATAGCCAACTTGTGTT-TAGGAATTTAAAAGACATGCTGGGAT AAAAGAT-AGGATACTCAGTCTTTGATAATAAA-CAAATTTCAGAAAAATTTGC CTAATTCATAGAGAAATG-GAAAAATAAAGGAAGACCTCAGCTATATTATGTC ACTCTA (SEQ ID NO:81).

The amino acid sequence corresponding to this DNA fragment was found to be: KHKEGSQIFYYRKPI-WKLVSKLTIVKVRIQFSEKNKQMKNN-FYQKIQLEEENLEK VEEKLIPEDSFQKYPQGKLRIIP-KKGSFRPIMTFLRKDKQKNIKLNLNQILMDSQL VFRNLKDMLGQKIGYSVFDNKQISEK-FAQFIEKWKNKGRPQLYYVTL (SEQ ID NO:82).

This amino acid sequence was then aligned with other telomerase (genes (EST2p, and Euplotes). The alignment is shown in FIG. 31. Consensus sequence is also shown in this Figure.

EXAMPLE 16

Identification of *Schizosaccharomyces pombe* Telomerase Sequences

In this Example, the tez1 sequence of *S. pomnbe* was identified as a homolog of the *E aediculatus* p123, and *S. cerevisiae* Est2p.

Figure 33A:
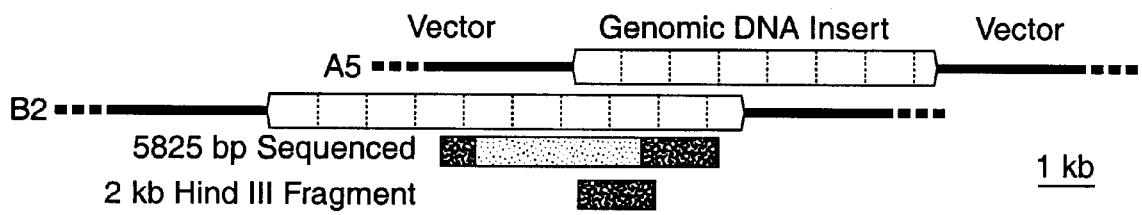
FIG. 33 is a schematic summary of the tez1+ sequencing experiments.
Figure 33B:
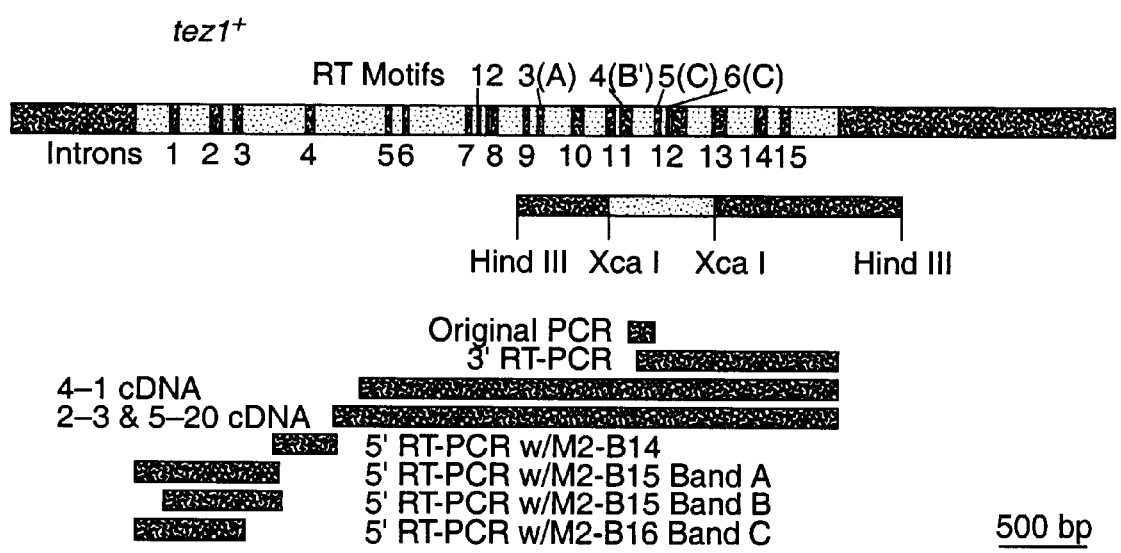

FIG. 33 provides an overall summary of these experiments. In this Figure, the top portion (Panel A) shows the relationship of two overlapping genomic clones, and the 5825 bp portion that was sequenced. The region designated at "tez1$^+$" is the protein coding region, with the flanking sequences indicated as well, the box underneath the 5825 bp region is an approximately 2 kb HindIII fragment that was used to make tez1 disruption construct, as described below.

The bottom half of FIG. 33 (Panel B) is a "close-up" schematic of this same region of DNA. The sequence designated as "original PCR" is the original degenerate PCR fragment that was generated with degenerate oligonucleotide primer pair designed based on Euplotes sequence motif 4 (B') and motif 5 (C), as described in previous Examples.

PCR With Degenerate Primers

Figure 35:
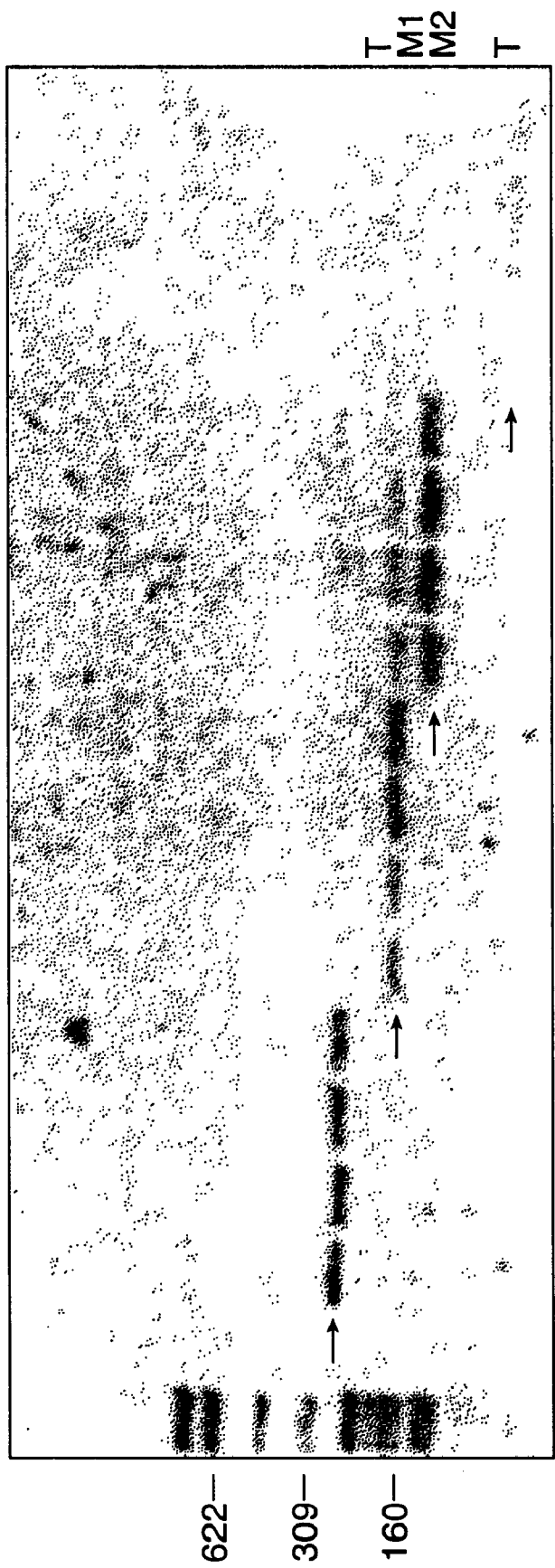
FIG. 35 (SEQ ID NO: 119, 121) shows the four major bands produced in PCR using the degenerate primers.

PCR using degenerate primers was used to find the homolog of the *E. aediculatus* p123 in *S. pombe*. FIG. 34 shows the sequences of the degenerate primers (designated as "poly 4" and "poly 1") used in this reaction. The PCR runs were conducted using the same buffer as described in previous Examples (See e.g., Example 10, above), with a 5 minute ramp time at 94° C., followed by 30 cycles of 94° C. for 30 seconds, 50° C. for 45 seconds, and 72° C. for 30 seconds, and 7 minutes at 72° C., followed by storage at 4° C. PCR runs were conducted using varied conditions, (i.e., various concentrations of *S. pombe* DNA and MgCl$_2$ concentrations). The PCR products were run on agarose gels and stained with ethidium bromide as described above. Several PCR runs resulted in the production of three bands (designated as "T," "M," and "B"). These bands were re-amplified and run on gels using the same conditions as described above. Four bands were observed following this re-amplification ("T," "M1," "M2," and "B"), as shown in FIG. 35. These four bands were then re-amplified using the same conditions as described above. The third band from the top of the lane in FIG. 35 was identified as containing the correct sequence for telomerase protein. The PCR product designated as M2 was found to show a reasonable match with other telomerase proteins, as indicated in FIG. 36. In addition to the alignment shown, this Figure also shows the actual sequence of tez1. In this Figure, the asterisks indicate residues shared with all four sequences (Oxytricha "Ot"; *E. aediculatus* "Ea_p123"; *S. cerevisiae* "Sc_p103"; and M2), while the circles (i.e., dots) indicate similar amino acid residues.

3' RT PCR

Figure 37:
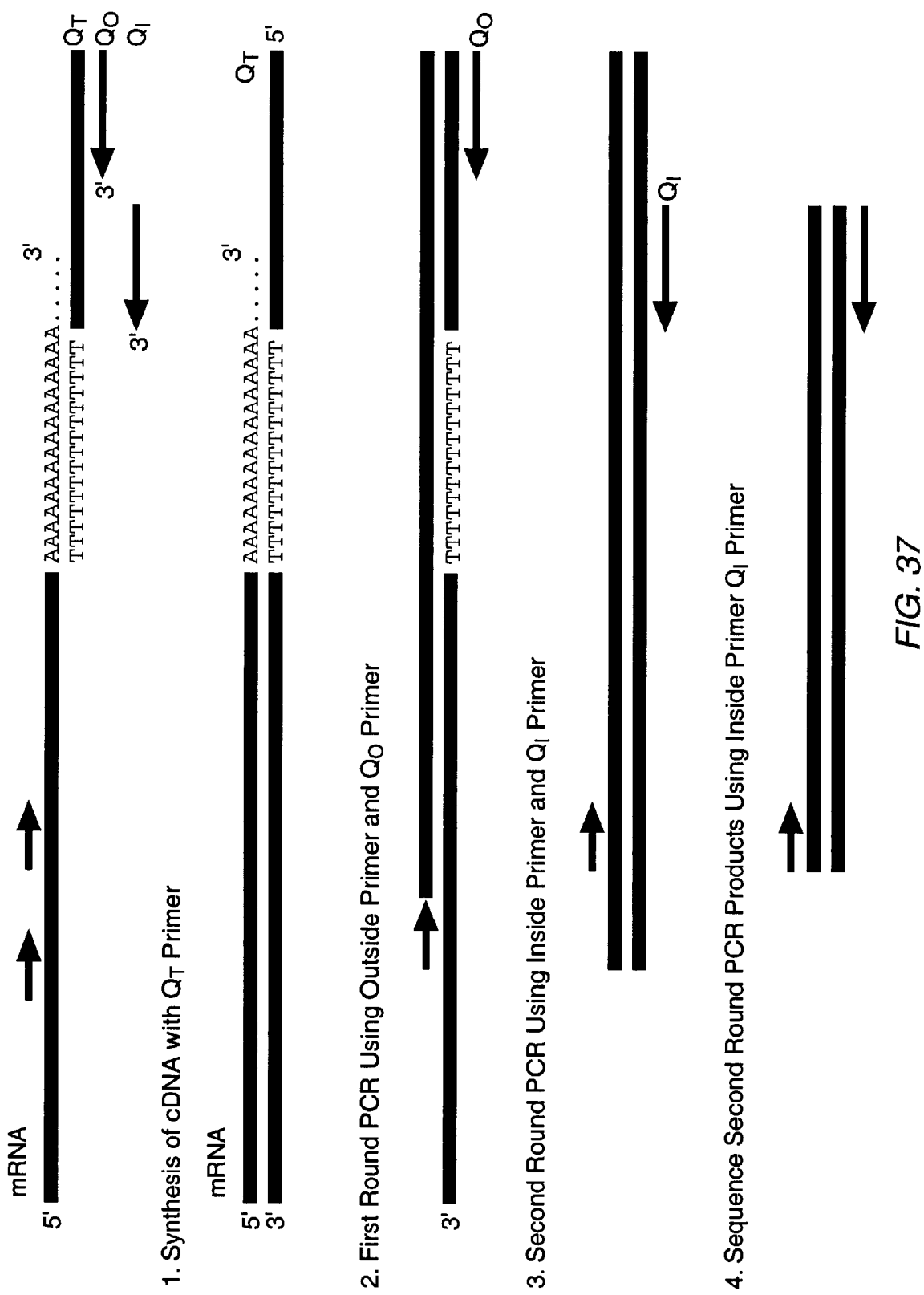
FIG. 37 (SEQ ID NOS: 131–132) is a schematic showing the 3' RT PCR strategy.

In order to obtain additional sequence information, 3' and 5' RT PCR were conducted on the telomerase candidate identified in FIG. 36. FIG. 37 provides a schematic of the 3' RT PCR strategy used. First, cDNA was prepared from mRNA using the oligonucleotide primer "$Q_T$" (5'-CCA GTG AGC AGA GTG ACG AGG ACT CGA GCT CAA GCT TTT TTT TTT TTT TT-3'; SEQ ID NO:102), then using this cDNA as a template for PCR with "$Q_0$" (5'-CCA GTG AGC AGA GTG ACG- 3'; SEQ ID NO:103), and a primer designed based on the original degenerated PCR reaction (i.e., "M2-T" with the sequence 5'-G TGT CAT TTC TAT ATG GAA GAT TTG ATT GAT G-3' (SEQ ID NO:109). The second PCR reaction (i.e., nested PCR) with "$Q_1$" (5'-GAG GAC TCG AGC TCA AGC-3'; SEQ ID NO:104), and another PCR primer designed with sequence derived from the original degenerate PCR reaction or "M2-T2" with the sequence 5'-AC CTA TCG TTT ACG AAA AAG AAA GGA TCA GTG-3'; SEQ ID NO:110). The buffers used in this PCR were the same as described above, with amplification conducted beginning with a ramp up of 94° for 5 min, followed by 30 cycles of 94° for 30 sec, and 55° C. for 30 sec, and 72° C. for 3 min), followed by 7 minutes at 72° C. The reaction products were stored at 4° C. until use.

Screening of Genomic and cDNA Libraries

Figure 38:
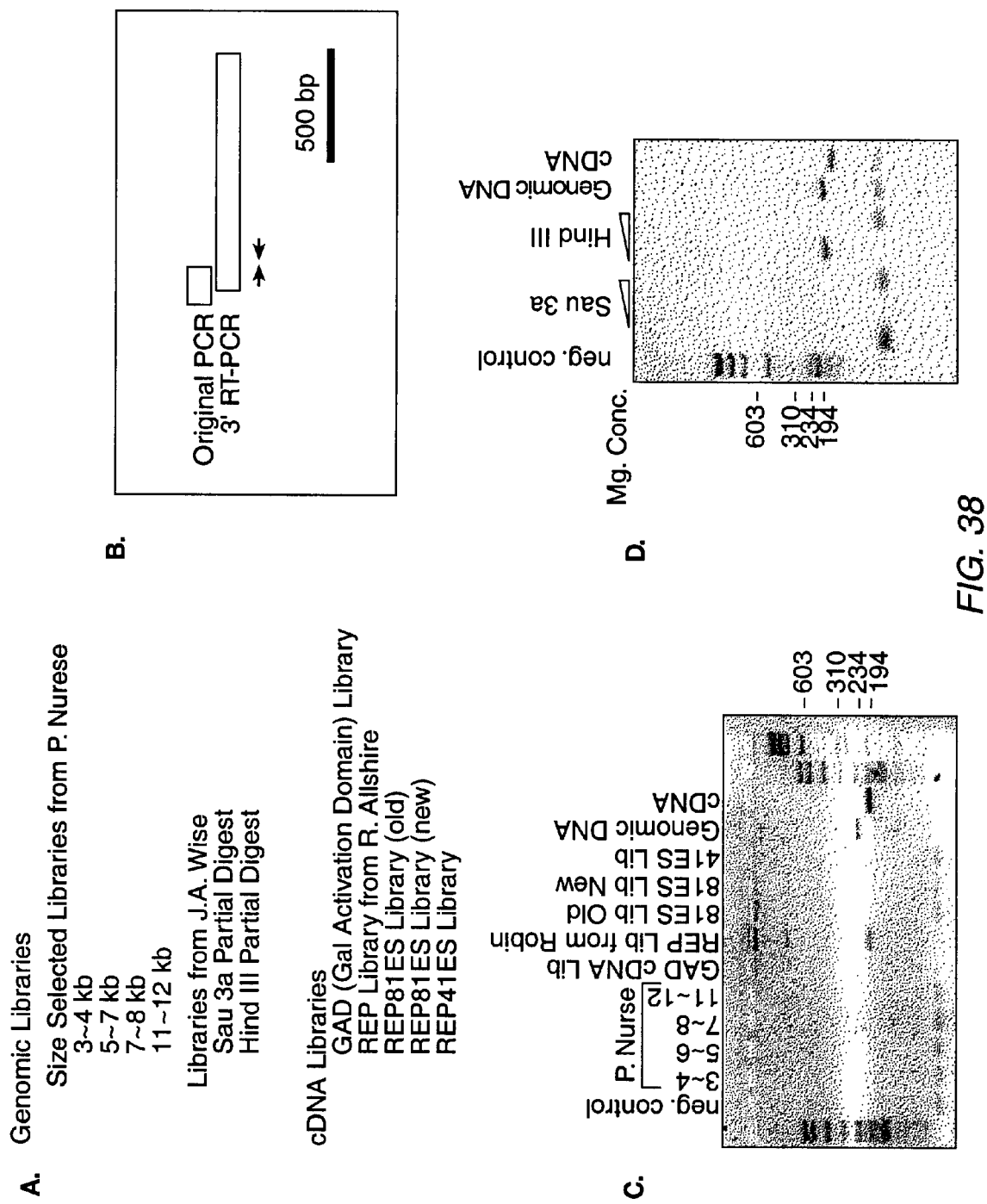
FIG. 38 shows the libraries and the results of screening libraries for *S. pombe* telomerase protein sequences.
Figure 39:
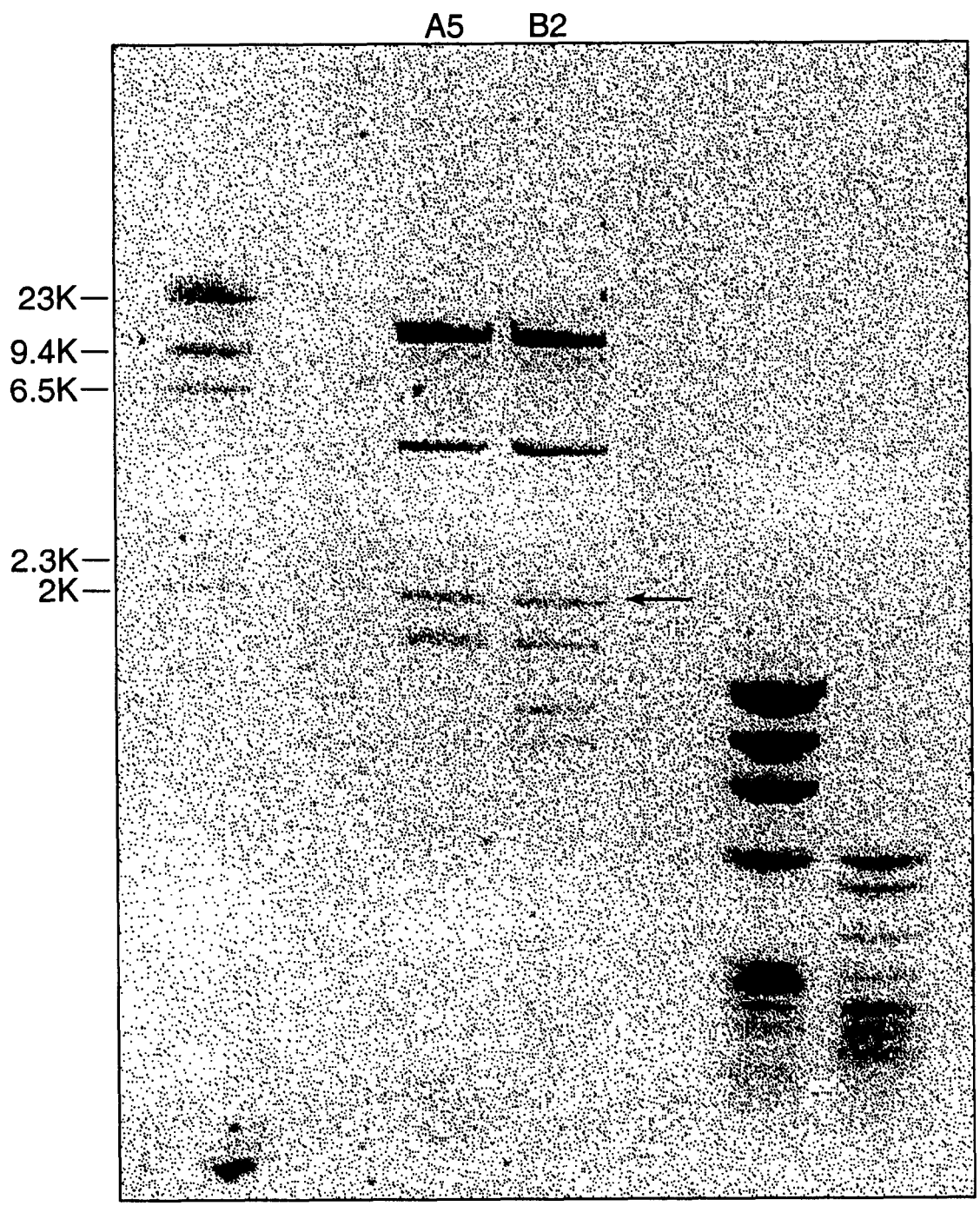
FIG. 39 shows the results obtained with the HindIII-digested positive genomic clones containing *S. pombe* telomerase sequence.

After obtaining this extra sequence information, several genomic and cDNA libraries were screened to identify any libraries that contain this telomerase candidate gene. The approach used, as well as the libraries and results are shown in FIG. 38. In this Figure, Panel A lists the libraries tested in this experiment; Panel B shows the regions used; Panels C and D show the dot blot hybridization results obtained with these libraries. Positive libraries were then screened by colony hybridization to obtain genomic and cDNA version of tez1 gene. In this experiment, approximately 3×10⁴ colonies from the HindIII genomic library were screened and six positive clones were identified (approximately 0.01%). DNA was then prepared from two independent clones (A5 and B2). FIG. 39 shows the results obtained with the HindIII-digested A5 and B2 positive genomic clones.

In addition, cDNA REP libraries were used. Approximately 3×10⁵ colonies were screened, and 5 positive clones were identified (0.002%). DNA was prepared from three independent clones (2-3, 4-1, and 5-20). In later experiments, it was determined that 2-3 and 5-20 contained identical inserts.

5' RT PCR

Figure 40:
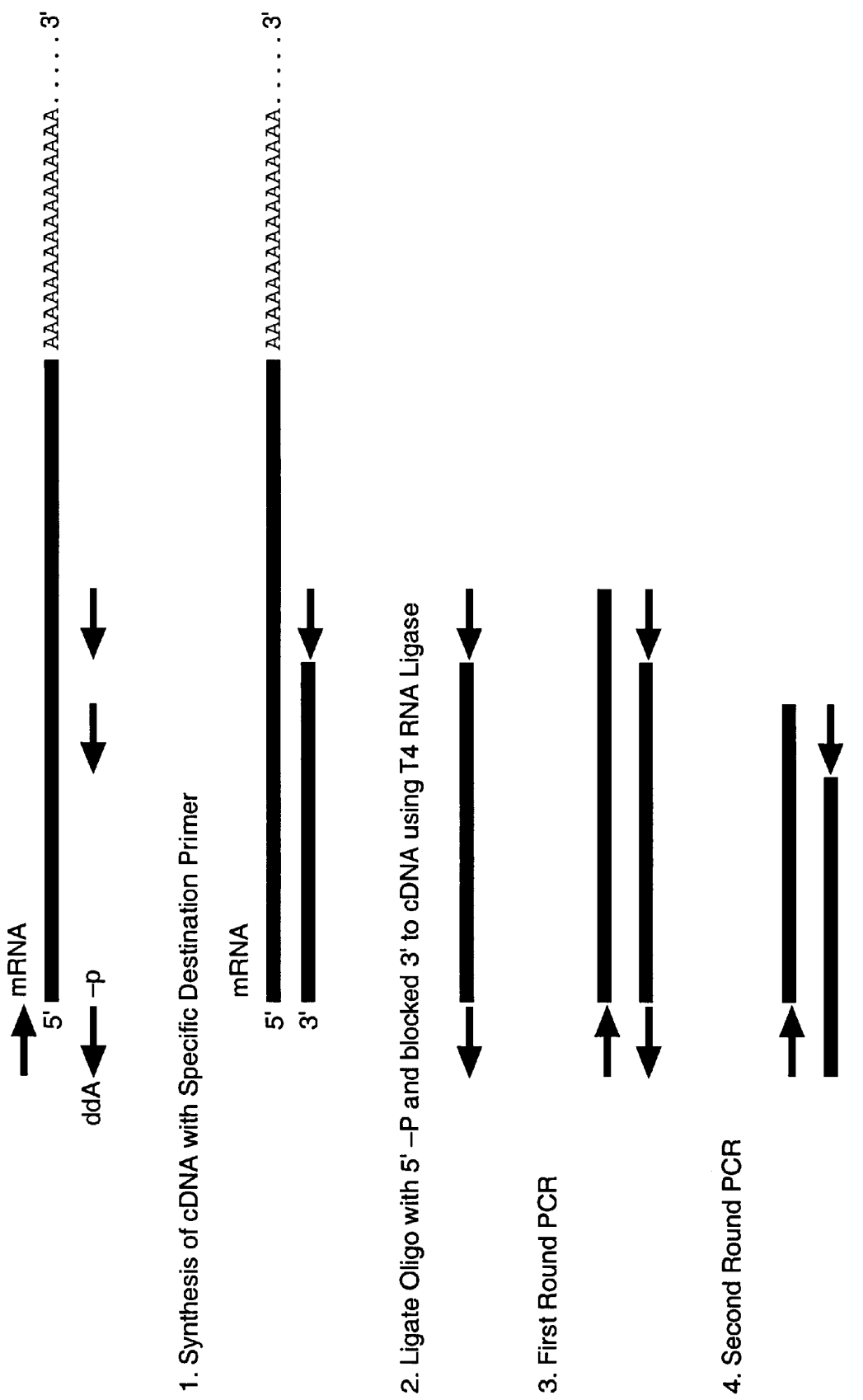
FIG. 40 is a schematic showing the 5' RT PCR strategy.

As the cDNA version of gene produced to this point was not complete, 5' RT-PCR was conducted in order to obtain a full length clone. The strategy is schematically shown in FIG. 40. In this experiment, cDNA was prepared using DNA oligonucleotide primer "M2-B" (5'-CAC TGA TCC TTT CTT TTT CGT AAA CGA TAG GT-3'; SEQ ID NO:105) and "M2-B2" (5'-C ATC AAT CAA ATC TTC CAT ATA GAA ATG ACA-3'; SEQ ID NO:106), designed from known regions of tez1 identified previously. An oligonucleotide linker PCR Adapt SfiI with a phosphorylated 5' end ("P") (P-GGG CCG TGT TGG CCT AGT TCT CTG CTC-3'; SEQ ID NO:107) was then ligated at the 3' end of this cDNA, and this construct was used as the template for nested PCR. In the first round of PCR, PCR Adapt SFI and M2-B were used as the primers; while PCR Adapt SfiII (5-GAG GAG GAG AAG AGC AGA GAA CTA GGC CAA CAC GCC CC-3'; SEQ ID NO:108), and M2-B2 (5'-ATC AAT CAA ATC TTC CAT ATA GAA ATG ACA-3'; SEQ ID NO:106) were used as primers in the second round. Nested PCR was used to increase specificity of reaction.

Sequence Alignments

Once the sequence of tez1 was identified, it was compared with sequences previously described. FIG. 41 shows the alignment of reverse transcriptase (RT) domains from telomerase catalytic subunits of S. pombe ("S.p. Tez1p"), S. cerevisiae ("S.c. Est2p"), and E. aediculatus p123 ("E.a. p123"). In this Figure, "h" indicates hydrophobic residues, while "p" indicates small polar residues, and "c" indicates charged residues. The amino acid residues indicated above the alignment shows the consensus RT motif of Y. Xiong and T. H. Eickbush (Y. Xiong and T. H. Eickbush, EMBO J., 9: 3353–3362 [1990]). The asterisks indicate the residues that are conserved for all three proteins. "Motif O" is identified herein as a motif specific to this telomerase subunit and not found in reverse transcriptases in general. It is therefore valuable in identifying other amino acid sequences as being good candidates for telomerase catalytic subunits.

FIG. 42 shows the alignment of entire sequences from Euplotes ("Ea_p123"), S. cerevisiae ("Sc_Est2p"), and S. pombe ("Sp_Tez1p"). In Panel A, the shaded areas indicate residues shared between two sequences. In Panel B, the shaded areas indicate residues shared between all three sequences.

Genetic Disruption of tez1

In this Example, the effects of disruption of tez1 were investigated. As telomerase is involved in telomere maintenance, it was hypothesized that if tez1 were indeed a telomerase component, disruption of tez1 was expected to cause gradual telomere shortening.

Figure 43:
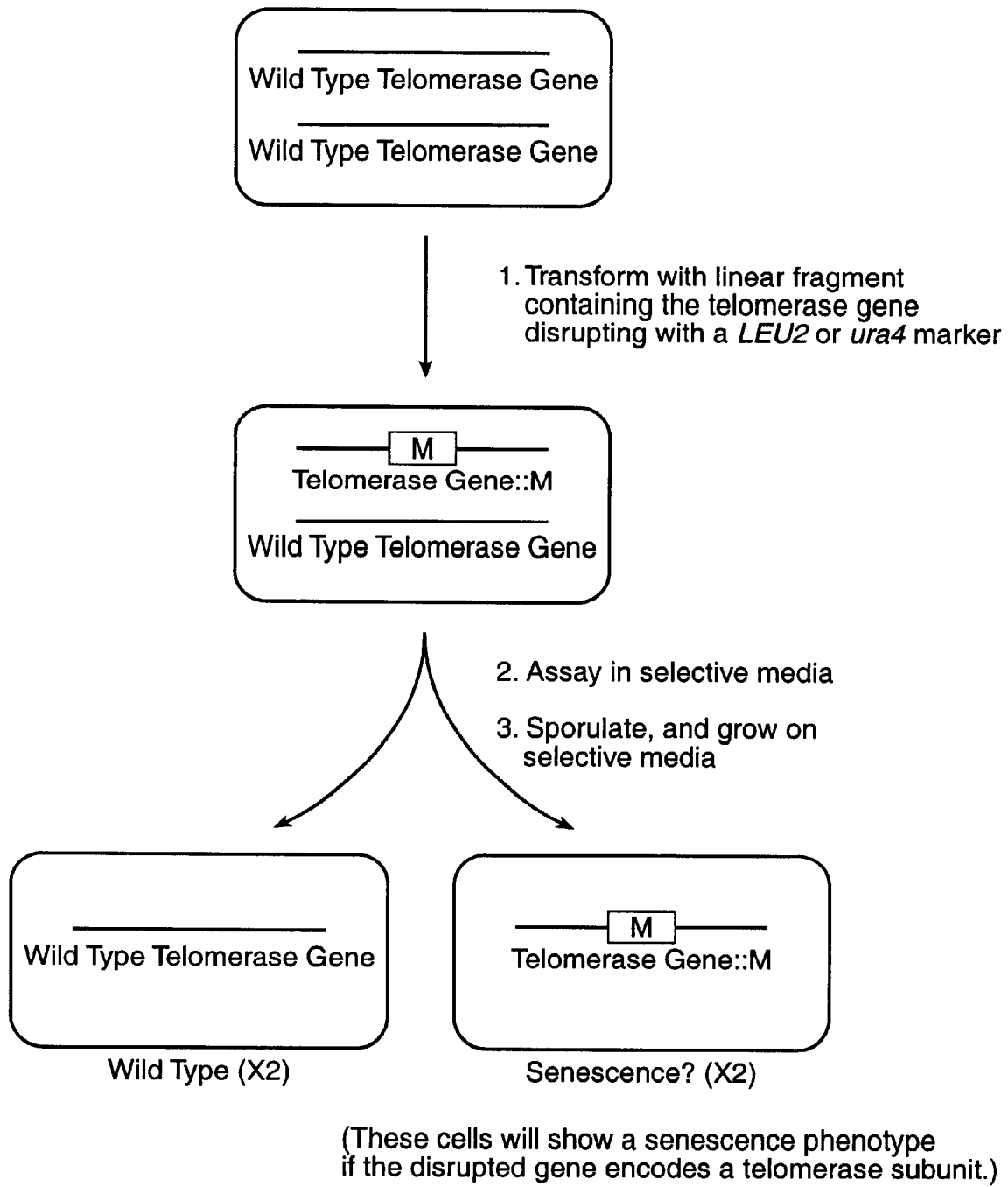
FIG. 43 shows the disruption strategy used with the telomerase genes in *S. pombe*.

In these experiments, homologous recombination was used to specifically disrupt the tez1 gene in S. pombe. This approach is schematically illustrated in FIG. 43. As indicated in FIG. 43, wild type tez1 was replaced with a fragment containing the ura4 or LEU2 marker.

Figure 44:
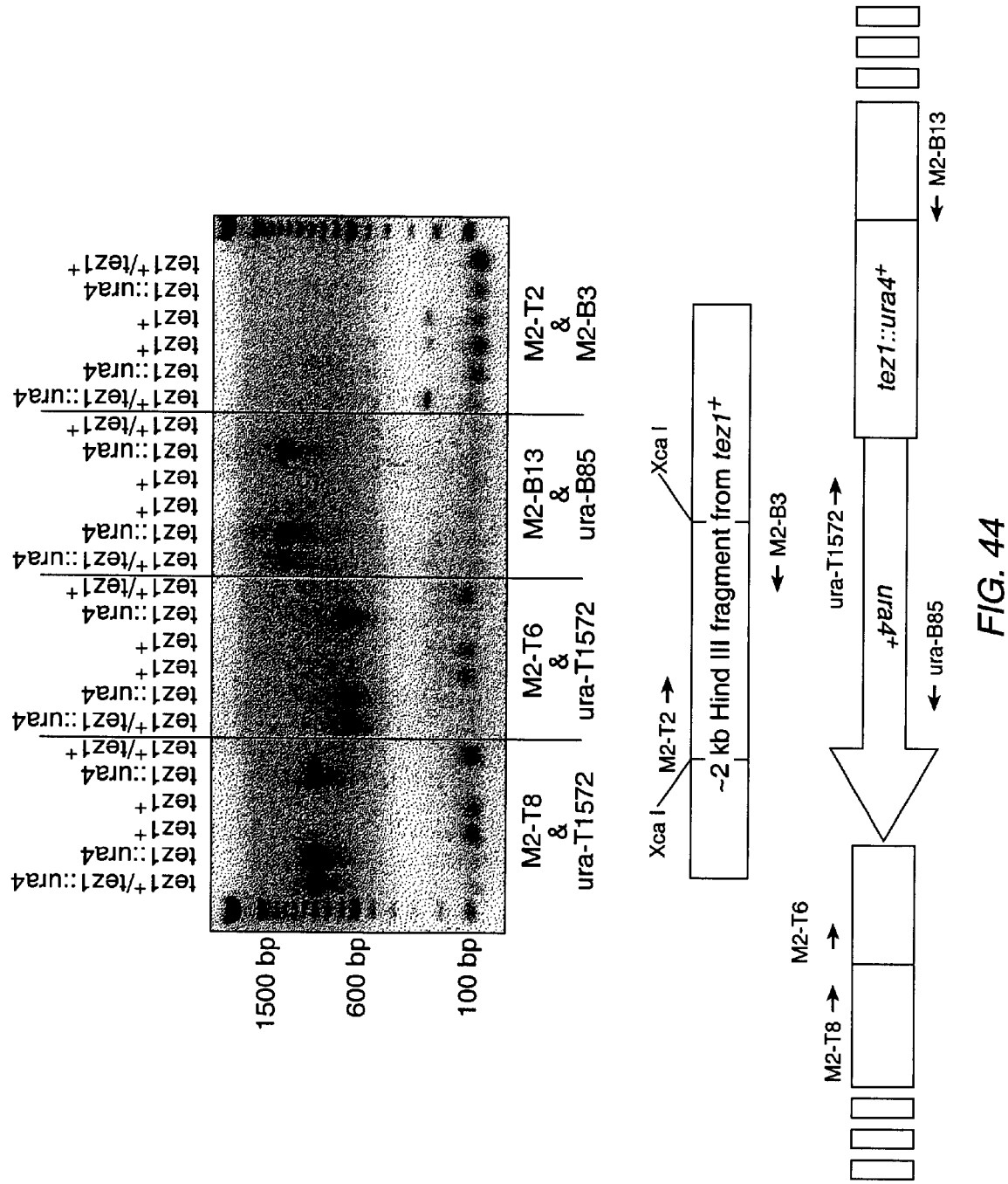
FIG. 44 shows the experimental results confirming disruption of tez1.
Figure 45:
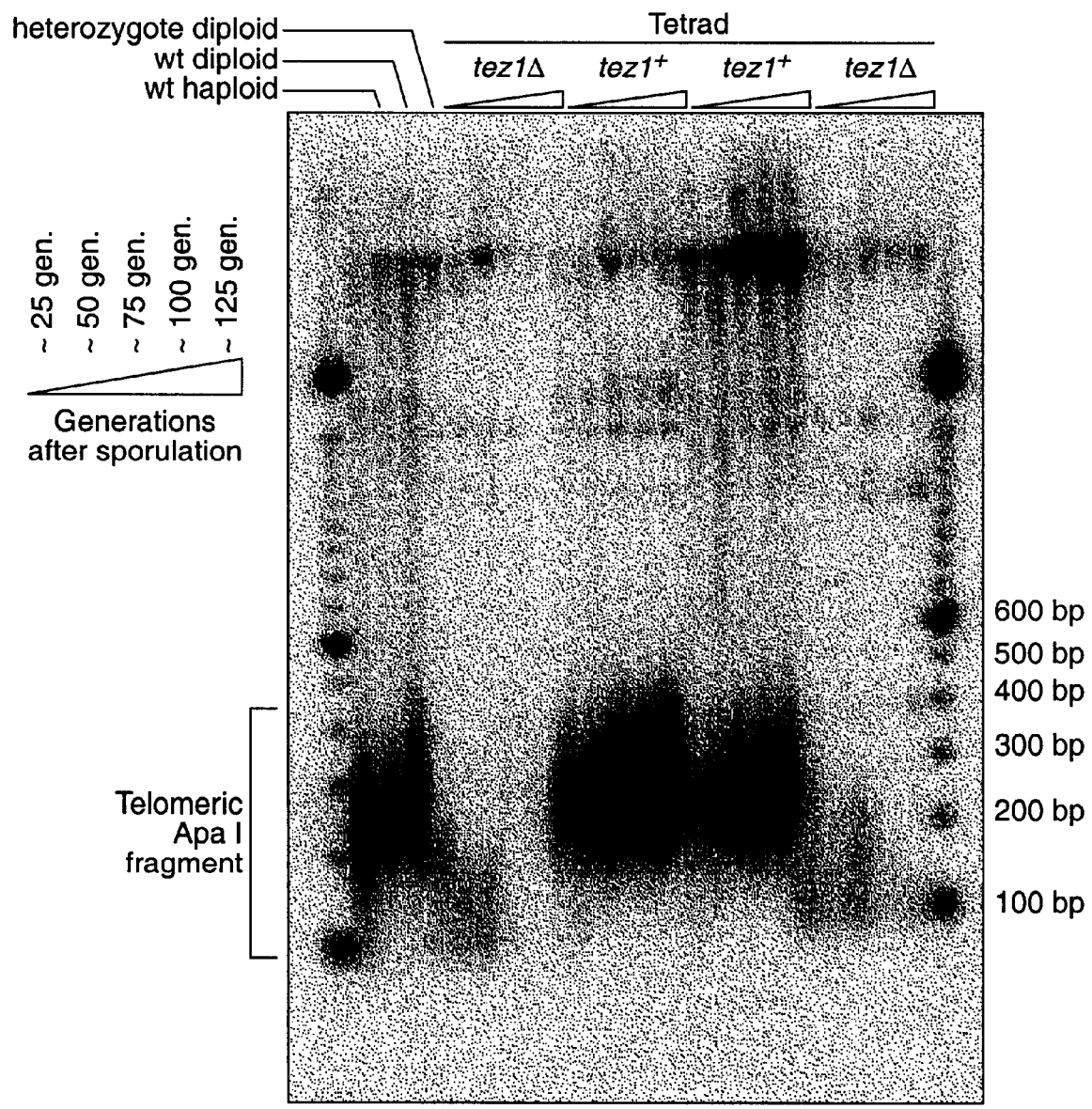
FIG. 45 shows the progressive shortening of telomeres in *S. pombe* due to tez1 disruption.

The disruption of tez1 gene was confirmed by PCR (FIG. 44), and Southern blot was performed to check for telomere length. FIG. 45 shows the Southern blot results for this experiment. Because an Apa I restriction enzyme site is present immediately adjacent to telomeric sequence in S. pombe, digestion of S. pombe genomic DNA preparations permits analysis of telomere length. Thus, DNA from S. pombe was digested with ApaI and the digestion products were run on an agarose gel and probed with a telomeric sequence-specific probe to determine whether the telomeres of disrupted S. pombe cells were shortened. The results are shown in FIG. 45. From these results, it was clear that disruption of the tez1 gene caused a shortening of the telomeres.

EXAMPLE 17

Cloning and Characterization of Human Telomerase Protein and cDNA

In this Example, the nucleic and amino acid sequence information for human telomerase was determined. Partial homologous sequences were first identified in a BLAST search conducted using the Euplotes 123 kDa peptide and nucleic acid sequences, as wells as Schizosaccharomyces protein and corresponding cDNA (tez1) sequences. The human sequences (also referred to as "hTCP1.1") were identified from a partial cDNA clone (GenBank accession #AA281296). Sequences from this clone were aligned with the sequences determined as described in previous Examples.

FIG. 25 shows the sequence alignment of the Euplotes ("p123"), Schizosaccharomyces ("tez1"), Est2p (i.e., the S. cerevisiae protein encoded by the Est2 nucleic acid sequence, and also referred to herein as "L8543.12"), and the human homolog identified in this comparison search.

The amino acid sequence of this aligned portion is provided in SEQ ID NO:67 (the cDNA sequence is provided in SEQ ID NO:62), while the portion of tez1 shown in FIG. 25 is provided in SEQ ID NO:63. The portion of Est2 shown in this Figure is also provided in SEQ ID NO:64, while the portion of p123 shown is also provided in SEQ ID NO:65. FIG. 29 shows the amino acid sequence of tez1 (SEQ ID NO:65), while FIG. 30 shows the DNA sequence of tez1 (SEQ ID NO:68). In FIG. 30, the introns and other non-coding regions, are shown in lower case, while the exons (i.e., coding regions) are shown in upper case.

As shown in FIG. 25, there are regions that are highly conserved among these proteins. For example, as shown in this Figure, there are regions of identity in "Motif 0," "Motif 1, "Motif 2," and "Motif 3." The identical amino acids are indicated with an asterisk (*), while the similar amino acid residues are indicated by a circle (●). This indicates that there are regions within the telomerase motifs that are conserved among a wide variety of eukaryotes, ranging from yeast to ciliates, to humans. It is contemplated that additional organisms will likewise contain such conserved regions of sequence. FIG. 27 shows the partial amino acid sequence of the clone encoding human telomerase motifs (SEQ ID NO:67), while FIG. 28 shows the corresponding DNA sequence of the Genbank #AA281296 clone.

Sanger dideoxy sequencing and other methods were used, as known in the art to obtain complete sequence information of the Genbank clone #AA281296. Some of the primers used in the sequencing are shown in Table 3. These primers were designed to hybridize to the clone (GenBank accession #AA281296), based on sequence complementarity to either plasmid backbone sequence or the sequence of the human cDNA insert in the clone.

TABLE 3

Primers

| Primer | Sequence | SEQ ID NO: |
|---|---|---|
| TCP1.1 | GTGAAGGCACTGTTCAGCG | SEQ ID NO:87 |
| TCP1.2 | GTGGATGATTTCTTGTTGG | SEQ ID NO:88 |
| TCP1.3 | ATGCTCCTGCGTTTGGTGG | SEQ ID NO:89 |
| TCP1.4 | CTGGACACTCAGCCCTTGG | SEQ ID NO:90 |
| TCP1.5 | GGCAGGTGTGCTGGACACT | SEQ ID NO:91 |
| TCP1.6 | TTTGATGATGCTGGCGATG | SEQ ID NO:92 |
| TCP1.7 | GGGGCTCGTCTTCTACAGG | SEQ ID NO:93 |
| TCP1.8 | CAGCAGGAGGATCTTGTAG | SEQ ID NO:94 |
| TCP1.9 | TGACCCCAGGAGTGGCACG | SEQ ID NO:95 |
| TCP1.10 | TCAAGCTGACTCGACACCG | SEQ ID NO:96 |
| TCP1.11 | CGGCGTGACAGGGCTGC | SEQ ID NO:97 |
| TCP1.12 | GCTGAAGGCTGAGTGTCC | SEQ ID NO:98 |
| TCP1.13 | TAGTCCATGTTCACAATCG | SEQ ID NO:99 |

From these experiments, it was determined that the EcoRI-NotI insert of the Genbank #AA281296 clone contains only a partial open reading frame for the human telomerase protein, although it may encode an active fragment of that protein. The open reading frame in the clone encodes an approximately 63 kD protein. The sequence of the longest open reading frame identified is shown in FIG. 47 (SEQ ID NO:100). The ORF begins at the ATG codon with the "met" indicated in the Figure. The poly A tail at the 3' end of the sequence is also shown. FIG. 48 shows a tentative alignment of telomerase reverse transcriptase proteins from the human sequence (human Telomerase Core Protein 1, "Hs TCP1"), E. aediculatus p123 ("Ep p123"), S. pombe tez1 ("Sp Tez1"), S. cerevisiae EST2 (Sc Est2"), and consensus sequence. In this Figure various motifs are indicated.

To obtain a full-length clone, probing of a cDNA library and 5'-RACE were used to obtain clones encoding portions of the previously uncloned regions. In these experiments, RACE (Rapid Amplification of cDNA Ends; See e.g., M. A. Frohman, "RACE: Rapid Amplification of cDNA Ends," in Innis et al. (eds), PCR Protocols: A Guide to Methods and Applications [1990], pp. 28–38; and Frohman et al., Proc. Natl. Acad. Sci., 85:8998–9002 [1988]) was used to generate material for sequence analysis. Four such clones were generated and used to provide additional 5' sequence information (pFWRP5, 6, 19, and 20).

In addition, human cDNA libraries (inserted into lambda) were probed with the EcoRI-NotI fragment of the clone (#AA281296). One lambda clone, designated "lambda 25-1.1," (ATCC accession #209024) was identified as containing complementary sequences. FIG. 54 shows a restriction map of this lambda clone. The human cDNA insert from this clone was subcloned as an EcoRI restriction fragment into the EcoRI site of commercially available phagemid pBluescriptIISK+(Stratagene), to create the plasmid "pGRN121," which was deposited with the ATCC (ATCC accession #209016). Preliminary results indicated that plasmid pGRN121 contains the entire open reading frame (ORF) sequence encoding the human telomerase protein.

Figure 49:
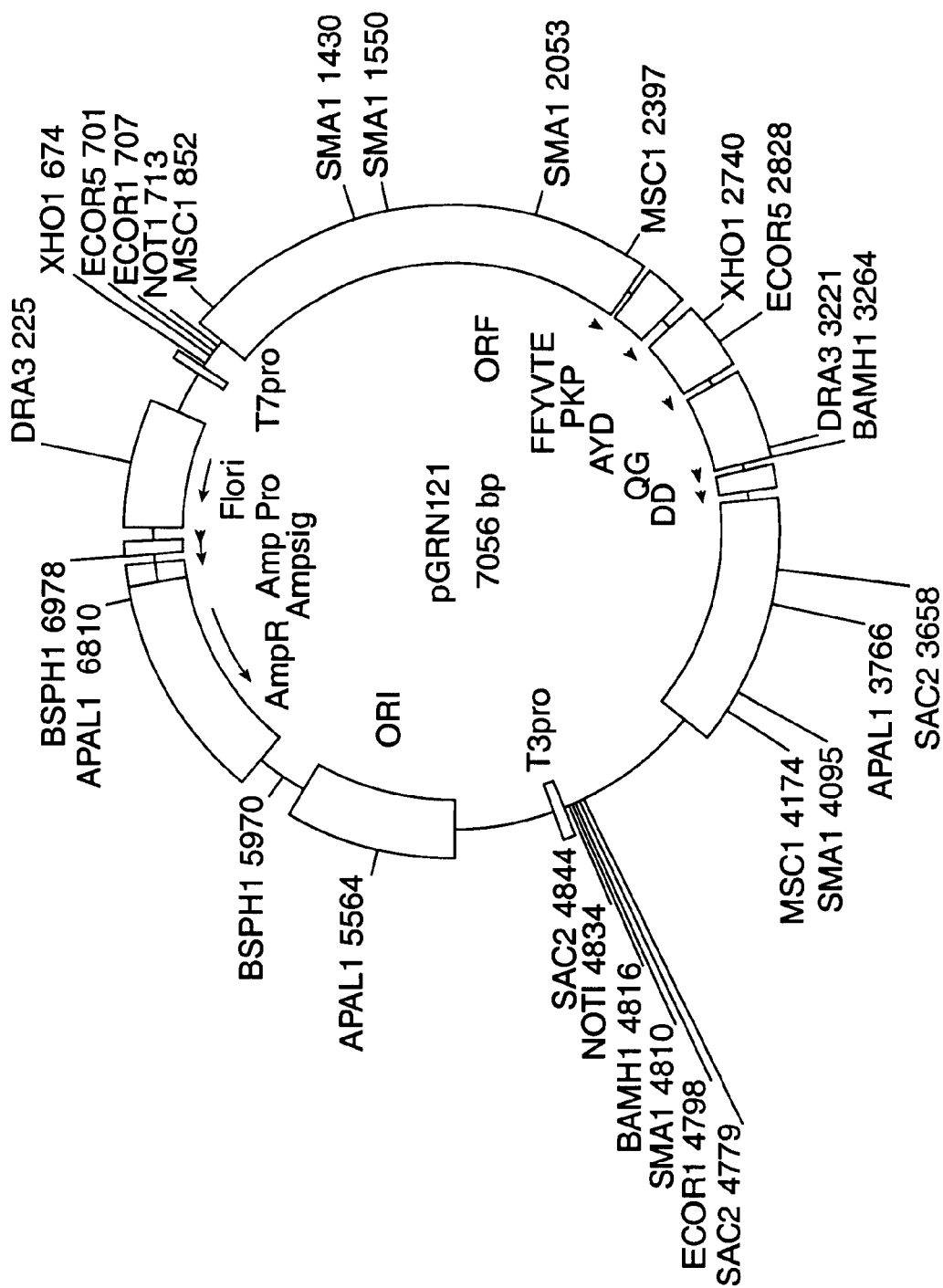
FIG. 49 provides a restriction and function map of plasmid pGRN121.

The cDNA insert of plasmid pGRN121 was sequenced using techniques known in the art. FIG. 49 provides a restriction site and function map of plasmid pGRN121 identified based on this preliminary work. The results of this preliminary sequence analysis are shown in FIG. 50. From this analysis. and as shown in FIG. 49, a putative start site for the coding region was identified at approximately 50 nucleotides from the EcoRI site (located at position 707), and the location of the telomerase-specific motifs, "FFYVTE" (SEQ ID NO:112), "PKP," "AYD," "QG," and "DD," were identified, in addition to a putative stop site at nucleotide #3571 (See, FIG. 51). FIG. 51 shows the DNA and corresponding amino acid sequences for the open reading frames in the sequence ("a" [SEQ ID NOS:174–201], "b" [SEQ ID NOS: 202–214], and "c" [SEQ ID NOS: 215–223]). However, due to the preliminary nature of the early sequencing work, the reading frames for the various motifs were found not to be in alignment.

Additional analysis conducted on the pGRN121 indicated that the plasmid contained significant portions from the 5'-end of the coding sequence not present on the Genbank accession #AA281296 clone. Furthermore, pGRN121 was found to contain a variant coding sequence that includes an insert of approximately 182 nucleotides. This insert was found to be absent from the Genbank accession #AA281296 clone. As with the E. aediculatus sequences, such variants can be tested in functional assays, such as telomerase assays to detect the presence of functional telomerase in a sample.

Figure 52:
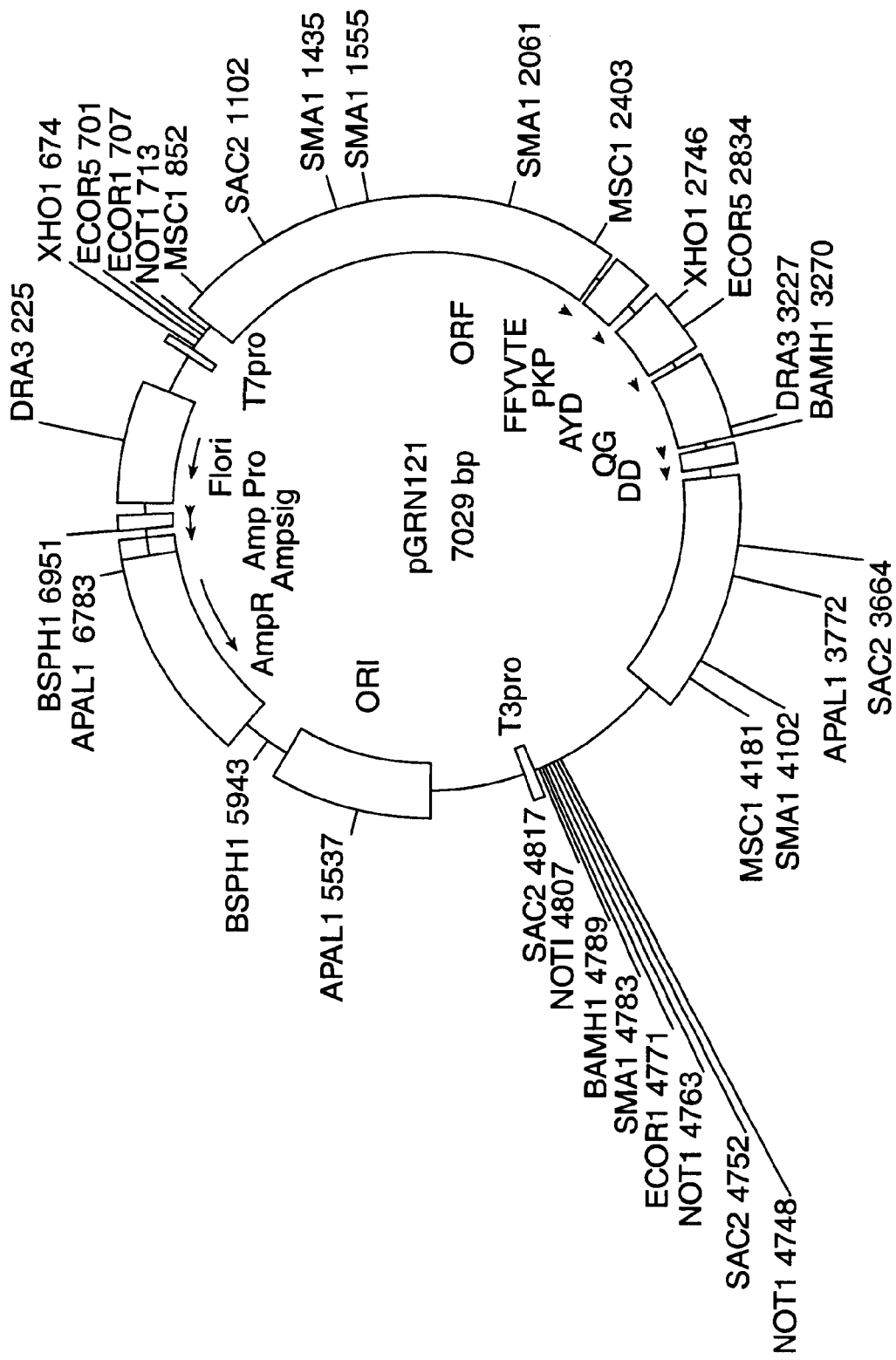
FIG. 52 provides a refined restriction and function map of plasmid pGRN121.

Further sequence analysis resolved the cDNA sequence of pGRN121, to provide a contiguous open reading frame that encodes a protein of molecular weight of approximately 127,000 daltons, and 1132 amino acids as shown in FIG. 53 (SEQ ID NOS:224 and 225). A refined map of pGRN121 based on this analysis, is provided in FIG. 52.

From the above, it is clear that the present invention provides nucleic acid and amino acid sequences, as well as other information regarding telomerase, telomerase protein subunits, and motifs from various organisms, in addition to methods for identification of homologous structures in other organisms in addition to those described herein.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

SEQUENCE LISTING (1) GENERAL INFORMATION:

(iii) NUMBER OF SEQUENCES: 225

(2) INFORMATION FOR SEQ ID NO: 1:

(i) SEQUENCE CHARACTERISTICS:
        (A) LENGTH: 3279 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 1:

```
AAAACCCCAA AACCCCAAAA CCCCTTTTAG AGCCCTGCAG TTGGAAATAT AACCTCAGTA      60

TTAATAAGCT CAGATTTTAA ATATTAATTA CAAAACCTAA ATGGAGGTTG ATGTTGATAA     120

TCAAGCTGAT AATCATGGCA TTCACTCAGC TCTTAAGACT TGTGAAGAAA TTAAAGAAGC     180

TAAAACGTTG TACTCTTGGA TCCAGAAAGT TATTAGATGA AGAAATCAAT CTCAAAGTCA     240

TTATAAAGAT TTAGAAGATA TTAAAATATT TGCGCAGACA AATATTGTTG CTACTCCACG     300

AGACTATAAT GAAGAAGATT TTAAAGTTAT TGCAAGAAAA GAAGTATTTT CAACTGGACT     360

AATGATCGAA CTTATTGACA AATGCTTAGT TGAACTTCTT TCATCAAGCG ATGTTTCAGA     420

TAGACAAAAA CTTCAATGAT TTGGATTTCA ACTTAAGGGA AATCAATTAG CAAAGACCCA     480

TTTATTAACA GCTCTTTCAA CTCAAAAGCA GTATTTCTTT CAAGACGAAT GGAACCAAGT     540

TAGAGCAATG ATTGGAAATG AGCTCTTCCG ACATCTCTAC ACTAAATATT TAATATTCCA     600

GCGAACTTCT GAAGGAACTC TTGTTCAATT TTGCGGGAAT AACGTTTTTG ATCATTTGAA     660

AGTCAACGAT AAGTTTGACA AAAAGCAAAA AGGTGGAGCA GCAGACATGA ATGAACCTCG     720

ATGTTGATCA ACCTGCAAAT ACAATGTCAA GAATGAGAAA GATCACTTTC TCAACAACAT     780

CAACGTGCCG AATTGGAATA ATATGAAATC AAGAACCAGA ATATTTTATT GCACTCATTT     840

TAATAGAAAT AACCAATTCT TCAAAAAGCA TGAGTTTGTG AGTAACAAAA ACAATATTTC     900

AGCGATGGAC AGAGCTCAGA CGATATTCAC GAATATATTC AGATTTAATA GAATTAGAAA     960

GAAGCTAAAA GATAAGGTTA TCGAAAAAAT TGCCTACATG CTTGAGAAAG TCAAAGATTT    1020

TAACTTCAAC TACTATTTAA CAAAATCTTG TCCTCTTCCA GAAAATTGGC GGGAACGGAA    1080

ACAAAAAATC GAAAACTTGA TAAATAAAAC TAGAGAAGAA AAGTCGAAGT ACTATGAAGA    1140

GCTGTTTAGC TACACAACTG ATAATAAATG CGTCACACAA TTTATTAATG AATTTTTCTA    1200

CAATATACTC CCCAAAGACT TTTTGACTGG AAGAAACCGT AAGAATTTTC AAAAGAAAGT    1260

TAAGAAATAT GTGGAACTAA ACAAGCATGA ACTCATTCAC AAAAACTTAT TGCTTGAGAA    1320

GATCAATACA AGAGAAATAT CATGGATGCA GGTTGAGACC TCTGCAAAGC ATTTTTATTA    1380

TTTTGATCAC GAAAACATCT ACGTCTTATG GAAATTGCTC CGATGGATAT TCGAGGATCT    1440

CGTCGTCTCG CTGATTAGAT GATTTTTCTA TGTCACCGAG CAACAGAAAA GTTACTCCAA    1500

AACCTATTAC TACAGAAAGA ATATTTGGGA CGTCATTATG AAAATGTCAA TCGCAGACTT    1560
```

-continued

| | |
|---|---|
| AAAGAAGGAA ACGCTTGCTG AGGTCCAAGA AAAAGAGGTT GAAGAATGGA AAAAGTCGCT | 1620 |
| TGGATTTGCA CCTGGAAAAC TCAGACTAAT ACCGAAGAAA ACTACTTTCC GTCCAATTAT | 1680 |
| GACTTTCAAT AAGAAGATTG TAAATTCAGA CCGGAAGACT ACAAAATTAA CTACAAATAC | 1740 |
| GAAGTTATTG AACTCTCACT TAATGCTTAA GACATTGAAG AATAGAATGT TAAAGATCC | 1800 |
| TTTTGGATTC GCTGTTTTTA ACTATGATGA TGTAATGAAA AAGTATGAGG AGTTTGTTTG | 1860 |
| CAAATGGAAG CAAGTTGGAC AACCAAAACT CTTCTTTGCA ACTATGGATA TCGAAAAGTG | 1920 |
| ATATGATAGT GTAAACAGAG AAAAACTATC AACATTCCTA AAAACTACTA AATTACTTTC | 1980 |
| TTCAGATTTC TGGATTATGA CTGCACAAAT TCTAAAGAGA AAGAATAACA TAGTTATCGA | 2040 |
| TTCGAAAAAC TTTAGAAAGA AAGAAATGAA AGATTATTTT AGACAGAAAT TCCAGAAGAT | 2100 |
| TGCACTTGAA GGAGGACAAT ATCCAACCTT ATTCAGTGTT CTTGAAAATG AACAAAATGA | 2160 |
| CTTAAATGCA AAGAAAACAT TAATTGTTGA AGCAAAGCAA AGAAATTATT TTAAGAAAGA | 2220 |
| TAACTTACTT CAACCAGTCA TTAATATTTG CCAATATAAT TACATTAACT TTAATGGGAA | 2280 |
| GTTTTATAAA CAAACAAAAG GAATTCCTCA AGGTCTTTGA GTTTCATCAA TTTTGTCATC | 2340 |
| ATTTTATTAT GCAACATTAG AGGAAAGCTC CTTAGGATTC CTTAGAGATG AATCAATGAA | 2400 |
| CCCTGAAAAT CCAAATGTTA ATCTTCTAAT GAGACTTACA GATGACTATC TTTTGATTAC | 2460 |
| AACTCAAGAG AATAATGCAG TATTGTTTAT TGAGAAACTT ATAAACGTAA GTCGTGAAAA | 2520 |
| TGGATTTAAA TTCAATATGA AGAAACTACA GACTAGTTTT CCATTAAGTC CAAGCAAATT | 2580 |
| TGCAAAATAC GGAATGGATA GTGTTGAGGA GCAAATATT GTTCAAGATT ACTGCGATTG | 2640 |
| GATTGGCATC TCAATTGATA TGAAAACTCT TGCTTTAATG CCAAATATTA ACTTGAGAAT | 2700 |
| AGAAGGAATT CTGTGTACAC TCAATCTAAA CATGCAAACA AAGAAAGCAT CAATGTGGCT | 2760 |
| CAAGAAGAAA CTAAAGTCGT TTTTAATGAA TAACATTACC CATTATTTTA GAAAGACGAT | 2820 |
| TACAACCGAA GACTTTGCGA ATAAAACTCT CAACAAGTTA TTTATATCAG GCGGTTACAA | 2880 |
| ATACATGCAA TGAGCCAAAG AATACAAGGA CCACTTTAAG AAGAACTTAG CTATGAGCAG | 2940 |
| TATGATCGAC TTAGAGGTAT CTAAAATTAT ATACTCTGTA ACCAGAGCAT TCTTTAAATA | 3000 |
| CCTTGTGTGC AATATTAAGG ATACAATTTT TGGAGAGGAG CATTATCCAG ACTTTTTCCT | 3060 |
| TAGCACACTG AAGCACTTTA TTGAAATATT CAGCACAAAA AAGTACATTT TCAACAGAGT | 3120 |
| TTGCATGATC CTCAAGGCAA AAGAAGCAAA GCTAAAAAGT GACCAATGTC AATCTCTAAT | 3180 |
| TCAATATGAT GCATAGTCGA CTATTCTAAC TTATTTTGGA AAGTTAATTT TCAATTTTTG | 3240 |
| TCTTATATAC TGGGGTTTTG GGGTTTTGGG GTTTTGGGG | 3279 |

(2) INFORMATION FOR SEQ ID NO: 2:

(i) SEQUENCE CHARACTERISTICS:
        (A) LENGTH: 1031 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 2:

```
Met Glu Val Asp Val Asp Asn Gln Ala Asp Asn His Gly Ile His Ser
1               5                   10                  15

Ala Leu Lys Thr Cys Glu Glu Ile Lys Glu Ala Lys Thr Leu Tyr Ser
            20                  25                  30

Trp Ile Gln Lys Val Ile Arg Cys Arg Asn Gln Ser Gln Ser His Tyr
        35                  40                  45
```

-continued

```
Lys Asp Leu Glu Asp Ile Lys Ile Phe Ala Gln Thr Asn Ile Val Ala
     50              55                  60
Thr Pro Arg Asp Tyr Asn Glu Asp Phe Lys Val Ile Ala Arg Lys
 65              70                  75                  80
Glu Val Phe Ser Thr Gly Leu Met Ile Glu Leu Ile Asp Lys Cys Leu
                 85                  90                  95
Val Glu Leu Leu Ser Ser Ser Asp Val Ser Asp Arg Gln Lys Leu Gln
                100                 105                 110
Cys Phe Gly Phe Gln Leu Lys Gly Asn Gln Leu Ala Lys Thr His Leu
             115                 120                 125
Leu Thr Ala Leu Ser Thr Gln Lys Gln Tyr Phe Phe Gln Asp Glu Trp
     130                 135                 140
Asn Gln Val Arg Ala Met Ile Gly Asn Glu Leu Phe Arg His Leu Tyr
145                 150                 155                 160
Thr Lys Tyr Leu Ile Phe Gln Arg Thr Ser Glu Gly Thr Leu Val Gln
                165                 170                 175
Phe Cys Gly Asn Asn Val Phe Asp His Leu Lys Val Asn Asp Lys Phe
             180                 185                 190
Asp Lys Lys Gln Lys Gly Gly Ala Ala Asp Met Asn Glu Pro Arg Cys
         195                 200                 205
Cys Ser Thr Cys Lys Tyr Asn Val Lys Asn Glu Lys Asp His Phe Leu
     210                 215                 220
Asn Asn Ile Asn Val Pro Asn Trp Asn Asn Met Lys Ser Arg Thr Arg
225                 230                 235                 240
Ile Phe Tyr Cys Thr His Phe Asn Arg Asn Asn Gln Phe Phe Lys Lys
                245                 250                 255
His Glu Phe Val Ser Asn Lys Asn Asn Ile Ser Ala Met Asp Arg Ala
             260                 265                 270
Gln Thr Ile Phe Thr Asn Ile Phe Arg Phe Asn Arg Ile Arg Lys Lys
         275                 280                 285
Leu Lys Asp Lys Val Ile Glu Lys Ile Ala Tyr Met Leu Glu Lys Val
     290                 295                 300
Lys Asp Phe Asn Phe Asn Tyr Tyr Leu Thr Lys Ser Cys Pro Leu Pro
305                 310                 315                 320
Glu Asn Trp Arg Glu Arg Lys Gln Lys Ile Glu Asn Leu Ile Asn Lys
                325                 330                 335
Thr Arg Glu Glu Lys Ser Lys Tyr Tyr Glu Glu Leu Phe Ser Tyr Thr
             340                 345                 350
Thr Asp Asn Lys Cys Val Thr Gln Phe Ile Asn Glu Phe Phe Tyr Asn
         355                 360                 365
Ile Leu Pro Lys Asp Phe Leu Thr Gly Arg Asn Arg Lys Asn Phe Gln
     370                 375                 380
Lys Lys Val Lys Tyr Val Glu Leu Asn Lys His Glu Leu Ile His
385                 390                 395                 400
Lys Asn Leu Leu Leu Glu Lys Ile Asn Thr Arg Glu Ile Ser Trp Met
                405                 410                 415
Gln Val Glu Thr Ser Ala Lys His Phe Tyr Tyr Phe Asp His Glu Asn
             420                 425                 430
Ile Tyr Val Leu Trp Lys Leu Leu Arg Trp Ile Phe Glu Asp Leu Val
         435                 440                 445
Val Ser Leu Ile Arg Cys Phe Phe Tyr Val Thr Glu Gln Gln Lys Ser
     450                 455                 460
```

-continued

```
Tyr Ser Lys Thr Tyr Tyr Tyr Arg Lys Asn Ile Trp Asp Val Ile Met
465                 470                 475                 480

Lys Met Ser Ile Ala Asp Leu Lys Lys Glu Thr Leu Ala Glu Val Gln
            485                 490                 495

Glu Lys Glu Val Glu Trp Lys Lys Ser Leu Gly Phe Ala Pro Gly
        500                 505                 510

Lys Leu Arg Leu Ile Pro Lys Lys Thr Thr Phe Arg Pro Ile Met Thr
    515                 520                 525

Phe Asn Lys Lys Ile Val Asn Ser Asp Arg Lys Thr Thr Lys Leu Thr
530                 535                 540

Thr Asn Thr Lys Leu Leu Asn Ser His Leu Met Leu Lys Thr Leu Lys
545                 550                 555                 560

Asn Arg Met Phe Lys Asp Pro Phe Gly Phe Ala Val Phe Asn Tyr Asp
            565                 570                 575

Asp Val Met Lys Lys Tyr Glu Glu Phe Val Cys Lys Trp Lys Gln Val
            580                 585                 590

Gly Gln Pro Lys Leu Phe Phe Ala Thr Met Asp Ile Glu Lys Cys Tyr
        595                 600                 605

Asp Ser Val Asn Arg Glu Lys Leu Ser Thr Phe Leu Lys Thr Thr Lys
    610                 615                 620

Leu Leu Ser Ser Asp Phe Trp Ile Met Thr Ala Gln Ile Leu Lys Arg
625                 630                 635                 640

Lys Asn Asn Ile Val Ile Asp Ser Lys Asn Phe Arg Lys Lys Glu Met
            645                 650                 655

Lys Asp Tyr Phe Arg Gln Lys Phe Gln Lys Ile Ala Leu Glu Gly Gly
            660                 665                 670

Gln Tyr Pro Thr Leu Phe Ser Val Leu Glu Asn Glu Gln Asn Asp Leu
        675                 680                 685

Asn Ala Lys Lys Thr Leu Ile Val Glu Ala Lys Gln Arg Asn Tyr Phe
    690                 695                 700

Lys Lys Asp Asn Leu Leu Gln Pro Val Ile Asn Ile Cys Gln Tyr Asn
705                 710                 715                 720

Tyr Ile Asn Phe Asn Gly Lys Phe Tyr Lys Gln Thr Lys Gly Ile Pro
            725                 730                 735

Gln Gly Leu Cys Val Ser Ser Ile Leu Ser Ser Phe Tyr Tyr Ala Thr
        740                 745                 750

Leu Glu Glu Ser Ser Leu Gly Phe Leu Arg Asp Glu Ser Met Asn Pro
    755                 760                 765

Glu Asn Pro Asn Val Asn Leu Leu Met Arg Leu Thr Asp Asp Tyr Leu
    770                 775                 780

Leu Ile Thr Thr Gln Glu Asn Asn Ala Val Leu Phe Ile Glu Lys Leu
785                 790                 795                 800

Ile Asn Val Ser Arg Glu Asn Gly Phe Lys Phe Asn Met Lys Lys Leu
            805                 810                 815

Gln Thr Ser Phe Pro Leu Ser Pro Ser Lys Phe Ala Lys Tyr Gly Met
            820                 825                 830

Asp Ser Val Glu Glu Gln Asn Ile Val Gln Asp Tyr Cys Asp Trp Ile
        835                 840                 845

Gly Ile Ser Ile Asp Met Lys Thr Leu Ala Leu Met Pro Asn Ile Asn
    850                 855                 860

Leu Arg Ile Glu Gly Ile Leu Cys Thr Leu Asn Leu Asn Met Gln Thr
865                 870                 875                 880
```

```
Lys Lys Ala Ser Met Trp Leu Lys Lys Leu Lys Ser Phe Leu Met
            885                 890                 895

Asn Asn Ile Thr His Tyr Phe Arg Lys Thr Ile Thr Thr Glu Asp Phe
            900                 905                 910

Ala Asn Lys Thr Leu Asn Lys Leu Phe Ile Ser Gly Gly Tyr Lys Tyr
            915                 920                 925

Met Gln Cys Ala Lys Glu Tyr Lys Asp His Phe Lys Lys Asn Leu Ala
            930                 935                 940

Met Ser Ser Met Ile Asp Leu Glu Val Ser Lys Ile Ile Tyr Ser Val
945                 950                 955                 960

Thr Arg Ala Phe Phe Lys Tyr Leu Val Cys Asn Ile Lys Asp Thr Ile
            965                 970                 975

Phe Gly Glu Glu His Tyr Pro Asp Phe Phe Leu Ser Thr Leu Lys His
            980                 985                 990

Phe Ile Glu Ile Phe Ser Thr Lys Lys Tyr Ile Phe Asn Arg Val Cys
            995                 1000                1005

Met Ile Leu Lys Ala Lys Glu Ala Lys Leu Lys Ser Asp Gln Cys Gln
            1010                1015                1020

Ser Leu Ile Gln Tyr Asp Ala
1025                1030
```

(2) INFORMATION FOR SEQ ID NO: 3:

(i) SEQUENCE CHARACTERISTICS:
        (A) LENGTH: 1762 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 3:

```
CCCCAAAACC CCAAAACCCC AAAACCCCTA TAAAAAAGA AAAAATTGAG GTAGTTTAGA      60

AATAAAATAT TATTCCCGCA CAAATGGAGA TGGATATTGA TTTGGATGAT ATAGAAAATT    120

TACTTCCTAA TACATTCAAC AAGTATAGCA GCTCTTGTAG TGACAAGAAA GGATGCAAAA    180

CATTGAAATC TGGCTCGAAA TCGCCTTCAT TGACTATTCC AAAGTTGCAA AACAATTAG     240

AGTTCTACTT CTCGGATGCA AATCTTTATA ACGATTCTTT CTTGAGAAAA TTAGTTTTAA    300

AAAGCGGAGA GCAAAGAGTA GAAATTGAAA CATTACTAAT GTTTAAATAA AATCAGGTAA    360

TGAGGATTAT TCTATTTTTT AGATCACTTC TTAAGGAGCA TTATGGAGAA AATTACTTAA    420

TACTAAAAGG TAAACAGTTT GGATTATTTC CCTAGCCAAC AATGATGAGT ATATTAAATT    480

CATATGAGAA TGAGTCAAAG GATCTCGATA CATCAGACTT ACCAAAGACA AACTCGCTAT    540

AAAACGCAAG AAAAAGTTTG ATAATCGAAC AGCAGAAGAA CTTATTGCAT TTACTATTCG    600

TATGGGTTTT ATTACAATTG TTTTAGGTAT CGACGGTGAA CTCCCGAGTC TTGAGACAAT    660

TGAAAAAGCT GTTTACAACT GAAGGAATCG CAGTTCTGAA AGTTCTGATG TGTATGCCAT    720

TATTTTGTGA ATTAATCTCA AATATCTTAT CTCAATTTAA TGGATAGCTA TAGAAACAAA    780

CCAAATAAAC CATGCAAGTT TAATGGAATA TACGTTAAAT CCTTTGGGAC AAATGCACAC    840

TGAATTTATA TTGGATTCTT AAAGCATAGA TACACAGAAT GCTTTAGAGA CTGATTTAGC    900

TTACAACAGA TTACCTGTTT TGATTACTCT TGCTCATCTC TTATATCTTT AAAAGAAGCA    960

GGCGAAATGA AAAGAAGACT AAAGAAAGAG ATTTCAAAAT TTGTTGATTC TTCTGTAACC   1020

GGAATTAACA ACAAGAATAT TAGCAACGAA AAAGAAGAAG AGCTATCACA ATCCTGATTC   1080
```

-continued

```
TTAAAGATTT CAAAAATTCC AGGTAAGAGA GATACATTCA TTAAAATTCA TATATTATAG   1140

TTTTTCATTT CACAGCTGTT ATTTTCTTTT ATCTTAACAA TATTTTTTGA TTAGCTGGAA   1200

GTAAAAAGTA TCAAATAAGA GAAGCGCTAG ACTGAGGTAA CTTAGCTTAT TCACATTCAT   1260

AGATCGACCT TCATATATCC AATACGATGA TAAGGAAACA GCAGTCATCC GTTTTAAAAA   1320

TAGTGCTATG AGGACTAAAT TTTTAGAGTC AAGAAATGGA GCCGAAATCT TAATCAAAAA   1380

GAATTGCGTC GATATTGCAA AAGAATCGAA CTCTAAATCT TTCGTTAATA AGTATTACCA   1440

ATCTTGATTG ATTGAAGAGA TTGACGAGGC AACTGCACAG AAGATCATTA AGAAAATAAA   1500

GTAACTTTTA TTAATTAGAG AATAAACTAA ATTACTAATA TAGAGATCAG CGATCTTCAA   1560

TTGACGAAAT AAAAGCTGAA CTAAAGTTAG ACAATAAAAA ATACAAACCT TGGTCAAAAT   1620

ATTGAGGAAG GAAAAGAAGA CCAGTTAGCA AAAGAAAAAA TAAGGCAATA AATAAAATGA   1680

GTACAGAAGT GAAGAAATAA AAGATTTATT TTTTTCAATA ATTTATTGAA AAGAGGGGTT   1740

TTGGGGTTTT GGGGTTTTGG GG                                           1762
```

(2) INFORMATION FOR SEQ ID NO: 4:

(i) SEQUENCE CHARACTERISTICS:
        (A) LENGTH: 552 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 4:

```
Pro Gln Asn Pro Lys Thr Pro Lys Pro Leu Lys Lys Lys Leu Arg
1               5                   10                  15

Phe Arg Asn Lys Ile Leu Phe Pro His Lys Trp Arg Trp Ile Leu Ile
            20                  25                  30

Trp Met Ile Lys Ile Tyr Phe Leu Ile His Ser Thr Ser Ile Ala Ala
                35                  40                  45

Leu Val Val Thr Arg Lys Asp Ala Lys His Cys Asn Leu Ala Arg Asn
        50                  55                  60

Arg Leu His Cys Leu Phe Gln Ser Cys Lys Asn Asn Ser Ser Thr Ser
65                  70                  75                  80

Arg Met Gln Ile Phe Ile Thr Ile Leu Ser Cys Glu Asn Phe Lys Ala
                85                  90                  95

Glu Ser Lys Glu Lys Leu Lys His Tyr Cys Leu Asn Lys Ile Arg Cys
            100                 105                 110

Gly Leu Phe Tyr Phe Leu Asp His Phe Leu Arg Ser Ile Met Glu Lys
        115                 120                 125

Ile Thr Tyr Lys Val Asn Ser Leu Asp Tyr Phe Pro Ser Gln Gln Cys
    130                 135                 140

Cys Val Tyr Ile His Met Arg Met Ser Gln Arg Ile Ser Ile His Gln
145                 150                 155                 160

Thr Tyr Gln Arg Gln Thr Arg Tyr Lys Thr Gln Glu Lys Val Cys Ser
                165                 170                 175

Asn Ser Arg Arg Thr Tyr Cys Ile Tyr Tyr Ser Tyr Gly Phe Tyr Tyr
            180                 185                 190

Asn Cys Phe Arg Tyr Arg Arg Cys Thr Pro Glu Ser Cys Asp Asn Cys
        195                 200                 205

Lys Ser Cys Leu Gln Leu Lys Glu Ser Gln Phe Cys Lys Phe Cys Val
    210                 215                 220
```

-continued

```
Cys His Tyr Phe Val Asn Ser Gln Ile Ser Tyr Leu Asn Leu Met Asp
225                 230                 235                 240

Ser Tyr Arg Asn Lys Pro Asn Lys Pro Cys Lys Phe Asn Gly Ile Tyr
                245                 250                 255

Val Lys Ser Phe Gly Thr Asn Ala His Cys Ile Tyr Ile Gly Phe Leu
                260                 265                 270

Lys His Arg Tyr Thr Glu Cys Phe Arg Asp Cys Phe Ser Leu Gln Gln
                275                 280                 285

Ile Thr Cys Phe Asp Tyr Ser Cys Ser Ser Leu Ile Ser Leu Lys Glu
290                 295                 300

Ala Gly Glu Met Lys Arg Arg Leu Lys Lys Glu Ile Ser Lys Phe Val
305                 310                 315                 320

Asp Ser Ser Val Thr Gly Ile Asn Asn Lys Asn Ile Ser Asn Glu Lys
                325                 330                 335

Glu Glu Glu Leu Ser Gln Ser Cys Phe Leu Lys Ile Ser Lys Ile Pro
                340                 345                 350

Gly Lys Arg Asp Thr Phe Ile Lys Ile His Ile Leu Phe Phe Ile Ser
                355                 360                 365

Gln Leu Leu Phe Ser Phe Ile Leu Thr Ile Phe Phe Asp Leu Glu Val
                370                 375                 380

Lys Ser Ile Lys Glu Lys Arg Thr Glu Val Thr Leu Ile His Ile His
385                 390                 395                 400

Arg Ser Thr Phe Ile Tyr Pro Ile Arg Cys Gly Asn Ser Ser His Pro
                405                 410                 415

Phe Lys Cys Tyr Glu Asp Ile Phe Arg Val Lys Lys Trp Ser Arg Asn
                420                 425                 430

Leu Asn Gln Lys Glu Leu Arg Arg Tyr Cys Lys Arg Ile Glu Leu Ile
                435                 440                 445

Phe Arg Val Leu Pro Ile Leu Ile Asp Cys Arg Asp Arg Gly Asn Cys
450                 455                 460

Thr Glu Asp His Arg Asn Lys Val Thr Phe Ile Asn Arg Ile Asn Ile
465                 470                 475                 480

Thr Asn Ile Glu Ile Ser Asp Leu Gln Leu Thr Lys Leu Leu Asn Ser
                485                 490                 495

Thr Ile Lys Asn Thr Asn Leu Gly Gln Asn Ile Glu Glu Gly Lys Glu
                500                 505                 510

Asp Gln Leu Ala Lys Glu Lys Ile Arg Gln Ile Lys Cys Val Gln Lys
                515                 520                 525

Cys Arg Asn Lys Arg Phe Ile Phe Phe Asn Asn Leu Leu Lys Arg Gly
                530                 535                 540

Val Leu Gly Phe Trp Gly Phe Gly
545                 550
```

(2) INFORMATION FOR SEQ ID NO: 5:

(i) SEQUENCE CHARACTERISTICS:
        (A) LENGTH: 562 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 5:

```
Pro Lys Thr Pro Lys Pro Gln Asn Pro Tyr Lys Lys Arg Lys Asn Cys
1               5                   10                  15
```

-continued

```
Gly Ser Leu Glu Ile Lys Tyr Tyr Ser Arg Thr Asn Gly Asp Gly Tyr
             20                  25                  30

Cys Phe Gly Cys Tyr Arg Lys Phe Thr Ser Tyr Ile Gln Gln Val Gln
             35                  40                  45

Leu Leu Gln Glu Arg Met Gln Asn Ile Glu Ile Trp Leu Glu Ile Ala
 50                  55                  60

Phe Ile Asp Tyr Ser Lys Val Ala Lys Thr Ile Arg Val Leu Leu Leu
 65                  70                  75                  80

Gly Cys Lys Ser Leu Arg Phe Phe Leu Glu Lys Ile Ser Phe Lys Lys
             85                  90                  95

Arg Arg Ala Lys Ser Arg Asn Cys Asn Ile Thr Asn Val Ile Lys Ser
            100                 105                 110

Gly Asn Glu Asp Tyr Ser Ile Phe Ile Thr Ser Gly Ala Leu Trp Arg
            115                 120                 125

Lys Leu Leu Asn Thr Lys Arg Thr Val Trp Ile Ile Ser Leu Ala Asn
            130                 135                 140

Asn Asp Glu Tyr Ile Lys Phe Ile Cys Glu Cys Val Lys Gly Ser Arg
145                 150                 155                 160

Tyr Ile Arg Leu Thr Lys Asp Lys Leu Ala Ile Lys Arg Lys Lys Lys
                165                 170                 175

Phe Asp Asn Arg Thr Ala Glu Glu Leu Ile Ala Phe Thr Ile Arg Met
            180                 185                 190

Gly Phe Ile Thr Ile Val Leu Gly Ile Asp Gly Glu Leu Pro Ser Leu
            195                 200                 205

Glu Thr Ile Glu Lys Ala Val Tyr Asn Cys Arg Asn Arg Ser Ser Glu
            210                 215                 220

Ser Ser Asp Val Tyr Ala Ile Ile Leu Cys Ile Asn Leu Lys Tyr Leu
225                 230                 235                 240

Ile Ser Ile Trp Ile Ala Ile Glu Thr Asn Gln Ile Asn His Ala Ser
                245                 250                 255

Leu Met Glu Tyr Thr Leu Asn Pro Leu Gly Gln Met His Thr Glu Phe
            260                 265                 270

Ile Leu Asp Ser Ser Ile Asp Thr Gln Asn Ala Leu Glu Thr Asp Leu
            275                 280                 285

Ala Tyr Asn Arg Leu Pro Val Leu Ile Thr Leu Ala His Leu Leu Tyr
            290                 295                 300

Leu Lys Lys Gln Ala Lys Cys Lys Glu Asp Arg Lys Arg Phe Gln Asn
305                 310                 315                 320

Leu Leu Ile Leu Leu Pro Glu Leu Thr Thr Arg Ile Leu Ala Thr Lys
            325                 330                 335

Lys Lys Lys Ser Tyr His Asn Pro Asp Ser Arg Phe Gln Lys Phe Gln
            340                 345                 350

Val Arg Glu Ile His Ser Leu Lys Phe Ile Tyr Tyr Ser Phe Ser Phe
            355                 360                 365

His Ser Cys Tyr Phe Leu Leu Ser Gln Tyr Phe Leu Ile Ser Trp Lys
            370                 375                 380

Lys Val Ser Asn Lys Arg Ser Ala Arg Leu Arg Leu Ser Leu Phe Thr
385                 390                 395                 400

Phe Ile Asp Arg Pro Ser Tyr Ile Gln Tyr Asp Asp Lys Glu Thr Ala
            405                 410                 415

Val Ile Arg Phe Lys Asn Ser Ala Met Arg Thr Lys Phe Leu Glu Ser
            420                 425                 430
```

-continued

```
Arg Asn Gly Ala Glu Ile Leu Ile Lys Lys Asn Cys Val Asp Ile Ala
        435                 440                 445

Lys Glu Ser Asn Ser Lys Ser Phe Val Asn Lys Tyr Tyr Gln Ser Cys
    450                 455                 460

Leu Ile Glu Glu Ile Asp Glu Ala Thr Ala Gln Lys Ile Ile Lys Glu
465                 470                 475                 480

Ile Lys Leu Leu Leu Ile Arg Glu Thr Lys Leu Leu Ile Arg Ser Ala
                485                 490                 495

Ile Phe Asn Cys Arg Asn Lys Ser Cys Thr Lys Val Arg Gln Lys Ile
            500                 505                 510

Gln Thr Leu Val Lys Ile Leu Arg Lys Glu Lys Lys Thr Ser Gln Lys
        515                 520                 525

Lys Lys Gly Asn Lys Asn Glu Tyr Arg Ser Glu Glu Ile Lys Asp Leu
    530                 535                 540

Phe Phe Ser Ile Ile Tyr Cys Lys Glu Gly Phe Trp Gly Phe Gly Val
545                 550                 555                 560

Leu Gly
```

(2) INFORMATION FOR SEQ ID NO: 6:

(i) SEQUENCE CHARACTERISTICS:
        (A) LENGTH: 560 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 6:

```
Pro Lys Pro Gln Asn Pro Lys Thr Pro Ile Lys Lys Glu Lys Ile Glu
1                   5                   10                  15

Val Val Lys Asn Ile Ile Pro Ala Gln Met Glu Met Asp Ile Asp Leu
                20                  25                  30

Asp Asp Ile Glu Asn Leu Leu Pro Asn Thr Phe Asn Lys Tyr Ser Ser
            35                  40                  45

Ser Cys Ser Asp Lys Lys Gly Cys Lys Thr Leu Lys Ser Gly Ser Lys
    50                  55                  60

Ser Pro Ser Leu Thr Ile Pro Lys Leu Gln Lys Gln Leu Glu Phe Tyr
65                  70                  75                  80

Phe Ser Asp Ala Asn Leu Tyr Asn Asp Ser Phe Leu Arg Lys Leu Val
                85                  90                  95

Leu Lys Ser Gly Glu Gln Arg Val Glu Ile Glu Thr Leu Leu Met Phe
            100                 105                 110

Lys Asn Gln Val Met Arg Ile Ile Leu Phe Phe Arg Ser Leu Leu Lys
        115                 120                 125

Glu His Tyr Gly Glu Asn Tyr Leu Ile Leu Lys Gly Lys Gln Phe Gly
    130                 135                 140

Leu Phe Pro Pro Thr Met Met Ser Ile Leu Asn Ser Tyr Glu Asn Glu
145                 150                 155                 160

Ser Lys Asp Leu Asp Thr Ser Asp Leu Pro Lys Thr Asn Ser Leu Asn
                165                 170                 175

Ala Arg Lys Ser Leu Ile Ile Glu Gln Gln Lys Asn Leu Leu His Leu
            180                 185                 190

Leu Phe Val Trp Val Leu Leu Gln Leu Phe Val Ser Thr Val Asn Ser
        195                 200                 205
```

```
Arg Val Leu Arg Gln Leu Lys Lys Leu Phe Thr Thr Glu Gly Ile Ala
    210                 215                 220

Val Leu Lys Val Leu Met Cys Met Pro Leu Phe Cys Glu Leu Ile Ser
225                 230                 235                 240

Asn Ile Leu Ser Gln Phe Asn Gly Leu Lys Gln Thr Lys Thr Met Gln
                245                 250                 255

Val Trp Asn Ile Arg Ile Leu Trp Asp Lys Cys Thr Leu Asn Leu Tyr
            260                 265                 270

Trp Ile Leu Lys Ala Ile His Arg Met Leu Arg Leu Ile Leu Thr Thr
        275                 280                 285

Asp Tyr Leu Phe Cys Leu Leu Leu Ile Ser Tyr Ile Phe Lys Arg
    290                 295                 300

Ser Arg Arg Asn Glu Lys Lys Thr Lys Glu Arg Asp Phe Lys Ile Cys
305                 310                 315                 320

Cys Phe Phe Cys Asn Arg Asn Gln Gln Glu Tyr Gln Arg Lys Arg Arg
                325                 330                 335

Arg Ala Ile Thr Ile Leu Ile Leu Lys Asp Phe Lys Asn Ser Arg Glu
            340                 345                 350

Arg Tyr Ile His Asn Ser Tyr Ile Ile Val Phe His Phe Thr Ala Val
        355                 360                 365

Ile Phe Phe Tyr Leu Asn Asn Ile Phe Cys Leu Ala Gly Ser Lys Lys
    370                 375                 380

Tyr Gln Ile Arg Glu Ala Leu Asp Cys Gly Asn Leu Ala Tyr Ser His
385                 390                 395                 400

Ser Ile Asp Leu His Ile Ser Asn Thr Met Ile Arg Lys Gln Gln Ser
                405                 410                 415

Ser Val Leu Lys Ile Val Leu Cys Gly Leu Asn Phe Ser Gln Glu Met
            420                 425                 430

Glu Pro Lys Ser Ser Lys Arg Ile Ala Ser Ile Leu Gln Lys Asn Arg
        435                 440                 445

Thr Leu Asn Leu Ser Leu Ile Ser Ile Thr Asn Leu Asp Cys Leu Lys
    450                 455                 460

Arg Leu Thr Arg Gln Leu His Arg Arg Ser Leu Lys Lys Ser Asn Phe
465                 470                 475                 480

Tyr Leu Glu Asn Lys Leu Asn Tyr Tyr Arg Asp Gln Arg Ser Ser Ile
                485                 490                 495

Asp Glu Ile Lys Ala Glu Leu Lys Leu Asp Asn Lys Tyr Lys Pro
            500                 505                 510

Trp Ser Lys Tyr Cys Gly Arg Lys Arg Pro Val Ser Lys Arg Lys
        515                 520                 525

Asn Lys Ala Ile Asn Lys Met Ser Thr Glu Val Lys Lys Ile Tyr
530                 535                 540

Phe Phe Gln Phe Ile Glu Lys Arg Gly Phe Gly Val Leu Gly Phe Trp
545                 550                 555                 560
```

(2) INFORMATION FOR SEQ ID NO: 7:

(i) SEQUENCE CHARACTERISTICS:
        (A) LENGTH: 719 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 7:

```
Met Glu Ile Glu Asn Asn Gln Ala Gln Gln Pro Lys Ala Glu Lys Leu
 1               5                  10                  15
Trp Trp Glu Leu Glu Leu Glu Met Gln Glu Asn Gln Asn Asp Ile Gln
                20                  25                  30
Val Arg Val Lys Ile Asp Asp Pro Lys Gln Tyr Leu Val Asn Val Thr
            35                  40                  45
Ala Ala Cys Leu Leu Gln Glu Gly Ser Tyr Tyr Gln Asp Lys Asp Glu
 50                  55                  60
Arg Arg Tyr Ile Ile Thr Lys Ala Leu Leu Glu Val Ala Glu Ser Asp
 65                  70                  75                  80
Pro Glu Phe Ile Cys Gln Leu Ala Val Tyr Ile Arg Asn Glu Leu Tyr
                85                  90                  95
Ile Arg Thr Thr Thr Asn Tyr Ile Val Ala Phe Cys Val Val His Lys
                100                 105                 110
Asn Thr Gln Pro Phe Ile Glu Lys Tyr Phe Asn Lys Ala Val Leu Leu
            115                 120                 125
Pro Asn Asp Leu Leu Glu Val Cys Glu Phe Ala Gln Val Leu Tyr Ile
130                 135                 140
Phe Asp Ala Thr Glu Phe Lys Asn Leu Tyr Leu Asp Arg Ile Leu Ser
145                 150                 155                 160
Gln Asp Ile Arg Lys Glu Leu Thr Phe Arg Lys Cys Leu Gln Arg Cys
                165                 170                 175
Val Arg Ser Lys Phe Ser Glu Phe Asn Glu Tyr Gln Leu Gly Lys Tyr
                180                 185                 190
Cys Thr Glu Ser Gln Arg Lys Lys Thr Met Phe Arg Tyr Leu Ser Val
            195                 200                 205
Thr Asn Lys Gln Lys Trp Asp Gln Thr Lys Lys Arg Lys Glu Asn
210                 215                 220
Leu Leu Thr Lys Leu Gln Ala Ile Lys Glu Ser Glu Asp Lys Ser Lys
225                 230                 235                 240
Arg Glu Thr Gly Asp Ile Met Asn Val Glu Asp Ala Ile Lys Ala Leu
                245                 250                 255
Lys Pro Ala Val Met Lys Lys Ile Ala Lys Arg Gln Asn Ala Met Lys
                260                 265                 270
Lys His Met Lys Ala Pro Lys Ile Pro Asn Ser Thr Leu Glu Ser Lys
            275                 280                 285
Tyr Leu Thr Phe Lys Asp Leu Ile Lys Phe Cys His Ile Ser Glu Pro
290                 295                 300
Lys Glu Arg Val Tyr Lys Ile Leu Gly Lys Tyr Pro Lys Thr Glu
305                 310                 315                 320
Glu Glu Tyr Lys Ala Ala Phe Gly Asp Ser Ala Ser Ala Pro Phe Asn
                325                 330                 335
Pro Glu Leu Ala Gly Lys Arg Met Lys Ile Glu Ile Ser Lys Thr Trp
            340                 345                 350
Glu Asn Glu Leu Ser Ala Lys Gly Asn Thr Ala Glu Val Trp Asp Asn
        355                 360                 365
Leu Ile Ser Ser Asn Gln Leu Pro Tyr Met Ala Met Leu Arg Asn Leu
370                 375                 380
Ser Asn Ile Leu Lys Ala Gly Val Ser Asp Thr Thr His Ser Ile Val
385                 390                 395                 400
Ile Asn Lys Ile Cys Glu Pro Lys Ala Val Glu Asn Ser Lys Met Phe
                405                 410                 415
```

```
Pro Leu Gln Phe Phe Ser Ala Ile Glu Ala Val Asn Glu Ala Val Thr
            420                 425                 430

Lys Gly Phe Lys Ala Lys Lys Arg Glu Asn Met Asn Leu Lys Gly Gln
            435                 440                 445

Ile Glu Ala Val Lys Glu Val Val Glu Lys Thr Asp Glu Glu Lys Lys
    450                 455                 460

Asp Met Glu Leu Glu Gln Thr Glu Glu Gly Phe Val Lys Val Asn
465                 470                 475                 480

Glu Gly Ile Gly Lys Gln Tyr Ile Asn Ser Ile Glu Leu Ala Ile Lys
                485                 490                 495

Ile Ala Val Asn Lys Asn Leu Asp Glu Ile Lys Gly His Thr Ala Ile
            500                 505                 510

Phe Ser Asp Val Ser Gly Ser Met Ser Thr Ser Met Ser Gly Gly Ala
            515                 520                 525

Lys Lys Tyr Gly Ser Val Arg Thr Cys Leu Glu Cys Ala Leu Val Leu
            530                 535                 540

Gly Leu Met Val Lys Gln Arg Cys Glu Lys Ser Ser Phe Tyr Ile Phe
545                 550                 555                 560

Ser Ser Pro Ser Ser Gln Cys Asn Lys Cys Tyr Leu Glu Val Asp Leu
                565                 570                 575

Pro Gly Asp Glu Leu Arg Pro Ser Met Gln Lys Leu Leu Gln Glu Lys
            580                 585                 590

Gly Lys Leu Gly Gly Gly Thr Asp Phe Pro Tyr Glu Cys Ile Asp Glu
            595                 600                 605

Trp Thr Lys Asn Lys Thr His Val Asp Asn Ile Val Ile Leu Ser Asp
            610                 615                 620

Met Met Ile Ala Glu Gly Tyr Ser Asp Ile Asn Val Arg Gly Ser Ser
625                 630                 635                 640

Ile Val Asn Ser Ile Lys Lys Tyr Lys Asp Glu Val Asn Pro Asn Ile
                645                 650                 655

Lys Ile Phe Ala Val Asp Leu Glu Gly Tyr Gly Lys Cys Leu Asn Leu
            660                 665                 670

Gly Asp Glu Phe Asn Glu Asn Asn Tyr Ile Lys Ile Phe Gly Met Ser
            675                 680                 685

Asp Ser Ile Leu Lys Phe Ile Ser Ala Lys Gln Gly Gly Ala Asn Met
            690                 695                 700

Val Glu Val Ile Lys Asn Phe Ala Leu Gln Lys Ile Gly Gln Lys
705                 710                 715

(2) INFORMATION FOR SEQ ID NO: 8:

(i) SEQUENCE CHARACTERISTICS:
        (A) LENGTH: 872 amino acids
        (B) TYPE: amino acid
        (C) STRANDEDNESS: not relevant
        (D) TOPOLOGY: not relevant (ii) MOLECULE TYPE: protein (xi) SEQUENCE DESCRIPTION: SEQ ID NO: 8:

Met Ser Arg Arg Asn Gln Lys Lys Pro Gln Ala Pro Ile Gly Asn Glu
1               5                   10                  15

Thr Asn Leu Asp Phe Val Leu Gln Asn Leu Glu Val Tyr Lys Ser Gln
            20                  25                  30

Ile Glu His Tyr Lys Thr Gln Gln Gln Ile Lys Glu Glu Asp Leu
            35                  40                  45
```

-continued

```
Lys Leu Leu Lys Phe Lys Asn Gln Asp Gln Asp Gly Asn Ser Gly Asn
     50                  55                  60

Asp Asp Asp Asp Glu Glu Asn Asn Ser Asn Lys Gln Gln Glu Leu Leu
65                  70                  75                  80

Arg Arg Val Asn Gln Ile Lys Gln Gln Val Gln Leu Ile Lys Lys Val
                 85                  90                  95

Gly Ser Lys Val Glu Lys Asp Leu Asn Leu Asn Glu Asp Glu Asn Lys
            100                 105                 110

Lys Asn Gly Leu Ser Glu Gln Gln Val Lys Glu Gln Leu Arg Thr
            115                 120                 125

Ile Thr Glu Glu Gln Val Lys Tyr Gln Asn Leu Val Phe Asn Met Asp
        130                 135                 140

Tyr Gln Leu Asp Leu Asn Glu Ser Gly Gly His Arg Arg His Arg Arg
145                 150                 155                 160

Glu Thr Asp Tyr Asp Thr Glu Lys Trp Phe Glu Ile Ser His Asp Gln
                165                 170                 175

Lys Asn Tyr Val Ser Ile Tyr Ala Asn Gln Lys Thr Ser Tyr Cys Trp
            180                 185                 190

Trp Leu Lys Asp Tyr Phe Asn Lys Asn Asn Tyr Asp His Leu Asn Val
        195                 200                 205

Ser Ile Asn Arg Leu Glu Thr Glu Ala Glu Phe Tyr Ala Phe Asp Asp
210                 215                 220

Phe Ser Gln Thr Ile Lys Leu Thr Asn Asn Ser Tyr Gln Thr Val Asn
225                 230                 235                 240

Ile Asp Val Asn Phe Asp Asn Asn Leu Cys Ile Leu Ala Leu Leu Arg
                245                 250                 255

Phe Leu Leu Ser Leu Glu Arg Phe Asn Ile Leu Asn Ile Arg Ser Ser
            260                 265                 270

Tyr Thr Arg Asn Gln Tyr Asn Phe Glu Lys Ile Gly Glu Leu Leu Glu
        275                 280                 285

Thr Ile Phe Ala Val Val Phe Ser His Arg His Leu Gln Gly Ile His
290                 295                 300

Leu Gln Val Pro Cys Glu Ala Phe Gln Tyr Leu Val Asn Ser Ser Ser
305                 310                 315                 320

Gln Ile Ser Val Lys Asp Ser Gln Leu Gln Val Tyr Ser Phe Ser Thr
                325                 330                 335

Asp Leu Lys Leu Val Asp Thr Asn Lys Val Gln Asp Tyr Phe Lys Phe
            340                 345                 350

Leu Gln Glu Phe Pro Arg Leu Thr His Val Ser Gln Gln Ala Ile Pro
        355                 360                 365

Val Ser Ala Thr Asn Ala Val Glu Asn Leu Asn Val Leu Leu Lys Lys
370                 375                 380

Val Lys His Ala Asn Leu Asn Leu Val Ser Ile Pro Thr Gln Phe Asn
385                 390                 395                 400

Phe Asp Phe Tyr Phe Val Asn Leu Gln His Leu Lys Leu Glu Phe Gly
                405                 410                 415

Leu Glu Pro Asn Ile Leu Thr Lys Gln Lys Leu Glu Asn Leu Leu Leu
            420                 425                 430

Ser Ile Lys Gln Ser Lys Asn Leu Lys Phe Leu Arg Leu Asn Phe Tyr
        435                 440                 445

Thr Tyr Val Ala Gln Glu Thr Ser Arg Lys Gln Ile Leu Lys Gln Ala
450                 455                 460
```

-continued

```
Thr Thr Ile Lys Asn Leu Lys Asn Asn Lys Asn Gln Glu Glu Thr Pro
465                 470                 475                 480

Glu Thr Lys Asp Glu Thr Pro Ser Glu Ser Thr Ser Gly Met Lys Phe
                485                 490                 495

Phe Asp His Leu Ser Glu Leu Thr Glu Leu Glu Asp Phe Ser Val Asn
                500                 505                 510

Leu Gln Ala Thr Gln Glu Ile Tyr Asp Ser Leu His Lys Leu Leu Ile
                515                 520                 525

Arg Ser Thr Asn Leu Lys Lys Phe Lys Leu Ser Tyr Lys Tyr Glu Met
530                 535                 540

Glu Lys Ser Lys Met Asp Thr Phe Ile Asp Leu Lys Asn Ile Tyr Glu
545                 550                 555                 560

Thr Leu Asn Asn Leu Lys Arg Cys Ser Val Asn Ile Ser Asn Pro His
                565                 570                 575

Gly Asn Ile Ser Tyr Glu Leu Thr Asn Lys Asp Ser Thr Phe Tyr Lys
                580                 585                 590

Phe Lys Leu Thr Leu Asn Gln Glu Leu Gln His Ala Lys Tyr Thr Phe
                595                 600                 605

Lys Gln Asn Glu Phe Gln Phe Asn Asn Val Lys Ser Ala Lys Ile Glu
                610                 615                 620

Ser Ser Ser Leu Glu Ser Leu Glu Asp Ile Asp Ser Leu Cys Lys Ser
625                 630                 635                 640

Ile Ala Ser Cys Lys Asn Leu Gln Asn Val Asn Ile Ile Ala Ser Leu
                645                 650                 655

Leu Tyr Pro Asn Asn Ile Gln Lys Asn Pro Phe Asn Lys Pro Asn Leu
                660                 665                 670

Leu Phe Phe Lys Gln Phe Glu Gln Leu Lys Asn Leu Glu Asn Val Ser
                675                 680                 685

Ile Asn Cys Ile Leu Asp Gln His Ile Leu Asn Ser Ile Ser Glu Phe
                690                 695                 700

Leu Glu Lys Asn Lys Lys Ile Lys Ala Phe Ile Leu Lys Arg Tyr Tyr
705                 710                 715                 720

Leu Leu Gln Tyr Tyr Leu Asp Tyr Thr Lys Leu Phe Lys Thr Leu Gln
                725                 730                 735

Gln Leu Pro Glu Leu Asn Gln Val Tyr Ile Asn Gln Gln Leu Glu Glu
                740                 745                 750

Leu Thr Val Ser Glu Val His Lys Gln Val Trp Glu Asn His Lys Gln
                755                 760                 765

Lys Ala Phe Tyr Glu Pro Leu Cys Glu Phe Ile Lys Glu Ser Ser Gln
770                 775                 780

Thr Leu Gln Leu Ile Asp Phe Asp Gln Asn Thr Val Ser Asp Asp Ser
785                 790                 795                 800

Ile Lys Lys Ile Leu Glu Ser Ile Ser Glu Ser Lys Tyr His His Tyr
                805                 810                 815

Leu Arg Leu Asn Pro Ser Gln Ser Ser Ser Leu Ile Lys Ser Glu Asn
                820                 825                 830

Glu Glu Ile Gln Glu Leu Leu Lys Ala Cys Asp Glu Lys Gly Val Leu
                835                 840                 845

Val Lys Ala Tyr Tyr Lys Phe Pro Leu Cys Leu Pro Thr Gly Thr Tyr
                850                 855                 860

Tyr Asp Tyr Asn Ser Asp Arg Trp
865                 870
```

(2) INFORMATION FOR SEQ ID NO: 9:

(i) SEQUENCE CHARACTERISTICS:
        (A) LENGTH: 83 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 9:

Asp Ile Asp Leu Asp Asp Ile Glu Asn Leu Leu Pro Asn Thr Phe Asn
1               5                   10                  15

Lys Tyr Ser Ser Ser Cys Ser Asp Lys Lys Gly Cys Lys Thr Leu Lys
            20                  25                  30

Ser Gly Ser Lys Ser Pro Ser Leu Thr Ile Pro Lys Leu Gln Lys Gln
        35                  40                  45

Leu Glu Phe Tyr Phe Ser Asp Ala Asn Leu Tyr Asn Asp Ser Phe Leu
    50                  55                  60

Arg Lys Leu Val Leu Lys Ser Gly Glu Gln Arg Val Glu Ile Glu Thr
65                  70                  75                  80

Leu Leu Met (2) INFORMATION FOR SEQ ID NO: 10:

(i) SEQUENCE CHARACTERISTICS:
        (A) LENGTH: 100 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 10:

Asn Val Lys Ser Ala Lys Ile Glu Ser Ser Ser Leu Glu Ser Leu Glu
1               5                   10                  15

Asp Ile Asp Ser Leu Cys Lys Ser Ile Ala Ser Cys Lys Asn Leu Gln
            20                  25                  30

Asn Val Asn Ile Ile Ala Ser Leu Leu Tyr Pro Asn Asn Ile Gln Lys
        35                  40                  45

Asn Pro Phe Asn Lys Pro Asn Leu Leu Phe Phe Lys Gln Phe Glu Gln
    50                  55                  60

Leu Lys Asn Leu Glu Asn Val Ser Ile Asn Cys Ile Leu Asp Gln His
65                  70                  75                  80

Ile Leu Asn Ser Ile Ser Glu Phe Leu Glu Lys Asn Lys Lys Ile Lys
                85                  90                  95

Ala Phe Ile Leu
            100

(2) INFORMATION FOR SEQ ID NO: 11:

(i) SEQUENCE CHARACTERISTICS:
        (A) LENGTH: 85 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 11:

Met Glu Met Asp Ile Asp Leu Asp Asp Ile Glu Asn Leu Leu Pro Asn
1               5                   10                  15

```
Thr Phe Asn Lys Tyr Ser Ser Cys Ser Asp Lys Lys Gly Cys Lys
            20                  25                  30

Thr Leu Lys Ser Gly Ser Lys Ser Pro Ser Leu Thr Ile Pro Lys Leu
            35                  40                  45

Gln Lys Gln Leu Glu Phe Tyr Phe Ser Asp Ala Asn Leu Tyr Asn Asp
 50                  55                  60

Ser Phe Leu Arg Lys Leu Val Leu Lys Ser Gly Glu Gln Arg Val Glu
 65                  70                  75                  80

Ile Glu Thr Leu Leu
                85
```

(2) INFORMATION FOR SEQ ID NO: 12:

(i) SEQUENCE CHARACTERISTICS:
        (A) LENGTH: 98 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 12:

```
Ile Glu Leu Ala Ile Lys Ile Ala Val Asn Lys Asn Leu Asp Glu Ile
 1                5                  10                  15

Lys Gly His Thr Ala Ile Phe Ser Asp Val Ser Gly Ser Met Ser Thr
            20                  25                  30

Ser Met Ser Gly Gly Ala Lys Lys Tyr Gly Ser Val Arg Thr Cys Leu
            35                  40                  45

Glu Cys Ala Leu Val Leu Gly Leu Met Val Lys Gln Arg Cys Glu Lys
 50                  55                  60

Ser Ser Phe Tyr Ile Phe Ser Pro Ser Ser Gln Cys Lys Cys Tyr
 65                  70                  75                  80

Leu Glu Val Asp Leu Pro Gly Asp Glu Leu Arg Pro Ser Met Gln Lys
                85                  90                  95

Leu Leu
```

(2) INFORMATION FOR SEQ ID NO: 13:

(i) SEQUENCE CHARACTERISTICS:
        (A) LENGTH: 69 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 13:

```
Gly Gln Pro Lys Leu Phe Phe Ala Thr Met Asp Ile Glu Lys Cys Tyr
 1                5                  10                  15

Asp Ser Val Asn Arg Glu Lys Leu Ser Thr Phe Leu Lys Thr Thr Lys
            20                  25                  30

Leu Leu Lys Phe Tyr Lys Gln Thr Lys Gly Ile Pro Gln Gly Leu Cys
            35                  40                  45

Val Ser Ser Ile Leu Ser Ser Phe Tyr Tyr Ala Thr Leu Glu Glu Ser
 50                  55                  60

Ser Leu Gly Phe Leu
 65
```

(2) INFORMATION FOR SEQ ID NO: 14:

(i) SEQUENCE CHARACTERISTICS:
        (A) LENGTH: 69 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 14:

```
Lys Asn Arg Asn Leu His Cys Thr Tyr Ile Asp Tyr Lys Lys Ala Phe
 1               5                  10                  15

Asp Ser Ile Pro His Ser Trp Leu Ile Gln Val Leu Glu Ile Tyr Lys
            20                  25                  30

Ile Asn Arg Gln Ile Ala Ile Lys Lys Gly Ile Tyr Gln Gly Asp Ser
        35                  40                  45

Leu Ser Pro Leu Trp Phe Cys Leu Ala Leu Asn Pro Leu Ser His Gln
    50                  55                  60

Leu His Asn Asp Arg
65
```

(2) INFORMATION FOR SEQ ID NO: 15:

(i) SEQUENCE CHARACTERISTICS:
        (A) LENGTH: 69 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 15:

```
Phe Gly Gly Ser Asn Trp Phe Arg Glu Val Asp Leu Lys Lys Cys Phe
 1               5                  10                  15

Asp Thr Ile Ser His Asp Leu Ile Ile Lys Glu Leu Lys Arg Tyr Ile
            20                  25                  30

Ser Asp His Val Pro Val Gly Pro Arg Val Cys Val Gln Gly Ala Pro
            35                  40                  45

Thr Ser Pro Ala Leu Cys Asn Ala Val Leu Leu Arg Leu Asp Arg Arg
    50                  55                  60

Leu Ala Gly Leu Ala
65
```

(2) INFORMATION FOR SEQ ID NO: 16:

(i) SEQUENCE CHARACTERISTICS:
        (A) LENGTH: 69 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 16:

```
Leu Lys Lys Lys Lys Ser Val Thr Val Leu Asp Val Gly Asp Ala Tyr
 1               5                  10                  15

Phe Ser Val Pro Leu Asp Glu Asp Phe Arg Lys Tyr Thr Ala Phe Thr
            20                  25                  30

Ile Pro Gly Ile Arg Tyr Gln Tyr Asn Val Leu Pro Gln Gly Trp Lys
        35                  40                  45
```

```
Gly Ser Pro Ala Ile Phe Gln Ser Ser Met Thr Lys Ile Leu Glu Pro
    50                  55                  60

Phe Arg Lys Gln Asn
65
```

(2) INFORMATION FOR SEQ ID NO: 17:

(i) SEQUENCE CHARACTERISTICS:
        (A) LENGTH: 69 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 17:

```
Val Leu Pro Glu Leu Tyr Phe Met Lys Phe Asp Val Lys Ser Cys Tyr
1               5                   10                  15

Asp Ser Ile Pro Arg Met Glu Cys Met Arg Ile Leu Lys Asp Ala Leu
            20                  25                  30

Lys Asn Lys Cys Tyr Ile Arg Glu Asp Gly Leu Phe Gln Gly Ser Ser
        35                  40                  45

Leu Ser Ala Pro Ile Val Asp Leu Val Tyr Asp Asp Leu Leu Glu Phe
    50                  55                  60

Tyr Ser Glu Phe Lys
65
```

(2) INFORMATION FOR SEQ ID NO: 18:

(i) SEQUENCE CHARACTERISTICS:
        (A) LENGTH: 54 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 18:

```
Leu Met Arg Leu Thr Asp Asp Tyr Leu Leu Ile Thr Thr Gln Glu Asn
1               5                   10                  15

Asn Ala Val Leu Phe Ile Glu Lys Leu Ile Asn Val Ser Arg Glu Asn
            20                  25                  30

Gly Phe Lys Phe Asn Met Lys Lys Leu Gln Thr Gln Asp Tyr Cys Asp
        35                  40                  45

Trp Ile Gly Ile Ser Ile
        50
```

(2) INFORMATION FOR SEQ ID NO: 19:

(i) SEQUENCE CHARACTERISTICS:
        (A) LENGTH: 54 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 19:

```
His Leu Ile Tyr Met Asp Asp Ile Lys Leu Tyr Ala Lys Asn Asp Lys
1               5                   10                  15

Glu Met Lys Lys Leu Ile Asp Thr Thr Thr Ile Phe Ser Asn Asp Ile
            20                  25                  30
```

```
Ser Met Gln Phe Gly Leu Asp Lys Cys Lys Thr Lys Cys Leu Tyr Lys
         35                  40                  45

Tyr Leu Gly Phe Gln Gln
 50

(2) INFORMATION FOR SEQ ID NO: 20:

(i) SEQUENCE CHARACTERISTICS:
        (A) LENGTH: 53 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 20:

Tyr Val Arg Tyr Ala Asp Asp Ile Leu Ile Gly Val Leu Gly Ser Lys
 1               5                  10                  15

Asn Lys Ile Ile Lys Arg Asp Leu Asn Asn Phe Leu Asn Ser Leu Gly
                 20                  25                  30

Leu Thr Ile Asn Glu Glu Lys Thr Leu Ile Glu Thr Pro Ala Arg Phe
             35                  40                  45

Leu Gly Tyr Asn Ile
 50

(2) INFORMATION FOR SEQ ID NO: 21:

(i) SEQUENCE CHARACTERISTICS:
        (A) LENGTH: 54 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 21:

Ile Tyr Gln Tyr Met Asp Asp Leu Tyr Val Gly Ser His Leu Glu Ile
 1               5                  10                  15

Gly His Arg Thr Lys Ile Glu Glu Leu Arg Gln His Leu Leu Arg Trp
                 20                  25                  30

Gly Leu Thr Thr Pro Asp Lys Lys His Gln Lys Glu Pro Pro Phe Leu
             35                  40                  45

Trp Met Gly Tyr Glu Leu
 50

(2) INFORMATION FOR SEQ ID NO: 22:

(i) SEQUENCE CHARACTERISTICS:
        (A) LENGTH: 49 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 22:

Ile Leu Lys Leu Ala Asp Asp Phe Leu Ile Ile Ser Thr Asp Gln Gln
 1               5                  10                  15

Gln Val Ile Asn Ile Lys Lys Leu Ala Met Gly Phe Gln Lys Tyr
                 20                  25                  30

Asn Ala Lys Ala Asn Arg Ile Arg Ser Lys Ser Ser Lys Gly Ile Phe
             35                  40                  45

Arg
```

(2) INFORMATION FOR SEQ ID NO: 23:

(i) SEQUENCE CHARACTERISTICS:
        (A) LENGTH: 39 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 23:

Leu Gln Lys Gln Leu Glu Phe Tyr Phe Ser Asp Ala Asn Leu Tyr Asn
1               5                   10                  15

Asp Ser Phe Leu Arg Lys Leu Val Leu Lys Ser Gly Glu Gln Arg Val
            20                  25                  30

Glu Ile Glu Thr Leu Leu Met
        35

(2) INFORMATION FOR SEQ ID NO: 24:

(i) SEQUENCE CHARACTERISTICS:
        (A) LENGTH: 37 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 24:

Ile Cys His Gln Glu Tyr Tyr Phe Gly Asp Phe Asn Leu Pro Arg Asp
1               5                   10                  15

Lys Phe Leu Lys Glu Gln Ile Lys Leu Asp Glu Gly Trp Val Pro Leu
            20                  25                  30

Glu Ile Met Ile Lys
        35

(2) INFORMATION FOR SEQ ID NO: 25:

(i) SEQUENCE CHARACTERISTICS:
        (A) LENGTH: 38 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 25:

Ile Cys Glu Gln Ile Glu Tyr Tyr Phe Gly Asp His Asn Leu Pro Arg
1               5                   10                  15

Asp Lys Phe Leu Lys Gln Gln Ile Leu Leu Asp Asp Gly Trp Val Pro
            20                  25                  30

Leu Glu Thr Met Ile Lys
        35

(2) INFORMATION FOR SEQ ID NO: 26:

(i) SEQUENCE CHARACTERISTICS:
        (A) LENGTH: 39 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 26:

Ile Leu Arg Gln Val Glu Tyr Tyr Phe Gly Asp Ala Asn Leu Asn Arg
1               5                   10                  15

Asp Lys Phe Leu Arg Glu Gln Ile Gly Lys Asn Glu Asp Gly Trp Val
            20                  25                  30

Pro Leu Ser Val Leu Val Thr
            35

(2) INFORMATION FOR SEQ ID NO: 27:

(i) SEQUENCE CHARACTERISTICS:
        (A) LENGTH: 38 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 27:

Cys Leu Lys Gln Val Glu Phe Tyr Phe Ser Glu Phe Asn Phe Pro Tyr
1               5                   10                  15

Asp Arg Phe Leu Arg Thr Thr Ala Glu Lys Asn Asp Gly Trp Val Pro
            20                  25                  30

Ile Ser Thr Ile Ala Thr
            35

(2) INFORMATION FOR SEQ ID NO: 28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 28:

TAGACCTGTT AGTGTACATT TGAATTGAAG C                        31

(2) INFORMATION FOR SEQ ID NO: 29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 29:

TAGACCTGTT AGGTTGGATT TGTGGCATCA                         30

(2) INFORMATION FOR SEQ ID NO: 30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 30:

CAAAACCCCA AAACCTAACA GGTCTA                                               26

(2) INFORMATION FOR SEQ ID NO: 31:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 31:

GCGGGAATTC TAATACGACT CACTATAGGG AAGAAACTCT GATGAGGCCG AAAGGCCGAA           60

ACTCCACGAA AGTGGAGTAA GTTTCTCGAT AATTGATCTG TAG                            103

(2) INFORMATION FOR SEQ ID NO: 32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 32:

CGGGGATCCT CTTCAAAAGA TGAGAGGACA GCAAAC                                    36

(2) INFORMATION FOR SEQ ID NO: 33:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 33:

CCCCAAAACC CCAAAACCCC AAAACCCCCA CAGGGGTTTT GGGGTTTTGG GGTTTTGGGG           60

(2) INFORMATION FOR SEQ ID NO: 34:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 34:

CCAAAACCCC AAAACCCCAA AACCCCCACA GGGGTTTTGG GGTTTTGGGG TTTTGGGG            58

(2) INFORMATION FOR SEQ ID NO: 35:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "DNA"

(xi) SEQUENCE DESCRIPTION: SEQ ID NO: 35:

AAAACCCCAA AACCCCAAAA CCCCCACAGG GGTTTTGGGG TTTTGGGGTT TTGGGG         56

(2) INFORMATION FOR SEQ ID NO: 36:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 36:

AACCCCAAAA CCCCAAAACC CCCACAGGGG TTTTGGGGTT TTGGGGTTTT GGGG           54

(2) INFORMATION FOR SEQ ID NO: 37:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 37:

CCCCAAAACC CCAAAACCCC CACAGGGGTT TTGGGGTTTT GGGGTTTT                  48

(2) INFORMATION FOR SEQ ID NO: 38:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 38:

AAAACCCCAA AACCCCAAAA CCCCCACAGG GGTTTTGGGG TTTTGGGGTT TT             52

(2) INFORMATION FOR SEQ ID NO: 39:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 39:

AACCCCAAAA CCCCAAAACC CCCACAGGGG TTTTGGGGTT TTGGGGTTTT                50

(2) INFORMATION FOR SEQ ID NO: 40:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "DNA"

(xi) SEQUENCE DESCRIPTION: SEQ ID NO: 40:

CCCCAAAACC CCAAAACCCC CACAGGGGTT TTGGGGTTTT GGGGTTTT                48

(2) INFORMATION FOR SEQ ID NO: 41:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 41:

CCAAAACCCC AAACCCCCA CAGGGGTTTT GGGGTTTTGG GGTTTT                   46

(2) INFORMATION FOR SEQ ID NO: 42:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 42:

AAAACCCCAA AACCCCCACA GGGGTTTTGG GGTTTTGGGG TTTT                    44

(2) INFORMATION FOR SEQ ID NO: 43:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "RNA"

(xi) SEQUENCE DESCRIPTION: SEQ ID NO: 43:

CAAAACCCCA AAACC                                                    15

(2) INFORMATION FOR SEQ ID NO: 44:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 44:

TTTTGGGG                                                             8

(2) INFORMATION FOR SEQ ID NO: 45:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "RNA"

(xi) SEQUENCE DESCRIPTION: SEQ ID NO: 45:

CAAAACCCCA AAACC                                                            15

(2) INFORMATION FOR SEQ ID NO: 46:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO: 46:

GGGGTTTT                                                                    8

(2) INFORMATION FOR SEQ ID NO: 47:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO: 47:

TCTRAARTAR TGDGTNADRT TRTTCAT                                               27

(2) INFORMATION FOR SEQ ID NO: 48:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO: 48:

GCGGATCCAT GAAYCCWGAR AAYCCWAAYG T                                          31

(2) INFORMATION FOR SEQ ID NO: 49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO: 49:

NNNGTNACHG GHATHAAYAA                                                       20

(2) INFORMATION FOR SEQ ID NO: 50:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
    (A) DESCRIPTION: /desc = "DNA"

(xi) SEQUENCE DESCRIPTION: SEQ ID NO: 50:

DGCDGTYTCY TGRTCRTTRT A                                                21

(2) INFORMATION FOR SEQ ID NO: 51:

(i) SEQUENCE CHARACTERISTICS:
        (A) LENGTH: 2421 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 51:

```
AACTCATTTA ATTACTAATT TAATCAACAA GATTGATAAA AAGCAGTAAA TAAAACCCAA         60

TAGATTTAAT TTAGAAAGTA TCAATTGAAA AATGGAAATT GAAAACAACT AAGCACAATA        120

GCCAAAAGCC GAAAAATTGT GGTGGGAACT TGAATTAGAT ATGCAAGAAA ACCAAAATGA        180

TATATAAGTT AGGGTTAAGA TTGACGATCC TAAGCAATAT CTCGTGAACG TCACTGCAGC        240

ATGTTTGTTG TAGGAAGGTA GTTACTACTA AGATAAAGAT GAAAGAAGAT ATATCATCAC        300

TAAAGCACTT CTTGAGGTGG CTGAGTCTGA TCCTGAGTTC ATCTGCTAGT TGGCAGTCTA        360

CATCCGTAAT GAACTTTACA TCAGAACTAC CACTAACTAC ATTGTAGCAT TTTGTGTTGT        420

CCACAAGAAT ACTCAACCAT TCATCGAAAA GTACTTCAAC AAAGCAGTAC TTTTGCCTAA        480

TGACTTACTG GAAGTCTGTG AATTTGCATA GGTTCTCTAT ATTTTTGATG CAACTGAATT        540

CAAAAATTTG TATCTTGATA GGATACTTTC ATAAGATATT CGTAAGGAAC TCACTTTCCG        600

TAAGTGTTTA CAAAGATGCG TCAGAAGCAA GTTTTCTGAA TTCAACGAAT ACTAACTTGG        660

TAAGTATTGC ACTGAATCCT AACGTAAGAA ACAATGTTC CGTTACCTCT CAGTTACCAA         720

CAAGTAAAAG TGGGATTAAA CTAAGAAGAA GAGAAAAGAG AATCTCTTAA CCAAACTTTA        780

GGCAATAAAG GAATCTGAAG ATAAGTCCAA GAGAGAAACT GGAGACATAA TGAACGTTGA        840

AGATGCAATC AAGGCTTTAA AACCAGCAGT TATGAAGAAA ATAGCCAAGA GATAGAATGC        900

CATGAAGAAA CACATGAAGG CACCTAAAAT TCCTAACTCT ACCTTGGAAT CAAAGTACTT        960

GACCTTCAAG GATCTCATTA AGTTCTGCCA TATTTCTGAG CCTAAAGAAA GAGTCTATAA       1020

GATCCTTGGT AAAAAATACC CTAAGACCGA AGAGGAATAC AAAGCAGCCT TTGGTGATTC       1080

TGCATCTGCA CCCTTCAATC CTGAATTGGC TGGAAAGCGT ATGAAGATTG AAATCTCTAA       1140

AACATGGGAA AATGAACTCA GTGCAAAAGG CAACACTGCT GAGGTTTGGG ATAATTTAAT       1200

TTCAAGCAAT TAACTCCCAT ATATGGCCAT GTTACGTAAC TTGTCTAACA TCTTAAAAGC       1260

CGGTGTTTCA GATACTACAC ACTCTATTGT GATCAACAAG ATTTGTGAGC CCAAGGCCGT       1320

TGAGAACTCC AAGATGTTCC CTCTTCAATT CTTTAGTGCC ATTGAAGCTG TTAATGAAGC       1380

AGTTACTAAG GGATTCAAGG CCAAGAAGAG AGAAAATATG AATCTTAAAG GTCAAATCGA       1440

AGCAGTAAAG GAAGTTGTTG AAAAAACCGA TGAAGAGAAG AAAGATATGG AGTTGGAGTA       1500

AACCGAAGAA GGAGAATTTG TTAAAGTCAA CGAAGGAATT GGCAAGCAAT ACATTAACTC       1560

CATTGAACTT GCAATCAAGA TAGCAGTTAA CAAGAATTTA GATGAAATCA AAGGACACAC       1620

TGCAATCTTC TCTGATGTTT CTGGTTCTAT GAGTACCTCA ATGTCAGGTG GAGCCAAGAA       1680

GTATGGTTCC GTTCGTACTT GTCTCGAGTG TGCATTAGTC CTTGGTTTGA TGGTAAAATA       1740
```

-continued

```
ACGTTGTGAA AAGTCCTCAT TCTACATCTT CAGTTCACCT AGTTCTCAAT GCAATAAGTG      1800

TTACTTAGAA GTTGATCTCC CTGGAGACGA ACTCCGTCCT TCTATGTAAA AACTTTTGCA      1860

AGAGAAAGGA AAACTTGGTG GTGGTACTGA TTTCCCCTAT GAGTGCATTG ATGAATGGAC      1920

AAAGAATAAA ACTCACGTAG ACAATATCGT TATTTTGTCT GATATGATGA TTGCAGAAGG      1980

ATATTCAGAT ATCAATGTTA GAGGCAGTTC CATTGTTAAC AGCATCAAAA AGTACAAGGA      2040

TGAAGTAAAT CCTAACATTA AAATCTTTGC AGTTGACTTA GAAGGTTACG GAAAGTGCCT      2100

TAATCTAGGT GATGAGTTCA ATGAAAACAA CTACATCAAG ATATTCGGTA TGAGCGATTC      2160

AATCTTAAAG TTCATTTCAG CCAAGCAAGG AGGAGCAAAT ATGGTCGAAG TTATCAAAAA      2220

CTTTGCCCTT CAAAAAATAG GACAAAAGTG AGTTTCTTGA GATTCTTCTA TAACAAAAAT      2280

CTCACCCCAC TTTTTTGTTT TATTGCATAG CCATTATGAA ATTTAAATTA TTATCTATTT      2340

ATTTAAGTTA CTTACATAGT TTATGTATCG CAGTCTATTA GCCTATTCAA ATGATTCTGC      2400

AAAGAACAAA AAGATTAAA A                                                2421
```

(2) INFORMATION FOR SEQ ID NO: 52:

(i) SEQUENCE CHARACTERISTICS:
        (A) LENGTH: 699 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 52:

```
Glu Leu Glu Leu Glu Met Gln Glu Asn Gln Asn Asp Ile Gln Val Arg
1               5                   10                  15

Val Lys Ile Asp Asp Pro Lys Gln Tyr Leu Val Asn Val Thr Ala Ala
            20                  25                  30

Cys Leu Leu Gln Glu Gly Ser Tyr Tyr Gln Asp Lys Asp Glu Arg Arg
        35                  40                  45

Tyr Ile Ile Thr Lys Ala Leu Leu Glu Val Ala Glu Ser Asp Pro Glu
    50                  55                  60

Phe Ile Cys Gln Leu Ala Val Tyr Ile Arg Asn Glu Leu Tyr Ile Arg
65                  70                  75                  80

Thr Thr Thr Asn Tyr Ile Val Ala Phe Cys Val Val His Lys Asn Thr
                85                  90                  95

Gln Pro Phe Ile Glu Lys Tyr Phe Asn Lys Ala Val Leu Leu Pro Asn
            100                 105                 110

Asp Leu Leu Glu Val Cys Glu Phe Ala Gln Val Leu Tyr Ile Phe Asp
        115                 120                 125

Ala Thr Glu Phe Lys Asn Leu Tyr Leu Asp Arg Ile Leu Ser Gln Asp
    130                 135                 140

Ile Arg Lys Glu Leu Thr Phe Arg Lys Cys Leu Gln Arg Cys Val Arg
145                 150                 155                 160

Ser Lys Phe Ser Glu Phe Asn Gly Tyr Gln Leu Gly Lys Tyr Cys Thr
                165                 170                 175

Glu Ser Gln Arg Lys Lys Thr Met Phe Arg Tyr Leu Ser Val Thr Asn
            180                 185                 190

Lys Gln Lys Trp Asp Gln Thr Lys Lys Arg Lys Glu Asn Leu Leu
            195                 200                 205

Thr Lys Leu Gln Ala Ile Lys Ser Glu Asp Lys Ser Lys Arg Glu
    210                 215                 220
```

-continued

```
Thr Gly Asp Ile Met Asn Val Glu Asp Ala Ile Lys Ala Leu Lys Pro
225                 230                 235                 240

Ala Val Met Lys Lys Ile Ala Lys Arg Gln Asn Ala Met Lys Lys His
            245                 250                 255

Met Lys Ala Pro Lys Ile Pro Asn Ser Thr Leu Glu Ser Lys Tyr Leu
            260                 265                 270

Thr Phe Lys Asp Leu Ile Lys Phe Cys His Ile Ser Glu Pro Lys Glu
        275                 280                 285

Arg Val Tyr Lys Ile Leu Gly Lys Lys Tyr Pro Lys Thr Glu Glu Glu
        290                 295                 300

Tyr Lys Ala Ala Phe Gly Asp Ser Ala Ser Ala Pro Phe Asn Pro Glu
305                 310                 315                 320

Leu Ala Gly Lys Arg Met Lys Ile Glu Ile Ser Lys Thr Trp Glu Asn
                325                 330                 335

Glu Leu Ser Ala Lys Gly Asn Thr Ala Glu Val Trp Asp Asn Leu Ile
            340                 345                 350

Ser Ser Asn Gln Leu Pro Tyr Met Ala Met Leu Arg Asn Leu Ser Asn
            355                 360                 365

Ile Leu Lys Ala Gly Val Ser Asp Thr Thr His Ser Ile Val Ile Asn
370                 375                 380

Lys Ile Cys Glu Pro Lys Ala Val Glu Asn Ser Lys Met Phe Pro Leu
385                 390                 395                 400

Gln Phe Phe Ser Ala Ile Glu Ala Val Asn Glu Ala Val Thr Lys Gly
                405                 410                 415

Phe Lys Ala Lys Lys Arg Glu Asn Met Asn Leu Lys Gly Gln Ile Glu
            420                 425                 430

Ala Val Lys Glu Val Val Glu Lys Thr Asp Glu Glu Lys Lys Asp Met
            435                 440                 445

Glu Leu Glu Gln Thr Glu Glu Gly Phe Val Lys Val Asn Glu Gly
450                 455                 460

Ile Gly Lys Gln Tyr Ile Asn Ser Ile Glu Leu Ala Ile Lys Ile Ala
465                 470                 475                 480

Val Asn Lys Asn Leu Asp Glu Ile Lys Gly His Thr Ala Ile Phe Ser
                485                 490                 495

Asp Val Ser Gly Ser Met Ser Thr Ser Met Ser Gly Gly Ala Lys Lys
            500                 505                 510

Tyr Gly Ser Val Arg Thr Cys Leu Glu Cys Ala Leu Val Leu Gly Leu
            515                 520                 525

Met Val Lys Gln Arg Cys Glu Lys Ser Ser Phe Tyr Ile Phe Ser Ser
530                 535                 540

Pro Ser Ser Gln Cys Asn Lys Cys Tyr Leu Glu Val Asp Leu Pro Gly
545                 550                 555                 560

Asp Glu Leu Arg Pro Ser Met Gln Lys Leu Leu Gln Glu Lys Gly Lys
            565                 570                 575

Leu Gly Gly Gly Thr Asp Phe Pro Tyr Glu Cys Ile Asp Glu Trp Thr
            580                 585                 590

Lys Asn Lys Thr His Val Asp Asn Ile Val Ile Leu Ser Asp Met Met
        595                 600                 605

Ile Ala Glu Gly Tyr Ser Asp Ile Asn Val Arg Gly Ser Ser Ile Val
        610                 615                 620

Asn Ser Ile Lys Lys Tyr Lys Asp Glu Val Asn Pro Asn Ile Lys Ile
625                 630                 635                 640
```

-continued

```
Phe Ala Val Asp Leu Glu Gly Tyr Gly Lys Cys Leu Asn Leu Gly Asp
                645                 650                 655
Glu Phe Asn Glu Asn Asn Tyr Ile Lys Ile Phe Gly Met Ser Asp Ser
            660                 665                 670
Ile Leu Lys Phe Ile Ser Ala Lys Gln Gly Gly Ala Asn Met Val Glu
        675                 680                 685
Val Ile Lys Asn Phe Ala Leu Gln Lys Ile Gly
    690                 695
```

(2) INFORMATION FOR SEQ ID NO: 53:

(i) SEQUENCE CHARACTERISTICS:
        (A) LENGTH: 2829 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 53:

```
TCAATACTAT TAATTAATAA ATAAAAAAAA GCAAACTACA AAGAAAATGT CAAGGCGTAA     60
CTAAAAAAAG CCATAGGCTC CTATAGGCAA TGAAACAAAT CTTGATTTTG TATTACAAAa    120
TCTAGAAGTT TACAAAAGCC AGATTGAGCA TTATAAGACC TAGTAGTAAT AGATCAAAGA    180
GGAGGATCTC AAGCTTTTAA AGTTCAAAAA TTAAGATTAG GATGGAAACT CTGGCAACGA    240
TGATGATGAT GAAGAAAACA ACTCAAATAA ATAATAAGAA TTATTAAGGA GAGTCAATTA    300
GATTAAGTAG CAAGTTTAAT TGATAAAAAA AGTTGGTTCT AAGGTAGAGA AAGATTTGAA    360
TTTGAACGAA GATGAAAACA AAAGAATGG ACTTTCTGAA TAGCAAGTGA AAGAAGAGTA     420
ATTAAGAACG ATTACTGAAG AATAGGTTAA GTATTAAAAT TTAGTATTTA ACATGGACTA    480
CCAGTTAGAT TTAAATGAGA GTGGTGGCCA TAGAAGACAC AGAAGAGAAA CAGATTATGA    540
TACTGAAAAA TGGTTTGAAA TATCTCATGA CCAAAAAAAT TATGTATCAA TTTACGCCAA    600
CTAAAAGACA TCATATTGTT GGTGGCTTAA AGATTATTTT AATAAAAACA ATTATGATCA    660
TCTTAATGTA AGCATTAACA GACTAGAAAC TGAAGCCGAA TTCTATGCCT TGATGATTT     720
TTCACAAACA ATCAAACTTA CTAATAATTC TTACTAGACT GTTAACATAG ACGTTAATTT    780
TGATAATAAT CTCTGTATAC TCGCATTGCT TAGATTTTTA TTATCACTAG AAAGATTCAA    840
TATTTTGAAT ATAAGATCTT CTTATACAAG AAATTAATAT AATTTTGAGA AAATTGGTGA    900
GCTACTTGAA ACTATCTTCG CAGTTGTCTT TTCTCATCGC CACTTACAAG GCATTCATTTT   960
ACAAGTTCCT TGCGAAGCGT TCTAATATTT AGTTAACTCC TCATCATAAA TTAGCGTTAA   1020
AGATAGCTAA TTATAGGTAT ACTCTTTCTC TACAGACTTA AAATTAGTTG ACACTAACAA   1080
AGTCCAAGAT TATTTTAAGT TCTTATAAGA ATTCCCTCGT TTGACTCATG TAAGCTAGTA   1140
GGCTATCCCA GTTAGTGCTA CTAACGCTGT AGAGAACCTC AATGTTTTAC TTAAAAAGGT   1200
CAAGCATGCT AATCTTAATT TAGTTTCTAT CCCTACCTAA TTCAATTTTG ATTTCTACTT   1260
TGTTAATTTA TAACATTTGA AATTAGAGTT TGGATTAGAA CCAAATATTT TGACAAAACA   1320
AAAGCTTGAA AATCTACTTT TGAGTATAAA ATAATCAAAA AATCTTAAAT TTTTAAGATT   1380
AAACTTTTAC ACCTACGTTG CTTAAGAAAC CTCCAGAAAA CAGATATTAA AACAAGCTAC   1440
AACAATCAAA AATCTCAAAA ACAATAAAAA TCAAGAAGAA ACTCCTGAAA CTAAAGATGA   1500
AACTCCAAGC GAAAGCACAA GTGGTATGAA ATTTTTTGAT CATCTTTCTG AATTAACCGA   1560
GCTTGAAGAT TTCAGCGTTA ACTTGTAAGC TACCCAAGAA ATTTATGATA GCTTGCACAA   1620
```

-continued

```
ACTTTTGATT AGATCAACAA ATTTAAAGAA GTTCAAATTA AGTTACAAAT ATGAAATGGA    1680

AAAGAGTAAA ATGGATACAT TCATAGATCT TAAGAATATT TATGAAACCT TAAACAATCT    1740

TAAAAGATGC TCTGTTAATA TATCAAATCC TCATGGAAAC ATTTCTTATG AACTGACAAA    1800

TAAAGATTCT ACTTTTTATA AATTTAAGCT GACCTTAAAC TAAGAATTAT AACACGCTAA    1860

GTATACTTTT AAGTAGAACG AATTTTAATT TAATAACGTT AAAAGTGCAA AAATTGAATC    1920

TTCCTCATTA GAAAGCTTAG AAGATATTGA TAGTCTTTGC AAATCTATTG CTTCTTGTAA    1980

AAATTTACAA AATGTTAATA TTATCGCCAG TTTGCTCTAT CCCAACAATA TTTAGAAAAA    2040

TCCTTTCAAT AAGCCCAATC TTCTATTTTT CAAGCAATTT GAATAATTGA AAAATTTGGA    2100

AAATGTATCT ATCAACTGTA TTCTTGATCA GCATATACTT AATTCTATTT CAGAATTCTT    2160

AGAAAAGAAT AAAAAAATAA AAGCATTCAT TTTGAAAAGA TATTATTTAT TACAATATTA    2220

TCTTGATTAT ACTAAATTAT TTAAAACACT TCAATAGTTA CCTGAATTAA ATTAAGTTTA    2280

CATTAATTAG CAATTAGAAG AATTGACTGT GAGTGAAGTA CATAAGTAAG TATGGGAAAA    2340

CCACAAGCAA AAAGCTTTCT ATGAACCATT ATGTGAGTTT ATCAAAGAAT CATCCTAAAC    2400

CCTTTAGCTA ATAGATTTTG ACCAAAACAC TGTAAGTGAT GACTCTATTA AAAAGATTTT    2460

AGAATCTATA TCTGAGTCTA AGTATCATCA TTATTTGAGA TTGAACCCTA GTTAATCTAG    2520

CAGTTTAATT AAATCTGAAA ACGAAGAAAT TTAAGAACTT CTCAAAGCTT GCGACGAAAA    2580

AGGTGTTTTA GTAAAAGCAT ACTATAAATT CCCTCTATGT TTACCAACTG GTACTTATTA    2640

CGATTACAAT TCAGATAGAT GGTGATTAAT TAAATATTAG TTTAAATAAA TATTAAATAT    2700

TGAATATTTC TTTGCTTATT ATTTGAATAA TACATACAAT AGTCATTTTT AGTGTTTTGA    2760

ATATATTTTA GTTATTAAT TCATTATTTT AAGTAAATAA TTATTTTTCA ATCATTTTTT    2820

AAAAAATCG                                                            2829
```

(2) INFORMATION FOR SEQ ID NO: 54:

(i) SEQUENCE CHARACTERISTICS:
        (A) LENGTH: 872 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 54:

```
Met Ser Arg Arg Asn Gln Lys Lys Pro Gln Ala Pro Ile Gly Asn Glu
 1               5                  10                  15

Thr Asn Leu Asp Phe Val Leu Gln Asn Leu Glu Val Tyr Lys Ser Gln
            20                  25                  30

Ile Glu His Tyr Lys Thr Gln Gln Gln Ile Lys Glu Glu Asp Leu
        35                  40                  45

Lys Leu Leu Lys Phe Lys Asn Gln Asp Gln Asp Gly Asn Ser Gly Asn
    50                  55                  60

Asp Asp Asp Asp Glu Glu Asn Asn Ser Asn Lys Gln Gln Glu Leu Leu
65                  70                  75                  80

Arg Arg Val Asn Gln Ile Lys Gln Gln Val Gln Leu Ile Lys Lys Val
                85                  90                  95

Gly Ser Lys Val Glu Lys Asp Leu Asn Leu Asn Glu Asp Glu Asn Lys
            100                 105                 110

Lys Asn Gly Leu Ser Glu Gln Gln Val Lys Glu Glu Gln Leu Arg Thr
        115                 120                 125
```

-continued

```
Ile Thr Glu Glu Gln Val Lys Tyr Gln Asn Leu Val Phe Asn Met Asp
    130                 135                 140

Tyr Gln Leu Asp Leu Asn Glu Ser Gly Gly His Arg Arg His Arg Arg
145                 150                 155                 160

Glu Thr Asp Tyr Asp Thr Glu Lys Trp Phe Glu Ile Ser His Asp Gln
                165                 170                 175

Lys Asn Tyr Val Ser Ile Tyr Ala Asn Gln Lys Thr Ser Tyr Cys Trp
            180                 185                 190

Trp Leu Lys Asp Tyr Phe Asn Lys Asn Tyr Asp His Leu Asn Val
        195                 200                 205

Ser Ile Asn Arg Leu Glu Thr Glu Ala Glu Phe Tyr Ala Phe Asp Asp
    210                 215                 220

Phe Ser Gln Thr Ile Lys Leu Thr Asn Asn Ser Tyr Gln Thr Val Asn
225                 230                 235                 240

Ile Asp Val Asn Phe Asp Asn Asn Leu Cys Ile Leu Ala Leu Leu Arg
                245                 250                 255

Phe Leu Leu Ser Leu Glu Arg Phe Asn Ile Leu Asn Ile Arg Ser Ser
            260                 265                 270

Tyr Thr Arg Asn Gln Tyr Asn Phe Glu Lys Ile Gly Glu Leu Leu Glu
        275                 280                 285

Thr Ile Phe Ala Val Val Phe Ser His Arg His Leu Gln Gly Ile His
    290                 295                 300

Leu Gln Val Pro Cys Glu Ala Phe Gln Tyr Leu Val Asn Ser Ser Ser
305                 310                 315                 320

Gln Ile Ser Val Lys Asp Ser Gln Leu Gln Val Tyr Ser Phe Ser Thr
                325                 330                 335

Asp Leu Lys Leu Val Asp Thr Asn Lys Val Gln Asp Tyr Phe Lys Phe
            340                 345                 350

Leu Gln Glu Phe Pro Arg Leu Thr His Val Ser Gln Gln Ala Ile Pro
        355                 360                 365

Val Ser Ala Thr Asn Ala Val Glu Asn Leu Asn Val Leu Leu Lys Lys
    370                 375                 380

Val Lys His Ala Asn Leu Asn Leu Val Ser Ile Pro Thr Gln Phe Asn
385                 390                 395                 400

Phe Asp Phe Tyr Phe Val Asn Leu Gln His Leu Lys Leu Glu Phe Gly
                405                 410                 415

Leu Glu Pro Asn Ile Leu Thr Lys Gln Lys Leu Glu Asn Leu Leu Leu
            420                 425                 430

Ser Ile Lys Gln Ser Lys Asn Leu Lys Phe Leu Arg Leu Asn Phe Tyr
        435                 440                 445

Thr Tyr Val Ala Gln Glu Thr Ser Arg Lys Gln Ile Leu Lys Gln Ala
    450                 455                 460

Thr Thr Ile Lys Asn Leu Lys Asn Asn Lys Asn Gln Glu Glu Thr Pre
465                 470                 475                 480

Glu Thr Lys Asp Glu Thr Pro Ser Glu Ser Thr Ser Gly Met Lys Phe
                485                 490                 495

Phe Asp His Leu Ser Glu Leu Thr Glu Leu Glu Asp Phe Ser Val Asn
            500                 505                 510

Leu Gln Ala Thr Gln Glu Ile Tyr Asp Ser Leu His Lys Leu Leu Ile
        515                 520                 525

Arg Ser Thr Asn Leu Lys Lys Phe Lys Leu Ser Tyr Lys Tyr Glu Met
    530                 535                 540
```

```
Glu Lys Ser Lys Met Asp Thr Phe Ile Asp Leu Lys Asn Ile Tyr Glu
545                 550                 555                 560

Thr Leu Asn Asn Leu Lys Arg Cys Ser Val Asn Ile Ser Asn Pro His
                565                 570                 575

Gly Asn Ile Ser Tyr Glu Leu Thr Asn Lys Asp Ser Thr Phe Tyr Lys
                580                 585                 590

Phe Lys Leu Thr Leu Asn Gln Glu Leu Gln His Ala Lys Tyr Thr Phe
                595                 600                 605

Lys Gln Asn Glu Phe Gln Phe Asn Asn Val Lys Ser Ala Lys Ile Glu
                610                 615                 620

Ser Ser Ser Leu Glu Ser Leu Glu Asp Ile Asp Ser Leu Cys Lys Ser
625                 630                 635                 640

Ile Ala Ser Cys Lys Asn Leu Gln Asn Val Asn Ile Ile Ala Ser Leu
                645                 650                 655

Leu Tyr Pro Asn Asn Ile Gln Lys Asn Pro Phe Asn Lys Pro Asn Leu
                660                 665                 670

Leu Phe Phe Lys Gln Phe Glu Gln Leu Lys Asn Leu Glu Asn Val Ser
                675                 680                 685

Ile Asn Cys Ile Leu Asp Gln His Ile Leu Asn Ser Ile Ser Glu Phe
690                 695                 700

Leu Glu Lys Asn Lys Lys Ile Lys Ala Phe Ile Leu Lys Arg Tyr Tyr
705                 710                 715                 720

Leu Leu Gln Tyr Tyr Leu Asp Tyr Thr Lys Leu Phe Lys Thr Leu Gln
                725                 730                 735

Gln Leu Pro Glu Leu Asn Gln Val Tyr Ile Asn Gln Gln Leu Glu Glu
                740                 745                 750

Leu Thr Val Ser Glu Val His Lys Gln Val Trp Glu Asn His Lys Gln
                755                 760                 765

Lys Ala Phe Tyr Glu Pro Leu Cys Glu Phe Ile Lys Glu Ser Ser Gln
                770                 775                 780

Thr Leu Gln Leu Ile Asp Phe Asp Gln Asn Thr Val Ser Asp Asp Ser
785                 790                 795                 800

Ile Lys Lys Ile Leu Glu Ser Ile Ser Glu Ser Lys Tyr His His Tyr
                805                 810                 815

Leu Arg Leu Asn Pro Ser Gln Ser Ser Ser Leu Ile Lys Ser Glu Asn
                820                 825                 830

Glu Glu Ile Gln Glu Leu Leu Lys Ala Cys Asp Glu Lys Gly Val Leu
                835                 840                 845

Val Lys Ala Tyr Tyr Lys Phe Pro Leu Cys Leu Pro Thr Gly Thr Tyr
850                 855                 860

Tyr Asp Tyr Asn Ser Asp Arg Trp
865                 870

(2) INFORMATION FOR SEQ ID NO: 55:

(i) SEQUENCE CHARACTERISTICS:
        (A) LENGTH: 884 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 55:

Met Lys Ile Leu Phe Glu Phe Ile Gln Asp Lys Leu Asp Ile Asp Leu
1               5                   10                  15
```

-continued

```
Gln Thr Asn Ser Thr Tyr Lys Glu Asn Leu Lys Cys Gly His Phe Asn
         20                  25                  30

Gly Leu Asp Glu Ile Leu Thr Thr Cys Phe Ala Leu Pro Asn Ser Arg
             35                  40                  45

Lys Ile Ala Leu Pro Cys Leu Pro Gly Asp Leu Ser His Lys Ala Val
 50                  55                  60

Ile Asp His Cys Ile Ile Tyr Leu Leu Thr Gly Glu Leu Tyr Asn Asn
 65                  70                  75                  80

Val Leu Thr Phe Gly Tyr Lys Ile Ala Arg Asn Glu Asp Val Asn Asn
                 85                  90                  95

Ser Leu Phe Cys His Ser Ala Asn Val Asn Val Thr Leu Leu Lys Gly
                 100                 105                 110

Ala Ala Trp Lys Met Phe His Ser Leu Val Gly Thr Tyr Ala Phe Val
             115                 120                 125

Asp Leu Leu Ile Asn Tyr Thr Val Ile Gln Phe Asn Gly Gln Phe Phe
             130                 135                 140

Thr Gln Ile Val Gly Asn Arg Cys Asn Glu Pro His Leu Pro Pro Lys
145                 150                 155                 160

Trp Val Gln Arg Ser Ser Ser Ser Ala Thr Ala Ala Gln Ile Lys
                 165                 170                 175

Gln Leu Thr Glu Pro Val Thr Asn Lys Gln Phe Leu His Lys Leu Asn
             180                 185                 190

Ile Asn Ser Ser Ser Phe Phe Pro Tyr Ser Lys Ile Leu Pro Ser Ser
             195                 200                 205

Ser Ser Ile Lys Lys Leu Thr Asp Leu Arg Glu Ala Ile Phe Pro Thr
         210                 215                 220

Asn Leu Val Lys Ile Pro Gln Arg Leu Lys Val Arg Ile Asn Leu Thr
225                 230                 235                 240

Leu Gln Lys Leu Leu Lys Arg His Lys Arg Leu Asn Tyr Val Ser Ile
                 245                 250                 255

Leu Asn Ser Ile Cys Pro Pro Leu Glu Gly Thr Val Leu Asp Leu Ser
             260                 265                 270

His Leu Ser Arg Gln Ser Pro Lys Glu Arg Val Leu Lys Phe Ile Ile
             275                 280                 285

Val Ile Leu Gln Lys Leu Leu Pro Gln Glu Met Phe Gly Ser Lys Lys
 290                 295                 300

Asn Lys Gly Lys Ile Ile Lys Asn Leu Asn Leu Leu Ser Leu Pro
305                 310                 315                 320

Leu Asn Gly Tyr Leu Pro Phe Asp Ser Leu Leu Lys Lys Leu Arg Leu
                 325                 330                 335

Lys Asp Phe Arg Trp Leu Phe Ile Ser Asp Ile Trp Phe Thr Lys His
             340                 345                 350

Asn Phe Glu Asn Leu Asn Gln Leu Ala Ile Cys Phe Ile Ser Trp Leu
             355                 360                 365

Phe Arg Gln Leu Ile Pro Lys Ile Ile Gln Thr Phe Phe Tyr Cys Thr
 370                 375                 380

Glu Ile Ser Ser Thr Val Thr Ile Val Tyr Phe Arg His Asp Thr Trp
385                 390                 395                 400

Asn Lys Leu Ile Thr Pro Phe Ile Val Glu Tyr Phe Lys Thr Tyr Leu
                 405                 410                 415

Val Glu Asn Asn Val Cys Arg Asn His Asn Ser Tyr Thr Leu Ser Asn
             420                 425                 430
```

-continued

```
Phe Asn His Ser Lys Met Arg Ile Ile Pro Lys Lys Ser Asn Asn Glu
            435                 440                 445

Phe Arg Ile Ile Ala Ile Pro Cys Arg Gly Ala Asp Glu Glu Glu Phe
        450                 455                 460

Thr Ile Tyr Lys Glu Asn His Lys Asn Ala Ile Gln Pro Thr Gln Lys
465                 470                 475                 480

Ile Leu Glu Tyr Leu Arg Asn Lys Arg Pro Thr Ser Phe Thr Lys Ile
                485                 490                 495

Tyr Ser Pro Thr Gln Ile Ala Asp Arg Ile Lys Glu Phe Lys Gln Arg
            500                 505                 510

Leu Leu Lys Lys Phe Asn Asn Val Leu Pro Glu Leu Tyr Phe Met Lys
        515                 520                 525

Phe Asp Val Lys Ser Cys Tyr Asp Ser Ile Pro Arg Met Glu Cys Met
    530                 535                 540

Arg Ile Leu Lys Asp Ala Leu Lys Asn Glu Asn Gly Phe Phe Val Arg
545                 550                 555                 560

Ser Gln Tyr Phe Phe Asn Thr Asn Thr Gly Val Leu Lys Leu Phe Asn
                565                 570                 575

Val Val Asn Ala Ser Arg Val Pro Lys Pro Tyr Glu Leu Tyr Ile Asp
            580                 585                 590

Asn Val Arg Thr Val His Leu Ser Asn Gln Asp Val Ile Asn Val Val
        595                 600                 605

Glu Met Glu Ile Phe Lys Thr Ala Leu Trp Val Glu Asp Lys Cys Tyr
    610                 615                 620

Ile Arg Glu Asp Gly Leu Phe Gln Gly Ser Ser Leu Ser Ala Pro Ile
625                 630                 635                 640

Val Asp Leu Val Tyr Asp Asp Leu Leu Glu Phe Tyr Ser Glu Phe Lys
                645                 650                 655

Ala Ser Pro Ser Gln Asp Thr Leu Ile Leu Lys Leu Ala Asp Asp Phe
            660                 665                 670

Leu Ile Ile Ser Thr Asp Gln Gln Val Ile Asn Ile Lys Lys Leu
        675                 680                 685

Ala Met Gly Gly Phe Gln Lys Tyr Asn Ala Lys Ala Asn Arg Asp Lys
    690                 695                 700

Ile Leu Ala Val Ser Ser Gln Ser Asp Asp Thr Val Ile Gln Phe
705                 710                 715                 720

Cys Ala Met His Ile Phe Val Lys Glu Leu Glu Val Trp Lys His Ser
                725                 730                 735

Ser Thr Met Asn Asn Phe His Ile Arg Ser Lys Ser Lys Gly Ile
            740                 745                 750

Phe Arg Ser Leu Ile Ala Leu Phe Asn Thr Arg Ile Ser Tyr Lys Thr
        755                 760                 765

Ile Asp Thr Asn Leu Asn Ser Thr Asn Thr Val Leu Met Gln Ile Asp
    770                 775                 780

His Val Val Lys Asn Ile Ser Glu Cys Tyr Lys Ser Ala Phe Lys Asp
785                 790                 795                 800

Leu Ser Ile Asn Val Thr Gln Asn Met Gln Phe His Ser Phe Leu Gln
                805                 810                 815

Arg Ile Ile Glu Met Thr Val Ser Gly Cys Pro Ile Thr Lys Cys Asp
            820                 825                 830

Pro Leu Ile Glu Tyr Glu Val Arg Phe Thr Ile Leu Asn Gly Phe Leu
        835                 840                 845
```

```
Glu Ser Leu Ser Ser Asn Thr Ser Lys Phe Lys Asp Asn Ile Ile Leu
    850                 855                 860

Leu Arg Lys Glu Ile Gln His Leu Gln Ala Tyr Ile Tyr Ile Tyr Ile
865                 870                 875                 880

His Ile Val Asn
```

(2) INFORMATION FOR SEQ ID NO: 56:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 56:

YARACHAARG GHATYCCHYA RGG            23

(2) INFORMATION FOR SEQ ID NO: 57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 57:

DGTDATNARN ARRTARTCRT C            21

(2) INFORMATION FOR SEQ ID NO: 58:

(i) SEQUENCE CHARACTERISTICS:
        (A) LENGTH: 42 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 58:

```
Leu Cys Val Ser Tyr Ile Leu Ser Ser Phe Tyr Tyr Ala Asn Leu Glu
1               5                   10                  15

Glu Asn Ala Leu Gln Phe Leu Arg Lys Glu Ser Met Asp Pro Glu Lys
            20                  25                  30

Pro Glu Thr Asn Leu Leu Met Arg Leu Thr
            35                  40
```

(2) INFORMATION FOR SEQ ID NO: 59:

(i) SEQUENCE CHARACTERISTICS:
        (A) LENGTH: 42 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 59:

```
Leu Cys Val Ser Ser Ile Leu Ser Ser Phe Tyr Tyr Ala Thr Leu Glu
1               5                   10                  15
```

```
Glu Ser Ser Leu Gly Phe Leu Arg Asp Glu Ser Met Asn Pro Glu Asn
         20                  25                  30

Pro Asn Val Asn Leu Leu Met Arg Leu Thr
         35                  40
```

(2) INFORMATION FOR SEQ ID NO: 60:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "RNA"

(ix) FEATURE:
        (A) NAME/KEY: modified_base
        (B) LOCATION: 12..25
        (D) OTHER INFORMATION: /mod_base= OTHER /note= "The residues
            located at these positions are 2-O-methylribonucleoti..."

(xi) SEQUENCE DESCRIPTION: SEQ ID NO: 60:

```
TAGACCTGTT AGGUUUUGGG GUUUUG                                      26
```

(2) INFORMATION FOR SEQ ID NO: 61:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 61:

```
GGGGTTTTGG GGTTTT                                                 16
```

(2) INFORMATION FOR SEQ ID NO: 62:

(i) SEQUENCE CHARACTERISTICS:
        (A) LENGTH: 389 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..389
        (D) OTHER INFORMATION: /note= "expressed sequence tag (EST)
            AA281296"

(xi) SEQUENCE DESCRIPTION: SEQ ID NO: 62:

```
GCCAAGTTCC TGCACTGGCT GATGAGTGTG TACGTCGTCG AGCTGCTCAG GTCTTTCTTT    60

TATGTCACGG AGACCACGTT TCAAAAGAAC AGGCTCTTTT TCTACCGGAA GAGTGTCTGG   120

AGCAAGTTGC AAAGCATTGG AATCAGACAG CACTTGAAGA GGGTGCAGCT GCGGGACGTG   180

TCGGAAGCAG AGGTCAGGCA GCATCGGGAA GCCAGGCCCG CCCTGCTGAC GTCCAGACTC   240

CGCTTCATCC CCAAGCCTGA CGGGCTGCGG CCGATTGTGA ACATGGACTA CGTCGTGGGA   300

GCCAGAACGT TCCGCAGAGA AAAGAGGGCC GAGCGTCTCA CCTCGAGGGT GAAGGCACTG   360

TTCAGCGTGC TCAACTACGA GCGGGCGCG                                    389
```

(2) INFORMATION FOR SEQ ID NO: 63:

(i) SEQUENCE CHARACTERISTICS:
        (A) LENGTH: 233 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..233
        (D) OTHER INFORMATION: /note= "TRT motifs from
            Schizosaccharomyces pombe tez1"

(xi) SEQUENCE DESCRIPTION: SEQ ID NO: 63:

```
Ile Ser Glu Ile Glu Trp Leu Val Leu Gly Lys Arg Ser Asn Ala Lys
  1               5                  10                  15

Met Cys Leu Ser Asp Phe Glu Lys Arg Lys Gln Ile Phe Ala Glu Phe
             20                  25                  30

Ile Tyr Trp Leu Tyr Asn Ser Phe Ile Ile Pro Ile Leu Gln Ser Phe
             35                  40                  45

Phe Tyr Ile Thr Glu Ser Ser Asp Leu Arg Asn Arg Thr Val Tyr Phe
 50                  55                  60

Arg Lys Asp Ile Trp Lys Leu Cys Arg Pro Phe Ile Thr Ser Met
 65                  70                  75                  80

Lys Met Glu Ala Phe Glu Lys Ile Asn Glu Asn Asn Val Arg Met Asp
                 85                  90                  95

Thr Gln Lys Thr Thr Leu Pro Pro Ala Val Ile Arg Leu Leu Pro Lys
                100                 105                 110

Lys Asn Thr Phe Arg Leu Ile Thr Asn Leu Arg Lys Arg Phe Leu Ile
                115                 120                 125

Lys Met Gly Ser Asn Lys Lys Met Leu Val Ser Thr Asn Gln Thr Leu
            130                 135                 140

Arg Pro Val Ala Ser Ile Leu Lys His Leu Ile Asn Glu Glu Ser Ser
145                 150                 155                 160

Gly Ile Pro Phe Asn Leu Glu Val Tyr Met Lys Leu Leu Thr Phe Lys
                165                 170                 175

Lys Asp Leu Leu Lys His Arg Met Phe Gly Arg Lys Lys Tyr Phe Val
                180                 185                 190

Arg Ile Asp Ile Lys Ser Cys Tyr Asp Arg Ile Lys Gln Asp Leu Met
                195                 200                 205

Phe Arg Ile Val Lys Lys Lys Leu Lys Asp Pro Glu Phe Val Ile Arg
210                 215                 220

Lys Tyr Ala Thr Ile His Ala Thr Ser
225                 230
```

(2) INFORMATION FOR SEQ ID NO: 64:

(i) SEQUENCE CHARACTERISTICS:
        (A) LENGTH: 233 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..233
        (D) OTHER INFORMATION: /note= "TRT motifs from Saccharomyces
            cerevisiae EST2"

(xi) SEQUENCE DESCRIPTION: SEQ ID NO: 64:

Leu Lys Asp Phe Arg Trp Leu Phe Ile Ser Asp Ile Trp Phe Thr Lys
1               5                   10                  15

His Asn Phe Glu Asn Leu Asn Gln Leu Ala Ile Cys Phe Ile Ser Trp
                20                  25                  30

Leu Phe Arg Gln Leu Ile Pro Lys Ile Ile Gln Thr Phe Phe Tyr Cys
            35                  40                  45

Thr Glu Ile Ser Ser Thr Val Thr Ile Val Tyr Phe Arg His Asp Thr
        50                  55                  60

Trp Asn Lys Leu Ile Thr Pro Phe Ile Val Glu Tyr Phe Lys Thr Tyr
65                  70                  75                  80

Leu Val Glu Asn Val Cys Arg Asn His Asn Ser Tyr Thr Leu Ser
                85                  90                  95

Asn Phe Asn His Ser Lys Met Arg Ile Ile Pro Lys Lys Ser Asn Asn
                100                 105                 110

Glu Phe Arg Ile Ile Ala Ile Pro Cys Arg Gly Ala Asp Glu Glu Glu
            115                 120                 125

Phe Thr Ile Tyr Lys Glu Asn His Lys Asn Ala Ile Gln Pro Thr Gln
        130                 135                 140

Lys Ile Leu Glu Tyr Leu Arg Asn Lys Arg Pro Thr Ser Phe Thr Lys
145                 150                 155                 160

Ile Tyr Ser Pro Thr Gln Ile Ala Asp Arg Ile Lys Glu Phe Lys Gln
                165                 170                 175

Arg Leu Leu Lys Lys Phe Asn Asn Val Leu Pro Glu Leu Tyr Phe Met
            180                 185                 190

Lys Phe Asp Val Lys Ser Cys Tyr Asp Ser Ile Pro Arg Met Glu Cys
        195                 200                 205

Met Arg Ile Leu Lys Asp Ala Leu Lys Asn Glu Asn Gly Phe Phe Val
    210                 215                 220

Arg Ser Gln Tyr Phe Phe Asn Thr Asn
225                 230

(2) INFORMATION FOR SEQ ID NO: 65:

(i) SEQUENCE CHARACTERISTICS:
        (A) LENGTH: 233 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..233
        (D) OTHER INFORMATION: /note= "TRT motifs from Euplotes
            aediculatus p123"

(xi) SEQUENCE DESCRIPTION: SEQ ID NO: 65:

Thr Arg Glu Ile Ser Trp Met Gln Val Glu Thr Ser Ala Lys His Phe
1               5                   10                  15

Tyr Tyr Phe Asp His Glu Asn Ile Tyr Val Leu Trp Lys Leu Leu Arg
                20                  25                  30

Trp Ile Phe Glu Asp Leu Val Val Ser Leu Ile Arg Cys Phe Phe Tyr
            35                  40                  45

Val Thr Glu Gln Gln Lys Ser Tyr Ser Lys Thr Tyr Tyr Arg Lys
        50                  55                  60

```
Asn Ile Trp Asp Val Ile Met Lys Met Ser Ile Ala Asp Leu Lys Lys
 65                  70                  75                  80

Glu Thr Leu Ala Glu Val Gln Glu Lys Glu Val Glu Trp Lys Lys
                 85                  90                  95

Ser Leu Gly Phe Ala Pro Gly Lys Leu Arg Leu Ile Pro Lys Lys Thr
            100                 105                 110

Thr Phe Arg Pro Ile Met Thr Phe Asn Lys Lys Ile Val Asn Ser Asp
            115                 120                 125

Arg Lys Thr Thr Lys Leu Thr Thr Asn Thr Lys Leu Leu Asn Ser His
        130                 135                 140

Leu Met Leu Lys Thr Leu Lys Asn Arg Met Phe Lys Asp Pro Phe Gly
145                 150                 155                 160

Phe Ala Val Phe Asn Tyr Asp Asp Val Met Lys Lys Tyr Glu Glu Phe
                165                 170                 175

Val Cys Lys Trp Lys Gln Val Gly Gln Pro Lys Leu Phe Phe Ala Thr
            180                 185                 190

Met Asp Ile Glu Lys Cys Tyr Asp Ser Val Asn Arg Glu Lys Leu Ser
            195                 200                 205

Thr Phe Leu Lys Thr Thr Lys Leu Leu Ser Ser Asp Phe Trp Ile Met
210                 215                 220

Thr Ala Gln Ile Leu Lys Arg Lys Asn
225                 230
```

(2) INFORMATION FOR SEQ ID NO: 66:

(i) SEQUENCE CHARACTERISTICS:
        (A) LENGTH: 2631 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..2631
        (D) OTHER INFORMATION: /note= "Saccharomyces cerevisiae
           EST2"

(xi) SEQUENCE DESCRIPTION: SEQ ID NO: 66:

```
ATTTATACTC ATGAAAATCT TATTCGAGTT CATTCAAGAC AAGCTTGACA TTGATCTACA     60

GACCAACAGT ACTTACAAAG AAAATTTAAA ATGTGGTCAC TTCAATGGCC TCGATGAAAT    120

TCTAACTACG TGTTTCGCAC TACCAAATTC AAGAAAAATA GCATTACCAT GCCTTCCTGG    180

TGACTTAAGC CACAAAGCAG TCATTGATCA CTGCATCATT TACCTGTTGA CGGGCGAATT    240

ATACAACAAC GTACTAACAT TTGGCTATAA AATAGCTAGA AATGAAGATG TCAACAATAG    300

TCTTTTTTGC CATTCTGCAA ATGTTAACGT TACGTTACTG AAAGGCGCTG CTTGGAAAAT    360

GTTCCACAGT TTGGTCGGTA CATACGCATT CGTTGATTTA TTGATCAATT ATACAGTAAT    420

TCAATTTAAT GGGCAGTTTT TCACTCAAAT CGTGGGTAAC AGATGTAACG AACCTCATCT    480

GCCGCCCAAA TGGGTCCAAC GATCATCCTC ATCATCCGCA ACTGCTGCGC AAATCAAACA    540

ACTTACAGAA CCAGTGACAA ATAAACAATT CTTACACAAG CTCAATATAA ATTCCTCTTC    600

TTTTTTTCCT TATAGCAAGA TCCTTCCTTC ATCATCATCT ATCAAAAAGC TAACTGACTT    660

GAGAGAAGCT ATTTTTCCCA CAAATTTGGT TAAAATTCCT CAGAGACTAA AGGTACGAAT    720

TAATTTGACG CTGCAAAAGC TATTAAAGAG ACATAAGCGT TTGAATTACG TTTCTATTTT    780

GAATAGTATT TGCCCACCAT TGGAAGGGAC CGTATTGGAC TTGTCGCATT TGAGTAGGCA    840
```

```
ATCACCAAAG GAACGAGTCT TGAAATTTAT CATTGTTATT TTACAGAAGT TATTACCCCA      900

AGAAATGTTT GGCTCAAAGA AAAATAAAGG AAAAATTATC AAGAATCTAA ATCTTTTATT      960

AAGTTTACCC TTAAATGGCT ATTTACCATT TGATAGTTTG TTGAAAAAGT TAAGATTAAA     1020

GGATTTTCGG TGGTTGTTCA TTTCTGATAT TTGGTTCACC AAGCACAATT TTGAAAACTT     1080

GAATCAATTG GCGATTTGTT TCATTTCCTG GCTATTTAGA CAACTAATTC CCAAAATTAT     1140

ACAGACTTTT TTTTACTGCA CCGAAATATC TTCTACAGTG ACAATTGTTT ACTTTAGACA     1200

TGATACTTGG AATAAACTTA TCACCCCTTT TATCGTAGAA TATTTTAAGA CGTACTTAGT     1260

CGAAAACAAC GTATGTAGAA ACCATAATAG TTACACGTTG TCCAATTTCA ATCATAGCAA     1320

AATGAGGATT ATACCAAAAA AAAGTAATAA TGAGTTCAGG ATTATTGCCA TCCCATGCAG     1380

AGGGGCAGAC GAAGAAGAAT TCACAATTTA TAAGGAGAAT CACAAAAATG CTATCCAGCC     1440

CACTCAAAAA ATTTTAGAAT ACCTAAGAAA CAAAAGGCCG ACTAGTTTTA CTAAAATATA     1500

TTCTCCAACG CAAATAGCTG ACCGTATCAA AGAATTTAAG CAGAGACTTT TAAAGAAATT     1560

TAATAATGTC TTACCAGAGC TTTATTTCAT GAAATTTGAT GTCAAATCTT GCTATGATTC     1620

CATACCAAGG ATGGAATGTA TGAGGATACT CAAGGATGCG CTAAAAAATG AAAATGGGTT     1680

TTTCGTTAGA TCTCAATATT TCTTCAATAC CAATACAGGT GTATTGAAGT TATTTAATGT     1740

TGTTAACGCT AGCAGAGTAC CAAAACCTTA TGAGCTATAC ATAGATAATG TGAGGACGGT     1800

TCATTTATCA AATCAGGATG TTATAAACGT TGTAGAGATG GAAATATTTA AACAGCTTT     1860

GTGGGTTGAA GATAAGTGCT ACATTAGAGA AGATGGTCTT TTTCAGGGCT CTAGTTTATC     1920

TGCTCCGATC GTTGATTTGG TGTATGACGA TCTTCTGGAG TTTTATAGCG AGTTTAAAGC     1980

CAGTCCTAGC CAGGACACAT TAATTTTAAA ACTGGCTGAC GATTTCCTTA ATATATCAAC     2040

AGACCAACAG CAAGTGATCA ATATCAAAAA GCTTGCCATG GGCGGATTTC AAAAATATAA     2100

TGCGAAAGCC AATAGAGACA AAATTTTAGC CGTAAGCTCC CAATCAGATG ATGATACGGT     2160

TATTCAATTT TGTGCAATGC ACATATTTGT TAAAGAATTG GAAGTTTGGA AACATTCAAG     2220

CACAATGAAT AATTTCCATA TCCGTTCGAA ATCTAGTAAA GGGATATTTC GAAGTTTAAT     2280

AGCGCTGTTT AACACTAGAA TCTCTTATAA AACAATTGAC ACAAATTTAA ATTCAACAAA     2340

CACCGTTCTC ATGCAAATTG ATCATGTTGT AAAGAACATT TCGGAATGTT ATAAATCTGC     2400

TTTTAAGGAT CTATCAATTA ATGTTACGCA AAATATGCAA TTTCATTCGT TCTTACAACG     2460

CATCATTGAA ATGACAGTCA GCGGTTGTCC AATTACGAAA TGTGATCCTT TAATCGAGTA     2520

TGAGGTACGA TTCACCATAT TGAATGGATT TTTGGAAAGC CTATCTTCAA ACACATCAAA     2580

ATTTAAAGAT AATATCATTC TTTTGAGAAA GGAAATTCAA CACTTGCAAG C             2631
```

(2) INFORMATION FOR SEQ ID NO: 67:

(i) SEQUENCE CHARACTERISTICS:
        (A) LENGTH: 129 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..129
        (D) OTHER INFORMATION: /note= "TRT motifs from human"

(xi) SEQUENCE DESCRIPTION: SEQ ID NO: 67:

```
Ala Lys Phe Leu His Trp Leu Met Ser Val Tyr Val Glu Leu Leu
1               5                   10                  15

Arg Ser Phe Phe Tyr Val Thr Glu Thr Thr Phe Gln Lys Asn Arg Leu
            20                  25                  30

Phe Phe Tyr Arg Lys Ser Val Trp Ser Lys Leu Gln Ser Ile Gly Ile
        35                  40                  45

Arg Gln His Leu Lys Arg Val Gln Leu Arg Glu Leu Ser Glu Ala Glu
    50                  55                  60

Val Arg Gln His Arg Glu Ala Arg Pro Ala Leu Leu Thr Ser Arg Leu
65                  70                  75                  80

Arg Phe Ile Pro Lys Pro Asp Gly Leu Arg Pro Ile Val Asn Met Asp
                85                  90                  95

Tyr Val Val Gly Ala Arg Thr Phe Arg Arg Glu Lys Arg Ala Glu Arg
                100                 105                 110

Leu Thr Ser Arg Val Lys Ala Leu Phe Ser Val Leu Asn Tyr Glu Arg
            115                 120                 125

Ala
```

(2) INFORMATION FOR SEQ ID NO: 68:

(i) SEQUENCE CHARACTERISTICS:
        (A) LENGTH: 5544 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(959..1216, 1273..1353, 1425..1543,
            1595..1857, 1894..2286, 2326..2396, 2436..2705,
            2746..2862, 2914..3083, 3125..3309, 3356..3504,
            3546..3759, 3797..4046, 4086..4252, 4296..4392,
            4435..4597)
        (D) OTHER INFORMATION: /note= "Schizosaccharomyces pombe
            telomerase catalytic subunit (TRT)"

(xi) SEQUENCE DESCRIPTION: SEQ ID NO: 68:

```
GGTACCGATT TACTTTCCTT TCTTCATAAG CTAATTGCTT CCTCGAACGC TCCTAAATCT      60

CTGGAAATAT TTTTACAAGA ACTCAATAAC AATACCAAGT CAAATTCCAA TATGAAGGTG     120

TTATTAGTGA TCGATAATAT TTCTATTTTA TCGGTCGTTA CCAAGTATAA GGACAAAAAG     180

AACAACTTCC TTCCCCCTAA AGACTTTTAC TTTATTAATT TACTTTTCAA ATATATTTCG     240

GGTTCGCTTA CTTTTAATCG TGGTACTGTT TTAGCTGCTA CTTCTAGCCA ACCGCGTGTT     300

TCTACCCCGT CATTGGATAT AGCTCTTGGA GTAGCTCACA GAAATCCTTA CAAATCTTCT     360

GATGAGACTA TATTAGATTC ATTACAGTCC GTGCATATTC TTAACATGGA GCCTTACACT     420

TTAGATGAGT CACGTCGCAT GATGGAGTAT TTGGTATCAT CCAACGTTTG CCTTGAAAAG     480

GTTGATAATT ATTTGCAAAA TCATGTCCTT AGTGGTGGTA ATCCGCGAAA GTTTTTTGAT     540

GCTTGCACAC GTCTAGCATG ATTGAGATAT TCAAAAATTT CTATCCACTA CAACTCCTTT     600

AACGCGGTTT TATTTTTCTA TTTTCTATTC TCATGTTGTT CCAAATATGT ATCATCTCGT     660

ATTAGGCTTT TTTCCGTTTT ACTCCTGGAA TCGTACCTTT TTCACTATTC CCCCTAATGA     720

ATAATCTAAA TTAGTTTCGC TTATAATTGA TAGTAGTAGA AAGATTGGTG ATTCTACTCG     780

TGTAATGTTA TTAGTTTAAA GATACTTTGC AAAACATTTA TTAGCTATCA TTATATAAAA     840
```

```
AAAATCCTAT AATTATAAAT ATTAATCAAT ATTTGCGGTC ACTATTTATT TAAAACGTTA      900

TGATCAGTAG GACACTTTGC ATATATATAG TTATGCTTAA TGGTTACTTG TAACTTGC        958

ATG ACC GAA CAC CAT ACC CCC AAA AGC AGG ATT CTT CGC TTT CTA GAG       1006
Met Thr Glu His His Thr Pro Lys Ser Arg Ile Leu Arg Phe Leu Glu
 1               5                  10                  15

AAT CAA TAT GTA TAC CTA TGT ACC TTA AAT GAT TAT GTA CAA CTT GTT       1054
Asn Gln Tyr Val Tyr Leu Cys Thr Leu Asn Asp Tyr Val Gln Leu Val
                 20                  25                  30

TTG AGA GGG TCG CCG GCA AGC TCG TAT AGC AAT ATA TGC GAA CGC TTG       1102
Leu Arg Gly Ser Pro Ala Ser Ser Tyr Ser Asn Ile Cys Glu Arg Leu
         35                  40                  45

AGA AGC GAT GTA CAA ACG TCC TTT TCT ATT TTT CTT CAT TCG ACT GTA       1150
Arg Ser Asp Val Gln Thr Ser Phe Ser Ile Phe Leu His Ser Thr Val
 50                  55                  60

GTC GGC TTC GAC AGT AAG CCA GAT GAA GGT GTT CAA TTT TCT TCT CCA       1198
Val Gly Phe Asp Ser Lys Pro Asp Glu Gly Val Gln Phe Ser Ser Pro
 65                  70                  75                  80

AAA TGC TCA CAG TCA GAG GTATATATAT TTTTGTTTTG ATTTTTTTCT              1246
Lys Cys Ser Gln Ser Glu
                 85

ATTCGGGATA GCTAATATAT GGGCAG CTA ATA GCG AAT GTT GTA AAA CAG ATG      1299
                             Leu Ile Ala Asn Val Val Lys Gln Met
                                              90                  95

TTC GAT GAA AGT TTT GAG CGT CGA AGG AAT CTA CTG ATG AAA GGG TTT       1347
Phe Asp Glu Ser Phe Glu Arg Arg Arg Asn Leu Leu Met Lys Gly Phe
                100                 105                 110

TCC ATG GTAAGGTATT CTAATTGTGA AATATTTACC TGCAATTACT GTTTCAAAGA        1403
Ser Met

GATTGTATTT AACCGATAAA G AAT CAT GAA GAT TTT CGA GCC ATG CAT GTA       1454
                        Asn His Glu Asp Phe Arg Ala Met His Val
                                     115                 120

AAC GGA GTA CAA AAT GAT CTC GTT TCT ACT TTT CCT AAT TAC CTT ATA       1502
Asn Gly Val Gln Asn Asp Leu Val Ser Thr Phe Pro Asn Tyr Leu Ile
 125                 130                 135

TCT ATA CTT GAG TCA AAA AAT TGG CAA CTT TTG TTA GAA AT                1543
Ser Ile Leu Glu Ser Lys Asn Trp Gln Leu Leu Leu Glu Ile
 140                 145                 150

GTAAATACCG GTTAAGATGT TGCGCACTTT GAACAAGACT GACAAGTATA G T ATC        1598
                                                              Ile

GGC AGT GAT GCC ATG CAT TAC TTA TTA TCC AAA GGA AGT ATT TTT GAG       1646
Gly Ser Asp Ala Met His Tyr Leu Leu Ser Lys Gly Ser Ile Phe Glu
 155                 160                 165                 170

GCT CTT CCA AAT GAC AAT TAC CTT CAG ATT TCT GGC ATA CCA CTT TTT       1694
Ala Leu Pro Asn Asp Asn Tyr Leu Gln Ile Ser Gly Ile Pro Leu Phe
                 175                 180                 185

AAA AAT AAT GTG TTT GAG GAA ACT GTG TCA AAA AAA AGA AAG CGA ACC       1742
Lys Asn Asn Val Phe Glu Glu Thr Val Ser Lys Lys Arg Lys Arg Thr
                 190                 195                 200

ATT GAA ACA TCC ATT ACT CAA AAT AAA AGC GCC CGC AAA GAA GTT TCC       1790
Ile Glu Thr Ser Ile Thr Gln Asn Lys Ser Ala Arg Lys Glu Val Ser
 205                 210                 215

TGG AAT AGC ATT TCA ATT AGT AGG TTT AGC ATT TTT TAC AGG TCA TCC       1838
Trp Asn Ser Ile Ser Ile Ser Arg Phe Ser Ile Phe Tyr Arg Ser Ser
 220                 225                 230

TAT AAG AAG TTT AAG CAA G GTAACTAATA CTGTTATCCT TCATAACTAA            1887
Tyr Lys Lys Phe Lys Gln
 235                 240
```

```
TTTTAG AT CTA TAT TTT AAC TTA CAC TCT ATT TGT GAT CGG AAC ACA        1934
       Asp Leu Tyr Phe Asn Leu His Ser Ile Cys Asp Arg Asn Thr
                    245                 250

GTA CAC ATG TGG CTT CAA TGG ATT TTT CCA AGG CAA TTT GGA CTT ATA      1982
Val His Met Trp Leu Gln Trp Ile Phe Pro Arg Gln Phe Gly Leu Ile
255                 260                 265                 270

AAC GCA TTT CAA GTG AAG CAA TTG CAC AAA GTG ATT CCA CTG GTA TCA      2030
Asn Ala Phe Gln Val Lys Gln Leu His Lys Val Ile Pro Leu Val Ser
                275                 280                 285

CAG AGT ACA GTT GTG CCC AAA CGT CTC CTA AAG GTA TAC CCT TTA ATT      2078
Gln Ser Thr Val Val Pro Lys Arg Leu Leu Lys Val Tyr Pro Leu Ile
                290                 295                 300

GAA CAA ACA GCA AAG CGA CTC CAT CGT ATT TCT CTA TCA AAA GTT TAC      2126
Glu Gln Thr Ala Lys Arg Leu His Arg Ile Ser Leu Ser Lys Val Tyr
                305                 310                 315

AAC CAT TAT TGC CCA TAT ATT GAC ACC CAC GAT GAT GAA AAA ATC CTT      2174
Asn His Tyr Cys Pro Tyr Ile Asp Thr His Asp Asp Glu Lys Ile Leu
                320                 325                 330

AGT TAT TCC TTA AAG CCG AAC CAG GTG TTT GCG TTT CTT CGA TCC ATT      2222
Ser Tyr Ser Leu Lys Pro Asn Gln Val Phe Ala Phe Leu Arg Ser Ile
335                 340                 345                 350

CTT GTT CGA GTG TTT CCT AAA TTA ATC TGG GGT AAC CAA AGG ATA TTT      2270
Leu Val Arg Val Phe Pro Lys Leu Ile Trp Gly Asn Gln Arg Ile Phe
                355                 360                 365

GAG ATA ATA TTA AAA G GTATTGTATA AAATTTATTA CCACTAACGA TTTTACCAG AC  2327
Glu Ile Ile Leu Lys                                             Asp
            370

CTC GAA ACT TTC TTG AAA TTA TCG AGA TAC GAG TCT TTT AGT TTA CAT      2375
Leu Glu Thr Phe Leu Lys Leu Ser Arg Tyr Glu Ser Phe Ser Leu His
                375                 380                 385

TAT TTA ATG AGT AAC ATA AAG GTAATATGCC AAATTTTTTT ACCATTAATT         2426
Tyr Leu Met Ser Asn Ile Lys
            390                 395

AACAATCAG ATT TCA GAA ATT GAA TGG CTA GTC CTT GGA AAA AGG TCA        2474
          Ile Ser Glu Ile Glu Trp Leu Val Leu Gly Lys Arg Ser
                      400                 405

AAT GCG AAA ATG TGC TTA AGT GAT TTT GAG AAA CGC AAG CAA ATA TTT      2522
Asn Ala Lys Met Cys Leu Ser Asp Phe Glu Lys Arg Lys Gln Ile Phe
            410                 415                 420

GCG GAA TTC ATC TAC TGG CTA TAC AAT TCG TTT ATA ATA CCT ATT TTA      2570
Ala Glu Phe Ile Tyr Trp Leu Tyr Asn Ser Phe Ile Ile Pro Ile Leu
425                 430                 435                 440

CAA TCT TTT TTT TAT ATC ACT GAA TCA AGT GAT TTA CGA AAT CGA ACT      2618
Gln Ser Phe Phe Tyr Ile Thr Glu Ser Ser Asp Leu Arg Asn Arg Thr
                445                 450                 455

GTT TAT TTT AGA AAA GAT ATT TGG AAA CTC TTG TGC CGA CCC TTT ATT      2666
Val Tyr Phe Arg Lys Asp Ile Trp Lys Leu Leu Cys Arg Pro Phe Ile
                460                 465                 470

ACA TCA ATG AAA ATG GAA GCG TTT GAA AAA ATA AAC GAG GTATTTAAA        2715
Thr Ser Met Lys Met Glu Ala Phe Glu Lys Ile Asn Glu
            475                 480                 485

GTATTTTTTG CAAAAAGCTA ATATTTTCAG AAC AAT GTT AGG ATG GAT ACT CAG     2769
                                  Asn Asn Val Arg Met Asp Thr Gln
                                                      490

AAA ACT ACT TTG CCT CCA GCA GTT ATT CGT CTA TTA CCT AAG AAG AAT      2817
Lys Thr Thr Leu Pro Pro Ala Val Ile Arg Leu Leu Pro Lys Lys Asn
        495                 500                 505

ACC TTT CGT CTC ATT ACG AAT TTA AGA AAA AGA TTC TTA ATA AAG          2862
Thr Phe Arg Leu Ile Thr Asn Leu Arg Lys Arg Phe Leu Ile Lys
510                 515                 520
```

-continued

```
GTATTAATTT TTGGTCATCA ATGTACTTTA CTTCTAATCT ATTATTAGCA G ATG GGT    2919
                                                       Met Gly
                                                       525

TCA AAC AAA AAA ATG TTA GTC AGT ACG AAC CAA ACT TTA CGA CCT GTG    2967
Ser Asn Lys Lys Met Leu Val Ser Thr Asn Gln Thr Leu Arg Pro Val
        530                 535                 540

GCA TCG ATA CTG AAA CAT TTA ATC AAT GAA GAA AGT AGT GGT ATT CCA    3015
Ala Ser Ile Leu Lys His Leu Ile Asn Glu Glu Ser Ser Gly Ile Pro
            545                 550                 555

TTT AAC TTG GAG GTT TAC ATG AAG CTT CTT ACT TTT AAG AAG GAT CTT    3063
Phe Asn Leu Glu Val Tyr Met Lys Leu Leu Thr Phe Lys Lys Asp Leu
    560                 565                 570

CTT AAG CAC CGA ATG TTT GG  GTAATTATAT AATGCGCGAT TCCTCATTAT       3113
Leu Lys His Arg Met Phe Gly
575                 580

TAATTTTGCA G G CGT AAG AAG TAT TTT GTA CGG ATA GAT ATA AAA TCC    3161
              Arg Lys Lys Tyr Phe Val Arg Ile Asp Ile Lys Ser
                          585                 590

TGT TAT GAT CGA ATA AAG CAA GAT TTG ATG TTT CGG ATT GTT AAA AAG    3209
Cys Tyr Asp Arg Ile Lys Gln Asp Leu Met Phe Arg Ile Val Lys Lys
            595                 600                 605

AAA CTC AAG GAT CCC GAA TTT GTA ATT CGA AAG TAT GCA ACC ATA CAT    3257
Lys Leu Lys Asp Pro Glu Phe Val Ile Arg Lys Tyr Ala Thr Ile His
610                 615                 620                 625

GCA ACA AGT GAC CGA GCT ACA AAA AAC TTT GTT AGT GAG GCG TTT TCC    3305
Ala Thr Ser Asp Arg Ala Thr Lys Asn Phe Val Ser Glu Ala Phe Ser
                630                 635                 640

TAT    T GTAAGTTTAT TTTTTCATTG GAATTTTTTA ACAAATTCTT TTTTAG TT    3357
Tyr                                                           Phe

GAT ATG GTG CCT TTT GAA AAA GTC GTG CAG TTA CTT TCT ATG AAA ACA    3405
Asp Met Val Pro Phe Glu Lys Val Val Gln Leu Leu Ser Met Lys Thr
            645                 650                 655

TCA GAT ACT TTG TTT GTT GAT TTT GTG GAT TAT TGG ACC AAA AGT TCT    3453
Ser Asp Thr Leu Phe Val Asp Phe Val Asp Tyr Trp Thr Lys Ser Ser
660                 665                 670                 675

TCT GAA ATT TTT AAA ATG CTC AAG GAA CAT CTC TCT GGA CAC ATT GTT    3501
Ser Glu Ile Phe Lys Met Leu Lys Glu His Leu Ser Gly His Ile Val
                680                 685                 690

AAG GTATACCAAT TGTTGAATTG TAATAACACT AATGAAACTA G ATA GGA AAT     3554
Lys                                                Ile Gly Asn
                                                           695

TCT CAA TAC CTT CAA AAA GTT GGT ATC CCT CAG GGC TCA ATT CTG TCA    3602
Ser Gln Tyr Leu Gln Lys Val Gly Ile Pro Gln Gly Ser Ile Leu Ser
            700                 705                 710

TCT TTT TTG TGT CAT TTC TAT ATG GAA GAT TTG ATT GAT GAA TAC CTA    3650
Ser Phe Leu Cys His Phe Tyr Met Glu Asp Leu Ile Asp Glu Tyr Leu
                715                 720                 725

TCG TTT ACG AAA AAG AAA GGA TCA GTG TTG TTA CGA GTA GTC GAC GAT    3698
Ser Phe Thr Lys Lys Lys Gly Ser Val Leu Leu Arg Val Val Asp Asp
            730                 735                 740

TTC CTC TTT ATA ACA GTT AAT AAA AAG GAT GCA AAA AAA TTT TTG AAT    3746
Phe Leu Phe Ile Thr Val Asn Lys Lys Asp Ala Lys Lys Phe Leu Asn
        745                 750                 755

TTA TCT TTA AGA    G GTGAGTTGCT GTCATTCCTA AGTTCTAACC GTTGAAG GA  3798
Leu Ser Leu Arg                                                Gly
760

TTT GAG AAA CAC AAT TTT TCT ACG AGC CTG GAG AAA ACA GTA ATA AAC    3846
Phe Glu Lys His Asn Phe Ser Thr Ser Leu Glu Lys Thr Val Ile Asn
765                 770                 775                 780
```

```
TTT GAA AAT AGT AAT GGG ATA ATA AAC AAT ACT TTT TTT AAT GAA AGC    3894
Phe Glu Asn Ser Asn Gly Ile Ile Asn Asn Thr Phe Phe Asn Glu Ser
                785                 790                 795

AAG AAA AGA ATG CCA TTC TTC GGT TTC TCT GTG AAC ATG AGG TCT CTT    3942
Lys Lys Arg Met Pro Phe Phe Gly Phe Ser Val Asn Met Arg Ser Leu
                800                 805                 810

GAT ACA TTG TTA GCA TGT CCT AAA ATT GAT GAA GCC TTA TTT AAC TCT    3990
Asp Thr Leu Leu Ala Cys Pro Lys Ile Asp Glu Ala Leu Phe Asn Ser
                815                 820                 825

ACA TCT GTA GAG CTG ACG AAA CAT ATG GGG AAA TCT TTT TTT TAC AAA    4038
Thr Ser Val Glu Leu Thr Lys His Met Gly Lys Ser Phe Phe Tyr Lys
                830                 835                 840

ATT CTA AG  GTATACTGTG TAACTGAATA ATAGCTGACA AATAATCAG A TCG       4089
Ile Leu Arg                                                Ser
845

AGC CTT GCA TCC TTT GCA CAA GTA TTT ATT GAC ATT ACC CAC AAT TCA    4137
Ser Leu Ala Ser Phe Ala Gln Val Phe Ile Asp Ile Thr His Asn Ser
                850                 855                 860

AAA TTC AAT TCT TGC TGC AAT ATA TAT AGG CTA GGA TAC TCT ATG TGT    4185
Lys Phe Asn Ser Cys Cys Asn Ile Tyr Arg Leu Gly Tyr Ser Met Cys
865                 870                 875                 880

ATG AGA GCA CAA GCA TAC TTA AAA AGG ATG AAG GAT ATA TTT ATT CCC    4233
Met Arg Ala Gln Ala Tyr Leu Lys Arg Met Lys Asp Ile Phe Ile Pro
                885                 890                 895

CAA AGA ATG TTC ATA ACG G GTGAGTACTT ATTTTAACTA GAAAAGTCAT         4282
Gln Arg Met Phe Ile Thr
                900

TAATTAACCT TAG  AT CTT TTG AAT GTT ATT GGA AGA AAA ATT TGG AAA     4330
                Asp Leu Leu Asn Val Ile Gly Arg Lys Ile Trp Lys
                    905                 910

AAG TTG GCC GAA ATA TTA GGA TAT ACG AGT AGG CGT TTC TTG TCC TCT    4378
Lys Leu Ala Glu Ile Leu Gly Tyr Thr Ser Arg Arg Phe Leu Ser Ser
915                 920                 925                 930

GCA GAA GTC AAA TG  GTACGTGTCG GTCTCGAGAC TTCAGCAATA TTGACACATC    4432
Ala Glu Val Lys Trp
                935

AG G CTT TTT TGT CTT GGA ATG AGA GAT GGT TTG AAA CCC TCT TTC AAA   4480
    Leu Phe Cys Leu Gly Met Arg Asp Gly Leu Lys Pro Ser Phe Lys
                940                 945                 950

TAT CAT CCA TGC TTC GAA CAG CTA ATA TAC CAA TTT CAG TCA TTG ACT    4528
Tyr His Pro Cys Phe Glu Gln Leu Ile Tyr Gln Phe Gln Ser Leu Thr
                955                 960                 965

GAT CTT ATC AAG CCG CTA AGA CCA GTT TTG CGA CAG GTG TTA TTT TTA    4576
Asp Leu Ile Lys Pro Leu Arg Pro Val Leu Arg Gln Val Leu Phe Leu
                970                 975                 980

CAT AGA AGA ATA GCT GAT TAATGTCATT TTCAATTTAT TATATACATC           4624
His Arg Arg Ile Ala Asp
                985

CTTTATTACT GGTGTCTTAA ACAATATTAT TACTAAGTAT AGCTGACCCC CAAAGCAAGC  4684

ATACTATAGG ATTTCTAGTA AAGTAAAATT AATCTCGTTA TTAGTTTTGA TTGACTTGTC  4744

TTTATCCTTA TACTTTTAAG AAAGATTGAC AGTGGTTGCT GACTACTGCC CACATGCCCA  4804

TTAAACGGGA GTGGTTAAAC ATTAAAAGTA ATACATGAGG CTAATCTCCT TTCATTTAGA  4864

ATAAGGAAAG TGGTTTTCTA TAATGAATAA TGCCCGCACT AATGCAAAAA GACGAAGATT  4924

ATCTTCTAAA CAAGGGGGAT TAAGCATATC CGAAGGAAAA GAGAGTAATA TACCCAGTGT  4984

TGTTGAAGAA AGCAAGGATA ATTTGGAACA AGCTTCTGCA GATGACAGGC TAAATTTTGG  5044

TGACCGAATT TTGGTAAAAG CCCCAGGTTA TCCATGGTGG CCGGCCTTGC TACTGAGACG  5104
```

| | | |
|---|---|---|
| AAAAGAAACT AAGGATAGTT TGAATACTAA TAGCTCATTT AATGTCTTAT ATAAGGTTTT | 5164 |
| GTTTTTTCCT GACTTCAATT TTGCATGGGT GAAAAGAAAT AGTGTTAAGC CATTATTGGA | 5224 |
| TTCCGAAATA GCCAAATTTC TTGGTTCCTC AAAGCGGAAG TCTAAAGAAC TTATTGAAGC | 5284 |
| TTATGAGGCT TCAAAAACTC CTCCTGATTT AAAGGAGGAA TCTTCCACCG ATGAGGAAAT | 5344 |
| GGATAGCTTA TCAGCTGCTG AGGAGAAGCC TAATTTTTTG CAAAAAAGAA AATATCATTG | 5404 |
| GGAGACATCT CTTGATGAAT CAGATGCGGA GAGTATCTCC AGCGGATCCT TGATGTCAAT | 5464 |
| AACTTCTATT TCTGAAATGT ATGGTCCTAC TGTCGCTTCG ACTTCTCGTA GCTCTACGCA | 5524 |
| GTTAAGTGAC CAAAGGTACC | 5544 |

(2) INFORMATION FOR SEQ ID NO: 69:

(i) SEQUENCE CHARACTERISTICS:
        (A) LENGTH: 988 amino acids
        (B) TYPE: amino acid
        (D) TOPOLOGY: linear (ii) MOLECULE TYPE: protein (xi) SEQUENCE DESCRIPTION: SEQ ID NO: 69:

```
Met Thr Glu His His Thr Pro Lys Ser Arg Ile Leu Arg Phe Leu Glu
  1               5                  10                  15

Asn Gln Tyr Val Tyr Leu Cys Thr Leu Asn Asp Tyr Val Gln Leu Val
             20                  25                  30

Leu Arg Gly Ser Pro Ala Ser Ser Tyr Ser Asn Ile Cys Glu Arg Leu
         35                  40                  45

Arg Ser Asp Val Gln Thr Ser Phe Ser Ile Phe Leu His Ser Thr Val
     50                  55                  60

Val Gly Phe Asp Ser Lys Pro Asp Glu Gly Val Gln Phe Ser Ser Pro
 65                  70                  75                  80

Lys Cys Ser Gln Ser Glu Leu Ile Ala Asn Val Val Lys Gln Met Phe
                 85                  90                  95

Asp Glu Ser Phe Glu Arg Arg Arg Asn Leu Leu Met Lys Gly Phe Ser
            100                 105                 110

Met Asn His Glu Asp Phe Arg Ala Met His Val Asn Gly Val Gln Asn
        115                 120                 125

Asp Leu Val Ser Thr Phe Pro Asn Tyr Leu Ile Ser Ile Leu Glu Ser
    130                 135                 140

Lys Asn Trp Gln Leu Leu Leu Glu Ile Ile Gly Ser Asp Ala Met His
145                 150                 155                 160

Tyr Leu Leu Ser Lys Gly Ser Ile Phe Glu Ala Leu Pro Asn Asp Asn
                165                 170                 175

Tyr Leu Gln Ile Ser Gly Ile Pro Leu Phe Lys Asn Asn Val Phe Glu
            180                 185                 190

Glu Thr Val Ser Lys Lys Arg Lys Arg Thr Ile Glu Thr Ser Ile Thr
        195                 200                 205

Gln Asn Lys Ser Ala Arg Lys Glu Val Ser Trp Asn Ser Ile Ser Ile
    210                 215                 220

Ser Arg Phe Ser Ile Phe Tyr Arg Ser Tyr Lys Lys Phe Lys Gln
225                 230                 235                 240

Asp Leu Tyr Phe Asn Leu His Ser Ile Cys Asp Arg Asn Thr Val His
                245                 250                 255

Met Trp Leu Gln Trp Ile Phe Pro Arg Gln Phe Gly Leu Ile Asn Ala
            260                 265                 270
```

-continued

```
Phe Gln Val Lys Gln Leu His Lys Val Ile Pro Leu Val Ser Gln Ser
        275                 280                 285

Thr Val Val Pro Lys Arg Leu Leu Lys Val Tyr Pro Leu Ile Glu Gln
        290                 295                 300

Thr Ala Lys Arg Leu His Arg Ile Ser Leu Ser Lys Val Tyr Asn His
305                 310                 315                 320

Tyr Cys Pro Tyr Ile Asp Thr His Asp Asp Glu Lys Ile Leu Ser Tyr
                325                 330                 335

Ser Leu Lys Pro Asn Gln Val Phe Ala Phe Leu Arg Ser Ile Leu Val
                340                 345                 350

Arg Val Phe Pro Lys Leu Ile Trp Gly Asn Gln Arg Ile Phe Glu Ile
                355                 360                 365

Ile Leu Lys Asp Leu Glu Thr Phe Leu Lys Leu Ser Arg Tyr Glu Ser
        370                 375                 380

Phe Ser Leu His Tyr Leu Met Ser Asn Ile Lys Ile Ser Glu Ile Glu
385                 390                 395                 400

Trp Leu Val Leu Gly Lys Arg Ser Asn Ala Lys Met Cys Leu Ser Asp
                405                 410                 415

Phe Glu Lys Arg Lys Gln Ile Phe Ala Glu Phe Ile Tyr Trp Leu Tyr
                420                 425                 430

Asn Ser Phe Ile Ile Pro Ile Leu Gln Ser Phe Tyr Ile Thr Glu
                435                 440                 445

Ser Ser Asp Leu Arg Asn Arg Thr Val Tyr Phe Arg Lys Asp Ile Trp
450                 455                 460

Lys Leu Leu Cys Arg Pro Phe Ile Thr Ser Met Lys Met Glu Ala Phe
465                 470                 475                 480

Glu Lys Ile Asn Glu Asn Asn Val Arg Met Asp Thr Gln Lys Thr Thr
                485                 490                 495

Leu Pro Pro Ala Val Ile Arg Leu Leu Pro Lys Lys Asn Thr Phe Arg
                500                 505                 510

Leu Ile Thr Asn Leu Arg Lys Arg Phe Leu Ile Lys Met Gly Ser Asn
        515                 520                 525

Lys Lys Met Leu Val Ser Thr Asn Gln Thr Leu Arg Pro Val Ala Ser
        530                 535                 540

Ile Leu Lys His Leu Ile Asn Glu Glu Ser Ser Gly Ile Pro Phe Asn
545                 550                 555                 560

Leu Glu Val Tyr Met Lys Leu Leu Thr Phe Lys Lys Asp Leu Leu Lys
                565                 570                 575

His Arg Met Phe Gly Arg Lys Tyr Phe Val Arg Ile Asp Ile Lys
                580                 585                 590

Ser Cys Tyr Asp Arg Ile Lys Gln Asp Leu Met Phe Arg Ile Val Lys
        595                 600                 605

Lys Lys Leu Lys Asp Pro Glu Phe Val Ile Arg Lys Tyr Ala Thr Ile
        610                 615                 620

His Ala Thr Ser Asp Arg Ala Thr Lys Asn Phe Val Ser Glu Ala Phe
625                 630                 635                 640

Ser Tyr Phe Asp Met Val Pro Phe Glu Lys Val Val Gln Leu Leu Ser
                645                 650                 655

Met Lys Thr Ser Asp Thr Leu Phe Val Asp Phe Val Asp Tyr Trp Thr
                660                 665                 670

Lys Ser Ser Ser Glu Ile Phe Lys Met Leu Lys Glu His Leu Ser Gly
        675                 680                 685
```

His Ile Val Lys Ile Gly Asn Ser Gln Tyr Leu Gln Lys Val Gly Ile
        690                 695                 700

Pro Gln Gly Ser Ile Leu Ser Ser Phe Leu Cys His Phe Tyr Met Glu
705                 710                 715                 720

Asp Leu Ile Asp Glu Tyr Leu Ser Phe Thr Lys Lys Gly Ser Val
                725                 730                 735

Leu Leu Arg Val Val Asp Asp Phe Leu Phe Ile Thr Val Asn Lys Lys
            740                 745                 750

Asp Ala Lys Lys Phe Leu Asn Leu Ser Leu Arg Gly Phe Glu Lys His
                755                 760                 765

Asn Phe Ser Thr Ser Leu Glu Lys Thr Val Ile Asn Phe Glu Asn Ser
770                 775                 780

Asn Gly Ile Ile Asn Asn Thr Phe Phe Asn Glu Ser Lys Lys Arg Met
785                 790                 795                 800

Pro Phe Phe Gly Phe Ser Val Asn Met Arg Ser Leu Asp Thr Leu Leu
                805                 810                 815

Ala Cys Pro Lys Ile Asp Glu Ala Leu Phe Asn Ser Thr Ser Val Glu
                820                 825                 830

Leu Thr Lys His Met Gly Lys Ser Phe Phe Tyr Lys Ile Leu Arg Ser
            835                 840                 845

Ser Leu Ala Ser Phe Ala Gln Val Phe Ile Asp Ile Thr His Asn Ser
        850                 855                 860

Lys Phe Asn Ser Cys Cys Asn Ile Tyr Arg Leu Gly Tyr Ser Met Cys
865                 870                 875                 880

Met Arg Ala Gln Ala Tyr Leu Lys Arg Met Lys Asp Ile Phe Ile Pro
                885                 890                 895

Gln Arg Met Phe Ile Thr Asp Leu Leu Asn Val Ile Gly Arg Lys Ile
                900                 905                 910

Trp Lys Lys Leu Ala Glu Ile Leu Gly Tyr Thr Ser Arg Arg Phe Leu
            915                 920                 925

Ser Ser Ala Glu Val Lys Trp Leu Phe Cys Leu Gly Met Arg Asp Gly
930                 935                 940

Leu Lys Pro Ser Phe Lys Tyr His Pro Cys Phe Glu Gln Leu Ile Tyr
945                 950                 955                 960

Gln Phe Gln Ser Leu Thr Asp Leu Ile Lys Pro Leu Arg Pro Val Leu
                965                 970                 975

Arg Gln Val Leu Phe Leu His Arg Arg Ile Ala Asp
            980                 985

(2) INFORMATION FOR SEQ ID NO: 70:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER /note= "N = guanosine
            modified by a biotin group"

(xi) SEQUENCE DESCRIPTION: SEQ ID NO: 70:

NCCTATTTYT TYTAYNNNAC NGA                                              23

(2) INFORMATION FOR SEQ ID NO: 71:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 71:

Phe Phe Tyr Xaa Thr Glu
1               5

(2) INFORMATION FOR SEQ ID NO: 72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 72:

CCAGATATNA DNARRAARTC RTC                                                    23

(2) INFORMATION FOR SEQ ID NO: 73:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER" /note= "Xaa = Phe,
            Ile or Leu"

(xi) SEQUENCE DESCRIPTION: SEQ ID NO: 73:

Asp Asp Phe Leu Xaa Ile
1               5

(2) INFORMATION FOR SEQ ID NO: 74:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 74:

ACAATGMGNH TNHTNCCNAA RAA                                                    23

(2) INFORMATION FOR SEQ ID NO: 75:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (ix) FEATURE:
            (A) NAME/KEY: Modified-site
            (B) LOCATION: 2..3
            (D) OTHER INFORMATION: /product= "OTHER" /note= "Xaa = Leu or
                Ile"

(xi) SEQUENCE DESCRIPTION: SEQ ID NO: 75:

Arg Xaa Xaa Pro Lys Lys
1               5

(2) INFORMATION FOR SEQ ID NO: 76:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 76:

ACGAATCKNG GDATNSWRTC RTARCA                                                    26

(2) INFORMATION FOR SEQ ID NO: 77:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 77:

Cys Tyr Asp Ser Ile Pro Arg
1               5

(2) INFORMATION FOR SEQ ID NO: 78:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 78:

CAATTCTCRT ARCANSWYTT DATRTC                                                    26

(2) INFORMATION FOR SEQ ID NO: 79:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 79:

Asp Ile Lys Ser Cys Tyr Asp
1               5

(2) INFORMATION FOR SEQ ID NO: 80:

(i) SEQUENCE CHARACTERISTICS:
            (A) LENGTH: 269 base pairs
            (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO: 80:

GATTACTCCC GAAGAAAGGA TCTTTCCGTC CAATCATGAC TTTCTTAAGA AAGGACAAGC      60

AAAAAAATAT TAAGTTAAAT CTAAATTAAA TTCTAATGGA TAGCCAACTT GTGTTTAGGA     120

ATTTAAAAGA CATGCTGGGA TAAAAGATAG GATACTCAGT CTTTGATAAT AAACAAATTT     180

CAGAAAAATT TGCCTAATTC ATAGAGAAAT GGAAAAATAA AGGAAGACCT CAGCTATATT     240

ATGTCACTCT AGACATAAAG ACTTGCTAC                                       269

(2) INFORMATION FOR SEQ ID NO: 81:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 81:

AAACACAAGG AAGGAAGTCA AATATTCTAT TACCGTAAAC CAATATGGAA ATTAGTGAGT      60

AAATTAACTA TTGTCAAAGT AAGAATTTAG TTTTCTGAAA AGAATAAATA AATGAAAAAT     120

AATTTTTATC AAAAAATTTA GCTTGAAGAG GAGAATTTGG AAAAAGTTGA AGAAAAATTG     180

ATACCAGAAG ATTCATTTTA GAAATACCCT CAAGGAAAGC TAAGGATTAT ACCTAAAAAA     240

GGATCTTTCC GTCCAATCAT GACTTTCTTA AGAAAGGACA AGCAAAAAAA TATTAAGTTA     300

AATCTAAATT AAATTCTAAT GGATAGCCAA CTTGTGTTTA GGAATTTAAA AGACATGCTG     360

GGATAAAAGA TAGGATACTC AGTCTTTGAT AATAAACAAA TTTCAGAAAA ATTTGCCTAA     420

TTCATAGAGA AATGGAAAAA TAAAGGAAGA CCTCAGCTAT ATTATGTCAC TCTA           474

(2) INFORMATION FOR SEQ ID NO: 82:

(i) SEQUENCE CHARACTERISTICS:
        (A) LENGTH: 158 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 82:

Lys His Lys Glu Gly Ser Gln Ile Phe Tyr Tyr Arg Lys Pro Ile Trp
  1               5                  10                  15

Lys Leu Val Ser Lys Leu Thr Ile Val Lys Val Arg Ile Gln Phe Ser
             20                  25                  30

Glu Lys Asn Lys Gln Met Lys Asn Asn Phe Tyr Gln Lys Ile Gln Leu
         35                  40                  45

Glu Glu Glu Asn Leu Glu Lys Val Glu Glu Lys Leu Ile Pro Glu Asp
     50                  55                  60

Ser Phe Gln Lys Tyr Pro Gln Gly Lys Leu Arg Ile Ile Pro Lys Lys
 65                  70                  75                  80

Gly Ser Phe Arg Pro Ile Met Thr Phe Leu Arg Lys Asp Lys Gln Lys
                 85                  90                  95

Asn Ile Lys Leu Asn Leu Asn Gln Ile Leu Met Asp Ser Gln Leu Val
            100                 105                 110

```
Phe Arg Asn Leu Lys Asp Met Leu Gly Gln Lys Ile Gly Tyr Ser Val
        115                 120                 125

Phe Asp Asn Lys Gln Ile Ser Glu Lys Phe Ala Gln Phe Ile Glu Lys
        130                 135                 140

Trp Lys Asn Lys Gly Arg Pro Gln Leu Tyr Tyr Val Thr Leu
145                 150                 155
```

(2) INFORMATION FOR SEQ ID NO: 83:

(i) SEQUENCE CHARACTERISTICS:
        (A) LENGTH: 157 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 83:

```
Phe Phe Tyr Cys Thr Glu Ile Ser Ser Thr Val Thr Ile Val Tyr Phe
1               5                   10                  15

Arg His Asp Thr Trp Asn Lys Leu Ile Thr Pro Phe Ile Val Glu Tyr
        20                  25                  30

Phe Lys Thr Tyr Leu Val Glu Asn Asn Val Cys Arg Asn His Asn Ser
        35                  40                  45

Tyr Thr Leu Ser Asn Phe Asn His Ser Lys Met Arg Ile Ile Pro Lys
    50                  55                  60

Lys Ser Asn Asn Glu Phe Arg Ile Ile Ala Ile Pro Cys Arg Gly Ala
65                  70                  75                  80

Asp Glu Glu Glu Phe Thr Ile Tyr Lys Glu Asn His Lys Asn Ala Ile
                85                  90                  95

Gln Pro Thr Gln Lys Ile Leu Glu Tyr Leu Arg Asn Lys Arg Pro Thr
                100                 105                 110

Ser Phe Thr Lys Ile Tyr Ser Pro Thr Gln Ile Ala Asp Arg Ile Lys
        115                 120                 125

Glu Phe Lys Gln Arg Leu Leu Lys Lys Phe Asn Asn Val Leu Pro Glu
        130                 135                 140

Leu Tyr Phe Met Lys Phe Asp Val Lys Ser Cys Tyr Asp
145                 150                 155
```

(2) INFORMATION FOR SEQ ID NO: 84:

(i) SEQUENCE CHARACTERISTICS:
        (A) LENGTH: 155 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 84:

```
Phe Phe Tyr Val Thr Glu Gln Gln Lys Ser Tyr Ser Lys Thr Tyr Tyr
1               5                   10                  15

Tyr Arg Lys Asn Ile Trp Asp Val Ile Met Lys Met Ser Ile Ala Asp
        20                  25                  30

Leu Lys Lys Glu Thr Leu Ala Glu Val Gln Glu Lys Glu Val Glu Glu
        35                  40                  45

Trp Lys Lys Ser Leu Gly Phe Ala Pro Gly Lys Leu Arg Leu Ile Pro
        50                  55                  60

Lys Lys Thr Thr Phe Arg Pro Ile Met Thr Phe Asn Lys Lys Ile Val
65                  70                  75                  80
```

```
Asn Ser Asp Arg Lys Thr Thr Lys Leu Thr Thr Asn Thr Lys Leu Leu
                85                  90                  95

Asn Ser His Leu Met Leu Lys Thr Leu Lys Asn Arg Met Phe Lys Asp
               100                 105                 110

Pro Phe Gly Phe Ala Val Phe Asn Tyr Asp Asp Val Met Lys Lys Tyr
           115                 120                 125

Glu Glu Phe Val Cys Lys Trp Lys Gln Val Gly Gln Pro Lys Leu Phe
       130                 135                 140

Phe Ala Thr Met Asp Ile Glu Lys Cys Tyr Asp
145                 150                 155
```

(2) INFORMATION FOR SEQ ID NO: 85:

(i) SEQUENCE CHARACTERISTICS:
        (A) LENGTH: 158 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 85:

```
Lys His Lys Glu Gly Ser Gln Ile Phe Tyr Tyr Arg Lys Pro Ile Trp
1               5                  10                  15

Lys Leu Val Ser Lys Leu Thr Ile Val Lys Val Arg Ile Gln Phe Ser
                20                  25                  30

Glu Lys Asn Lys Gln Met Lys Asn Asn Phe Tyr Gln Lys Ile Gln Leu
                35                  40                  45

Glu Glu Glu Asn Leu Glu Lys Val Glu Glu Lys Leu Ile Pro Glu Asp
            50                  55                  60

Ser Phe Gln Lys Tyr Pro Gln Gly Lys Leu Arg Ile Ile Pro Lys Lys
65                  70                  75                  80

Gly Ser Phe Arg Pro Ile Met Thr Phe Leu Arg Lys Asp Lys Gln Lys
                85                  90                  95

Asn Ile Lys Leu Asn Leu Asn Gln Ile Leu Met Asp Ser Gln Leu Val
               100                 105                 110

Phe Arg Asn Leu Lys Asp Met Leu Gly Gln Lys Ile Gly Tyr Ser Val
           115                 120                 125

Phe Asp Asn Lys Gln Ile Ser Glu Lys Phe Ala Gln Phe Ile Glu Lys
           130                 135                 140

Trp Lys Asn Lys Gly Arg Pro Gln Leu Tyr Tyr Val Thr Leu
145                 150                 155
```

(2) INFORMATION FOR SEQ ID NO: 86:

(i) SEQUENCE CHARACTERISTICS:
        (A) LENGTH: 1007 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 86:

```
Glu Val Asp Val Asp Asn Gln Ala Asp Asn His Gly Ile His Ser Ala
1               5                  10                  15

Leu Lys Thr Cys Glu Glu Ile Lys Glu Ala Lys Thr Leu Tyr Ser Trp
                20                  25                  30

Ile Gln Lys Val Ile Arg Cys Arg Asn Gln Ser Gln Ser His Tyr Lys
                35                  40                  45
```

```
Asp Leu Glu Asp Ile Lys Ile Phe Ala Gln Thr Asn Ile Val Ala Thr
 50                  55                  60

Pro Arg Asp Tyr Asn Glu Glu Asp Phe Lys Val Ile Ala Arg Lys Glu
 65                  70                  75                  80

Val Phe Ser Thr Gly Leu Met Ile Glu Leu Ile Asp Lys Cys Leu Val
                 85                  90                  95

Glu Leu Leu Ser Ser Ser Asp Val Ser Asp Arg Gln Lys Leu Gln Cys
            100                 105                 110

Phe Gly Phe Gln Leu Lys Gly Asn Gln Leu Ala Lys Thr His Leu Leu
        115                 120                 125

Thr Ala Leu Ser Thr Gln Lys Gln Tyr Phe Gln Asp Glu Trp Asn
130                 135                 140

Gln Val Arg Ala Met Ile Gly Asn Glu Leu Phe Arg His Leu Tyr Thr
145                 150                 155                 160

Lys Tyr Leu Ile Phe Gln Arg Thr Ser Glu Gly Thr Leu Val Gln Phe
                165                 170                 175

Cys Gly Asn Asn Val Phe Asp His Leu Lys Val Asn Asp Lys Phe Asp
            180                 185                 190

Lys Lys Gln Lys Gly Gly Ala Ala Asp Met Asn Glu Pro Arg Cys Cys
        195                 200                 205

Ser Thr Cys Lys Tyr Asn Val Lys Asn Glu Lys Asp His Phe Leu Asn
    210                 215                 220

Asn Ile Asn Val Pro Asn Trp Asn Asn Met Lys Ser Arg Thr Arg Ile
225                 230                 235                 240

Phe Tyr Cys Thr His Phe Asn Arg Asn Gln Phe Phe Lys Lys His
                245                 250                 255

Glu Phe Val Ser Asn Lys Asn Asn Ile Ser Ala Met Asp Arg Ala Gln
            260                 265                 270

Thr Ile Phe Thr Asn Ile Phe Arg Phe Asn Arg Ile Arg Lys Lys Leu
        275                 280                 285

Lys Asp Lys Val Ile Glu Lys Ile Ala Tyr Met Leu Glu Lys Val Lys
    290                 295                 300

Asp Phe Asn Phe Asn Tyr Tyr Leu Thr Lys Ser Cys Pro Leu Pro Glu
305                 310                 315                 320

Asn Trp Arg Glu Arg Lys Gln Lys Ile Glu Asn Leu Ile Asn Lys Thr
                325                 330                 335

Arg Glu Glu Lys Ser Lys Tyr Tyr Glu Glu Leu Phe Ser Tyr Thr Thr
            340                 345                 350

Asp Asn Lys Cys Val Thr Gln Phe Ile Asn Glu Phe Phe Tyr Asn Ile
        355                 360                 365

Leu Pro Lys Asp Phe Leu Thr Gly Arg Asn Arg Lys Asn Phe Gln Lys
370                 375                 380

Lys Val Lys Lys Tyr Val Glu Leu Asn Lys His Glu Leu Ile His Lys
385                 390                 395                 400

Asn Leu Leu Leu Glu Lys Ile Asn Thr Arg Glu Ile Ser Trp Met Gln
                405                 410                 415

Val Glu Thr Ser Ala Lys His Phe Tyr Tyr Phe Asp His Glu Asn Ile
            420                 425                 430

Tyr Val Leu Trp Lys Leu Leu Arg Trp Ile Phe Glu Asp Leu Val Val
        435                 440                 445

Ser Leu Ile Arg Cys Phe Phe Tyr Val Thr Glu Gln Gln Lys Ser Tyr
450                 455                 460
```

-continued

```
Ser Lys Thr Tyr Tyr Tyr Arg Lys Asn Ile Trp Asp Val Ile Met Lys
465                 470                 475                 480

Met Ser Ile Ala Asp Leu Lys Lys Glu Thr Leu Ala Glu Val Gln Glu
            485                 490                 495

Lys Glu Val Glu Glu Trp Lys Lys Ser Leu Gly Phe Ala Pro Gly Lys
        500                 505                 510

Leu Arg Leu Ile Pro Lys Lys Thr Thr Phe Arg Pro Ile Met Thr Phe
    515                 520                 525

Asn Lys Lys Ile Val Asn Ser Asp Arg Lys Thr Thr Lys Leu Thr Thr
530                 535                 540

Asn Thr Lys Leu Leu Asn Ser His Leu Met Leu Lys Thr Leu Lys Asn
545                 550                 555                 560

Arg Met Phe Lys Asp Pro Phe Gly Phe Ala Val Phe Asn Tyr Asp Asp
            565                 570                 575

Val Met Lys Lys Tyr Glu Glu Phe Val Cys Lys Trp Lys Gln Val Gly
        580                 585                 590

Gln Pro Lys Leu Phe Phe Ala Thr Met Asp Ile Glu Lys Cys Tyr Asp
        595                 600                 605

Ser Val Asn Arg Glu Lys Leu Ser Thr Phe Leu Lys Thr Thr Lys Leu
610                 615                 620

Leu Ser Ser Asp Phe Trp Ile Met Thr Ala Gln Ile Leu Lys Arg Lys
625                 630                 635                 640

Asn Asn Ile Val Ile Asp Ser Lys Asn Phe Arg Lys Lys Glu Met Lys
            645                 650                 655

Asp Tyr Phe Arg Gln Lys Phe Gln Lys Ile Ala Leu Glu Gly Gly Gln
        660                 665                 670

Tyr Pro Thr Leu Phe Ser Val Leu Glu Asn Glu Gln Asn Asp Leu Asn
        675                 680                 685

Ala Lys Lys Thr Leu Ile Val Glu Ala Lys Gln Arg Asn Tyr Phe Lys
690                 695                 700

Lys Asp Asn Leu Leu Gln Pro Val Ile Asn Ile Cys Gln Tyr Asn Tyr
705                 710                 715                 720

Ile Asn Phe Asn Gly Lys Phe Tyr Lys Gln Thr Lys Gly Ile Pro Gln
            725                 730                 735

Gly Leu Cys Val Ser Ser Ile Leu Ser Ser Phe Tyr Tyr Ala Thr Leu
        740                 745                 750

Glu Glu Ser Ser Leu Gly Phe Leu Arg Asp Glu Ser Met Asn Pro Glu
        755                 760                 765

Asn Pro Asn Val Asn Leu Leu Met Arg Leu Thr Asp Asp Tyr Leu Leu
770                 775                 780

Ile Thr Thr Gln Glu Asn Asn Ala Val Leu Phe Ile Glu Lys Leu Ile
785                 790                 795                 800

Asn Val Ser Arg Glu Asn Gly Phe Lys Phe Asn Met Lys Lys Leu Gln
            805                 810                 815

Thr Ser Phe Pro Leu Ser Pro Ser Lys Phe Ala Lys Tyr Gly Met Asp
        820                 825                 830

Ser Val Glu Glu Gln Asn Ile Val Gln Asp Tyr Cys Asp Trp Ile Gly
        835                 840                 845

Ile Ser Ile Asp Met Lys Thr Leu Ala Leu Met Pro Asn Ile Asn Leu
850                 855                 860

Arg Ile Glu Gly Ile Leu Cys Thr Leu Asn Leu Asn Met Gln Thr Lys
865                 870                 875                 880
```

```
Lys Ala Ser Met Trp Leu Lys Lys Lys Leu Lys Ser Phe Leu Met Asn
            885                 890                 895

Asn Ile Thr His Tyr Phe Arg Lys Thr Ile Thr Thr Glu Asp Phe Ala
        900                 905                 910

Asn Lys Thr Leu Asn Lys Leu Phe Ile Ser Gly Gly Tyr Lys Tyr Met
        915                 920                 925

Gln Cys Ala Lys Glu Tyr Lys Asp His Phe Lys Lys Asn Leu Ala Met
    930                 935                 940

Ser Ser Met Ile Asp Leu Glu Val Ser Lys Ile Ile Tyr Ser Val Thr
945                 950                 955                 960

Arg Ala Phe Phe Lys Tyr Leu Val Cys Asn Ile Lys Asp Thr Ile Phe
                965                 970                 975

Gly Glu Glu His Tyr Pro Asp Phe Phe Leu Ser Thr Leu Lys His Phe
            980                 985                 990

Ile Glu Ile Phe Ser Thr Lys Lys Tyr Ile Phe Asn Arg Val Cys
            995                 1000                1005
```

(2) INFORMATION FOR SEQ ID NO: 87:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 87:

GTGAAGGCAC TGTTCAGCG                                                        19

(2) INFORMATION FOR SEQ ID NO: 88:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 88:

GTGGATGATT TCTTGTTGG                                                        19

(2) INFORMATION FOR SEQ ID NO: 89:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 89:

ATGCTCCTGC GTTTGGTGG                                                        19

(2) INFORMATION FOR SEQ ID NO: 90:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 90:

CTGGACACTC AGCCCTTGG                                                                                    19

(2) INFORMATION FOR SEQ ID NO: 91:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 91:

GGCAGGTGTG CTGGACACT                                                                                    19

(2) INFORMATION FOR SEQ ID NO: 92:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 92:

TTTGATGATG CTGGCGATG                                                                                    19

(2) INFORMATION FOR SEQ ID NO: 93:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 93:

GGGGCTCGTC TTCTACAGG                                                                                    19

(2) INFORMATION FOR SEQ ID NO: 94:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 94:

CAGCAGGAGG ATCTTGTAG                                                                                    19

(2) INFORMATION FOR SEQ ID NO: 95:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 95:

TGACCCCAGG AGTGGCACG                                                                                    19

(2) INFORMATION FOR SEQ ID NO: 96:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 96:

```
TCAAGCTGAC TCGACACCG                                         19
```

(2) INFORMATION FOR SEQ ID NO: 97:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 97:

```
CGGCGTGACA GGGCTGC                                           17
```

(2) INFORMATION FOR SEQ ID NO: 98:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 98:

```
GCTGAAGGCT GAGTGTCC                                          18
```

(2) INFORMATION FOR SEQ ID NO: 99:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 99:

```
TAGTCCATGT TCACAATCG                                         19
```

(2) INFORMATION FOR SEQ ID NO: 100:

(i) SEQUENCE CHARACTERISTICS:
        (A) LENGTH: 2171 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 22..1716
        (D) OTHER INFORMATION: /note= "EcoRI-NotI insert of clone
            712562 encoding 63 kDa telomerase protein"

(xi) SEQUENCE DESCRIPTION: SEQ ID NO: 100:

```
GCCAAGTTCC TGCACTGGCT GATGAGTGTG TACGTCGTCG AGCTGCTCAG GTCTTTCTTT    60
```

-continued

```
TATGTCACGG AGACCACGTT TCAAAAGAAC AGGCTCTTTT TCTACCGGAA GAGTGTCTGG      120

AGCAAGTTGC AAAGCATTGG AATCAGACAG CACTTGAAGA GGGTGCAGCT GCGGGAGCTG      180

TCGGAAGCAG AGGTCAGGCA GCATCGGGAA GCCAGGCCCG CCCTGCTGAC GTCCAGACTC      240

CGCTTCATCC CCAAGCCTGA CGGGCTGCGG CCGATTGTGA ACATGGACTA CGTCGTGGGA      300

GCCAGAACGT TCCGCAGAGA AAAGARGGCC GAGCGTCTCA CCTCGAGGGT GAAGGCACTG      360

TTCAGCGTGC TCAACTACGA GCGGGCGCGG CGCCCCGGCC TCCTGGGCGC CTCTGTGCTG      420

GGCCTGGACG ATATCCACAG GGCCTGGCGC ACCTTCGTGC TGCGTGTGCG GGCCCAGGAC      480

CCGCCGCCTG AGCTGTACTT TGTCAAGGTG GATGTGACGG GCGCGTACGA CACCATCCCC      540

CAGGACAGGC TCACGGAGGT CATCGCCAGC ATCATCAAAC CCCAGAACAC GTACTGCGTG      600

CGTCGGTATG CCGTGGTCCA GAAGGCCGCC ATGGGCACGT CCGCAAGGCC TTCAAGAGCC      660

ACGTCCTACG TCCAGTGCCA GGGGATCCCG CAGGGCTCCA TCCTCTCCAC GCTGCTCTGC      720

AGCCTGTGCT ACGGCGACAT GGAGAACAAG CTGTTTGCGG GGATTCGGCG GGACGGGCTG      780

CTCCTGCGTT TGGTGGATGA TTTCTTGTTG GTGACACCTC ACCTCACCCA CGCGAAAACC      840

TTCCTCAGGA CCCTGGTCCG AGGTGTCCCT GAGTATGGCT GCGTGGTGAA CTTGCGGAAG      900

ACAGTGGTGA ACTTCCCTGT AGAAGACGAG GCCCTGGGTG GCACGGCTTT TGTTCAGATG      960

CCGGCCCACG GCCTATTCCC CTGGTGCGGC CTGCTGCTGG ATACCCGGAC CCTGGAGGTG      1020

CAGAGCGACT ACTCCAGCTA TGCCCGGACC TCCATCAGAG CCAGTCTCAC CTTCAACCGC      1080

GGCTTCAAGG CTGGGAGGAA CATGCGTCGC AAACTCTTTG GGGTCTTGCG GCTGAAGTGT      1140

CACAGCCTGT TTCTGGATTT GCAGGTGAAC AGCCTCCAGA CGGTGTGCAC CAACATCTAC      1200

AAGATCCTCC TGCTGCAGGC GTACAGGTTT CACGCATGTG TGCTGCAGCT CCCATTTCAT      1260

CAGCAAGTTT GGAAGAACCC ACATTTTTCC TGCGCGTCAT CTCTGACACG GCTCCCTCTG      1320

CTACTCCATC CTGAAAGCCA AGAACGCAGG GATGTCGCTG GGGGCCAAGG GCGCCGCCGG      1380

CCCTCTGCCC TCCGAGGCCG TGCAGTGGCT GTGCCACCAA GCATTCCTGC TCAAGCTGAC      1440

TCGACACCGT GTCACCTACG TGCCACTCCT GGGGTCACTC AGGACAGCCC AGACGCAGCT      1500

GAGTCGGAAG CTCCCGGGGA CGACGCTGAC TGCCCTGGAG GCCGCAGCCA ACCCGGCACT      1560

GCCCTCAGAC TTCAAGACCA TCCTGGACTG ATGGCCACCC GCCACAGCC AGGCCGAGAG      1620

CAGACACCAG CAGCCCTGTC ACGCCGGGCT TATACGTCCC AGGGAGGGAG GGGCGGCCCA      1680

CACCCAGGCC TGCACCGCTG GGAGTCTGAG GCCTGAGTGA GTGTTTGGCC GAGGCCTGCA      1740

TGTCCGGCTG AAGGCTGAGT GTCCGGCTGA GGCCTGAGCG AGTGTCCAGC CAAGGGCTGA      1800

GTGTCCAGCA CACCTGCGTT TTCACTTCCC CACAGGCTGG CGTTCGGTCC ACCCCAGGGC      1860

CAGCTTTTCC TCACCAGGAG CCCGGCTTCC ACTCCCCACA TAGGAATAGT CCATCCCCAG      1920

ATTCGCCATT GTTCACCCTT CGCCCTGCCT TCCTTTGCCT TCCACCCCCA CCATTCAGGT      1980

GGAGACCCTG AGAAGGACCC TGGGAGCTTT GGGAATTTGG AGTGACCAAA GGTGTGCCCT      2040

GTACACAGGC GAGGACCCTG CACCTGGATG GGGGTCCCTG TGGGTCAAAT TGGGGGGAGG      2100

TGCTGTGGGA GTAAAATACT GAATATATGA GTTTTTCAGT TTTGGAAAAA AAAAAAAAAA      2160

AAAAAAAAA A                                                             2171
```

(2) INFORMATION FOR SEQ ID NO: 101:

(i) SEQUENCE CHARACTERISTICS:
      (A) LENGTH: 564 amino acids
      (B) TYPE: amino acid (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..564
        (D) OTHER INFORMATION: /note= "63 kDa telomerase protein
            encoded by ORF of EcoRI-NotI insert of clone 712562"

(xi) SEQUENCE DESCRIPTION: SEQ ID NO: 101:

```
Met Ser Val Tyr Val Val Glu Leu Leu Arg Ser Phe Phe Tyr Val Thr
1               5                   10                  15

Glu Thr Thr Phe Gln Lys Asn Arg Leu Phe Phe Tyr Arg Lys Ser Val
            20                  25                  30

Trp Ser Lys Leu Gln Ser Ile Gly Ile Arg Gln His Leu Lys Arg Val
        35                  40                  45

Gln Leu Arg Glu Leu Ser Glu Ala Glu Val Arg Gln His Arg Glu Ala
    50                  55                  60

Arg Pro Ala Leu Leu Thr Ser Arg Leu Arg Phe Ile Pro Lys Pro Asp
65                  70                  75                  80

Gly Leu Arg Pro Ile Val Asn Met Asp Tyr Val Val Gly Ala Arg Thr
                85                  90                  95

Phe Arg Arg Glu Lys Xaa Ala Glu Arg Leu Thr Ser Arg Val Lys Ala
            100                 105                 110

Leu Phe Ser Val Leu Asn Tyr Glu Arg Ala Arg Arg Pro Gly Leu Leu
        115                 120                 125

Gly Ala Ser Val Leu Gly Leu Asp Asp Ile His Arg Ala Trp Arg Thr
130                 135                 140

Phe Val Leu Arg Val Arg Ala Gln Asp Pro Pro Glu Leu Tyr Phe
145                 150                 155                 160

Val Lys Val Asp Val Thr Gly Ala Tyr Asp Thr Ile Pro Gln Asp Arg
                165                 170                 175

Leu Thr Glu Val Ile Ala Ser Ile Ile Lys Pro Gln Asn Thr Tyr Cys
            180                 185                 190

Val Arg Arg Tyr Ala Val Val Gln Lys Ala Ala Met Gly Thr Ser Ala
        195                 200                 205

Arg Pro Ser Arg Ala Thr Ser Tyr Val Gln Cys Gln Gly Ile Pro Gln
210                 215                 220

Gly Ser Ile Leu Ser Thr Leu Leu Cys Ser Leu Cys Tyr Gly Asp Met
225                 230                 235                 240

Glu Asn Lys Leu Phe Ala Gly Ile Arg Arg Asp Gly Leu Leu Leu Arg
                245                 250                 255

Leu Val Asp Asp Phe Leu Leu Val Thr Pro His Leu Thr His Ala Lys
            260                 265                 270

Thr Phe Leu Arg Thr Leu Val Arg Gly Val Pro Glu Tyr Gly Cys Val
        275                 280                 285

Val Asn Leu Arg Lys Thr Val Val Asn Phe Pro Val Glu Asp Glu Ala
        290                 295                 300

Leu Gly Gly Thr Ala Phe Val Gln Met Pro Ala His Gly Leu Phe Pro
305                 310                 315                 320

Trp Cys Gly Leu Leu Leu Asp Thr Arg Thr Leu Glu Val Gln Ser Asp
                325                 330                 335

Tyr Ser Ser Tyr Ala Arg Thr Ser Ile Arg Ala Ser Leu Thr Phe Asn
            340                 345                 350
```

—continued

```
Arg Gly Phe Lys Ala Gly Arg Asn Met Arg Arg Lys Leu Phe Gly Val
        355                 360                 365

Leu Arg Leu Lys Cys His Ser Leu Phe Leu Asp Leu Gln Val Asn Ser
    370                 375                 380

Leu Gln Thr Val Cys Thr Asn Ile Tyr Lys Ile Leu Leu Leu Gln Ala
385                 390                 395                 400

Tyr Arg Phe His Ala Cys Val Leu Gln Leu Pro Phe His Gln Gln Val
                405                 410                 415

Trp Lys Asn Pro His Phe Ser Cys Ala Ser Ser Leu Thr Arg Leu Pro
            420                 425                 430

Leu Leu Leu His Pro Glu Ser Gln Glu Arg Arg Asp Val Ala Gly Gly
        435                 440                 445

Gln Gly Arg Arg Pro Ser Ala Leu Arg Gly Arg Ala Val Ala Val
450                 455                 460

Pro Pro Ser Ile Pro Ala Gln Ala Asp Ser Thr Pro Cys His Leu Arg
465                 470                 475                 480

Ala Thr Pro Gly Val Thr Gln Asp Ser Pro Asp Ala Ala Glu Ser Glu
                485                 490                 495

Ala Pro Gly Asp Asp Ala Asp Cys Pro Gly Gly Arg Ser Gln Pro Gly
                500                 505                 510

Thr Ala Leu Arg Leu Gln Asp His Pro Gly Leu Met Ala Thr Arg Pro
            515                 520                 525

Gln Pro Gly Arg Glu Gln Thr Pro Ala Ala Leu Ser Arg Arg Ala Tyr
            530                 535                 540

Thr Ser Gln Gly Gly Arg Gly Gly Pro His Pro Gly Leu His Arg Trp
545                 550                 555                 560

Glu Ser Glu Ala (2) INFORMATION FOR SEQ ID NO: 102:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 102:

CCAGTGAGCA GAGTGACGAG GACTCGAGCT CAAGCTTTTT TTTTTTTTTT            50

(2) INFORMATION FOR SEQ ID NO: 103:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 103:

CCAGTGAGCA GAGTGACG                                               18

(2) INFORMATION FOR SEQ ID NO: 104:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 104:

GAGGACTCGA GCTCAAGC                                                    18

(2) INFORMATION FOR SEQ ID NO: 105:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 105:

CACTGATCCT TTCTTTTTCG TAAACGATAG GT                                    32

(2) INFORMATION FOR SEQ ID NO: 106:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 106:

CATCAATCAA ATCTTCCATA TAGAAATGAC A                                     31

(2) INFORMATION FOR SEQ ID NO: 107:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER /note= "N =
                5'-phosphorylated guanosine"

(xi) SEQUENCE DESCRIPTION: SEQ ID NO: 107:

NGGCCGTGTT GGCCTAGTTC TCTGCTC                                          27

(2) INFORMATION FOR SEQ ID NO: 108:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 108:

GAGGAGGAGA AGAGCAGAGA ACTAGGCCAA CACGCCCC                              38

(2) INFORMATION FOR SEQ ID NO: 109:

(i) SEQUENCE CHARACTERISTICS:
            (A) LENGTH: 32 base pairs
            (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO: 109:

GTGTCATTTC TATATGGAAG ATTTGATTGA TG                32

(2) INFORMATION FOR SEQ ID NO: 110:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 110:

ACCTATCGTT TACGAAAAAG AAAGGATCAG TG                32

(2) INFORMATION FOR SEQ ID NO: 111:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 111:

GAGTGACATA ATATACGTGA                              20

(2) INFORMATION FOR SEQ ID NO: 112:

(i) SEQUENCE CHARACTERISTICS:
            (A) LENGTH: 24 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 112:

Phe Phe Tyr Val Thr Glu Thr Thr Phe Gln Lys Asn Arg Leu Phe Phe
1               5                   10                  15

Tyr Arg Lys Ser Val Trp Ser Lys
            20

(2) INFORMATION FOR SEQ ID NO: 113:

(i) SEQUENCE CHARACTERISTICS:
            (A) LENGTH: 23 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 113:

Arg Gln His Leu Lys Arg Val Gln Leu Arg Asp Val Ser Glu Ala Glu
1               5                   10                  15

Val Arg Gln His Arg Glu Ala
            20

(2) INFORMATION FOR SEQ ID NO: 114:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 114:

```
Ala Arg Thr Phe Arg Arg Glu Lys Arg Ala Glu Arg Leu Thr Ser Arg
1               5                   10                  15

Val Lys Ala Leu Phe Ser Val Leu Asn Tyr Glu
            20                  25
```

(2) INFORMATION FOR SEQ ID NO: 115:

(i) SEQUENCE CHARACTERISTICS:
        (A) LENGTH: 28 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 115:

```
Ala Lys Phe Leu His Trp Leu Met Ser Val Tyr Val Val Glu Leu Leu
1               5                   10                  15

Arg Ser Phe Phe Tyr Val Thr Glu Thr Thr Phe Gln
            20                  25
```

(2) INFORMATION FOR SEQ ID NO: 116:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 116:

```
Leu Phe Phe Tyr Arg Lys Ser Val Trp Ser Lys Leu Gln Ser Ile Gly
1               5                   10                  15

Ile Arg Gln His Leu Lys Arg Val Gln Leu Arg Asp Val Ser
            20                  25                  30
```

(2) INFORMATION FOR SEQ ID NO: 117:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 117:

```
Pro Ala Leu Leu Thr Ser Arg Leu Arg Phe Ile Pro Lys Pro Asp Gly
1               5                   10                  15

Leu Arg Pro Ile Val Asn Met Asp Tyr Val Val
            20                  25
```

(2) INFORMATION FOR SEQ ID NO: 118:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 118:

YARACHAARG GHATYCCHYA RGG                                                   23

(2) INFORMATION FOR SEQ ID NO: 119:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 119:

Gln Thr Lys Gly Ile Pro Gln Gly
1               5

(2) INFORMATION FOR SEQ ID NO: 120:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 120:

NGTNATDARD ARRTARTCRT C                                                     21

(2) INFORMATION FOR SEQ ID NO: 121:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 121:

Asp Asp Tyr Leu Leu Ile Thr
1               5

(2) INFORMATION FOR SEQ ID NO: 122:

(i) SEQUENCE CHARACTERISTICS:
        (A) LENGTH: 55 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 122:

Lys Gly Ile Pro Gln Gly Leu Cys Val Ser Ser Ile Leu Ser Ser Phe
1               5                   10                  15

Tyr Tyr Ala Thr Leu Glu Glu Ser Ser Leu Gly Phe Leu Arg Asp Glu
                20                  25                  30

```
Ser Met Asn Pro Glu Asn Pro Asn Val Asn Leu Leu Met Arg Leu Thr
         35                  40                  45

Asp Asp Tyr Leu Leu Ile Thr
         50                  55
```

(2) INFORMATION FOR SEQ ID NO: 123:

(i) SEQUENCE CHARACTERISTICS:
        (A) LENGTH: 34 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 123:

```
Ser Ile Leu Ser Ser Phe Leu Cys His Phe Tyr Met Glu Asp Leu Ile
 1               5                  10                  15

Asp Glu Tyr Leu Ser Phe Thr Lys Lys Gly Ser Val Leu Leu Arg
         20                  25                  30

Val Val
```

(2) INFORMATION FOR SEQ ID NO: 124:

(i) SEQUENCE CHARACTERISTICS:
        (A) LENGTH: 49 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 124:

```
Asp Gly Leu Phe Gln Gly Ser Ser Leu Ser Ala Pro Ile Val Asp Leu
 1               5                  10                  15

Val Tyr Asp Asp Leu Leu Glu Phe Tyr Ser Glu Phe Lys Ala Ser Pro
         20                  25                  30

Ser Gln Asp Thr Leu Ile Leu Lys Leu Ala Asp Asp Phe Leu Ile Ile
         35                  40                  45

Ser
```

(2) INFORMATION FOR SEQ ID NO: 125:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 125:

```
Gln Lys Val Gly Ile Pro Gln Gly
 1               5
```

(2) INFORMATION FOR SEQ ID NO: 126:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 126:

CAAAAAGTTG GTATCCCTCA GGG                                                      23

(2) INFORMATION FOR SEQ ID NO: 127:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 127:

AGACCAAAGG AATTCCATCA GGCTCAATTC TGTCATCTTT TTTGTGTCAT TTCTATATGG              60

AAGATTTGAT TGATGAATAC CTATCGTTTA CGAAAAAGAA AGGATCAGTG TTGTTACGAG             120

TAGTCGACGA CTACCTCCTC ATCACC                                                 146

(2) INFORMATION FOR SEQ ID NO: 128:

(i) SEQUENCE CHARACTERISTICS:
        (A) LENGTH: 47 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 128:

Lys Gly Ile Pro Ser Gly Ser Ile Leu Ser Phe Leu Cys His Phe
1               5                  10                  15

Tyr Met Glu Asp Leu Ile Asp Glu Tyr Leu Ser Phe Thr Lys Lys Lys
            20                  25                  30

Gly Ser Val Leu Leu Arg Val Val Asp Asp Tyr Leu Leu Ile Thr
            35                  40                  45

(2) INFORMATION FOR SEQ ID NO: 129:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 129:

GACGATTTCC TCTTTATAAC A                                                       21

(2) INFORMATION FOR SEQ ID NO: 130:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 130:

Asp Asp Phe Leu Phe Ile Thr
1               5

(2) INFORMATION FOR SEQ ID NO: 131:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 131:

AAAAAAAAAA AAAAAA                                    16

(2) INFORMATION FOR SEQ ID NO: 132:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 132:

TTTTTTTTTT TTTTTTT                                   17

(2) INFORMATION FOR SEQ ID NO: 133:

(i) SEQUENCE CHARACTERISTICS:
        (A) LENGTH: 35 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..35
        (D) OTHER INFORMATION: /note= "motif 0 peptide from
            Schizosaccharomyces pombe tez1p"

(xi) SEQUENCE DESCRIPTION: SEQ ID NO: 133:

Trp Leu Tyr Asn Ser Phe Ile Ile Pro Ile Leu Gln Ser Phe Phe Tyr
1             5                   10               15

Ile Thr Glu Ser Ser Asp Leu Arg Asn Arg Thr Val Tyr Phe Arg Lys
           20                 25               30

Asp Ile Trp
        35

(2) INFORMATION FOR SEQ ID NO: 134:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "motif 1 and 2 peptide from
            Schizosaccharomyces pombe tez1p"

(xi) SEQUENCE DESCRIPTION: SEQ ID NO: 134:

Ala Val Ile Arg Leu Leu Pro Lys Lys Asn Thr Phe Arg Leu Ile Thr
1             5                   10               15

Asn Leu Arg Lys Arg Phe
        20

```
(2) INFORMATION FOR SEQ ID NO: 135:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..26
        (D) OTHER INFORMATION: /note= "motif 3(A) peptide from
            Schizosaccharomyces pombe tez1p"

(xi) SEQUENCE DESCRIPTION: SEQ ID NO: 135:

Lys Lys Tyr Phe Val Arg Ile Asp Ile Lys Ser Cys Tyr Asp Arg Ile
1               5                   10                  15

Lys Gln Asp Leu Met Phe Arg Ile Val Lys
            20                  25

(2) INFORMATION FOR SEQ ID NO: 136:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..32
        (D) OTHER INFORMATION: /note= "motif 4(B') peptide from
            Schizosaccharomyces pombe tez1p"

(xi) SEQUENCE DESCRIPTION: SEQ ID NO: 136:

Tyr Leu Gln Lys Val Gly Ile Pro Gln Gly Ser Ile Leu Ser Ser Phe
1               5                   10                  15

Leu Cys His Phe Tyr Met Glu Asp Leu Ile Asp Glu Tyr Leu Ser Phe
            20                  25                  30

(2) INFORMATION FOR SEQ ID NO: 137:

(i) SEQUENCE CHARACTERISTICS:
        (A) LENGTH: 49 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..49
        (D) OTHER INFORMATION: /note= "motif 5(C) and 6(D) peptide
            from Schizosaccharomyces pombe tez1p"

(xi) SEQUENCE DESCRIPTION: SEQ ID NO: 137:

Val Leu Leu Arg Val Val Asp Asp Phe Leu Phe Ile Thr Val Asn Lys
1               5                   10                  15

Lys Asp Ala Lys Lys Phe Leu Asn Leu Ser Leu Arg Gly Phe Glu Lys
            20                  25                  30

His Asn Phe Ser Thr Ser Leu Glu Lys Thr Val Ile Asn Phe Glu Asn
                35                  40                  45

Ser
```

(2) INFORMATION FOR SEQ ID NO: 138:

(i) SEQUENCE CHARACTERISTICS:
       (A) LENGTH: 34 amino acids
       (B) TYPE: amino acid
       (C) STRANDEDNESS: <Unknown>
       (D) TOPOLOGY: linear (ii) MOLECULE TYPE: peptide (ix) FEATURE:
       (A) NAME/KEY: Peptide
       (B) LOCATION: 1..34
       (D) OTHER INFORMATION: /note= "motif 0 peptide from
           Saccharomyces cerevisiae EST2p"

(xi) SEQUENCE DESCRIPTION: SEQ ID NO: 138:

Trp Leu Phe Arg Gln Leu Ile Pro Lys Ile Ile Gln Thr Phe Phe Tyr
1               5                   10                  15

Cys Thr Glu Ile Ser Ser Thr Val Thr Ile Val Tyr Phe Arg His Asp
            20                  25                  30

Thr Trp (2) INFORMATION FOR SEQ ID NO: 139:

(i) SEQUENCE CHARACTERISTICS:
       (A) LENGTH: 25 amino acids
       (B) TYPE: amino acid
       (C) STRANDEDNESS: <Unknown>
       (D) TOPOLOGY: linear (ii) MOLECULE TYPE: peptide (ix) FEATURE:
       (A) NAME/KEY: Peptide
       (B) LOCATION: 1..25
       (D) OTHER INFORMATION: /note= "motif 1 and 2 peptide from
           Saccharomyces cerevisiae EST2p"

(xi) SEQUENCE DESCRIPTION: SEQ ID NO: 139:

Ser Lys Met Arg Ile Ile Pro Lys Lys Ser Asn Asn Glu Phe Arg Ile
1               5                   10                  15

Ile Ala Ile Pro Cys Arg Gly Ala Asp
            20                  25

(2) INFORMATION FOR SEQ ID NO: 140:

(i) SEQUENCE CHARACTERISTICS:
       (A) LENGTH: 26 amino acids
       (B) TYPE: amino acid
       (C) STRANDEDNESS: <Unknown>
       (D) TOPOLOGY: linear (ii) MOLECULE TYPE: peptide (ix) FEATURE:
       (A) NAME/KEY: Peptide
       (B) LOCATION: 1..26
       (D) OTHER INFORMATION: /note= "motif 3(A) peptide from
           Saccharomyces cerevisiae EST2p"

(xi) SEQUENCE DESCRIPTION: SEQ ID NO: 140:

Glu Leu Tyr Phe Met Lys Phe Asp Val Lys Ser Cys Tyr Asp Ser Ile
1               5                   10                  15

Pro Arg Met Glu Cys Met Arg Ile Leu Lys
            20                  25

```
(2) INFORMATION FOR SEQ ID NO: 141:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..32
        (D) OTHER INFORMATION: /note= "motif 4(B') peptide from
            Saccharomyces cerevisiae EST2p"

(xi) SEQUENCE DESCRIPTION: SEQ ID NO: 141:

Tyr Ile Arg Glu Asp Gly Leu Phe Gln Gly Ser Ser Leu Ser Ala Pro
1               5                   10                  15

Ile Val Asp Leu Val Tyr Asp Leu Leu Glu Phe Tyr Ser Glu Phe
            20                  25                  30

(2) INFORMATION FOR SEQ ID NO: 142:

(i) SEQUENCE CHARACTERISTICS:
        (A) LENGTH: 49 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..49
        (D) OTHER INFORMATION: /note= "motif 5(C) peptide from
            Saccharomyces cerevisiae EST2p"

(xi) SEQUENCE DESCRIPTION: SEQ ID NO: 142:

Leu Ile Leu Lys Leu Ala Asp Asp Phe Leu Ile Ile Ser Thr Asp Gln
1               5                   10                  15

Gln Gln Val Ile Asn Ile Lys Lys Leu Ala Met Gly Gly Phe Gln Lys
            20                  25                  30

Tyr Asn Ala Lys Ala Asn Arg Asp Lys Ile Leu Ala Val Ser Ser Gln
            35                  40                  45

Ser (2) INFORMATION FOR SEQ ID NO: 143:

(i) SEQUENCE CHARACTERISTICS:
        (A) LENGTH: 35 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..35
        (D) OTHER INFORMATION: /note= "motif 0 peptide from Euplotes
            aediculatus p123"

(xi) SEQUENCE DESCRIPTION: SEQ ID NO: 143:

Trp Ile Phe Glu Asp Leu Val Val Ser Leu Ile Arg Cys Phe Phe Tyr
1               5                   10                  15
```

```
Val Thr Glu Gln Gln Lys Ser Tyr Ser Lys Thr Tyr Tyr Tyr Arg Lys
         20                  25                  30

Asn Ile Trp
        35
```

(2) INFORMATION FOR SEQ ID NO: 144:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..23
        (D) OTHER INFORMATION: /note= "motif 1 and 2 peptide from
            Euplotes aediculatus p123"

(xi) SEQUENCE DESCRIPTION: SEQ ID NO: 144:

```
Gly Lys Leu Arg Leu Ile Pro Lys Lys Thr Thr Phe Arg Pro Ile Met
1               5                   10                  15

Thr Phe Asn Lys Lys Ile Val
            20
```

(2) INFORMATION FOR SEQ ID NO: 145:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..26
        (D) OTHER INFORMATION: /note= "motif 3(A) peptide from
            Euplotes aediculatus p123"

(xi) SEQUENCE DESCRIPTION: SEQ ID NO: 145:

```
Lys Leu Phe Phe Ala Thr Met Asp Ile Glu Lys Cys Tyr Asp Ser Val
1               5                   10                  15

Asn Arg Glu Lys Leu Ser Thr Phe Leu Lys
            20                  25
```

(2) INFORMATION FOR SEQ ID NO: 146:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..32
        (D) OTHER INFORMATION: /note= "motif 4(B') peptide from
            Euplotes aediculatus p123"

(xi) SEQUENCE DESCRIPTION: SEQ ID NO: 146:

```
Tyr Lys Gln Thr Lys Gly Ile Pro Gln Gly Leu Cys Val Ser Ser Ile
1               5                   10                  15
```

```
Leu Ser Ser Phe Tyr Tyr Ala Thr Leu Glu Glu Ser Ser Leu Gly Phe
            20                  25                  30
```

(2) INFORMATION FOR SEQ ID NO: 147:

(i) SEQUENCE CHARACTERISTICS:
        (A) LENGTH: 49 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..49
        (D) OTHER INFORMATION: /note= "motif 5(C) and 6(D) peptide
            from Euplotes aediculatus p123"

(xi) SEQUENCE DESCRIPTION: SEQ ID NO: 147:

```
Leu Leu Met Arg Leu Thr Asp Asp Tyr Leu Leu Ile Thr Thr Gln Glu
1               5                  10                  15

Asn Asn Ala Val Leu Phe Ile Glu Lys Leu Ile Asn Val Ser Arg Glu
            20                  25                  30

Asn Gly Phe Lys Phe Asn Met Lys Lys Leu Gln Thr Ser Phe Pro Leu
        35                  40                  45

Ser
```

(2) INFORMATION FOR SEQ ID NO: 148:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "motif 1 peptide from Euplotes
            aediculatus p123"

(xi) SEQUENCE DESCRIPTION: SEQ ID NO: 148:

```
Leu Val Val Ser Leu Ile Arg Cys Phe Phe Tyr Val Thr Glu Gln Gln
1               5                  10                  15

Lys Ser Tyr Ser Lys Thr
            20
```

(2) INFORMATION FOR SEQ ID NO: 149:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..30
        (D) OTHER INFORMATION: /note= "motif 0 peptide from Euplotes
            aediculatus p123"

(xi) SEQUENCE DESCRIPTION: SEQ ID NO: 149:

```
Lys Ser Leu Gly Phe Ala Pro Gly Lys Leu Arg Leu Ile Pro Lys Lys
1               5                  10                  15
```

```
Thr Thr Phe Arg Pro Ile Met Thr Phe Asn Lys Lys Ile Val
            20                  25                  30
```

(2) INFORMATION FOR SEQ ID NO: 150:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..27
        (D) OTHER INFORMATION: /note= "motif A peptide from Euplotes
            aediculatus p123"

(xi) SEQUENCE DESCRIPTION: SEQ ID NO: 150:

```
Pro Lys Leu Phe Phe Ala Thr Met Asp Ile Glu Lys Cys Tyr Asp Ser
1               5                   10                  15
Val Asn Arg Glu Lys Leu Ser Thr Phe Leu Lys
            20                  25
```

(2) INFORMATION FOR SEQ ID NO: 151:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..27
        (D) OTHER INFORMATION: /note= "motif B peptide from Euplotes
            aediculatus p123"

(xi) SEQUENCE DESCRIPTION: SEQ ID NO: 151:

```
Asn Gly Lys Phe Tyr Lys Gln Thr Lys Gly Ile Pro Gln Gly Leu Cys
1               5                   10                  15
Val Ser Ser Ile Leu Ser Ser Phe Tyr Tyr Ala
            20                  25
```

(2) INFORMATION FOR SEQ ID NO: 152:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 22
        (D) OTHER INFORMATION: /note= "motif C peptide from Euplotes
            aediculatus p123"

(xi) SEQUENCE DESCRIPTION: SEQ ID NO: 152:

```
Pro Asn Val Asn Leu Leu Met Arg Leu Thr Asp Asp Tyr Leu Leu Ile
1               5                   10                  15
Thr Thr Gln Glu Asn Asn
            20
```

```
(2) INFORMATION FOR SEQ ID NO: 153:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "motif D peptide from Euplotes
            aediculatus p123"

(xi) SEQUENCE DESCRIPTION: SEQ ID NO: 153:

Asn Val Ser Arg Glu Asn Gly Phe Lys Phe Asn Met Lys Lys Leu
1               5                  10                  15

(2) INFORMATION FOR SEQ ID NO: 154:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "motif 1 peptide from
            Schizosaccharomyces pombe tez1"

(xi) SEQUENCE DESCRIPTION: SEQ ID NO: 154:

Phe Ile Ile Pro Ile Leu Gln Ser Phe Phe Tyr Ile Thr Glu Ser Ser
1               5                  10                  15

Asp Leu Arg Asn Arg Thr
            20

(2) INFORMATION FOR SEQ ID NO: 155:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..30
        (D) OTHER INFORMATION: /note= "motif 0 peptide from
            Schizosaccharomyces pombe tez1"

(xi) SEQUENCE DESCRIPTION: SEQ ID NO: 155:

Gln Lys Thr Thr Leu Pro Pro Ala Val Ile Arg Leu Leu Pro Lys Lys
1               5                  10                  15

Asn Thr Phe Arg Leu Ile Thr Asn Leu Arg Lys Arg Phe Leu
            20                  25                  30

(2) INFORMATION FOR SEQ ID NO: 156:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear
```

(ii) MOLECULE TYPE: peptide (ix) FEATURE:
              (A) NAME/KEY: Peptide
              (B) LOCATION: 1..27
              (D) OTHER INFORMATION: /note= "motif A peptide from
                  Schizosaccharomyces pombe tez1"

(xi) SEQUENCE DESCRIPTION: SEQ ID NO: 156:

Arg Lys Lys Tyr Phe Val Arg Ile Asp Ile Lys Ser Cys Tyr Asp Arg
1               5                   10                  15

Ile Lys Gln Asp Leu Met Phe Arg Ile Val Lys
            20                  25

(2) INFORMATION FOR SEQ ID NO: 157:

(i) SEQUENCE CHARACTERISTICS:
              (A) LENGTH: 27 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Peptide
              (B) LOCATION: 1..27
              (D) OTHER INFORMATION: /note= "motif B peptide from
                  Schizosaccharomyces pombe tez1"

(xi) SEQUENCE DESCRIPTION: SEQ ID NO: 157:

Gly Asn Ser Gln Tyr Leu Gln Lys Val Gly Ile Pro Gln Gly Ser Ile
1               5                   10                  15

Leu Ser Ser Phe Leu Cys His Phe Tyr Met Glu
            20                  25

(2) INFORMATION FOR SEQ ID NO: 158:

(i) SEQUENCE CHARACTERISTICS:
              (A) LENGTH: 22 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Peptide
              (B) LOCATION: 1..22
              (D) OTHER INFORMATION: /note= "motif C peptide from
                  Schizosaccharomyces pombe tez1"

(xi) SEQUENCE DESCRIPTION: SEQ ID NO: 158:

Lys Lys Gly Ser Val Leu Leu Arg Val Val Asp Asp Phe Leu Phe Ile
1               5                   10                  15

Thr Val Asn Lys Lys Asp
            20

(2) INFORMATION FOR SEQ ID NO: 159:

(i) SEQUENCE CHARACTERISTICS:
              (A) LENGTH: 15 amino acids
              (B) TYPE: amino acid
              (C) STRANDEDNESS: <Unknown>
              (D) TOPOLOGY: linear (ii) MOLECULE TYPE: peptide

```
    (ix) FEATURE:
         (A) NAME/KEY: Peptide
         (B) LOCATION: 1..15
         (D) OTHER INFORMATION: /note= "motif D peptide from
             Schizosaccharomyces pombe tez1"

(xi) SEQUENCE DESCRIPTION: SEQ ID NO: 159:

Leu Asn Leu Ser Leu Arg Gly Phe Glu Lys His Asn Phe Ser Thr
1               5                   10                  15

(2) INFORMATION FOR SEQ ID NO: 160:

(i) SEQUENCE CHARACTERISTICS:
         (A) LENGTH: 22 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Peptide
         (B) LOCATION: 1..22
         (D) OTHER INFORMATION: /note= "motif 1 peptide from
             Saccharomyces cerevisiae EST2"

(xi) SEQUENCE DESCRIPTION: SEQ ID NO: 160:

Leu Ile Pro Lys Ile Ile Gln Thr Phe Phe Tyr Cys Thr Glu Ile Ser
1               5                   10                  15

Ser Thr Val Thr Ile Val
            20

(2) INFORMATION FOR SEQ ID NO: 161:

(i) SEQUENCE CHARACTERISTICS:
         (A) LENGTH: 32 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Peptide
         (B) LOCATION: 1..32
         (D) OTHER INFORMATION: /note= "motif 0 peptide from
             Saccharomyces cerevisiae EST2"

(xi) SEQUENCE DESCRIPTION: SEQ ID NO: 161:

Thr Leu Ser Asn Phe Asn His Ser Lys Met Arg Ile Ile Pro Lys Lys
1               5                   10                  15

Ser Asn Asn Glu Phe Arg Ile Ile Ala Ile Pro Cys Arg Gly Ala Asp
            20                  25                  30

(2) INFORMATION FOR SEQ ID NO: 162:

(i) SEQUENCE CHARACTERISTICS:
         (A) LENGTH: 27 amino acids
         (B) TYPE: amino acid
         (C) STRANDEDNESS: <Unknown>
         (D) TOPOLOGY: linear (ii) MOLECULE TYPE: peptide (ix) FEATURE:
         (A) NAME/KEY: Peptide
         (B) LOCATION: 1..27
         (D) OTHER INFORMATION: /note= "motif A peptide from
             Saccharomyces cerevisiae EST2"
```

(xi) SEQUENCE DESCRIPTION: SEQ ID NO: 162:

Pro Glu Leu Tyr Phe Met Lys Phe Asp Val Lys Ser Cys Tyr Asp Ser
1               5                   10                  15
Ile Pro Arg Met Glu Cys Met Arg Ile Leu Lys
            20                  25

(2) INFORMATION FOR SEQ ID NO: 163:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..27
        (D) OTHER INFORMATION: /note= "motif B peptide from
            Saccharomyces cerevisiae EST2"

(xi) SEQUENCE DESCRIPTION: SEQ ID NO: 163:

Glu Asp Lys Cys Tyr Ile Arg Glu Asp Gly Leu Phe Gln Gly Ser Ser
1               5                   10                  15
Leu Ser Ala Pro Ile Val Asp Leu Val Tyr Asp
            20                  25

(2) INFORMATION FOR SEQ ID NO: 164:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "motif C peptide from
            Saccharomyces cerevisiae EST2"

(xi) SEQUENCE DESCRIPTION: SEQ ID NO: 164:

Ser Gln Asp Thr Leu Ile Leu Lys Leu Ala Asp Asp Phe Leu Ile Ile
1               5                   10                  15
Ser Thr Asp Gln Gln Gln
            20

(2) INFORMATION FOR SEQ ID NO: 165:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "motif D peptide from
            Saccharomyces cerevisiae EST2"

(xi) SEQUENCE DESCRIPTION: SEQ ID NO: 165:

Lys Lys Leu Ala Met Gly Gly Phe Gln Lys Tyr Asn Ala Lys Ala
1               5                   10                  15

(2) INFORMATION FOR SEQ ID NO: 166:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "motif 1 peptide from human
            telomerase core protein 1 (TCP1)"

(xi) SEQUENCE DESCRIPTION: SEQ ID NO: 166:

```
Tyr Val Val Glu Leu Leu Arg Ser Phe Phe Tyr Val Thr Glu Thr Thr
 1               5                  10                  15

Phe Gln Lys Asn Arg Leu
            20
```

(2) INFORMATION FOR SEQ ID NO: 167:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..30
        (D) OTHER INFORMATION: /note= "motif 0 peptide from human
            telomerase core protein 1 (TCP1)"

(xi) SEQUENCE DESCRIPTION: SEQ ID NO: 167:

```
Ala Arg Pro Ala Leu Leu Thr Ser Arg Leu Arg Phe Ile Pro Lys Pro
 1               5                  10                  15

Asp Gly Leu Arg Pro Ile Val Asn Met Asp Tyr Val Val Gly
            20                  25                  30
```

(2) INFORMATION FOR SEQ ID NO: 168:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..27
        (D) OTHER INFORMATION: /note= "motif A peptide from human
            telomerase core protein 1 (TCP1)"

(xi) SEQUENCE DESCRIPTION: SEQ ID NO: 168:

```
Pro Glu Leu Tyr Phe Val Lys Val Asp Val Thr Gly Ala Tyr Asp Thr
 1               5                  10                  15

Ile Pro Gln Asp Arg Leu Thr Glu Val Ile Ala
            20                  25
```

```
(2) INFORMATION FOR SEQ ID NO: 169:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Protein
        (B) LOCATION: 1..27
        (D) OTHER INFORMATION: /note= "motif B peptide from human
             telomerase core protein 1 (TCP1)"

(xi) SEQUENCE DESCRIPTION: SEQ ID NO: 169:

Arg Ala Thr Ser Tyr Val Gln Cys Gln Gly Ile Pro Gln Gly Ser Ile
 1               5                  10                  15

Leu Ser Thr Leu Leu Cys Ser Leu Cys Tyr Gly
                20                  25

(2) INFORMATION FOR SEQ ID NO: 170:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "motif C peptide from human
             telomerase core protein 1 (TCP1)"

(xi) SEQUENCE DESCRIPTION: SEQ ID NO: 170:

Arg Arg Asp Gly Leu Leu Leu Arg Leu Val Asp Asp Phe Leu Leu Val
 1               5                  10                  15

Thr Pro His Leu Thr His
                20

(2) INFORMATION FOR SEQ ID NO: 171:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "motif D peptide from human
             telomerase core protein 1 (TCP1)"

(xi) SEQUENCE DESCRIPTION: SEQ ID NO: 171:

Leu Arg Thr Leu Val Arg Gly Val Pro Glu Tyr Gly Cys Val Val
 1               5                  10                  15

(2) INFORMATION FOR SEQ ID NO: 172:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear
```

(ii) MOLECULE TYPE: peptide (xi) SEQUENCE DESCRIPTION: SEQ ID NO: 172:

Phe Phe Tyr Val Thr Glu
1               5

(2) INFORMATION FOR SEQ ID NO: 173:

(i) SEQUENCE CHARACTERISTICS:
        (A) LENGTH: 4029 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY:
        (B) LOCATION: 1..4029
        (D) OTHER INFORMATION: /note= "preliminary sequence for
            human TRT cDNA insert of plasmid pGRN121"

(xi) SEQUENCE DESCRIPTION: SEQ ID NO: 173:

| | | | | | |
|---|---|---|---|---|---|
| GCAGCGCTGC | GTCCTGCTGC | GCACGTGGGA | AGCCCTGGCC | CCGGCCACCC | CCGCGATGCC | 60 |
| GCGCGCTCCC | CGCTGCCGAG | CCGTGCGCTC | CCTGCTGCGC | AGCCACTACC | GCGAGGTGCT | 120 |
| GCCGCTGGCC | ACGTTCGTGC | GGCGCCTGGG | GCCCCAGGGC | TGGCGGCTGG | TGCAGCGCGG | 180 |
| GGACCCGGCG | GCTTTCCGCG | CGNTGGTGGC | CCANTGCNTG | GTGTGCGTGC | CCTGGGANGN | 240 |
| ANGGCNGCCC | CCCGCCGCCC | CCTCCTTCCG | CCAGGTGTCC | TGCCTGAANG | ANCTGGTGGC | 300 |
| CCGAGTGCTG | CANANGCTGT | GCGANCGCGG | CGCGAANAAC | GTGCTGGCCT | TCGGCTTCGC | 360 |
| GCTGCTGGAC | GGGGCCCGCG | GGGGCCCCCC | CGAGGCCTTC | ACCACCAGCG | TGCGCAGCTA | 420 |
| CCTGCCCAAC | ACGGTGACCG | ACGCACTGCG | GGGGAGCGGG | GCGTGGGGGC | TGCTGCTGCG | 480 |
| CCGCGTGGGC | GACGACGTGC | TGGTTCACCT | GCTGGCACGC | TGCGCGNTNT | TTGTGCTGGT | 540 |
| GGNTCCCAGC | TGCGCCTACC | ANGTGTGCGG | GCCGCCGCTG | TACCAGCTCG | GCGCTGCNAC | 600 |
| TCAGGCCCGG | CCCCCGCCAC | ACGCTANTGG | ACCCGAANGC | GTCTGGGATC | CAACGGGCCT | 660 |
| GGAACCATAG | CGTCAGGGAG | GCCGGGGTCC | CCCTGGGCTG | CCAGCCCCGG | GTGCGAGGAG | 720 |
| GCGCGGGGGC | AGTGCCAGCC | GAAGTCTGCC | GTTGCCCAAG | AGGCCCAGGC | GTGGCGCTGC | 780 |
| CCCTGAGCCG | GAGCGGACGC | CCGTTGGGCA | GGGGTCCTGG | GCCCACCCGG | GCAGGACGCC | 840 |
| TGGACCGAGT | GACCGTGGTT | TCTGTGTGGT | GTCACCTGCC | AGACCCGCCG | AAGAAGCCAC | 900 |
| CTCTTTGGAG | GGTGCGCTCT | CTGGCACGCG | CCACTCCCAC | CCATCCGTGG | GCCGCCAGCA | 960 |
| CCACGCGGGC | CCCCCATCCA | CATCGCGGCC | ACCACGTCCT | GGGACACGCC | TTGTCCCCCG | 1020 |
| GTGTACGCCG | AGACCAAGCA | CTTCCTCTAC | TCCTCAGGCG | ACAAGNACAC | TGCGNCCCTC | 1080 |
| CTTCCTACTC | AATATATCTG | AGGCCCAGCC | TGACTGGCGT | TCGGGAGGTT | CGTGGAGACA | 1140 |
| NTCTTTCTGG | TTCCAGGCCT | TGGATGCCAG | GATTCCCCGC | AGGTTGCCCC | GCCTGCCCCA | 1200 |
| GCGNTACTGG | CAAATGCGGC | CCCTGTTTCT | GGAGCTGCTT | GGGAACCACG | CGCAGTGCCC | 1260 |
| CTACGGGGTG | TTCCTCAAGA | CGCACTGCCC | GCTGCGAGCT | GCGGTCACCC | CAGCAGCCGG | 1320 |
| TGTCTGTGCC | CGGGAGAAGC | CCCAGGGCTC | TGTGGCGGCC | CCCGAGGAGG | AGGAACACAG | 1380 |
| ACCCCCGTCG | CCTGGTGCAG | CTGCTCCGCC | AGCACAGCAG | CCCCTGGCAG | GTGTACGGCT | 1440 |
| TCGTGCGGGC | CTGCCTGCGC | CGGCTGGTGC | CCCCAGGCCT | CTGGGCTCC | AGGCACAACG | 1500 |
| AACGCCGCTT | CCTCAGGAAC | ACCAAGAAGT | TCATCTCCCT | GGGGAAGCAT | GCCAAGCTCT | 1560 |
| CGCTGCAGGA | GCTGACGTGG | AAGATGAGCG | TGCGGGACTG | CGCTTGGCTG | CGCAGGAGCC | 1620 |

```
CAGGGGTTGG CTGTGTTCCG GCCGCAGAGC ACCGTCTGCG TGAGGAGATC CTGGCCAAGT    1680

TCCTGCACTG GCTGATGAGT GTGTACGTCG TCGAGCTGCT CAGGTCTTTC TTTTATGTCA    1740

CGGAGACCAC GTTTCAAAAG AACAGGCTCT TTTTCTACCG GAAGAGTGTC TGGAGCAAGT    1800

TGCAAAGCAT TGGAATCAGA CAGCACTTGA AGAGGGTGCA GCTGCGGGAG CTGTCGGAAG    1860

CAGAGGTCAG GCAGCATCGG GAAGCCAGGC CCGCCCTGCT GACGTCCAGA CTCCGCTTCA    1920

TCCCCAAGCC TGACGGGCTG CGGCCGATTG TGAACATGGA CTACGTCGTG GGAGCCAGAA    1980

CGTTCCGCAG AGAAAAGAGG GCCGAGCGTC TCACCTCGAG GGTGAAGGCA CTGTTCAGCG    2040

TGCTCAACTA CGAGCGGGCG CGGCGCCCCG GCCTCCTGGG CGCCTCTGTG CTGGGCCTGG    2100

ACGATATCCA CAGGGCCTGG CGCACCTTCG TGCTGCGTGT GCGGGCCCAG GACCCGCCGC    2160

CTGAGCTGTA CTTTGTCAAG GTGGATGTGA CGGGCGCGTA CGACACCATC CCCCAGGACA    2220

GGCTCACGGA GGTCATCGCC AGCATCATCA AACCCCAGAA CACGTACTGC GTGCGTCGGT    2280

ATGCCGTGGT CCAGAAGGCC GCCCATGGGC ACGTCCGCAA GGCCTTCAAG AGCCACGTCT    2340

CTACCTTGAC AGACCTCCAG CCGTACATGC GACAGTTCGT GGCTCACCTG CAGGANAACA    2400

GCCCGCTGAG GGATGCCGTC GTCATCGAGC AGAGCTCCTC CCTGAATGAG GCCAGCAGTG    2460

GCCTCTTCGA CGTCTTCCTA CGCTTCATGT GCCACCACGC CGTGCGCATC AGGGGCAAGT    2520

CCTACGTCCA GTGCCAGGGG ATCCCGCAGG GCTCCATCCT CTCCACGCTG CTCTGCAGCC    2580

TGTGCTACGG CGACATGGAG AACAAGTGT TTGCGGGGAT TCGGCGGGAC GGGCTGCTCC    2640

TGCGTTTGGT GGATGATTTC TTGTTGGTGA CACCTCACCT CACCCACGCG AAAACCTTCC    2700

TCAGGACCCT GGTCCGAGGT GTCCCTGAGT ATGGCTGCGT GGTGAACTTG CGGAAGACAG    2760

TGGTGAACTT CCCTGTAGAA GACGAGGCCC TGGGTGGCAC GGCTTTTGTT CAGATGCCGG    2820

CCCACGGCCT ATTCCCCTGG TGCGGCCTGC TGCTGGATAC CCGGACCCTG GAGGTGCAGA    2880

GCGACTACTC CAGCTATGCC CGGACCTCCA TCAGAGCCA TCTCACCTTC AACCGCGGCT    2940

TCAAGGCTGG GAGGAACATG CGTCGCAAAC TCTTTGGGGT CTTGCGGCTG AAGTGTCACA    3000

GCCTGTTTCT GGATTTGCAG GTGAACAGCC TCCAGACGGT GTGCACCAAC ATCTACAAGA    3060

TCCTCCTGCT GCAGGCGTAC AGGTTTCACG CATGTGTGCT GCAGCTCCCA TTTCATCAGC    3120

AAGTTTGGAA GAACCCCACA TTTTTCCTGC GCGTCATCTC TGACACGGCC TCCCTCTGCT    3180

ACTCCATCCT GAAAGCCAAG AACGCAGGGA TGTCGCTGGG GGCCAAGGGC GCCGCCGGCC    3240

CTCTGCCCTC CGAGGCCGTG CAGTGGCTGT GCCACCAAGC ATTCCTGCTC AAGCTGACTC    3300

GACACCGTGT CACCTACGTG CCACTCCTGG GGTCACTCAG GACAGCCCAG ACGCAGCTGA    3360

GTCGGAAGCT CCCCGGGACG ACGCTGACTG CCCTGGAGGC CGCAGCCAAC CCGGCACTGC    3420

CCTCAGACTT CAAGACCATC CTGGACTGAT GGCCACCCGC CCACAGCCAG CCGAGAGCA    3480

GACACCAGCA GCCCTGTCAC GCCGGGCTCT ACGTCCCAGG GAGGGAGGGG CGGCCCACAC    3540

CCAGGCCCGC ACCGCTGGGA GTCTGAGGCC TGAGTGAGTG TTTGGCCGAG GCCTGCATGT    3600

CCGGCTGAAG GCTGAGTGTC CGGCTGAGGC CTGAGCGAGT GTCCAGCCAA GGGCTGAGTG    3660

TCCAGCACAC CTGCCGTCTT CACTTCCCCA CAGGCTGGCG CTCGGCTCCA CCCCAGGGCC    3720

AGCTTTTCCT CACCAGGAGC CCGGCTTCCA CTCCCCACAT AGGAATAGTC CATCCCCAGA    3780

TTCGCCATTG TTCACCCCTC GCCCTGCCCT CCTTTGCCTT CCACCCCCAC CATCCAGGTG    3840

GAGACCCTGA GAAGGACCCT GGGAGCTCTG GGAATTTGGA GTGACCAAAG GTGTGCCCTG    3900

TACACAGGCG AGGACCCTGC ACCTGGATGG GGGTCCCTGT GGGTCAAATT GGGGGGAGGT    3960
```

GCTGTGGGAG TAAAATACTG AATATATGAG TTTTTCAGTT TTGAAAAAAA AAAAAAAAAA    4020

AAAAAAAAA                                                            4029

(2) INFORMATION FOR SEQ ID NO: 174:

(i) SEQUENCE CHARACTERISTICS:
        (A) LENGTH: 261 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 174:

```
Ala Ala Leu Arg Pro Ala Ala His Val Gly Ser Pro Gly Pro Gly His
1               5                  10                  15

Pro Arg Asp Ala Ala Arg Ser Pro Leu Pro Ser Arg Ala Leu Pro Ala
            20                  25                  30

Ala Gln Pro Leu Pro Arg Gly Ala Ala Gly His Val Arg Ala Ala
        35                  40                  45

Pro Gly Ala Pro Gly Leu Ala Ala Gly Ala Ala Arg Gly Pro Gly Gly
    50                  55                  60

Phe Pro Arg Xaa Gly Gly Pro Xaa Xaa Gly Val Arg Ala Leu Gly Xaa
65                  70                  75                  80

Xaa Ala Ala Pro Arg Arg Pro Leu Leu Pro Pro Gly Val Leu Pro Glu
                85                  90                  95

Xaa Xaa Gly Gly Pro Ser Ala Ala Xaa Ala Val Arg Xaa Arg Arg Glu
            100                 105                 110

Xaa Arg Ala Gly Leu Arg Leu Arg Ala Ala Gly Arg Gly Pro Arg Gly
        115                 120                 125

Pro Pro Arg Gly Leu His His Gln Arg Ala Gln Leu Pro Ala Gln His
    130                 135                 140

Gly Asp Arg Arg Thr Ala Gly Glu Arg Gly Val Gly Ala Ala Ala Ala
145                 150                 155                 160

Pro Arg Gly Arg Arg Ala Gly Ser Pro Ala Gly Thr Leu Arg Xaa
                165                 170                 175

Xaa Cys Ala Gly Gly Ser Gln Leu Arg Leu Pro Xaa Val Arg Ala Ala
            180                 185                 190

Ala Val Pro Ala Arg Arg Cys Xaa Ser Gly Pro Ala Pro Ala Thr Arg
        195                 200                 205

Xaa Trp Thr Arg Xaa Arg Leu Gly Ser Asn Gly Pro Gly Thr Ile Ala
    210                 215                 220

Ser Gly Arg Pro Gly Ser Pro Trp Ala Ala Ser Pro Gly Cys Glu Glu
225                 230                 235                 240

Ala Arg Gly Gln Cys Gln Pro Lys Ser Ala Val Ala Gln Glu Ala Gln
                245                 250                 255

Ala Trp Arg Cys Pro
            260
```

(2) INFORMATION FOR SEQ ID NO: 175:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: linear (ii) MOLECULE TYPE: peptide -continued (xi) SEQUENCE DESCRIPTION: SEQ ID NO: 175:

Ala Gly Ala Asp Ala Arg Trp Ala Gly Val Leu Gly Pro Pro Gly Gln
1               5                   10                  15

Asp Ala Trp Thr Glu
            20

(2) INFORMATION FOR SEQ ID NO: 176:

(i) SEQUENCE CHARACTERISTICS:
         (A) LENGTH: 82 amino acids
         (B) TYPE: amino acid
         (C) STRANDEDNESS: <Unknown>
         (D) TOPOLOGY: linear (ii) MOLECULE TYPE: peptide (xi) SEQUENCE DESCRIPTION: SEQ ID NO: 176:

Pro Trp Phe Leu Cys Gly Val Thr Cys Gln Thr Arg Arg Ser His
1               5                   10                  15

Leu Phe Gly Gly Cys Ala Leu Trp His Ala Pro Leu Pro Pro Ile Arg
                20                  25                  30

Gly Pro Pro Ala Pro Arg Gly Pro Pro Ile His Ile Ala Ala Thr Thr
                35                  40                  45

Ser Trp Asp Thr Pro Cys Pro Pro Val Tyr Ala Glu Thr Lys His Phe
    50                  55                  60

Leu Tyr Ser Ser Gly Asp Lys Xaa Thr Ala Xaa Leu Leu Pro Thr Gln
65                  70                  75                  80

Tyr Ile (2) INFORMATION FOR SEQ ID NO: 177:

(i) SEQUENCE CHARACTERISTICS:
         (A) LENGTH: 153 amino acids
         (B) TYPE: amino acid
         (C) STRANDEDNESS: <Unknown>
         (D) TOPOLOGY: linear (ii) MOLECULE TYPE: peptide (xi) SEQUENCE DESCRIPTION: SEQ ID NO: 177:

Leu Ala Phe Gly Arg Phe Val Glu Thr Xaa Phe Leu Val Pro Gly Leu
1               5                   10                  15

Gly Cys Gln Asp Ser Pro Gln Val Ala Pro Pro Ala Pro Ala Xaa Leu
                20                  25                  30

Ala Asn Ala Ala Pro Val Ser Gly Ala Ala Trp Glu Pro Arg Ala Val
                35                  40                  45

Pro Leu Arg Gly Val Pro Gln Asp Ala Leu Pro Ala Ala Ser Cys Gly
    50                  55                  60

His Pro Ser Ser Arg Cys Leu Cys Pro Gly Glu Ala Pro Gly Leu Cys
65                  70                  75                  80

Gly Gly Pro Arg Gly Gly Gly Thr Gln Thr Pro Val Ala Trp Cys Ser
                85                  90                  95

Cys Ser Ala Ser Thr Ala Ala Pro Gly Arg Cys Thr Ala Ser Cys Gly
                100                 105                 110

Pro Ala Cys Ala Gly Trp Cys Pro Gln Ala Ser Gly Ala Pro Gly Thr
                115                 120                 125

-continued

```
Thr Asn Ala Ala Ser Ser Gly Thr Pro Arg Ser Ser Pro Trp Gly
    130                 135                 140
Ser Met Pro Ser Ser Arg Cys Arg Ser
145                 150
```

(2) INFORMATION FOR SEQ ID NO: 178:

(i) SEQUENCE CHARACTERISTICS:
        (A) LENGTH: 35 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 178:

```
Ala Cys Gly Thr Ala Leu Gly Cys Ala Gly Ala Gln Gly Leu Ala Val
1               5                   10                  15
Phe Arg Pro Gln Ser Thr Val Cys Val Arg Arg Ser Trp Pro Ser Ser
                20                  25                  30
Cys Thr Gly
        35
```

(2) INFORMATION FOR SEQ ID NO: 179:

(i) SEQUENCE CHARACTERISTICS:
        (A) LENGTH: 43 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 179:

```
Val Cys Thr Ser Ser Ser Cys Ser Gly Leu Ser Phe Met Ser Arg Arg
1               5                   10                  15
Pro Arg Phe Lys Arg Thr Gly Ser Phe Ser Thr Gly Arg Val Ser Gly
                20                  25                  30
Ala Ser Cys Lys Ala Leu Glu Ser Asp Ser Thr
        35                  40
```

(2) INFORMATION FOR SEQ ID NO: 180:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 180:

```
Arg Gly Cys Ser Cys Gly Ser Cys Arg Lys Gln Arg Ser Gly Ser Ile
1               5                   10                  15
Gly Lys Pro Gly Pro Pro Cys
                20
```

(2) INFORMATION FOR SEQ ID NO: 181:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide

```
    (xi) SEQUENCE DESCRIPTION: SEQ ID NO: 181:

Arg Pro Asp Ser Ala Ser Ser Pro Ser Leu Thr Gly Cys Gly Arg Leu
1               5                   10                  15

(2) INFORMATION FOR SEQ ID NO: 182:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 182:

Thr Trp Thr Thr Ser Trp Glu Pro Glu Arg Ser Ala Glu Lys Arg Gly
1               5                   10                  15

Pro Ser Val Ser Pro Arg Gly
            20

(2) INFORMATION FOR SEQ ID NO: 183:

(i) SEQUENCE CHARACTERISTICS:
        (A) LENGTH: 54 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 183:

Arg His Cys Ser Ala Cys Ser Thr Thr Ser Gly Arg Gly Ala Pro Ala
1               5                   10                  15

Ser Trp Ala Pro Leu Cys Trp Ala Trp Thr Ile Ser Thr Gly Pro Gly
            20                  25                  30

Ala Pro Ser Cys Cys Val Cys Gly Pro Arg Thr Arg Arg Leu Ser Cys
            35                  40                  45

Thr Leu Ser Arg Trp Met
    50

(2) INFORMATION FOR SEQ ID NO: 184:

(i) SEQUENCE CHARACTERISTICS:
        (A) LENGTH: 52 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 184:

Arg Ala Arg Thr Thr Pro Ser Pro Arg Thr Gly Ser Arg Arg Ser Ser
1               5                   10                  15

Pro Ala Ser Ser Asn Pro Arg Thr Arg Thr Ala Cys Val Gly Met Pro
            20                  25                  30

Trp Ser Arg Arg Pro Pro Met Gly Thr Ser Ala Arg Pro Ser Arg Ala
            35                  40                  45

Thr Ser Leu Pro
    50
```

(2) INFORMATION FOR SEQ ID NO: 185:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 185:

```
Gln Thr Ser Ser Arg Thr Cys Asp Ser Ser Trp Leu Thr Cys Arg Xaa
1               5                   10                  15

Thr Ala Arg
```

(2) INFORMATION FOR SEQ ID NO: 186:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 186:

```
Gly Met Pro Ser Ser Ser Arg Ala Pro Pro
1               5                   10
```

(2) INFORMATION FOR SEQ ID NO: 187:

(i) SEQUENCE CHARACTERISTICS:
        (A) LENGTH: 74 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 187:

```
Met Arg Pro Ala Val Ala Ser Ser Thr Ser Ser Tyr Ala Ser Cys Ala
1               5                   10                  15

Thr Thr Pro Cys Ala Ser Gly Ala Ser Pro Thr Ser Ser Ala Arg Gly
            20                  25                  30

Ser Arg Arg Ala Pro Ser Ser Pro Arg Cys Ser Ala Ala Cys Ala Thr
            35                  40                  45

Ala Thr Trp Arg Thr Ser Cys Leu Arg Gly Phe Gly Gly Thr Gly Cys
        50                  55                  60

Ser Cys Val Trp Trp Met Ile Ser Cys Trp
65                  70
```

(2) INFORMATION FOR SEQ ID NO: 188:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 188:

```
His Leu Thr Ser Pro Thr Arg Lys Pro Ser Ser Gly Pro Trp Ser Glu
1               5                   10                  15

Val Ser Leu Ser Met Ala Ala Trp
            20
```

(2) INFORMATION FOR SEQ ID NO: 189:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 189:

Thr Cys Gly Arg Gln Trp
1               5

(2) INFORMATION FOR SEQ ID NO: 190:

(i) SEQUENCE CHARACTERISTICS:
        (A) LENGTH: 70 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 190:

Lys Thr Arg Pro Trp Val Ala Arg Leu Leu Phe Arg Cys Arg Pro Thr
1               5                   10                  15

Ala Tyr Ser Pro Gly Ala Ala Cys Cys Trp Ile Pro Gly Pro Trp Arg
                20                  25                  30

Cys Arg Ala Thr Thr Pro Ala Met Pro Gly Pro Pro Ser Glu Pro Val
            35                  40                  45

Ser Pro Ser Thr Ala Ala Ser Arg Leu Gly Gly Thr Cys Val Ala Asn
        50                  55                  60

Ser Leu Gly Ser Cys Gly
65                  70

(2) INFORMATION FOR SEQ ID NO: 191:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 191:

Ser Val Thr Ala Cys Phe Trp Ile Cys Arg
1               5                   10

(2) INFORMATION FOR SEQ ID NO: 192:

(i) SEQUENCE CHARACTERISTICS:
        (A) LENGTH: 55 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 192:

Thr Ala Ser Arg Arg Cys Ala Pro Thr Ser Thr Arg Ser Ser Cys Cys
1               5                   10                  15

Arg Arg Thr Gly Phe Thr His Val Cys Cys Ser Ser His Phe Ile Ser
                20                  25                  30

```
Lys Phe Gly Arg Thr Pro His Phe Ser Cys Ala Ser Ser Leu Thr Arg
        35              40                  45

Pro Pro Ser Ala Thr Pro Ser
    50              55
```

(2) INFORMATION FOR SEQ ID NO: 193:

(i) SEQUENCE CHARACTERISTICS:
        (A) LENGTH: 34 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 193:

```
Lys Pro Arg Thr Gln Gly Cys Arg Trp Gly Pro Arg Ala Pro Pro Ala
1               5                   10                  15

Leu Cys Pro Pro Arg Pro Cys Ser Gly Cys Ala Thr Lys His Ser Cys
        20                  25                  30

Ser Ser
```

(2) INFORMATION FOR SEQ ID NO: 194:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 194:

```
Leu Asp Thr Val Ser Pro Thr Cys His Ser Trp Gly His Ser Gly Gln
1               5                   10                  15

Pro Arg Arg Ser
        20
```

(2) INFORMATION FOR SEQ ID NO: 195:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 195:

```
Val Gly Ser Ser Arg Gly Arg Arg
1               5
```

(2) INFORMATION FOR SEQ ID NO: 196:

(i) SEQUENCE CHARACTERISTICS:
        (A) LENGTH: 61 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 196:

```
Leu Pro Trp Arg Pro Gln Pro Thr Arg His Cys Pro Gln Thr Ser Arg
1               5                   10                  15
```

```
Pro Ser Trp Thr Asp Gly His Pro Pro Thr Ala Arg Pro Arg Ala Asp
            20                  25                  30

Thr Ser Ser Pro Val Thr Pro Gly Ser Thr Ser Gln Gly Gly Arg Gly
            35                  40                  45

Gly Pro His Pro Gly Pro His Arg Trp Glu Ser Glu Ala
            50                  55                  60
```

(2) INFORMATION FOR SEQ ID NO: 197:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 197:

```
Val Ser Val Trp Pro Arg Pro Ala Cys Pro Ala Glu Gly
1               5                   10
```

(2) INFORMATION FOR SEQ ID NO: 198:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 198:

```
Gly Leu Ser Glu Cys Pro Ala Lys Gly
1               5
```

(2) INFORMATION FOR SEQ ID NO: 199:

(i) SEQUENCE CHARACTERISTICS:
        (A) LENGTH: 34 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 199:

```
Val Ser Ser Thr Pro Ala Val Phe Thr Ser Pro Gln Ala Gly Ala Arg
1               5                   10                  15

Leu His Pro Arg Ala Ser Phe Ser Pro Gly Ala Arg Leu Pro Leu
            20                  25                  30

Pro Thr
```

(2) INFORMATION FOR SEQ ID NO: 200:

(i) SEQUENCE CHARACTERISTICS:
        (A) LENGTH: 70 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 200:

```
Ser Ile Pro Arg Phe Ala Ile Val His Pro Ser Pro Cys Pro Pro Leu
1               5                   10                  15
```

-continued

```
Pro Ser Thr Pro Thr Ile Gln Val Glu Thr Leu Arg Arg Thr Leu Gly
             20                  25                  30

Ala Leu Gly Ile Trp Ser Asp Gln Arg Cys Ala Leu Tyr Thr Gly Glu
         35                  40                  45

Asp Pro Ala Pro Gly Trp Gly Ser Leu Trp Val Lys Leu Gly Gly Gly
 50                  55                  60

Ala Val Gly Val Lys Tyr
 65              70
```

(2) INFORMATION FOR SEQ ID NO: 201:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 201:

```
Ile Tyr Glu Phe Phe Ser Phe Glu Lys Lys Lys Lys Lys Lys Lys Lys
 1               5                  10                  15
```

(2) INFORMATION FOR SEQ ID NO: 202:

(i) SEQUENCE CHARACTERISTICS:
        (A) LENGTH: 222 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 202:

```
Gln Arg Cys Val Leu Leu Arg Thr Trp Glu Ala Leu Ala Pro Ala Thr
 1               5                  10                  15

Pro Ala Met Pro Arg Ala Pro Arg Cys Arg Ala Val Arg Ser Leu Leu
             20                  25                  30

Arg Ser His Tyr Arg Glu Val Leu Pro Leu Ala Thr Phe Val Arg Arg
         35                  40                  45

Leu Gly Pro Gln Gly Trp Arg Leu Val Gln Arg Gly Asp Pro Ala Ala
 50                  55                  60

Phe Arg Ala Xaa Val Ala Xaa Cys Xaa Val Cys Val Pro Trp Xaa Xaa
 65                  70                  75                  80

Xaa Xaa Pro Pro Ala Ala Pro Ser Phe Arg Gln Val Ser Cys Leu Xaa
             85                  90                  95

Xaa Leu Val Ala Arg Val Leu Xaa Xaa Leu Cys Xaa Arg Gly Ala Xaa
            100                 105                 110

Asn Val Leu Ala Phe Gly Phe Ala Leu Leu Asp Gly Ala Arg Gly Gly
            115                 120                 125

Pro Pro Glu Ala Phe Thr Thr Ser Val Arg Ser Tyr Leu Pro Asn Thr
130                 135                 140

Val Thr Asp Ala Leu Arg Gly Ser Gly Ala Trp Gly Leu Leu Leu Arg
145                 150                 155                 160

Arg Val Gly Asp Asp Val Leu Val His Leu Leu Ala Arg Cys Ala Xaa
                165                 170                 175

Phe Val Leu Val Xaa Pro Ser Cys Ala Tyr Xaa Val Cys Gly Pro Pro
            180                 185                 190

Leu Tyr Gln Leu Gly Ala Ala Thr Gln Ala Arg Pro Pro His Ala
            195                 200                 205
```

```
Xaa Gly Pro Glu Xaa Val Trp Asp Pro Thr Gly Leu Glu Pro
    210             215                 220
```

(2) INFORMATION FOR SEQ ID NO: 203:

(i) SEQUENCE CHARACTERISTICS:
        (A) LENGTH: 330 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 203:

```
Arg Gln Gly Gly Arg Gly Pro Pro Gly Leu Pro Ala Pro Gly Ala Arg
1               5                   10                  15

Arg Arg Gly Gly Ser Ala Ser Arg Ser Leu Pro Leu Pro Lys Arg Pro
            20                  25                  30

Arg Arg Gly Ala Ala Pro Glu Pro Glu Arg Thr Pro Val Gly Gln Gly
            35                  40                  45

Ser Trp Ala His Pro Gly Arg Thr Pro Gly Pro Ser Asp Arg Gly Phe
    50                  55                  60

Cys Val Val Ser Pro Ala Arg Pro Ala Glu Glu Ala Thr Ser Leu Glu
65                  70                  75                  80

Gly Ala Leu Ser Gly Thr Arg His Ser His Pro Ser Val Gly Arg Gln
                85                  90                  95

His His Ala Gly Pro Pro Ser Thr Ser Arg Pro Pro Arg Pro Gly Thr
                100                 105                 110

Arg Leu Val Pro Arg Cys Thr Pro Arg Pro Ser Thr Ser Ser Thr Pro
            115                 120                 125

Gln Ala Thr Xaa Thr Leu Arg Pro Ser Phe Leu Leu Asn Ile Ser Glu
    130                 135                 140

Ala Gln Pro Asp Trp Arg Ser Gly Gly Ser Trp Arg Xaa Ser Phe Trp
145                 150                 155                 160

Phe Gln Ala Leu Asp Ala Arg Ile Pro Arg Arg Leu Pro Arg Leu Pro
                165                 170                 175

Gln Arg Tyr Trp Gln Met Arg Pro Leu Phe Leu Glu Leu Leu Gly Asn
            180                 185                 190

His Ala Gln Cys Pro Tyr Gly Val Phe Leu Lys Thr His Cys Pro Leu
            195                 200                 205

Arg Ala Ala Val Thr Pro Ala Ala Gly Val Cys Ala Arg Glu Lys Pro
            210                 215                 220

Gln Gly Ser Val Ala Ala Pro Glu Glu Glu His Arg Pro Pro Ser
225                 230                 235                 240

Pro Gly Ala Ala Ala Pro Pro Ala Gln Gln Pro Leu Ala Gly Val Arg
                245                 250                 255

Leu Arg Ala Gly Leu Pro Ala Pro Gly Ala Pro Arg Pro Leu Gly
                260                 265                 270

Leu Gln Ala Gln Arg Thr Pro Leu Pro Gln Glu His Gln Glu Val His
            275                 280                 285

Leu Pro Gly Glu Ala Cys Gln Ala Leu Ala Gly Ala Asp Val Glu
    290                 295                 300

Asp Glu Arg Ala Gly Leu Arg Leu Ala Ala Gln Glu Pro Arg Gly Trp
305                 310                 315                 320

Leu Cys Ser Gly Arg Arg Ala Pro Ser Ala
                325                 330
```

(2) INFORMATION FOR SEQ ID NO: 204:

(i) SEQUENCE CHARACTERISTICS:
        (A) LENGTH: 89 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 204:

```
Gly Asp Pro Gly Gln Val Pro Ala Leu Ala Asp Glu Cys Val Arg Arg
1               5                   10                  15

Arg Ala Ala Gln Val Phe Leu Leu Cys His Gly Asp His Val Ser Lys
            20                  25                  30

Glu Gln Ala Leu Phe Leu Pro Glu Glu Cys Leu Glu Gln Val Ala Lys
        35                  40                  45

His Trp Asn Gln Thr Ala Leu Glu Glu Gly Ala Ala Gly Ala Val
50                  55                  60

Gly Ser Arg Gly Gln Ala Ala Ser Gly Ser Gln Ala Arg Pro Ala Asp
65                  70                  75                  80

Val Gln Thr Pro Leu His Pro Gln Ala
                85
```

(2) INFORMATION FOR SEQ ID NO: 205:

(i) SEQUENCE CHARACTERISTICS:
        (A) LENGTH: 76 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 205:

```
Arg Ala Ala Ala Asp Cys Glu His Gly Leu Arg Gly Ser Gln Asn
1               5                   10                  15

Val Pro Gln Arg Lys Glu Gly Arg Ala Ser His Leu Glu Gly Glu Gly
            20                  25                  30

Thr Val Gln Arg Ala Gln Leu Arg Ala Gly Ala Ala Pro Arg Pro Pro
        35                  40                  45

Gly Arg Leu Cys Ala Gly Pro Gly Arg Tyr Pro Gln Gly Leu Ala His
50                  55                  60

Leu Arg Ala Ala Cys Ala Gly Pro Gly Pro Ala Ala
65                  70                  75
```

(2) INFORMATION FOR SEQ ID NO: 206:

(i) SEQUENCE CHARACTERISTICS:
        (A) LENGTH: 94 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 206:

```
Ala Val Leu Cys Gln Gly Gly Cys Asp Gly Arg Val Arg His His Pro
1               5                   10                  15

Pro Gly Gln Ala His Gly Gly His Arg Gln His His Gln Thr Pro Glu
            20                  25                  30

His Val Leu Arg Ala Ser Val Cys Arg Gly Pro Glu Gly Arg Pro Trp
        35                  40                  45
```

```
Ala Arg Pro Gln Gly Leu Gln Glu Pro Arg Leu Tyr Leu Asp Arg Pro
 50                  55                  60

Pro Ala Val His Ala Thr Val Arg Gly Ser Pro Ala Gly Xaa Gln Pro
 65                  70                  75                  80

Ala Glu Gly Cys Arg Arg His Arg Ala Glu Leu Leu Pro Glu
                 85                  90
```

(2) INFORMATION FOR SEQ ID NO: 207:

(i) SEQUENCE CHARACTERISTICS:
        (A) LENGTH: 68 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 207:

```
Gly Gln Gln Trp Pro Leu Arg Arg Leu Pro Thr Leu His Val Pro Pro
 1               5                  10                  15

Arg Arg Ala His Gln Gly Gln Val Leu Arg Pro Val Pro Gly Asp Pro
                 20                  25                  30

Ala Gly Leu His Pro Leu His Ala Ala Leu Gln Pro Val Leu Arg Arg
                 35                  40                  45

His Gly Glu Gln Ala Val Cys Gly Asp Ser Ala Gly Arg Ala Ala Pro
 50                  55                  60

Ala Phe Gly Gly
 65
```

(2) INFORMATION FOR SEQ ID NO: 208:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 208:

```
Phe Leu Val Gly Asp Thr Ser Pro His Pro Arg Glu Asn Leu Pro Gln
 1               5                  10                  15

Asp Pro Gly Pro Arg Cys Pro
                 20
```

(2) INFORMATION FOR SEQ ID NO: 209:

(i) SEQUENCE CHARACTERISTICS:
        (A) LENGTH: 144 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 209:

```
Val Trp Leu Arg Gly Glu Leu Ala Glu Asp Ser Gly Glu Leu Pro Cys
 1               5                  10                  15

Arg Arg Arg Gly Pro Gly Trp His Gly Phe Cys Ser Asp Ala Gly Pro
                 20                  25                  30

Arg Pro Ile Pro Leu Val Arg Pro Ala Ala Gly Tyr Pro Asp Pro Gly
                 35                  40                  45
```

```
Gly Ala Glu Arg Leu Leu Gln Leu Cys Pro Asp Leu His Gln Ser Gln
        50                  55                  60

Ser His Leu Gln Pro Arg Leu Gln Gly Trp Glu His Ala Ser Gln
 65                  70                  75                  80

Thr Leu Trp Gly Leu Ala Ala Glu Val Ser Gln Pro Val Ser Gly Phe
                    85                  90                  95

Ala Gly Glu Gln Pro Pro Asp Gly Val His Gln His Leu Gln Asp Pro
                100                 105                 110

Pro Ala Ala Gly Val Gln Val Ser Arg Met Cys Ala Ala Pro Ile
                115                 120                 125

Ser Ser Ala Ser Leu Glu Glu Pro His Ile Phe Pro Ala Arg His Leu
        130                 135                 140
```

(2) INFORMATION FOR SEQ ID NO: 210:

(i) SEQUENCE CHARACTERISTICS:
        (A) LENGTH: 137 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 210:

```
His Gly Leu Pro Leu Leu His Pro Glu Ser Gln Glu Arg Arg Asp
 1               5                  10                  15

Val Ala Gly Gly Gln Gly Arg Arg Pro Ser Ala Leu Arg Gly Arg
                20                  25                  30

Ala Val Ala Val Pro Pro Ser Ile Pro Ala Gln Ala Asp Ser Thr Pro
        35                  40                  45

Cys His Leu Arg Ala Thr Pro Gly Val Thr Gln Asp Ser Pro Asp Ala
        50                  55                  60

Ala Glu Ser Glu Ala Pro Gly Asp Asp Ala Asp Cys Pro Gly Gly Arg
 65                  70                  75                  80

Ser Gln Pro Gly Thr Ala Leu Arg Leu Gln Asp His Pro Gly Leu Met
                    85                  90                  95

Ala Thr Arg Pro Gln Pro Gly Arg Glu Gln Thr Pro Ala Ala Leu Ser
                100                 105                 110

Arg Arg Ala Leu Arg Pro Arg Glu Gly Gly Ala Ala His Thr Gln Ala
            115                 120                 125

Arg Thr Ala Gly Ser Leu Arg Pro Glu
        130                 135
```

(2) INFORMATION FOR SEQ ID NO: 211:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 211:

```
Val Phe Gly Arg Gly Leu His Val Arg Leu Lys Ala Glu Cys Pro Ala
 1               5                  10                  15

Glu Ala
```

(2) INFORMATION FOR SEQ ID NO: 212:

(i) SEQUENCE CHARACTERISTICS:
        (A) LENGTH: 71 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 212:

Ala Ser Val Gln Pro Arg Ala Glu Cys Pro Ala His Leu Pro Ser Ser
1               5                   10                  15

Leu Pro His Arg Leu Ala Leu Gly Ser Thr Pro Gly Pro Ala Phe Pro
                20                  25                  30

His Gln Glu Pro Gly Phe His Ser Pro His Arg Asn Ser Pro Ser Pro
            35                  40                  45

Asp Ser Pro Leu Phe Thr Pro Arg Pro Ala Leu Leu Cys Leu Pro Pro
        50                  55                  60

Pro Pro Ser Arg Trp Arg Pro
65              70

(2) INFORMATION FOR SEQ ID NO: 213:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 213:

Glu Gly Pro Trp Glu Leu Trp Glu Phe Gly Val Thr Lys Gly Val Pro
1               5                   10                  15

Cys Thr Gln Ala Arg Thr Leu His Leu Asp Gly Gly Pro Cys Gly Ser
                20                  25                  30

Asn Trp Gly Glu Val Leu Trp Glu
            35                  40

(2) INFORMATION FOR SEQ ID NO: 214:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 214:

Asn Thr Glu Tyr Met Ser Phe Ser Val Leu Lys Lys Lys Lys Lys Lys
1               5                   10                  15

Lys Lys (2) INFORMATION FOR SEQ ID NO: 215:

(i) SEQUENCE CHARACTERISTICS:
        (A) LENGTH: 94 amino acids
        (B) TYPE: amino acid
        (C) STRANDEDNESS: <Unknown>
        (D) TOPOLOGY: linear (ii) MOLECULE TYPE: peptide -continued (xi) SEQUENCE DESCRIPTION: SEQ ID NO: 215:

Ser Ala Ala Ser Cys Cys Ala Arg Gly Lys Pro Trp Pro Arg Pro Pro
1               5                   10                  15

Pro Arg Cys Arg Ala Leu Pro Ala Ala Glu Pro Cys Ala Pro Cys Cys
            20                  25                  30

Ala Ala Thr Thr Ala Arg Cys Cys Arg Trp Pro Arg Ser Cys Gly Ala
        35                  40                  45

Trp Gly Pro Arg Ala Gly Gly Trp Cys Ser Ala Gly Thr Arg Arg Leu
50                  55                  60

Ser Ala Arg Trp Trp Pro Xaa Ala Trp Cys Ala Cys Pro Gly Xaa Xaa
65                  70                  75                  80

Gly Xaa Pro Pro Pro Pro Pro Ser Ala Arg Cys Pro Ala
            85                  90

(2) INFORMATION FOR SEQ ID NO: 216:

(i) SEQUENCE CHARACTERISTICS:
        (A) LENGTH: 49 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 216:

Xaa Xaa Trp Trp Pro Glu Cys Cys Xaa Xaa Cys Ala Xaa Ala Ala Arg
1               5                   10                  15

Xaa Thr Cys Trp Pro Ser Ala Ser Arg Cys Trp Thr Gly Pro Ala Gly
            20                  25                  30

Ala Pro Pro Arg Pro Ser Pro Pro Ala Cys Ala Ala Thr Cys Pro Thr
        35                  40                  45

Arg (2) INFORMATION FOR SEQ ID NO: 217:

(i) SEQUENCE CHARACTERISTICS:
        (A) LENGTH: 1003 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 217:

Pro Thr His Cys Gly Gly Ala Gly Arg Gly Cys Cys Cys Ala Ala
1               5                   10                  15

Trp Ala Thr Thr Cys Trp Phe Thr Cys Trp His Ala Ala Arg Xaa Leu
            20                  25                  30

Cys Trp Trp Xaa Pro Ala Ala Pro Thr Xaa Cys Ala Gly Arg Arg Cys
        35                  40                  45

Thr Ser Ser Ala Leu Xaa Leu Arg Pro Gly Pro Arg His Thr Leu Xaa
50                  55                  60

Asp Pro Xaa Ala Ser Gly Ile Gln Arg Ala Trp Asn His Ser Val Arg
65                  70                  75                  80

Glu Ala Gly Val Pro Leu Gly Cys Gln Pro Arg Val Arg Gly Ala
            85                  90                  95

Gly Ala Val Pro Ala Glu Val Cys Arg Cys Pro Arg Gly Pro Gly Val
            100                 105                 110

-continued

```
Ala Leu Pro Leu Ser Arg Ser Gly Arg Pro Leu Gly Arg Gly Pro Gly
            115                 120                 125

Pro Thr Arg Ala Gly Arg Leu Asp Arg Val Thr Val Ser Val Trp
130                 135                 140

Cys His Leu Pro Asp Pro Lys Lys Pro Pro Leu Trp Arg Val Arg
145                 150                 155                 160

Ser Leu Ala Arg Ala Thr Pro Thr His Pro Trp Ala Ala Ser Thr Thr
                165                 170                 175

Arg Ala Pro His Pro His Arg Gly His His Val Leu Gly His Ala Leu
            180                 185                 190

Ser Pro Gly Val Arg Arg Asp Gln Ala Leu Pro Leu Leu Arg Arg
            195                 200                 205

Gln Xaa His Cys Xaa Pro Pro Ser Tyr Ser Ile Tyr Leu Arg Pro Ser
    210                 215                 220

Leu Thr Gly Val Arg Glu Val Arg Gly Asp Xaa Leu Ser Gly Ser Arg
225                 230                 235                 240

Pro Trp Met Pro Gly Phe Pro Ala Gly Cys Pro Ala Cys Pro Ser Xaa
                245                 250                 255

Thr Gly Lys Cys Gly Pro Cys Phe Trp Ser Cys Leu Gly Thr Thr Arg
                260                 265                 270

Ser Ala Pro Thr Gly Cys Ser Ser Arg Thr Ala Arg Cys Glu Leu
            275                 280                 285

Arg Ser Pro Gln Gln Pro Val Ser Val Pro Gly Arg Ser Pro Arg Ala
290                 295                 300

Leu Trp Arg Pro Pro Arg Arg Asn Thr Asp Pro Arg Arg Leu Val
305                 310                 315                 320

Gln Leu Leu Arg Gln His Ser Ser Pro Trp Gln Val Tyr Gly Phe Val
                325                 330                 335

Arg Ala Cys Leu Arg Arg Leu Val Pro Pro Gly Leu Trp Gly Ser Arg
                340                 345                 350

His Asn Glu Arg Arg Phe Leu Arg Asn Thr Lys Lys Phe Ile Ser Leu
            355                 360                 365

Gly Lys His Ala Lys Leu Ser Leu Gln Glu Leu Thr Trp Lys Met Ser
            370                 375                 380

Val Arg Asp Cys Ala Trp Leu Arg Arg Ser Pro Gly Val Gly Cys Val
385                 390                 395                 400

Pro Ala Ala Glu His Arg Leu Arg Glu Glu Ile Leu Ala Lys Phe Leu
                405                 410                 415

His Trp Leu Met Ser Val Tyr Val Val Glu Leu Leu Arg Ser Phe Phe
                420                 425                 430

Tyr Val Thr Glu Thr Thr Phe Gln Lys Asn Arg Leu Phe Phe Tyr Arg
            435                 440                 445

Lys Ser Val Trp Ser Lys Leu Gln Ser Ile Gly Ile Arg Gln His Leu
            450                 455                 460

Lys Arg Val Gln Leu Arg Glu Leu Ser Glu Ala Glu Val Arg Gln His
465                 470                 475                 480

Arg Glu Ala Arg Pro Ala Leu Leu Thr Ser Arg Leu Arg Phe Ile Pro
                485                 490                 495

Lys Pro Asp Gly Leu Arg Pro Ile Val Asn Met Asp Tyr Val Val Gly
            500                 505                 510

Ala Arg Thr Phe Arg Arg Glu Lys Arg Ala Glu Arg Leu Thr Ser Arg
            515                 520                 525
```

-continued

```
Val Lys Ala Leu Phe Ser Val Leu Asn Tyr Glu Arg Ala Arg Pro
    530                 535                 540

Gly Leu Leu Gly Ala Ser Val Leu Gly Leu Asp Asp Ile His Arg Ala
545                 550                 555                 560

Trp Arg Thr Phe Val Leu Arg Val Arg Ala Gln Asp Pro Pro Glu
                565                 570                 575

Leu Tyr Phe Val Lys Val Asp Val Thr Gly Ala Tyr Asp Thr Ile Pro
                580                 585                 590

Gln Asp Arg Leu Thr Glu Val Ile Ala Ser Ile Ile Lys Pro Gln Asn
                595                 600                 605

Thr Tyr Cys Val Arg Arg Tyr Ala Val Val Gln Lys Ala Ala His Gly
    610                 615                 620

His Val Arg Lys Ala Phe Lys Ser His Val Ser Thr Leu Thr Asp Leu
625                 630                 635                 640

Gln Pro Tyr Met Arg Gln Phe Val Ala His Leu Gln Xaa Asn Ser Pro
                645                 650                 655

Leu Arg Asp Ala Val Val Ile Glu Gln Ser Ser Ser Leu Asn Glu Ala
                660                 665                 670

Ser Ser Gly Leu Phe Asp Val Phe Leu Arg Phe Met Cys His His Ala
    675                 680                 685

Val Arg Ile Arg Gly Lys Ser Tyr Val Gln Cys Gln Gly Ile Pro Gln
690                 695                 700

Gly Ser Ile Leu Ser Thr Leu Leu Cys Ser Leu Cys Tyr Gly Asp Met
705                 710                 715                 720

Glu Asn Lys Leu Phe Ala Gly Ile Arg Arg Asp Gly Leu Leu Leu Arg
                725                 730                 735

Leu Val Asp Asp Phe Leu Leu Val Thr Pro His Leu Thr His Ala Lys
                740                 745                 750

Thr Phe Leu Arg Thr Leu Val Arg Gly Val Pro Glu Tyr Gly Cys Val
    755                 760                 765

Val Asn Leu Arg Lys Thr Val Val Asn Phe Pro Val Glu Asp Glu Ala
770                 775                 780

Leu Gly Gly Thr Ala Phe Val Gln Met Pro Ala His Gly Leu Phe Pro
785                 790                 795                 800

Trp Cys Gly Leu Leu Leu Asp Thr Arg Thr Leu Glu Val Gln Ser Asp
                805                 810                 815

Tyr Ser Ser Tyr Ala Arg Thr Ser Ile Arg Ala Ser Leu Thr Phe Asn
                820                 825                 830

Arg Gly Phe Lys Ala Gly Arg Asn Met Arg Arg Lys Leu Phe Gly Val
    835                 840                 845

Leu Arg Leu Lys Cys His Ser Leu Phe Leu Asp Leu Gln Val Asn Ser
850                 855                 860

Leu Gln Thr Val Cys Thr Asn Ile Tyr Lys Ile Leu Leu Leu Gln Ala
865                 870                 875                 880

Tyr Arg Phe His Ala Cys Val Leu Gln Leu Pro Phe His Gln Gln Val
                885                 890                 895

Trp Lys Asn Pro Thr Phe Phe Leu Arg Val Ile Ser Asp Thr Ala Ser
                900                 905                 910

Leu Cys Tyr Ser Ile Leu Lys Ala Lys Asn Ala Gly Met Ser Leu Gly
    915                 920                 925

Ala Lys Gly Ala Ala Gly Pro Leu Pro Ser Glu Ala Val Gln Trp Leu
930                 935                 940
```

```
Cys His Gln Ala Phe Leu Leu Lys Leu Thr Arg His Arg Val Thr Tyr
945                 950                 955                 960

Val Pro Leu Leu Gly Ser Leu Arg Thr Ala Gln Thr Gln Leu Ser Arg
                965                 970                 975

Lys Leu Pro Gly Thr Thr Leu Thr Ala Leu Glu Ala Ala Asn Pro
                980                 985                 990

Ala Leu Pro Ser Asp Phe Lys Thr Ile Leu Asp
            995                 1000
```

(2) INFORMATION FOR SEQ ID NO: 218:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 218:

```
Trp Pro Pro Ala His Ser Gln Ala Glu Ser Arg His Gln Gln Pro Cys
1               5                   10                  15

His Ala Gly Leu Tyr Val Pro Gly Arg Glu Gly Arg Pro Thr Pro Arg
                20                  25                  30

Pro Ala Pro Leu Gly Val
            35
```

(2) INFORMATION FOR SEQ ID NO: 219:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 219:

```
Gly Leu Ser Glu Cys Leu Ala Glu Ala Cys Met Ser Gly
1               5                   10
```

(2) INFORMATION FOR SEQ ID NO: 220:

(i) SEQUENCE CHARACTERISTICS:
        (A) LENGTH: 91 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 220:

```
Arg Leu Ser Val Arg Leu Arg Pro Glu Arg Val Ser Ser Gln Gly Leu
1               5                   10                  15

Ser Val Gln His Thr Cys Arg Leu His Phe Pro Thr Gly Trp Arg Ser
                20                  25                  30

Ala Pro Pro Gln Gly Gln Leu Phe Leu Thr Arg Ser Pro Ala Ser Thr
                35                  40                  45

Pro His Ile Gly Ile Val His Pro Gln Ile Arg His Cys Ser Pro Leu
50                  55                  60
```

```
Ala Leu Pro Ser Phe Ala Phe His Pro His Pro Gly Gly Asp Pro
 65                  70                  75                  80

Glu Lys Asp Pro Gly Ser Ser Gly Asn Leu Glu
                 85                  90
```

(2) INFORMATION FOR SEQ ID NO: 221:

(i) SEQUENCE CHARACTERISTICS:
        (A) LENGTH: 34 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 221:

```
Pro Lys Val Cys Pro Val His Arg Arg Gly Pro Cys Thr Trp Met Gly
 1               5                  10                  15

Val Pro Val Gly Gln Ile Gly Gly Arg Cys Cys Gly Ser Lys Ile Leu
                 20                  25                  30

Asn Ile
```

(2) INFORMATION FOR SEQ ID NO: 222:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 222:

```
Val Phe Gln Phe
 1
```

(2) INFORMATION FOR SEQ ID NO: 223:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 223:

```
Lys Lys Lys Lys Lys Lys Lys Lys
 1               5
```

(2) INFORMATION FOR SEQ ID NO: 224:

(i) SEQUENCE CHARACTERISTICS:
        (A) LENGTH: 4015 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 56..3454
        (D) OTHER INFORMATION: /product= "hTRT" /note= "human
            telomerase reverse transcriptase (hTRT) catalytic protein
            component"

(xi) SEQUENCE DESCRIPTION: SEQ ID NO: 224:

```
GCAGCGCTGC GTCCTGCTGC GCACGTGGGA AGCCCTGGCC CCGGCCACCC CCGCG ATG        58
                                                              Met
                                                                1

CCG CGC GCT CCC CGC TGC CGA GCC GTG CGC TCC CTG CTG CGC AGC CAC        106
Pro Arg Ala Pro Arg Cys Arg Ala Val Arg Ser Leu Leu Arg Ser His
            5               10              15

TAC CGC GAG GTG CTG CCG CTG GCC ACG TTC GTG CGG CGC CTG GGG CCC        154
Tyr Arg Glu Val Leu Pro Leu Ala Thr Phe Val Arg Arg Leu Gly Pro
        20              25              30

CAG GGC TGG CGG CTG GTG CAG CGC GGG GAC CCG GCG GCT TTC CGC GCG        202
Gln Gly Trp Arg Leu Val Gln Arg Gly Asp Pro Ala Ala Phe Arg Ala
    35              40              45

CTG GTG GCC CAG TGC CTG GTG TGC GTG CCC TGG GAC GCA CGG CCG CCC        250
Leu Val Ala Gln Cys Leu Val Cys Val Pro Trp Asp Ala Arg Pro Pro
50              55              60              65

CCC GCC GCC CCC TCC TTC CGC CAG GTG TCC TGC CTG AAG GAG CTG GTG        298
Pro Ala Ala Pro Ser Phe Arg Gln Val Ser Cys Leu Lys Glu Leu Val
                70              75              80

GCC CGA GTG CTG CAG AGG CTG TGC GAG CGC GGC GCG AAG AAC GTG CTG        346
Ala Arg Val Leu Gln Arg Leu Cys Glu Arg Gly Ala Lys Asn Val Leu
            85              90              95

GCC TTC GGC TTC GCG CTG CTG GAC GGG GCC CGC GGG GGC CCC CCC GAG        394
Ala Phe Gly Phe Ala Leu Leu Asp Gly Ala Arg Gly Gly Pro Pro Glu
        100             105             110

GCC TTC ACC ACC AGC GTG CGC AGC TAC CTG CCC AAC ACG GTG ACC GAC        442
Ala Phe Thr Thr Ser Val Arg Ser Tyr Leu Pro Asn Thr Val Thr Asp
    115             120             125

GCA CTG CGG GGG AGC GGG GCG TGG GGG CTG CTG CTG CGC CGC GTG GGC        490
Ala Leu Arg Gly Ser Gly Ala Trp Gly Leu Leu Leu Arg Arg Val Gly
130             135             140             145

GAC GAC GTG CTG GTT CAC CTG CTG GCA CGC TGC GCG CTC TTT GTG CTG        538
Asp Asp Val Leu Val His Leu Leu Ala Arg Cys Ala Leu Phe Val Leu
                150             155             160

GTG GCT CCC AGC TGC GCC TAC CAG GTG TGC GGG CCG CCG CTG TAC CAG        586
Val Ala Pro Ser Cys Ala Tyr Gln Val Cys Gly Pro Pro Leu Tyr Gln
            165             170             175

CTC GGC GCT GCC ACT CAG GCC CGG CCC CCG CCA CAC GCT AGT GGA CCC        634
Leu Gly Ala Ala Thr Gln Ala Arg Pro Pro Pro His Ala Ser Gly Pro
        180             185             190

CGA AGG CGT CTG GGA TGC GAA CGG GCC TGG AAC CAT AGC GTC AGG GAG        682
Arg Arg Arg Leu Gly Cys Glu Arg Ala Trp Asn His Ser Val Arg Glu
    195             200             205

GCC GGG GTC CCC CTG GGC CTG CCA GCC CCG GGT GCG AGG AGG CGC GGG        730
Ala Gly Val Pro Leu Gly Leu Pro Ala Pro Gly Ala Arg Arg Arg Gly
210             215             220             225

GGC AGT GCC AGC CGA AGT CTG CCG TTG CCC AAG AGG CCC AGG CGT GGC        778
Gly Ser Ala Ser Arg Ser Leu Pro Leu Pro Lys Arg Pro Arg Arg Gly
                230             235             240

GCT GCC CCT GAG CCG GAG CGG ACG CCC GTT GGG CAG GGG TCC TGG GCC        826
Ala Ala Pro Glu Pro Glu Arg Thr Pro Val Gly Gln Gly Ser Trp Ala
            245             250             255

CAC CCG GGC AGG ACG CGT GGA CCG AGT GAC CGT GGT TTC TGT GTG GTG        874
His Pro Gly Arg Thr Arg Gly Pro Ser Asp Arg Gly Phe Cys Val Val
        260             265             270

TCA CCT GCC AGA CCC GCC GAA GAA GCC ACC TCT TTG GAG GGT GCG CTC        922
Ser Pro Ala Arg Pro Ala Glu Glu Ala Thr Ser Leu Glu Gly Ala Leu
    275             280             285
```

-continued

```
TCT GGC ACG CGC CAC TCC CAC CCA TCC GTG GGC CGC CAG CAC CAC GCG     970
Ser Gly Thr Arg His Ser His Pro Ser Val Gly Arg Gln His His Ala
290                 295                 300                 305

GGC CCC CCA TCC ACA TCG CGG CCA CCA CGT CCC TGG GAC ACG CCT TGT    1018
Gly Pro Pro Ser Thr Ser Arg Pro Pro Arg Pro Trp Asp Thr Pro Cys
                310                 315                 320

CCC CCG GTG TAC GCC GAG ACC AAG CAC TTC CTC TAC TCC TCA GGC GAC    1066
Pro Pro Val Tyr Ala Glu Thr Lys His Phe Leu Tyr Ser Ser Gly Asp
            325                 330                 335

AAG GAG CAG CTG CGG CCC TCC TTC CTA CTC AGC TCT CTG AGG CCC AGC    1114
Lys Glu Gln Leu Arg Pro Ser Phe Leu Leu Ser Ser Leu Arg Pro Ser
        340                 345                 350

CTG ACT GGC GCT CGG AGG CTC GTG GAG ACC ATC TTT CTG GGT TCC AGG    1162
Leu Thr Gly Ala Arg Arg Leu Val Glu Thr Ile Phe Leu Gly Ser Arg
    355                 360                 365

CCC TGG ATG CCA GGG ACT CCC CGC AGG TTG CCC CGC CTG CCC CAG CGC    1210
Pro Trp Met Pro Gly Thr Pro Arg Arg Leu Pro Arg Leu Pro Gln Arg
370                 375                 380                 385

TAC TGG CAA ATG CGG CCC CTG TTT CTG GAG CTG CTT GGG AAC CAC GCG    1258
Tyr Trp Gln Met Arg Pro Leu Phe Leu Glu Leu Leu Gly Asn His Ala
                390                 395                 400

CAG TGC CCC TAC GGG GTG CTC CTC AAG ACG CAC TGC CCG CTG CGA GCT    1306
Gln Cys Pro Tyr Gly Val Leu Leu Lys Thr His Cys Pro Leu Arg Ala
                405                 410                 415

GCG GTC ACC CCA GCA GCC GGT GTC TGT GCC CGG GAG AAG CCC CAG GGC    1354
Ala Val Thr Pro Ala Ala Gly Val Cys Ala Arg Glu Lys Pro Gln Gly
            420                 425                 430

TCT GTG GCG GCC CCC GAG GAG GAG GAC ACA GAC CCC CGT CGC CTG GTG    1402
Ser Val Ala Ala Pro Glu Glu Glu Asp Thr Asp Pro Arg Arg Leu Val
        435                 440                 445

CAG CTG CTC CGC CAG CAC AGC AGC CCC TGG CAG GTG TAC GGC TTC GTG    1450
Gln Leu Leu Arg Gln His Ser Ser Pro Trp Gln Val Tyr Gly Phe Val
450                 455                 460                 465

CGG GCC TGC CTG CGC CGG CTG GTG CCC CCA GGC CTC TGG GGC TCC AGG    1498
Arg Ala Cys Leu Arg Arg Leu Val Pro Pro Gly Leu Trp Gly Ser Arg
                470                 475                 480

CAC AAC GAA CGC CGC TTC CTC AGG AAC ACC AAG AAG TTC ATC TCC CTG    1546
His Asn Glu Arg Arg Phe Leu Arg Asn Thr Lys Lys Phe Ile Ser Leu
                485                 490                 495

GGG AAG CAT GCC AAG CTC TCG CTG CAG GAG CTG ACG TGG AAG ATG AGC    1594
Gly Lys His Ala Lys Leu Ser Leu Gln Glu Leu Thr Trp Lys Met Ser
            500                 505                 510

GTG CGG GAC TGC GCT TGG CTG CGC AGG AGC CCA GGG GTT GGC TGT GTT    1642
Val Arg Asp Cys Ala Trp Leu Arg Arg Ser Pro Gly Val Gly Cys Val
        515                 520                 525

CCG GCC GCA GAG CAC CGT CTG CGT GAG GAG ATC CTG GCC AAG TTC CTG    1690
Pro Ala Ala Glu His Arg Leu Arg Glu Glu Ile Leu Ala Lys Phe Leu
530                 535                 540                 545

CAC TGG CTG ATG AGT GTG TAC GTC GTC GAG CTG CTC AGG TCT TTC TTT    1738
His Trp Leu Met Ser Val Tyr Val Val Glu Leu Leu Arg Ser Phe Phe
                550                 555                 560

TAT GTC ACG GAG ACC ACG TTT CAA AAG AAC AGG CTC TTT TTC TAC CGG    1786
Tyr Val Thr Glu Thr Thr Phe Gln Lys Asn Arg Leu Phe Phe Tyr Arg
            565                 570                 575

AAG AGT GTC TGG AGC AAG TTG CAA AGC ATT GGA ATC AGA CAG CAC TTG    1834
Lys Ser Val Trp Ser Lys Leu Gln Ser Ile Gly Ile Arg Gln His Leu
        580                 585                 590

AAG AGG GTG CAG CTG CGG GAG CTG TCG GAA GCA GAG GTC AGG CAG CAT    1882
Lys Arg Val Gln Leu Arg Glu Leu Ser Glu Ala Glu Val Arg Gln His
    595                 600                 605
```

```
CGG GAA GCC AGG CCC GCC CTG CTG ACG TCC AGA CTC CGC TTC ATC CCC       1930
Arg Glu Ala Arg Pro Ala Leu Leu Thr Ser Arg Leu Arg Phe Ile Pro
610                 615                 620                 625

AAG CCT GAC GGG CTG CGG CCG ATT GTG AAC ATG GAC TAC GTC GTG GGA       1978
Lys Pro Asp Gly Leu Arg Pro Ile Val Asn Met Asp Tyr Val Val Gly
                630                 635                 640

GCC AGA ACG TTC CGC AGA GAA AAG AGG GCC GAG CGT CTC ACC TCG AGG       2026
Ala Arg Thr Phe Arg Arg Glu Lys Arg Ala Glu Arg Leu Thr Ser Arg
            645                 650                 655

GTG AAG GCA CTG TTC AGC GTG CTC AAC TAC GAG CGG GCG CGG CGC CCC       2074
Val Lys Ala Leu Phe Ser Val Leu Asn Tyr Glu Arg Ala Arg Arg Pro
    660                 665                 670

GGC CTC CTG GGC GCC TCT GTG CTG GGC CTG GAC GAT ATC CAC AGG GCC       2122
Gly Leu Leu Gly Ala Ser Val Leu Gly Leu Asp Asp Ile His Arg Ala
675                 680                 685

TGG CGC ACC TTC GTG CTG CGT GTG CGG GCC CAG GAC CCG CCG CCT GAG       2170
Trp Arg Thr Phe Val Leu Arg Val Arg Ala Gln Asp Pro Pro Pro Glu
690                 695                 700                 705

CTG TAC TTT GTC AAG GTG GAT GTG ACG GGC GCG TAC GAC ACC ATC CCC       2218
Leu Tyr Phe Val Lys Val Asp Val Thr Gly Ala Tyr Asp Thr Ile Pro
                710                 715                 720

CAG GAC AGG CTC ACG GAG GTC ATC GCC AGC ATC ATC AAA CCC CAG AAC       2266
Gln Asp Arg Leu Thr Glu Val Ile Ala Ser Ile Ile Lys Pro Gln Asn
            725                 730                 735

ACG TAC TGC GTG CGT CGG TAT GCC GTG GTC CAG AAG GCC GCC CAT GGG       2314
Thr Tyr Cys Val Arg Arg Tyr Ala Val Val Gln Lys Ala Ala His Gly
        740                 745                 750

CAC GTC CGC AAG GCC TTC AAG AGC CAC GTC TCT ACC TTG ACA GAC CTC       2362
His Val Arg Lys Ala Phe Lys Ser His Val Ser Thr Leu Thr Asp Leu
    755                 760                 765

CAG CCG TAC ATG CGA CAG TTC GTG GCT CAC CTG CAG GAG ACC AGC CCG       2410
Gln Pro Tyr Met Arg Gln Phe Val Ala His Leu Gln Glu Thr Ser Pro
770                 775                 780                 785

CTG AGG GAT GCC GTC GTC ATC GAG CAG AGC TCC TCC CTG AAT GAG GCC       2458
Leu Arg Asp Ala Val Val Ile Glu Gln Ser Ser Ser Leu Asn Glu Ala
                790                 795                 800

AGC AGT GGC CTC TTC GAC GTC TTC CTA CGC TTC ATG TGC CAC CAC GCC       2506
Ser Ser Gly Leu Phe Asp Val Phe Leu Arg Phe Met Cys His His Ala
            805                 810                 815

GTG CGC ATC AGG GGC AAG TCC TAC GTC CAG TGC CAG GGG ATC CCG CAG       2554
Val Arg Ile Arg Gly Lys Ser Tyr Val Gln Cys Gln Gly Ile Pro Gln
        820                 825                 830

GGC TCC ATC CTC TCC ACG CTG CTC TGC AGC CTG TGC TAC GGC GAC ATG       2602
Gly Ser Ile Leu Ser Thr Leu Leu Cys Ser Leu Cys Tyr Gly Asp Met
    835                 840                 845

GAG AAC AAG CTG TTT GCG GGG ATT CGG CGG GAC GGG CTG CTC CTG CGT       2650
Glu Asn Lys Leu Phe Ala Gly Ile Arg Arg Asp Gly Leu Leu Leu Arg
850                 855                 860                 865

TTG GTG GAT GAT TTC TTG TTG GTG ACA CCT CAC CTC ACC CAC GCG AAA       2698
Leu Val Asp Asp Phe Leu Leu Val Thr Pro His Leu Thr His Ala Lys
                870                 875                 880

ACC TTC CTC AGG ACC CTG GTC CGA GGT GTC CCT GAG TAT GGC TGC GTG       2746
Thr Phe Leu Arg Thr Leu Val Arg Gly Val Pro Glu Tyr Gly Cys Val
            885                 890                 895

GTG AAC TTG CGG AAG ACA GTG GTG AAC TTC CCT GTA GAA GAC GAG GCC       2794
Val Asn Leu Arg Lys Thr Val Val Asn Phe Pro Val Glu Asp Glu Ala
        900                 905                 910

CTG GGT GGC ACG GCT TTT GTT CAG ATG CCG GCC CAC GGC CTA TTC CCC       2842
Leu Gly Gly Thr Ala Phe Val Gln Met Pro Ala His Gly Leu Phe Pro
    915                 920                 925
```

```
TGG TGC GGC CTG CTG CTG GAT ACC CGG ACC CTG GAG GTG CAG AGC GAC      2890
Trp Cys Gly Leu Leu Leu Asp Thr Arg Thr Leu Glu Val Gln Ser Asp
930                 935                 940                 945

TAC TCC AGC TAT GCC CGG ACC TCC ATC AGA GCC AGT CTC ACC TTC AAC      2938
Tyr Ser Ser Tyr Ala Arg Thr Ser Ile Arg Ala Ser Leu Thr Phe Asn
                950                 955                 960

CGC GGC TTC AAG GCT GGG AGG AAC ATG CGT CGC AAA CTC TTT GGG GTC      2986
Arg Gly Phe Lys Ala Gly Arg Asn Met Arg Arg Lys Leu Phe Gly Val
            965                 970                 975

TTG CGG CTG AAG TGT CAC AGC CTG TTT CTG GAT TTG CAG GTG AAC AGC      3034
Leu Arg Leu Lys Cys His Ser Leu Phe Leu Asp Leu Gln Val Asn Ser
        980                 985                 990

CTC CAG ACG GTG TGC ACC AAC ATC TAC AAG ATC CTC CTG CTG CAG GCG      3082
Leu Gln Thr Val Cys Thr Asn Ile Tyr Lys Ile Leu Leu Leu Gln Ala
    995                 1000                1005

TAC AGG TTT CAC GCA TGT GTG CTG CAG CTC CCA TTT CAT CAG CAA GTT      3130
Tyr Arg Phe His Ala Cys Val Leu Gln Leu Pro Phe His Gln Gln Val
1010                1015                1020                1025

TGG AAG AAC CCC ACA TTT TTC CTG CGC GTC ATC TCT GAC ACG GCC TCC      3178
Trp Lys Asn Pro Thr Phe Phe Leu Arg Val Ile Ser Asp Thr Ala Ser
                1030                1035                1040

CTC TGC TAC TCC ATC CTG AAA GCC AAG AAC GCA GGG ATG TCG CTG GGG      3226
Leu Cys Tyr Ser Ile Leu Lys Ala Lys Asn Ala Gly Met Ser Leu Gly
            1045                1050                1055

GCC AAG GGC GCC GCC GGC CCT CTG CCC TCC GAG GCC GTG CAG TGG CTG      3274
Ala Lys Gly Ala Ala Gly Pro Leu Pro Ser Glu Ala Val Gln Trp Leu
        1060                1065                1070

TGC CAC CAA GCA TTC CTG CTC AAG CTG ACT CGA CAC CGT GTC ACC TAC      3322
Cys His Gln Ala Phe Leu Leu Lys Leu Thr Arg His Arg Val Thr Tyr
    1075                1080                1085

GTG CCA CTC CTG GGG TCA CTC AGG ACA GCC CAG ACG CAG CTG AGT CGG      3370
Val Pro Leu Leu Gly Ser Leu Arg Thr Ala Gln Thr Gln Leu Ser Arg
1090                1095                1100                1105

AAG CTC CCG GGG ACG ACG CTG ACT GCC CTG GAG GCC GCA GCC AAC CCG      3418
Lys Leu Pro Gly Thr Thr Leu Thr Ala Leu Glu Ala Ala Ala Asn Pro
                1110                1115                1120

GCA CTG CCC TCA GAC TTC AAG ACC ATC CTG GAC TGATGGCCAC CCGCCCACAG    3471
Ala Leu Pro Ser Asp Phe Lys Thr Ile Leu Asp
            1125                1130

CCAGGCCGAG AGCAGACACC AGCAGCCCTG TCACGCCGGG CTCTACGTCC CAGGGAGGGA    3531

GGGGCGGCCC ACACCCAGGC CCGCACCGCT GGGAGTCTGA GGCCTGAGTG AGTGTTTGGC    3591

CGAGGCCTGC ATGTCCGGCT GAAGGCTGAG TGTCCGGCTG AGGCCTGAGC GAGTGTCCAG    3651

CCAAGGGCTG AGTGTCCAGC ACACCTGCCG TCTTCACTTC CCCACAGGCT GGCGCTCGGC    3711

TCCACCCCAG GGCCAGCTTT TCCTCACCAG GAGCCCGGCT TCCACTCCCC ACATAGGAAT    3771

AGTCCATCCC CAGATTCGCC ATTGTTCACC CCTCGCCCTG CCCTCCTTTG CCTTCCACCC    3831

CCACCATCCA GGTGGAGACC CTGAGAAGGA CCCTGGGAGC TCTGGGAATT TGGAGTGACC    3891

AAAGGTGTGC CCTGTACACA GGCGAGGACC CTGCACCTGG ATGGGGTCC CTGTGGGTCA     3951

AATTGGGGGG AGGTGCTGTG GGAGTAAAAT ACTGAATATA TGAGTTTTTC AGTTTTGAAA    4011

AAAA                                                                  4015
```

(2) INFORMATION FOR SEQ ID NO: 225:

(i) SEQUENCE CHARACTERISTICS:
        (A) LENGTH: 1132 amino acids
        (B) TYPE: amino acid
        (D) TOPOLOGY: linear (ii) MOLECULE TYPE: protein (xi) SEQUENCE DESCRIPTION: SEQ ID NO: 225:

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365
```

-continued

```
Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780
```

```
Pro Leu Arg Asp Ala Val Val Ile Glu Gln Ser Ser Leu Asn Glu
785                 790                 795                 800

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
            850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln Gln
        1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Ala Gly Pro Leu Pro Ser Glu Ala Val Gln Trp
            1060                1065                1070

Leu Cys His Gln Ala Phe Leu Leu Lys Leu Thr Arg His Arg Val Thr
        1075                1080                1085

Tyr Val Pro Leu Leu Gly Ser Leu Arg Thr Ala Gln Thr Gln Leu Ser
        1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
                1125                1130
```

We claim:
1. An isolated polypeptide consisting of the amino acid sequence shown in SEQ. ID. NO. 69.

* * * * *

UNITED STATES PATENT AND TRADEMARK OFFICE
CERTIFICATE OF CORRECTION

PATENT NO.       : 6,309,867 B1                                          Page 1 of 1
APPLICATION NO.  : 09/430323
DATED            : October 30, 2001
INVENTOR(S)      : Cech et al.

It is certified that error appears in the above-identified patent and that said Letters Patent is hereby corrected as shown below:

Column 1, line 14, please add:
--This invention was made with Government support under Grant No. GM28039, awarded by the National Institutes of Health. The Government has certain rights in this invention.-- after "abandoned".

Signed and Sealed this

First Day of August, 2006

JON W. DUDAS
*Director of the United States Patent and Trademark Office*